US012559559B2

(12) United States Patent
Knoechel et al.

(10) Patent No.: US 12,559,559 B2
(45) Date of Patent: Feb. 24, 2026

(54) TARGETING GALECTIN-9 AS A THERAPEUTIC STRATEGY FOR T-CELL EXHAUSTION IN T-CELL ACUTE LYMPHOBLASTIC LEUKEMIA

(71) Applicants:DANA-FARBER CANCER INSTITUTE, INC., Boston, MA (US); THE BRIGHAM AND WOMEN'S HOSPITAL, INC., Boston, MA (US)

(72) Inventors: Birgit Knoechel, Brookline, MA (US); Jens G. Lohr, Brookline, MA (US); Praveen Anand, Allston, MA (US); Amy Guillaumet-Adkins, Allston, MA (US); Jon Aster, Lexington, MA (US)

(73) Assignees: DANA-FARBER CANCER INSTITUTE, INC., Boston, MA (US); THE BRIGHAM AND WOMEN'S HOSPITAL, INC., Boston, MA (US)

( * ) Notice: Subject to any disclaimer, the term of this patent is extended or adjusted under 35 U.S.C. 154(b) by 999 days.

(21) Appl. No.: 17/622,507

(22) PCT Filed: Jul. 10, 2020

(86) PCT No.: PCT/US2020/041570
§ 371 (c)(1),
(2) Date: Dec. 23, 2021

(87) PCT Pub. No.: WO2021/007503
PCT Pub. Date: Jan. 14, 2021

(65) Prior Publication Data
US 2022/0242955 A1      Aug. 4, 2022

Related U.S. Application Data

(60) Provisional application No. 62/872,987, filed on Jul. 11, 2019.

(51) Int. Cl.
| | |
|---|---|
| *A61K 39/395* | (2006.01) |
| *A61K 39/00* | (2006.01) |
| *C07K 16/28* | (2006.01) |
| *G01N 33/574* | (2006.01) |

(52) U.S. Cl.
CPC ... *C07K 16/2851* (2013.01); *G01N 33/57426* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 11,629,191 B2 * | 4/2023 | Koide | ............ A61P 37/06 424/133.1 |
| 2019/0077869 A1 | 3/2019 | Fiedler | |

FOREIGN PATENT DOCUMENTS

| | | |
|---|---|---|
| WO | 2019084553 A1 | 5/2019 |

OTHER PUBLICATIONS

Mohammed et al. Galectin-9 as a Predictive Marker for the Onset of Immune-Related Adverse Effects Associated with Anti-CCR4 MoAb Therapy in Patients with Adult T Cell Leukemia. Tohoku J. Exp. Med., 2017, 241,201-208 (Year: 2017).*

Edwards et al., The remarkable flexibility of the human antibody repertoire; isolation of over one thousand different antibodies to a single protein, BLyS. J Mol Biol. Nov. 14, 2003;334(1): 103-18. (Year: 2003).*

Lloyd et al., Modelling the human immune response: performance of a 1011 human antibody repertoire against a broad panel of therapeutically relevant antigens. Protein Eng Des Sel. Mar. 2009;22(3):159-68. (Year: 2009).*

Goel et al., Plasticity within the antigen-combining site may manifest as molecular mimicry in the humoral immune response. J Immunol. Dec. 15, 2004; 173(12):7358-67. (Year: 2004).*

Kanyavuz et al., Breaking the law: unconventional strategies for antibody diversification. Nat Rev Immunol. Jun. 2019; 19(6):355-368. (Year: 2019).*

Aibar S., et al., "SCENIC: Single-Cell Regulatory Network Inference and Clustering", Nat Methods 14, pp. 1083-1086, doi:10.1038/nmeth.4463, 2017.

Alencar A.J., et al., "Immune-checkpoint Inhibition as First-line Therapy for Hodgkin Lymphoma", Nature Reviews, Clinical Oncology, vol. 16, Oct. 2019, pp. 599-600.

Alexandrov L. B., et al., "Signatures of Mutational Processes in Human Cancer", Nature, vol. 500, 415-421, 11 Pages, doi:10.1038/nature12477, 2013.

Anastas J.N., et al., "Re-programing Chromatin with a Bifunctional LSD1/ HDAC Inhibitor Induces Therapeutic Differentiation in DIPG" Cancer Cell 36, 528-544, e510, Nov. 11, 2019, 28 Pages.

Anders S., et al., "A Python Framework to Work with High-Throughput Sequencing Data", Bioinformatics 31, doi: 10.1093/bioinformatics/btu638, 2015, pp. 166-169.

Aran D., et al., "xCell: Digitally Portraying the Tissue Cellular Heterogeneity Landscape", Genome Biol 18, 220, doi: 10.1186/s13059-017-1349-1, 2017, pp. 1-14.

Aster J.C., et al., "The Varied Roles of Notch in Cancer", Annual Review of Pathology, vol. 12, 2017, pp. 245-275.

Beck B., et al., "Unravelling Cancer Stem Cell Potential", Nature Reviews Cancer, vol. 13, Oct. 2013, pp. 727-738.

Bell J.J., et al., "The Earliest Thymic Progenitors for T Cells Possess Myeloid Lineage Potential", Nature, vol. 452, Apr. 10, 2008, pp. 764-767.

Beltran A., et al., "A Phase II Trial of the Aurora Kinase A Inhibitor Alisertib for Patients with Castration-resistant and Neuroendocrine Prostate Cancer: Efficacy and Biomarkers", doi: 10.1158/1078-0432.CCR-18-1912, Epub Sep. 19, 2018, Clinical Cancer Research, vol. 25, No. 1, Jan. 1, 2019, pp. 43-51.

Beltran H., et al., "The Role of Lineage Plasticity in Prostate Cancer Therapy Resistance", Clinical Cancer Research, Epub Jul. 30, 2019, doi: 10.1158/1078-0432.CCR-19-1423, Dec. 1, 2019, vol. 25, No. 23, pp. 6916-6924.

(Continued)

*Primary Examiner* — Maher M Haddad
(74) *Attorney, Agent, or Firm* — Mueting Raasch Group

(57) ABSTRACT

The present invention relates to compositions and methods for treating early T-cell precursor acute lymphoblastic leukemia (ETP T-ALL).

15 Claims, 111 Drawing Sheets

Specification includes a Sequence Listing.

(56) References Cited

OTHER PUBLICATIONS

Belver L., et al., "The Genetics and Mechanisms of T Cell Acute Lymphoblastic Leukaemia", Nature Reviews, Cancer, vol. 16, Aug. 2016, pp. 494-507.

Boegel S., et al., "HLA Typing from RNA-Seq Sequence Reads", Genome Medicine 4, 102, doi:10.1186/gm403, 2012, pp. 1-12.

Bolger A.M., et al., "Trimmomatic: A Flexible Trimmer for Illumina Sequence Data", Bioinformatics 30, pp. 2114-2120, doi:10.1093/bioinformatics/btu170, 2014.

Boratyn G.M., et al., "Magic-BLAST, an Accurate DNA and RNA-seq Aligner for Long and Short Reads", BMC Bioinformatics, vol. 20, No. 405, 2019, pp. 1-19.

Butler A., et al., "Integrating Single-Cell Transcriptomic Data Across Different Conditions, Technologies, and Species", Nature Biotechnology, vol. 36, No. 5, 411-420, doi:10.1038/nbt.4096, Jun. 2018, 33 Pages.

Cao H., et al., "The Role of CD44 in Fetal and Adult Hematopoietic Stem Cell Regulation", Haematologica, vol. 101, No. 1, 2016, pp. 26-37.

Carrette F., et al., "IL-7 signaling and CD127 Receptor Regulation in the Control of T Cell Homeostasis", Seminars in Immunology, vol. 24, No. 3, 209-217, 2012, pp. 1-18.

Chen C., et al., "Global Analysis of Induced Transcription Factors and Cofactors Identifies Tfdp2 as an Essential Coregulator during Terminal Erythropoiesis", Experimental Hematology, vol. 42, 464-476.e.5, doi:10.1016/j.exphem.2014.03.001, Jun. 2014, pp. 1-23.

Chen L., et al., "Molecular Mechanisms of T Cell Co-Stimulation and Co-Inhibition", Nature Reviews Immunology, doi:10.1038/nri3405, 2013, 227-242, pp. 1-30.

Cibulskis K., et al., "Sensitive Detection of Somatic Point Mutations in Impure and Heterogeneous Cancer Samples", Nature Biotechnology, vol. 31, No. 3, doi:10.1038/nbt.2514, 213-219, 2013, 9 Pages.

Civin C., et al., "Antigenic Analysis of Hematopoiesis. III. A Hematopoietic Progenitor Cell Surface Antigen Defined by a Monoclonal Antibody Raised Against KG-1a Cells", The Journal of Immunology, vol. 133, No. 1, 1984, pp. 157-165.

Coustan-Smith E., et al., "Early T-Cell Precursor Leukaemia: A Subtype of Very High-Risk Acute Lymphoblastic Leukaemia", Lancet Oncology, vol. 10, No. 2, 147-156, doi:10.1016/S1470-2045(08)70314-0, Feb. 2009, pp. 1-19.

Cullion K., et al., "Targeting the Notch1 and mTOR Pathways in a Mouse T-ALL Model", Blood, vol. 113, No. 24, Jun. 11, 2009, pp. 6172-6181.

Dail M., et al., "Loss of Oncogenic Notch1 with Resistance to a PI3K Inhibitor in T-cell Leukaemia", Nature, 512-516, vol. 513, No. 7519, doi:10.1038/nature13495, 2014, 27 Pages.

De Bie J., et al., "Single-cell Sequencing Reveals the Origin and the Order of Mutation Acquisition in T-cell Acute Lymphoblastic Leukemia" Leukemia, vol. 32, 2018, pp. 1358-1369.

Dobin A., et al., "STAR: Ultrafast Universal RNA-seq Aligner", Bioinformatics, vol. 29, No. 1, doi:10.1093/bioinformatics/bts635, 2013, pp. 15-21.

Eisenhauer., E.A., et al., "New Response Evaluation Criteria in Solid Tumours: Revised RECIST Guideline (version 1.1)", European Journal of Cancer, vol. 45, 2009, pp. 228-247.

Fan J., et al., "Characterizing Transcriptional Heterogeneity through Pathway and Gene Set Overdispersion Analysis", Nature Methods, vol. 13, 241-244, doi:10.1038/nmeth.3734, 2016, pp. 1-17.

Fernandez J.M., et al., "The BLUEPRINT Data Analysis Portal", Cell Systems 3, 491-495, doi:10.1016/j.cels.2016.10.021, Nov. 23, 2016, 11 Pages.

Filbin M.G., et al., "Developmental and Oncogenic Programs in H3K27M Gliomas Dissected by Single-cell RNA-seq", Science, 360(6386):331-335, doi:10.1126/science.aao4750, Apr. 20, 2018, pp. 1-11.

Galen P.V., et al., "Single-Cell RNA-Seq Reveals AML Hierarchies Relevant to Disease Progression and Immunity", Cell, vol. 176, No. 6, e1224, 1265-1281, 2019, 42 Pages.

Haydu J.E., et al. "Early T-Cell Precursor Acute Lymphoblastic Leukaemia", Curr Opin Hematol 20, pp. 369-373, doi:10.1097/MOH.0b013e3283623c61, 2013.

Heng T.S.P., et al., "The Immunological Genome Project: Networks of Gene Expression in Immune Cells", Nature Immunology, vol. 9, No. 10, doi:10.1038/ni1008-1091, Oct. 2008, pp. 1091-1094.

Hosokawa H., et al., "Bcl11b Sets Pro-t Cell Fate by Site-specific Cofactor Recruitment and by Repressing Id2 and Zbtb16", Nature Immunology, vol. 19, No. 12, 1427-1440, 2018, pp. 1-36.

Hu H., et al., "AnimalTFDB 3.0: A Comprehensive Resource for Annotation and Prediction of Animal Transcription Factors", Nucleic Acids Research, vol. 47, doi:10.1093/nar/gky822, 2019, pp. D33-D38.

International Preliminary Report on Patentability for International Application No. PCT/US2020/041570, mailed Jan. 20, 2022, 8 Pages.

International Search Report and Written Opinion for International Application No. PCT/US2020/041570, mailed Oct. 16, 2020, 10 Pages.

Jurtz V., et al., "NetMHCpan-4.0: Improved Peptide-MHC Class I Interaction Predictions Integrating Eluted Ligand and Peptide Binding Affinity Data1", Journal of Immunology, vol. 199, No. 9, 3360-3368, doi:10.4049/jimmunol.1700893, Nov. 2017, pp. 1-24.

Katsumura K.R., et al., "Human Leukemia Mutations Corrupt but Do Not Abrogate GATA-2 Function", PNAS, Proc Natl Acad Sci USA, vol. 115, No. 43, 2018, pp. E10109-E10118.

Kikushige Y., et al., "A TIM-3/Gal-9 Autocrine Stimulatory Loop Drives Self-Renewal of Human Myeloid Leukemia Stem Cells and Leukemic Progression", Cell Stem Cell 17, doi:10.1016/j.stem.2015.07.011, 2015, pp. 341-352.

Kluk M.J., et al., "Validation and Implementation of a Custom Next-Generation Sequencing Clinical Assay for Hematologic Malignancies", The Journal of Molecular Diagnostics, vol. 18, No. 4, doi:10.1016/j.jmoldx.2016.02.003, Jul. 2016, pp. 507-515.

Knoechel B., et al., "An Epigenetic Mechanism of Resistance to Targeted Therapy in T cell Acute Lymphoblastic Leukemia", Nature Genetics, vol. 46, No. 4, 364-370, doi:10.1038/ng.2913, Apr. 2014, pp. 1-21.

Knoechel B., et al., "Complete Hematologic Response of Early T-cell Progenitor Acute Lymphoblastic Leukemia to the Gamma-Secretase Inhibitor BMS-906024: Genetic and Epigenetic Findings in an Outlier Case", Cold Spring Harbor, Molecular Case Studies 1, a000539, doi:10.1101/mcs.a000539, 2015, pp. 1-13.

Kumar M. P., et al., "Analysis of Single-Cell RNA-Seq Identifies Cell-Cell Communication Associated with Tumor Characteristics", Cell Reports 25, 1458-1468 e1454, doi:10.1016/j.celrep.2018.10.047, Nov. 6, 2018, 16 Pages.

La Manno G., et al., "RNA Velocity of Single Cells", Nature, vol. 560, No. 7719, 494-498, doi:10.1038/s41586-018-0414-6, Aug. 2018, pp. 1-36.

Lahortiga I., et al., "Duplication of the MYB Oncogene in T Cell Acute Lymphoblastic Leukemia", Nature Genetics, doi:10.1038/ng2025, vol. 39, No. 5, May 2007, pp. 593-595.

Li B., et al., "RSEM: Accurate Transcript Quantification from RNA-Seq Data with or without a Reference Genome", BMC Bioinformatics 12, 323, doi:10.1186/1471-2105-12-323, 2011, pp. 1-16.

Liaw A., at al., "Classification and Regression by Random Forest", vol. 23, 2001.

Litzow M.R., et al., "How I Treat T-cell Acute Lymphoblastic Leukemia in Adults", Blood, vol. 126, No. 7, doi:10.1182/blood-2014-10-551895, Aug. 13, 2015, pp. 833-841.

Liu Y., et al., "The Genomic Landscape of Pediatric and Young Adult T-Lineage Acute Lymphoblastic Leukemia", Nature Genetics, vol. 49, No. 8, 1211-1218, doi: 10.1038/ng.3909, Aug. 2017, 10 Pages.

Livak K.J., et al., "Analysis of Relative Gene Expression Data Using Real-Time Quantitative PCR and the 2(-Delta Delta C(T)) Method", Methods, vol. 25, doi:10.1006/meth.2001.1262, 2001, pp. 402-408.

Luc S., et al., "Bcl11a Deficiency Leads to Hematopoietic Stem Cell Defects with an Aging-like Phenotype", Cell Reports 16, Sep. 20, 2016, pp. 3181-3194.

(56)　　　　　References Cited

OTHER PUBLICATIONS

Luksza M., et al., "A Neoantigen Fitness Model Predicts Tumor Response to Checkpoint Blockade Immunotherapy", Nature, vol. 551, No. 7681, 517-520, doi:10.1038/nature24473, Nov. 23, 2017, pp. 1-31.

Lun A.T.L., et al., "A Step-by-Step Workflow for Low-Level Analysis of Single-Cell RNA-seq Data with Bioconductor", F1000Res 5, 2122, doi:10.12688/f1000research.9501.2, 2016, pp. 1-71.

Marrack P., et al., "Type I Interferons Keep Activated T Cells Alive", The Journal of experimental medicine, vol. 189, No. 3, 1999, pp. 521-529.

McKenzie M.D., et al., "Interconversion between Tumorigenic and Differentiated States in Acute Myeloid Leukemia", Cell Stem Cell 25, 258-272, Aug. 1, 2019, 25 Pages.

Meacham C.E., et al., "Tumour Heterogeneity and Cancer Cell Plasticity", Nature, vol. 501, Sep. 19, 2013, pp. 328-337.

Miller A.B., et al., "Reporting Results of Cancer Treatment". Cancer, vol. 47, 1981, pp. 207-214.

Miller B.C., et al., "Subsets of Exhausted CD8+ T Cells Differentially Mediate Tumor Control and Respond to Checkpoint Blockade", Nature Immunology, vol. 20, doi:10.1038/s41590-019-0312-6, 326-336, Mar. 2019, 18 Pages.

MU., et al., "SOX2 Promotes Lineage Plasticity and Antiandrogen Resistance in TP53- and RB1-deficient Prostate Cancer", Science, vol. 355, No. 6320, 84-88, Jan. 6, 2017, pp. 1-12.

Muller S., et al., "CONICS Integrates scRNA-seq with DNA Sequencing to Map Gene Expression to Tumor Sub-clones", Bioinformatics, vol. 34, No. 18, doi:10.1093/bioinformatics/bty316, 2018, pp. 3217-3219.

Munoz P., et al., "CD38 Signaling in T Cells is Initiated within a Subset of Membrane Rafts Containing Lck and the CD3-zeta Subunit of the T Cell Antigen Receptor", The Journal of Biological Chemistry, vol. 279, No. 50, 2003, pp. 50791-50802.

NCBI: "Galectin-9 Isoform X1 [Homo sapiens]", XP_016880112.1, Retrieved date: Feb. 19, 2025, pp. 1-2.

NCBI: "Predicted: Homo sapiens Galectin 9 (LGALS9), Transcript Variant X1, mRNA", XM_017024623.2, Retrieved date: Feb. 19, 2025, pp. 1-2.

Neftel C., et al., "An Integrative Model of Cellular States, Plasticity, and Genetics for Glioblastoma", Cell, vol. 178, No. 4, 835-849, e821, Aug. 8, 2019, 37 Pages.

Newman A.M., et al., "Robust Enumeration of Cell Subsets from Tissue Expression Profiles", Nature Methods, 453-457, vol. 12, No. 5, 2015, pp. 1-20.

Ntziachristos P., et al., "Genetic Inactivation of the Polycomb Repressive Complex 2 in T Cell Acute Lymphoblastic Leukemia", Nature Medicine, vol. 18, No. 2, 298-301, Feb. 2012, 7 Pages.

Palacios E.H., et al., "Function of the Src-family Kinases, Lck and Fyn, in T-cell Development and Activation", Oncogene, vol. 23, 2004, pp. 7990-8000.

Palomero T., et al., "Mutational Loss of PTEN Induces Resistance to NOTCH1 Inhibition in T-cell Leukemia", Nature Medicine, vol. 13, No. 10, 1203-1210, doi:10.1038/nm1636, Oct. 2007, pp. 1-16.

Palomero T., et al., "Therapeutic Targeting of NOTCH1 Signaling in T-ALL", Clinical Lymphoma Myeloma, 9(Suppl 3):S205, 2009, 13 Pages.

Pardoll D.M., et al., "The Blockade of Immune Checkpoints in Cancer Immunotherapy", Nature Reviews Cancer, vol. 12, Apr. 2012, pp. 252-264.

Park S-M., et al., "IKZF2 Drives Leukemia Stem Cell Self-Renewal and Inhibits Myeloid Differentiation", Cell Stem Cell 24, 153-165, Jan. 3, 2019, 21 Pages.

Patel A. P., et al., "Single-cell RNA-seq Highlights Intratumoral Heterogeneity in Primary Glioblastoma", Science, vol. 344, No. 6190, 1396-1401, doi: 10.1126/science.1254257, Jun. 20, 2014, pp. 1-13.

Pellin D., et al., "A Comprehensive Single Cell Transcriptional Landscape of Human Hematopoietic Progenitors", Nature Communications, vol. 10, No. 2395, doi:10.1038/s41467-019-10291-0, 2019, pp. 1-15.

Picelli S., et al., "Full-Length RNA-seq from Single Cells Using Smart-seq2", Nature Protocols, vol. 9, No. 1, doi:10.1038/nprot.2014.006, 2014, pp. 171-181.

Pimentel H., et al., "A Dynamic Intron Retention Program Enriched in RNA Processing Genes Regulates Gene Expression During Terminal Erythropoiesis", Nucleic AcidsResearch, vol. 44, No. 2, 2016, pp. 838-851, doi:10.1093/nar/gkv1168.

Pinnell N., et al., "The PIAS-like Coactivator Zmiz1 Is a Direct and Selective Cofactor of Notch1 in T Cell Development and Leukemia", Immunity 43, doi:10.1016/j.immuni.2015.10.007, Nov. 17, 2015, pp. 870-883.

Potter N., et al., "Single Cell Analysis of Clonal Architecture in Acute Myeloid Leukaemia", Leukemia, vol. 33, 2019, pp. 1113-1123.

Pui C.H., et al., "Treatment of Acute Lymphoblastic Leukemia", The New England Journal of Medicine, vol. 354, doi:10.1056/NEJMra052603, 2006, pp. 166-178.

Rakowski L.A., et al., "Convergence of the ZMIZ1 and NOTCH1 Pathways at C-MYC in Acute T Lymphoblastic Leukemias", Cancer Research, vol. 73, No. 2, 930-941, doi: 10.1158/0008-5472.CAN-12-1389, Jan. 15, 2013, pp. 1-17.

Ramezani-Rad P., et al., "SOX4 Enables Oncogenic Survival Signals in Acute Lymphoblastic Leukemia", Blood, vol. 121, No. 1, doi:10.1182/blood-2012-05-428938, Jan. 3, 2013, pp. 148-155.

Sasca D., et al., "NCAM1 (CD56) Promotes Leukemogenesis and Confers Drug Resistance in AML", Blood, vol. 133, No. 21, May 23, 2019, pp. 2305-2319.

Schena M., et al., "Parallel Human Genome Analysis: Microarray-based Expression Monitoring of 1000 Genes", Proceedings of the National Academy of Sciences USA, vol. 93, No. 2, Oct. 1996, pp. 10614-10619.

Schlenner S.M., et al., "Fate Mapping Reveals Separate Origins of T Cells and Myeloid Lineages in the Thymus", Immunity 32, Mar. 26, 2010, pp. 426-436.

Schubert M., et al., "Perturbation-Response Genes Reveal Signaling Footprints in Cancer Gene Expression", Nature Communications, vol. 9, No. 20, 2018, pp. 1-11, doi:10.1038/s41467-017-02391-6.

Shlush L.I., et al., "Tracing the Origins of Relapse in Acute Myeloid Leukaemia to Stem Cells", Nature, 104-108, vol. 547, Jul. 6, 2017, 17 Pages.

Smart A.C., et al., "Intron Retention is a Source of Neoepitopes in Cancer", Nature Biotechnology, vol. 36, No. 11, 1056-1058, Dec. 2018, pp. 1-11, doi: 10.1038/nbt.4239.

Suva M.L., et al., "Single-Cell RNA Sequencing in Cancer: Lessons Learned and Emerging Challenges", Molecular Cell, vol. 75, No. 1, Jul. 11, 2019, pp. 7-12.

Suva M.L., et al., "Reconstructing and Reprogramming the Tumor-Propagating Potential of Glioblastoma Stem-like Cells", Cell, vol. 157, No. 3, Apr. 24, 2014, pp. 580-594.

Tatarek J., et al., "Notch1 Inhibition Targets the Leukemia-Initiating Cells in a Tal1/Lmo2 Mouse Model of T-ALL", Blood, vol. 118, No. 6 , 2011, pp. 1579-1590, doi:10.1182/blood-2010-08-300343.

Thoms J.A.I., et al., "ERG Promotes T-Acute Lymphoblastic Leukemia and is Transcriptionally Regulated In Leukemic Cells By A Stem Cell Enhancer", Blood, vol. 117, No. 26, 2011, pp. 7079-7089, doi:10.1182/blood-2010-12-317990.

Tirosh I., et al., Dissecting the Multicellular Ecosystem of Metastatic Melanoma by Single-cell RNA-seq, Science, vol. 352, No. 6282, 189-196, doi:10.1126/science.aad0501, Apr. 8, 2016, pp. 1-23.

Topalian S.L., et al., "Mechanism-driven Biomarkers to Guide Immune Checkpoint Blockade in Cancer Therapy", Nature Reviews Cancer, vol. 16, No. 5, 275-287, May 2016, pp. 1-30.

Trapnell C., et al., "Pseudo-temporal Ordering of Individual Cells Reveals Dynamics and Regulators of Cell Fate Decisions", Nature Biotechnology, vol. 32, No. 4, 381-386, doi:10.1038/nbt.2859, Apr. 2014, pp. 1-12.

Uckelmann H.J., et al., "Location, Location, Location: Mutant NPM1c Cytoplasmic Localization Is Required to Maintain Stem Cell Genes in AML", Cancer Cell 34, Sep. 10, 2018, pp. 355-357.

Van Der Auwera G.A., et al., "From FastQ Data to High Confidence Variant Calls: the Genome Analysis Toolkit Best Practices Pipe-

(56) References Cited

OTHER PUBLICATIONS line", Current Protocols in Bioinformatics, vol. 11, No. 1110, 11-33, 2013, pp. 1-43, doi:10.1002/0471250953.billlos43.

Venteicher A.S., et al., "Decoupling Genetics, Lineages, and Microenvironment in IDH-mutant Gliomas by Single-cell RNA-seq", Science, vol. 355, No. 6332, Mar. 31, 2017, pp. 1-29.

Vlierberghe P.V., et al., "ETV6 Mutations in Early Immature Human T Cell Leukemias", Journal of Experimental Medicine, vol. 208, No. 13, 2011, pp. 2571-2579, doi:10.1084/jem.20112239.

Vlierberghe P.V., et al., "The Molecular Basis of T Cell Acute Lymphoblastic Leukemia", The Journal of Clinical Investigation, vol. 122, No. 10, Oct. 2012, pp. 3398-3406, doi:10.1172/JCI61269.

Wada H., et al., "Adult T-cell Progenitors Retain Myeloid Potential", Nature, vol. 452, Apr. 10, 2008, pp. 768-772.

Wang H., et al., "Transcriptional Regulation of JARID1B/KDM5B Histone Demethylase by Ikaros, Histone Deacetylase 1 (HDAC1), and Casein Kinase 2 (CK2) in B-cell Acute Lymphoblastic Leukemia", Journal of Biological Chemistry, vol. 291, No. 08, Feb. 19, 2016, pp. 4004-4018, doi:10.1074/jbc.M115.679332.

Wang X., et al., "The Characteristics of Hematopoietic Stem Cells from Autoimmune-prone Mice and the Role of Neural Cell Adhesion Molecules in Abnormal Proliferation of These Cells in MRL/lpr mice", Haematologica, vol. 92, No. 3, 2007, pp. 300-307.

Wang Z., et al., "RNA-Seq: A Revolutionary Tool for Transcriptomics", Nature Reviews Genetics, vol. 10, No. 1, 57-63, Jan. 2009, pp. 1-16.

Watson P.A., et al., "Emerging Mechanisms of Resistance to Androgen Receptor Inhibitors in Prostate Cancer", Nature Reviews Cancer, vol. 15, No. 12, 701-711, Dec. 2015, pp. 1-27.

Weng A.P., et al., "Activating Mutations of NOTCH1 in Human T Cell Acute Lymphoblastic Leukemia", Science, vol. 306, doi:10.1126/science.1102160, Oct. 8, 2004, pp. 269-271.

Wherry E. J., et al., "Molecular and Cellular Insights into T cell Exhaustion", Nature Reviews Immunology, vol. 15, No. 8, 486-499, doi:10.1038/nri3862, Aug. 2015, pp. 1-29.

Wolchok J.D., et al., "Guidelines for the Evaluation of Immune Therapy Activity in Solid Tumors: Immune-Related Response Criteria", Clinical Cancer Research, vol. 15, No. 23, Dec. 1, 2009, pp. 7412-7420.

Wolf F.A., et al., "SCANPY: Large-Scale Single-Cell Gene Expression Data Analysis", Genome Biology, vol. 19, No. 15, doi:10.1186/s13059-017-1382-0, 2018, pp. 1-5.

Yashiro-Ohtani Y., et al., "Long-range Enhancer Activity Determines Myc Sensitivity to Notch Inhibitors in T Cell Leukemia", PNAS, USA., Nov. 4, 2014, pp. E4946-E4953.

Yoshida H., et al., "X-ray Structures of Human Galectin-9 C-Terminal Domain in Complexes with a Biantennary Oligosaccharide and Sialyllactose", The Journal of Biological Chemistry, vol. 285, No. 47, doi:10.1074/jbc.M110.163402, Nov. 2010, pp. 36969-36976.

Zemmour D., et al., "Single-cell Gene Expression Reveals a Landscape of Regulatory T cell Phenotypes Shaped by the TCR", Nature Immunology, vol. 19, No. 3, 291-301, doi:10.1038/s41590-018-0051-0, Mar. 2018, pp. 1-34.

Zhang J., et al., "Deregulation of DUX4 and ERG in Acute Lymphoblastic Leukemia", Nature Genetics, vol. 48, No. 12, 1481-1489, 2016, pp. 1-29.

Zhang J., et al., "The Genetic Basis of Early T-cell Precursor Acute Lymphoblastic Leukaemia", Nature, vol. 481, doi:10.1038/nature10725, Jan. 12, 2012, pp. 157-163.

Zhu C., et al., "The Tim-3 Ligand Galectin-9 Negatively Regulates T Helper Type 1 Immunity", Nature Immunology, vol. 6, doi:10.1038/ni1271, Dec. 2005, pp. 1245-1252.

Real et al., "NOTCH inhibition and glucocorticoid therapy in T-cell acute lymphoblastic leukemia," Leukemia, vol. 23, No. 8, Aug. 2009, pp. 1374-1377.

Rytting et al., "Augmented Berlin-Frankfurt-Munster Therapy in Adolescents and Young Adults (AYA) with Acute Lymphoblastic Leukemia (ALL)," Cancer, vol. 120, No. 23, Dec. 2014, pp. 3660-3668.

Sanchez et al., "Targeting PI3K Signaling in Acute Lymphoblastic Leukemia," International Journal of Molecular Sciences, vol. 20, No. 2, Article 412, Jan. 2019, pp. 1-14.

Henry C.J., et al., "Lyt-200, a Humanized Anti-Galectin-9 Antibody, Exhibits Preclinical Efficacy in Models of Hematological Malignancies", 605.Molecular Pharmacology and Drug Resistance: Lymphoid Neoplasms, Nov. 15, 2022, Blood, vol. 140 (Supplement 1), 8837, 2 pages.

Lee M., et al., "AlphaGal9Ab Treatment As a Novel Therapy for Blood Cancer", 618.Acute Lymphoblastic Leukemias: Biomarkers, Molecular Markers and Minimal Residual Disease in Diagnosis and Prognosis, Blood, The 65th ASH Annual Meeting Abstracts, vol. 142, Supplement 1, Nov. 2, 2023, p. 6056.

Lu R-M., et al., "Development of Therapeutic Antibodies for the Treatment of Diseases," Journal of Biomedical Science, 2020, vol. 27, No. 1(1), pp. 1-30.

* cited by examiner

5 ETP T-ALL patients
4 normal donors

Blood /
Bone marrow

Single cell
sorting

CD45low -> enriched for leukemia
CD45high CD3+ -> T cells
CD45high CD19+ -> B cells
CD45high CD14+ -> Monocytes PAGODA2 multilevel clusters

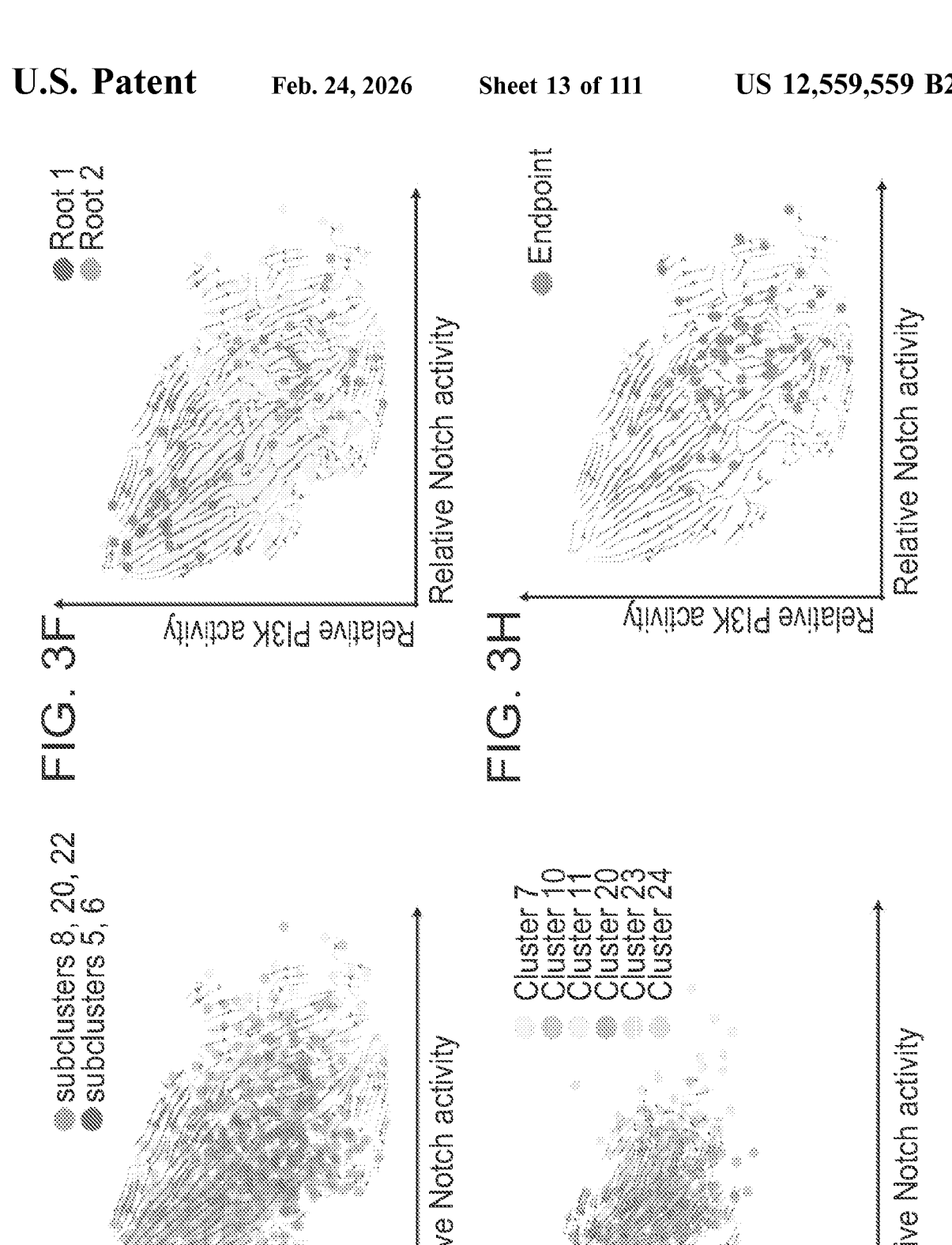

FIG. 5C
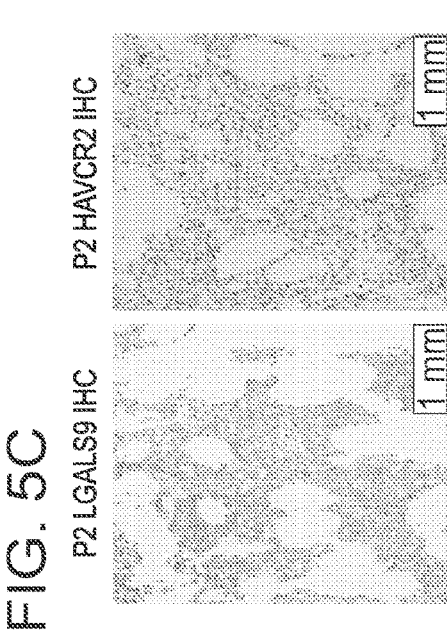
P2 LGALS9 IHC     P2 HAVCR2 IHC
FIG. 5E
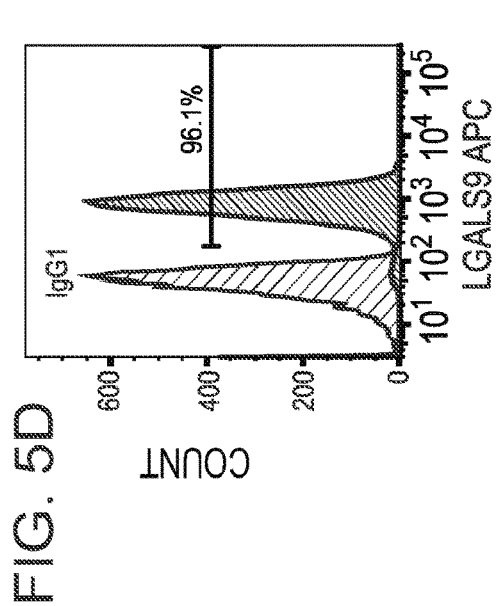
FIG. 5B
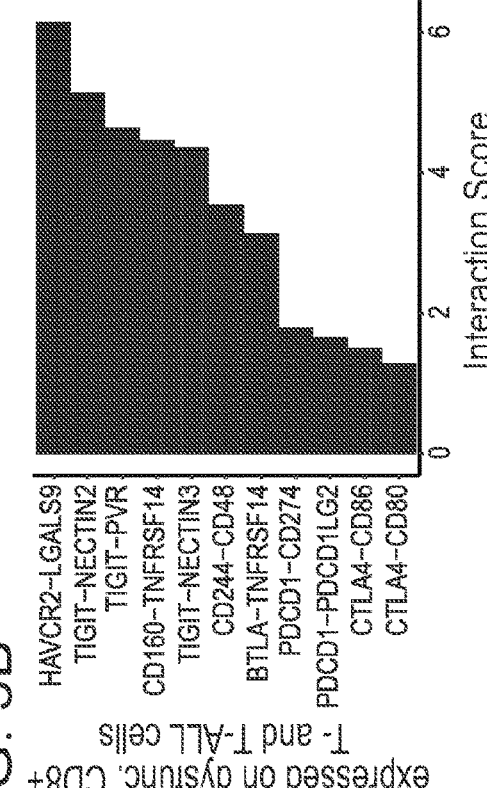
FIG. 5D Expression of markers genes from Cluster 1 in Immgen dataset

| FIG. 7B-1 | FIG. 7B-2 | FIG. 7B-3 | FIG. 7B-4 |
|-----------|-----------|-----------|-----------|
| FIG. 7B-5 | FIG. 7B-6 | FIG. 7B-7 | FIG. 7B-8 |

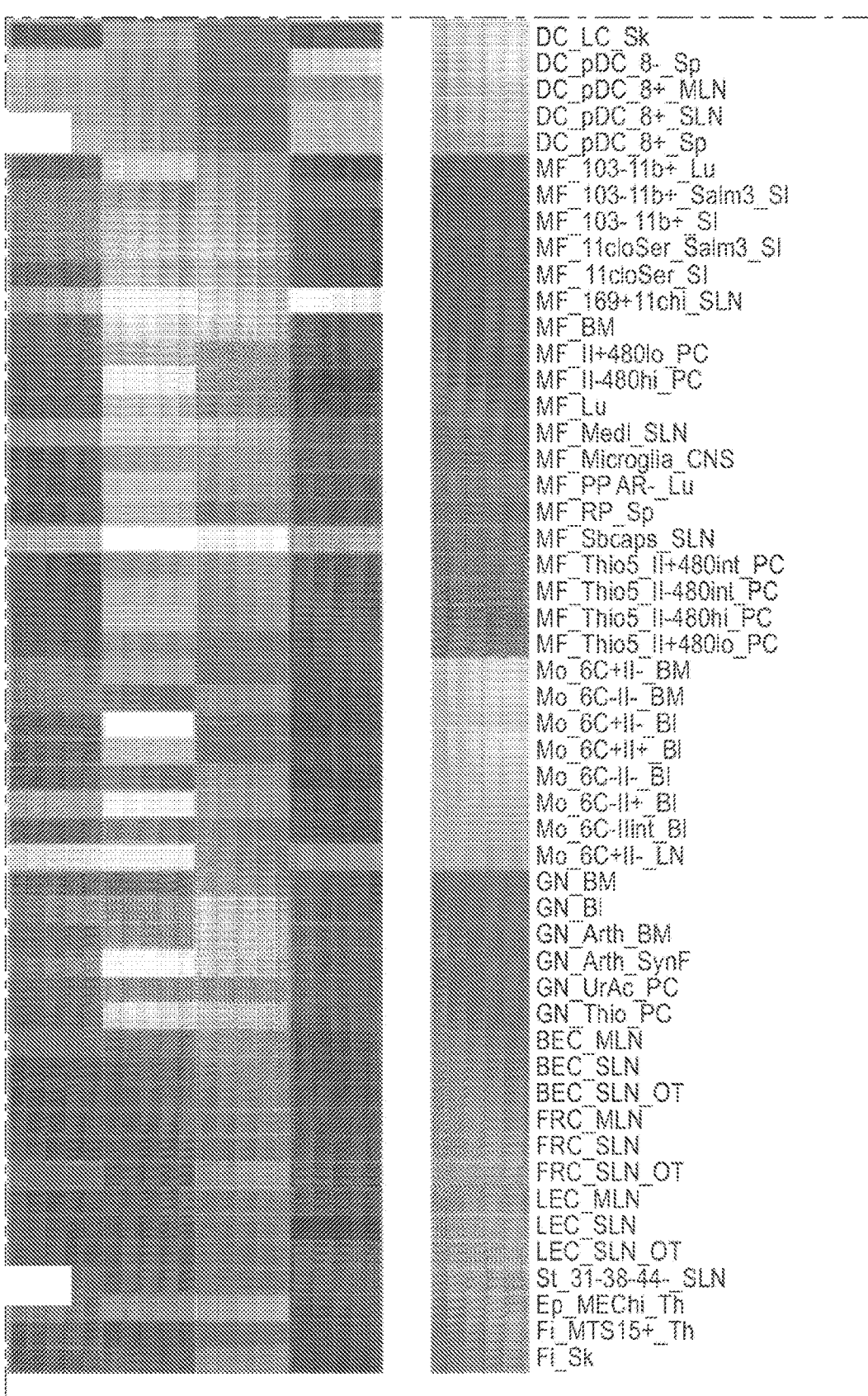

DC_LC_Sk
DC_pDC_8-_Sp
DC_pDC_8+_MLN
DC_pDC_8+_SLN
DC_pDC_8+_Sp
MF_103-11b+_Lu
MF_103-11b+_Salm3_SI
MF_103-_11b+_SI
MF_11cloSer_Salm3_SI
MF_11cloSer_SI
MF_169+11chi_SLN
MF_BM
MF_II+480lo_PC
MF_II-480hi_PC
MF_Lu
MF_Medl_SLN
MF_Microglia_CNS
MF_PPAR-_Lu
MF_RP_Sp
MF_Sbcaps_SLN
MF_Thio5_II+480int_PC
MF_Thio5_II-480int_PC
MF_Thio5_II-480hi_PC
MF_Thio5_II+480lo_PC
Mo_6C+II-_BM
Mo_6C-II-_BM
Mo_6C+II-_Bl
Mo_6C+II+_Bl
Mo_6C-II-_Bl
Mo_6C-II+_Bl
Mo_6C-IIint_Bl
Mo_6C+II-_LN
GN_BM
GN_Bl
GN_Arth_BM
GN_Arth_SynF
GN_UrAc_PC
GN_Thio_PC
BEC_MLN
BEC_SLN
BEC_SLN_OT
FRC_MLN
FRC_SLN
FRC_SLN_OT
LEC_MLN
LEC_SLN
LEC_SLN_OT
St_31-38-44-_SLN
Ep_MEChi_Th
Fi_MTS15+_Th
Fi_Sk

Expression of markers genes from Cluster 7 in Immgen dataset

| FIG. 7C | | |
|---|---|---|
| FIG. 7C-1 | FIG. 7C-2 | FIG. 7C-3 | FIG. 7C-4 |
| FIG. 7C-5 | FIG. 7C-6 | FIG. 7C-7 | FIG. 7C-8 |

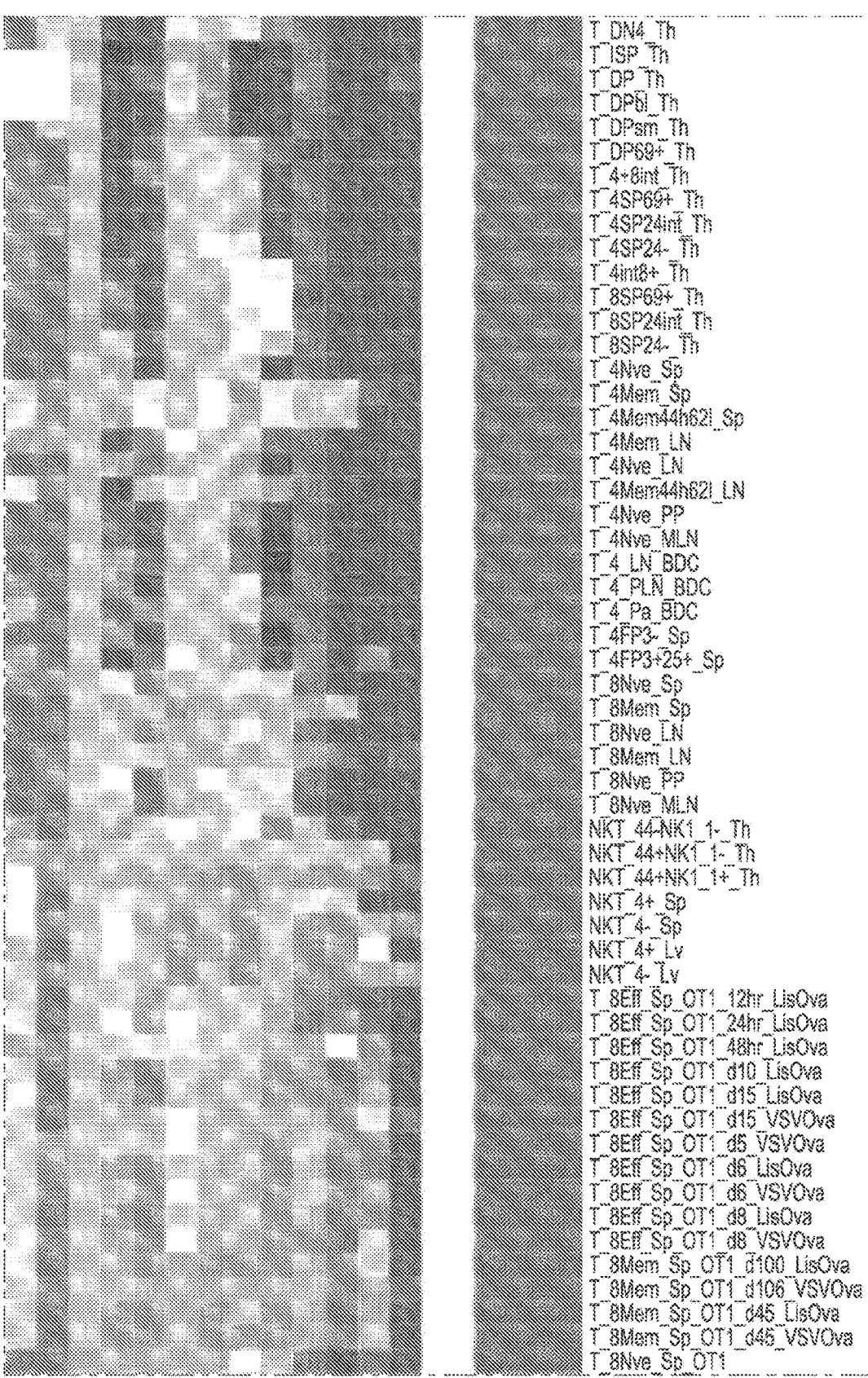

T_DN4_Th
T_ISP_Th
T_DP_Th
T_DP8l_Th
T_DPsm_Th
T_DP69+_Th
T_4+8int_Th
T_4SP69+_Th
T_4SP24int_Th
T_4SP24-_Th
T_4int8+_Th
T_8SP69+_Th
T_8SP24int_Th
T_8SP24-_Th
T_4Nve_Sp
T_4Mem_Sp
T_4Mem44h62l_Sp
T_4Mem_LN
T_4Nve_LN
T_4Mem44h62l_LN
T_4Nve_PP
T_4Nve_MLN
T_4_LN_BDC
T_4_PLN_BDC
T_4_Pa_BDC
T_4FP3-_Sp
T_4FP3+25+_Sp
T_8Nve_Sp
T_8Mem_Sp
T_8Nve_LN
T_8Mem_LN
T_8Nve_PP
T_8Nve_MLN
NKT_44-NK1_1-_Th
NKT_44+NK1_1-_Th
NKT_44+NK1_1+_Th
NKT_4+_Sp
NKT_4-_Sp
NKT_4+_Lv
NKT_4-_Lv
T_8Eff_Sp_OT1_12hr_LisOva
T_8Eff_Sp_OT1_24hr_LisOva
T_8Eff_Sp_OT1_48hr_LisOva
T_8Eff_Sp_OT1_d10_LisOva
T_8Eff_Sp_OT1_d15_LisOva
T_8Eff_Sp_OT1_d15_VSVOva
T_8Eff_Sp_OT1_d5_VSVOva
T_8Eff_Sp_OT1_d6_LisOva
T_8Eff_Sp_OT1_d6_VSVOva
T_8Eff_Sp_OT1_d8_LisOva
T_8Eff_Sp_OT1_d8_VSVOva
T_8Mem_Sp_OT1_d100_LisOva
T_8Mem_Sp_OT1_d106_VSVOva
T_8Mem_Sp_OT1_d45_LisOva
T_8Mem_Sp_OT1_d45_VSVOva
T_8Nve_Sp_OT1

Expression of markers genes from Cluster 8 in Immgen dataset

| FIG. 7D | | |
|---|---|---|
| FIG. 7D-1 | FIG. 7D-2 | FIG. 7D-3 | FIG. 7D-4 |
| FIG. 7D-5 | FIG. 7D-6 | FIG. 7D-7 | FIG. 7D-8 |
| FIG. 7D-9 | FIG. 7D-10 | FIG. 7D-11 | FIG. 7D-12 |

FIG. 7D

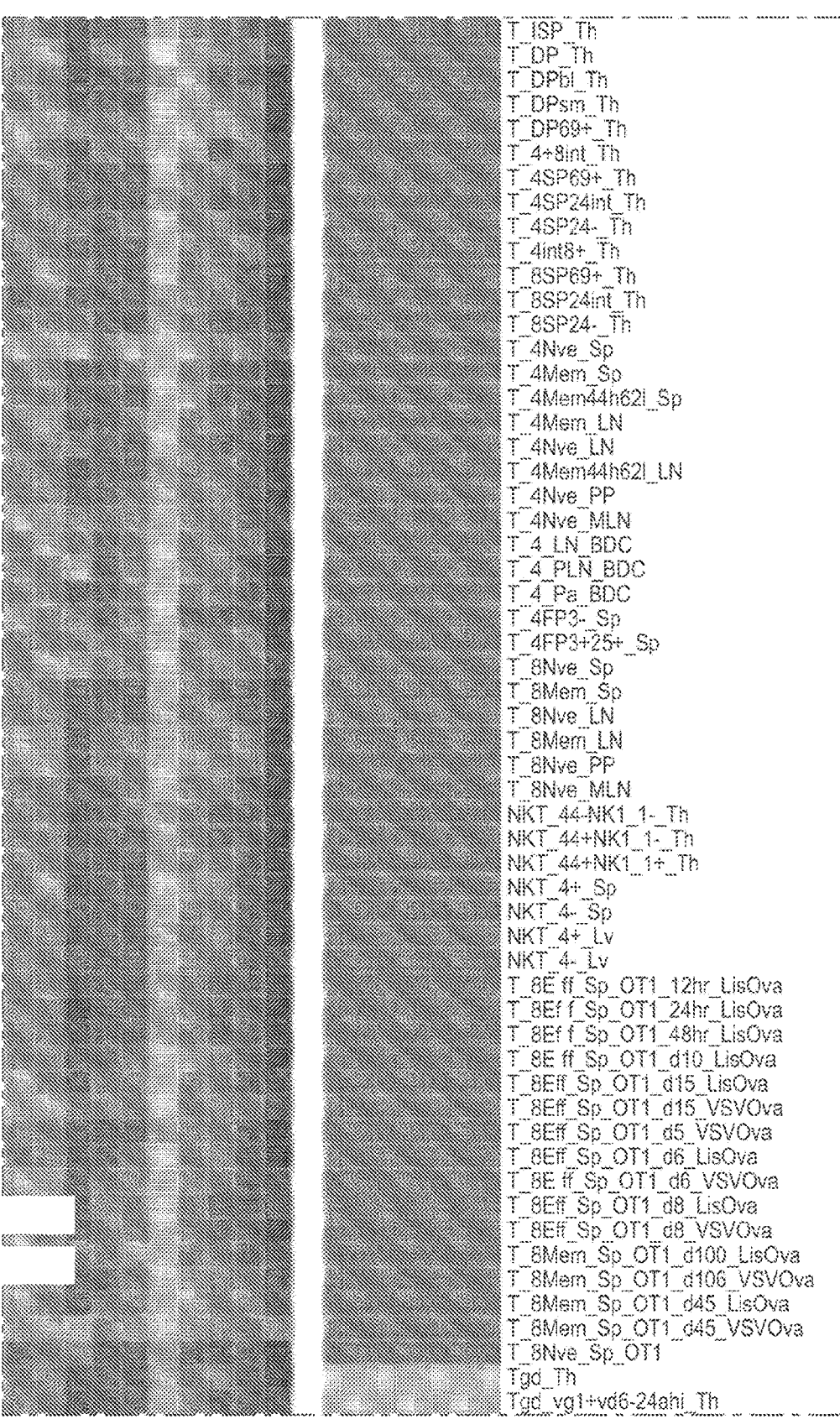

T_ISP_Th
T_DP_Th
T_DPbl_Th
T_DPsm_Th
T_DP69+_Th
T_4+8int_Th
T_4SP69+_Th
T_4SP24int_Th
T_4SP24-_Th
T_4int8+_Th
T_8SP69+_Th
T_8SP24int_Th
T_8SP24-_Th
T_4Nve_Sp
T_4Mem_Sp
T_4Mem44h62l_Sp
T_4Mem_LN
T_4Nve_LN
T_4Mem44h62l_LN
T_4Nve_PP
T_4Nve_MLN
T_4_LN_BDC
T_4_PLN_BDC
T_4_Pa_BDC
T_4FP3-_Sp
T_4FP3+25+_Sp
T_8Nve_Sp
T_8Mem_Sp
T_8Nve_LN
T_8Mem_LN
T_8Nve_PP
T_8Nve_MLN
NKT_44-NK1_1-_Th
NKT_44+NK1_1-_Th
NKT_44+NK1_1+_Th
NKT_4+_Sp
NKT_4-_Sp
NKT_4+_Lv
NKT_4-_Lv
T_8Eff_Sp_OT1_12hr_LisOva
T_8Eff_Sp_OT1_24hr_LisOva
T_8Eff_Sp_OT1_48hr_LisOva
T_8Eff_Sp_OT1_d10_LisOva
T_8Eff_Sp_OT1_d15_LisOva
T_8Eff_Sp_OT1_d15_VSVOva
T_8Eff_Sp_OT1_d5_VSVOva
T_8Eff_Sp_OT1_d6_LisOva
T_8Eff_Sp_OT1_d6_VSVOva
T_8Eff_Sp_OT1_d8_LisOva
T_8Eff_Sp_OT1_d8_VSVOva
T_8Mem_Sp_OT1_d100_LisOva
T_8Mem_Sp_OT1_d106_VSVOva
T_8Mem_Sp_OT1_d45_LisOva
T_8Mem_Sp_OT1_d45_VSVOva
T_8Nve_Sp_OT1
Tgd_Th
Tgd_vg1+vd6-24ahi_Th

FIG. 7D-2

Expression of markers genes from Cluster 10 in Immgen dataset

| FIG. 7E | | | |
|---|---|---|---|
| FIG. 7E-1 | FIG. 7E-2 | FIG. 7E-3 | FIG. 7E-4 |
| FIG. 7E-5 | FIG. 7E-6 | FIG. 7E-7 | FIG. 7E-8 |
| FIG. 7E-9 | FIG. 7E-10 | FIG. 7E-11 | FIG. 7E-12 |

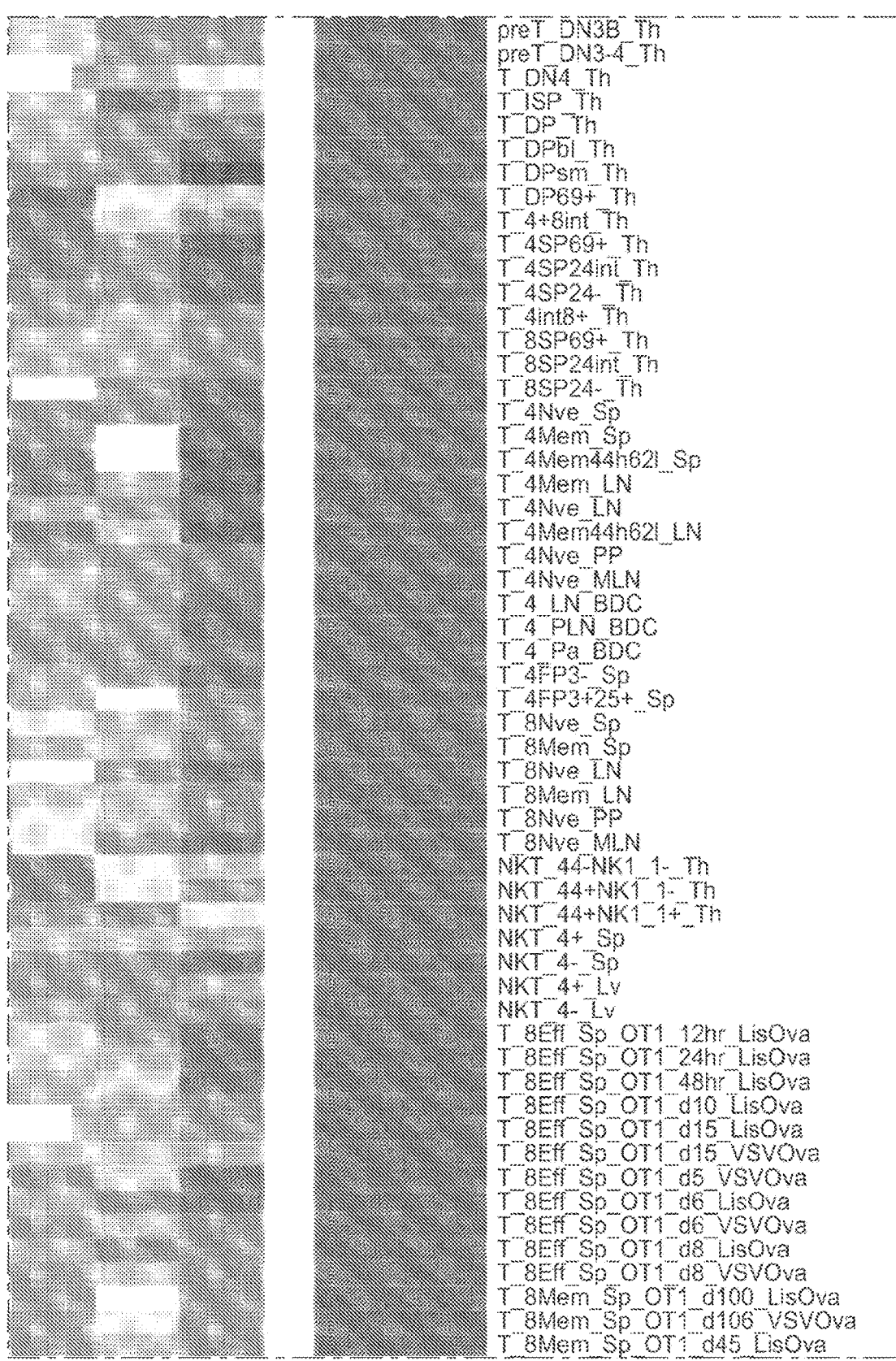

preT_DN3B_Th
preT_DN3-4_Th
T_DN4_Th
T_ISP_Th
T_DP_Th
T_DPbl_Th
T_DPsm_Th
T_DP69+_Th
T_4+8int_Th
T_4SP69+_Th
T_4SP24int_Th
T_4SP24-_Th
T_4int8+_Th
T_8SP69+_Th
T_8SP24int_Th
T_8SP24-_Th
T_4Nve_Sp
T_4Mem_Sp
T_4Mem44h62l_Sp
T_4Mem_LN
T_4Nve_LN
T_4Mem44h62l_LN
T_4Nve_PP
T_4Nve_MLN
T_4_LN_BDC
T_4_PLN_BDC
T_4_Pa_BDC
T_4FP3-_Sp
T_4FP3+25+_Sp
T_8Nve_Sp
T_8Mem_Sp
T_8Nve_LN
T_8Mem_LN
T_8Nve_PP
T_8Nve_MLN
NKT_44-NK1_1-_Th
NKT_44+NK1_1-_Th
NKT_44+NK1_1+_Th
NKT_4+_Sp
NKT_4-_Sp
NKT_4+_Lv
NKT_4-_Lv
T_8Eff_Sp_OT1_12hr_LisOva
T_8Eff_Sp_OT1_24hr_LisOva
T_8Eff_Sp_OT1_48hr_LisOva
T_8Eff_Sp_OT1_d10_LisOva
T_8Eff_Sp_OT1_d15_LisOva
T_8Eff_Sp_OT1_d15_VSVOva
T_8Eff_Sp_OT1_d5_VSVOva
T_8Eff_Sp_OT1_d6_LisOva
T_8Eff_Sp_OT1_d6_VSVOva
T_8Eff_Sp_OT1_d8_LisOva
T_8Eff_Sp_OT1_d8_VSVOva
T_8Mem_Sp_OT1_d100_LisOva
T_8Mem_Sp_OT1_d106_VSVOva
T_8Mem_Sp_OT1_d45_LisOva

FIG. 7E-2

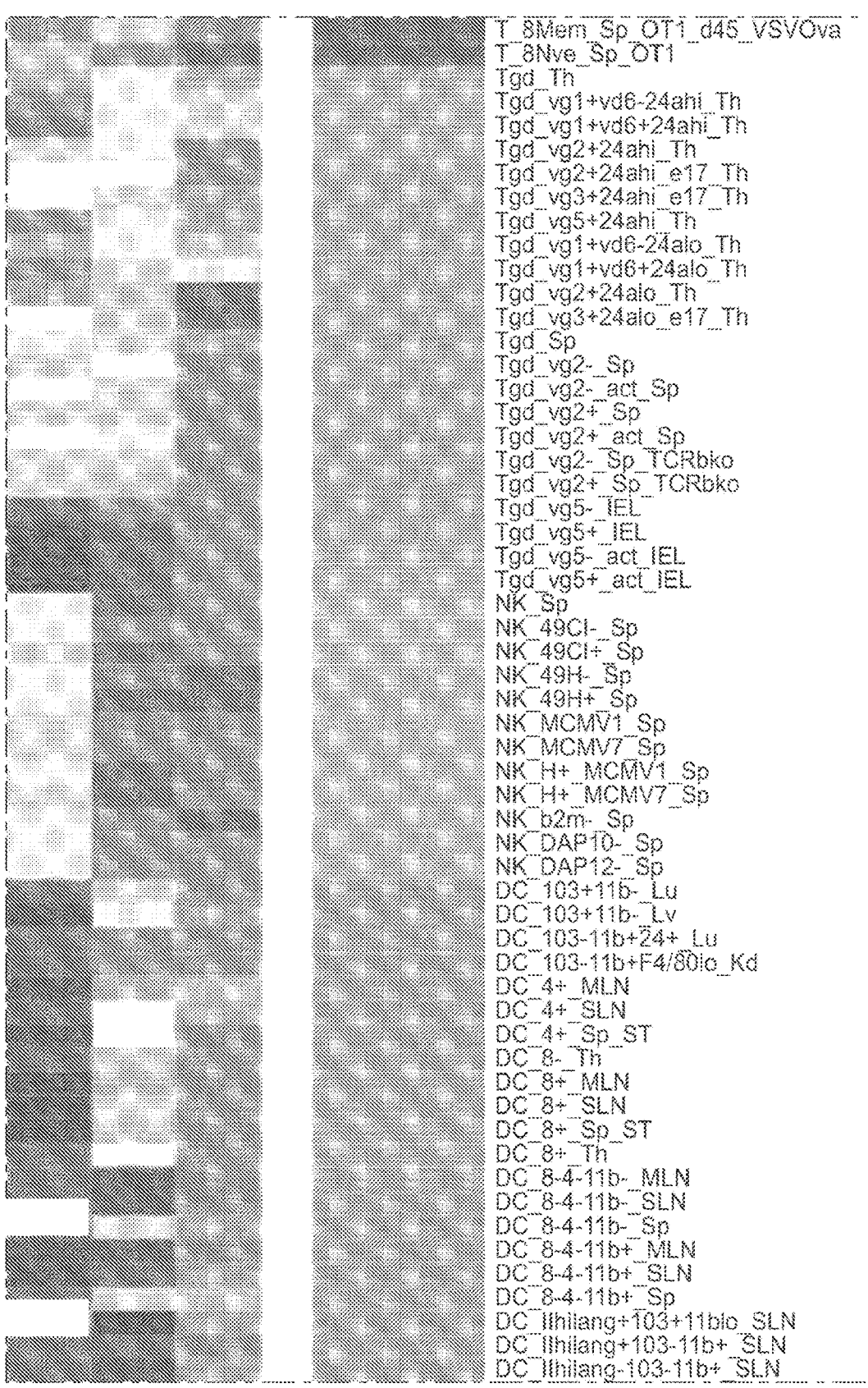

T_8Mem_Sp_OT1_d45_VSVOva
T_8Nve_Sp_OT1
Tgd_Th
Tgd_vg1+vd6-24ahi_Th
Tgd_vg1+vd6+24ahi_Th
Tgd_vg2+24ahi_Th
Tgd_vg2+24ahi_e17_Th
Tgd_vg3+24ahi_e17_Th
Tgd_vg5+24ahi_Th
Tgd_vg1+vd6-24alo_Th
Tgd_vg1+vd6+24alo_Th
Tgd_vg2+24alo_Th
Tgd_vg3+24alo_e17_Th
Tgd_Sp
Tgd_vg2-_Sp
Tgd_vg2-_act_Sp
Tgd_vg2+_Sp
Tgd_vg2+_act_Sp
Tgd_vg2-_Sp_TCRbko
Tgd_vg2+_Sp_TCRbko
Tgd_vg5-_IEL
Tgd_vg5+_IEL
Tgd_vg5-_act_IEL
Tgd_vg5+_act_IEL
NK_Sp
NK_49CI-_Sp
NK_49CI+_Sp
NK_49H-_Sp
NK_49H+_Sp
NK_MCMV1_Sp
NK_MCMV7_Sp
NK_H+_MCMV1_Sp
NK_H+_MCMV7_Sp
NK_b2m-_Sp
NK_DAP10-_Sp
NK_DAP12-_Sp
DC_103+11b-_Lu
DC_103+11b-_Lv
DC_103-11b+24+_Lu
DC_103-11b+F4/80io_Kd
DC_4+_MLN
DC_4+_SLN
DC_4+_Sp_ST
DC_8-_Th
DC_8+_MLN
DC_8+_SLN
DC_8+_Sp_ST
DC_8+_Th
DC_8-4-11b-_MLN
DC_8-4-11b-_SLN
DC_8-4-11b-_Sp
DC_8-4-11b+_MLN
DC_8-4-11b+_SLN
DC_8-4-11b+_Sp
DC_llhilang+103+11bio_SLN
DC_llhilang+103-11b+_SLN
DC_llhilang-103-11b+_SLN

FIG. 7E-3

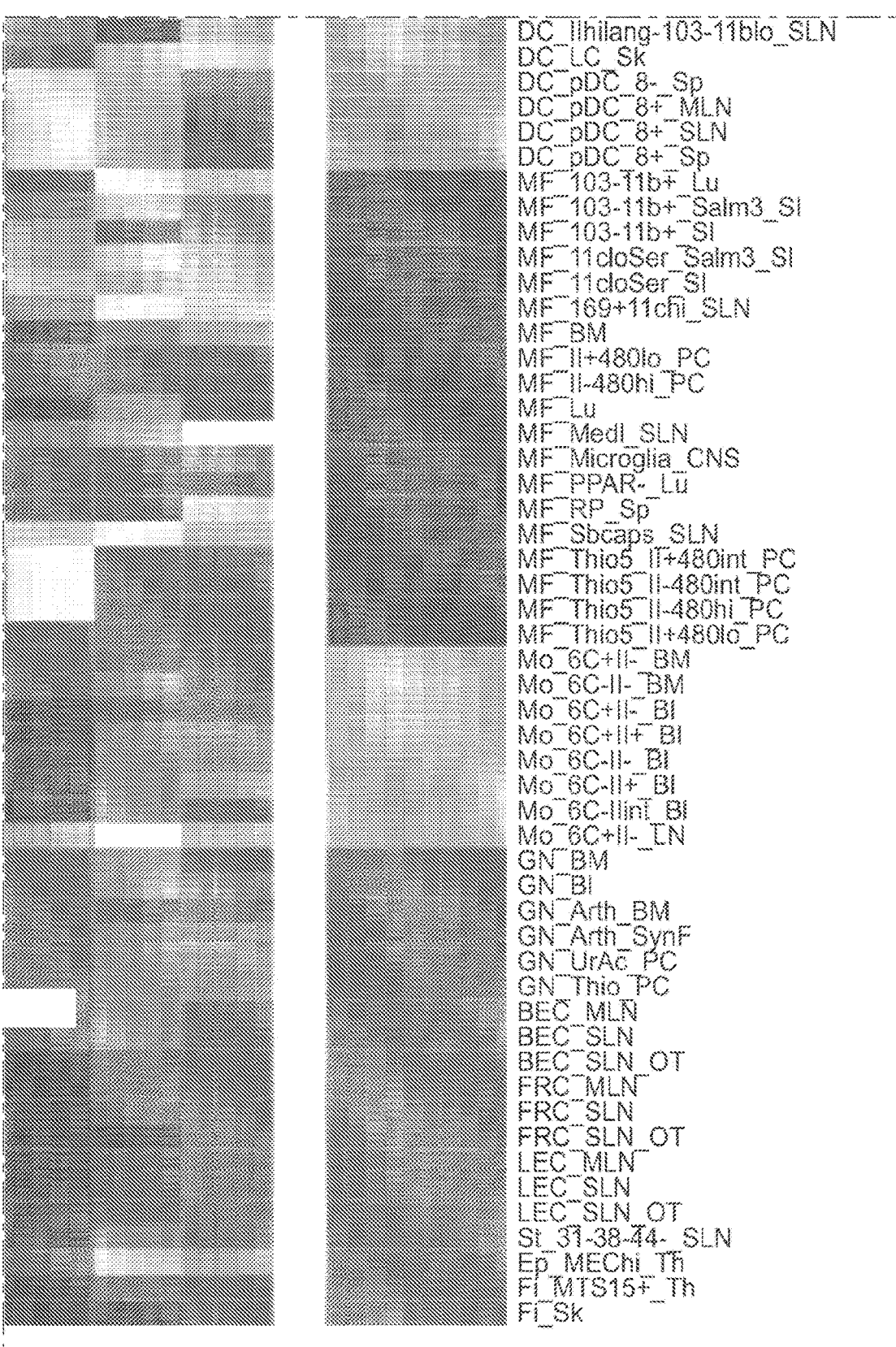

DC_Ilhilang-103-11blo_SLN
DC_LC_Sk
DC_pDC_8-_Sp
DC_pDC_8+_MLN
DC_pDC_8+_SLN
DC_pDC_8+_Sp
MF_103-11b+_Lu
MF_103-11b+_Salm3_SI
MF_103-11b+_SI
MF_11doSer_Salm3_SI
MF_11doSer_SI
MF_169+11chi_SLN
MF_BM
MF_II+480lo_PC
MF_II-480hi_PC
MF_Lu
MF_Medl_SLN
MF_Microglia_CNS
MF_PPAR-_Lu
MF_RP_Sp
MF_Sbcaps_SLN
MF_Thio5_II+480int_PC
MF_Thio5_II-480int_PC
MF_Thio5_II-480hi_PC
MF_Thio5_II+480lo_PC
Mo_6C+II-_BM
Mo_6C-II-_BM
Mo_6C+II-_Bl
Mo_6C+II+_Bl
Mo_6C-II-_Bl
Mo_6C-II+_Bl
Mo_6C-IIint_Bl
Mo_6C+II-_LN
GN_BM
GN_Bl
GN_Arth_BM
GN_Arth_SynF
GN_UrAc_PC
GN_Thio_PC
BEC_MLN
BEC_SLN
BEC_SLN_OT
FRC_MLN
FRC_SLN
FRC_SLN_OT
LEC_MLN
LEC_SLN
LEC_SLN_OT
SI_31-38-44-_SLN
Ep_MEChi_Th
Fl_MTS15+_Th
Fl_Sk

Expression of markers genes from Cluster 11 in Immgen dataset

| FIG. 7F | | | |
|---|---|---|---|
| FIG. 7F-1 | FIG. 7F-2 | FIG. 7F-3 | FIG. 7F-4 |
| FIG. 7F-5 | FIG. 7F-6 | FIG. 7F-7 | FIG. 7F-8 |
| FIG. 7F-9 | FIG. 7F-10 | FIG. 7F-11 | FIG. 7F-12 |

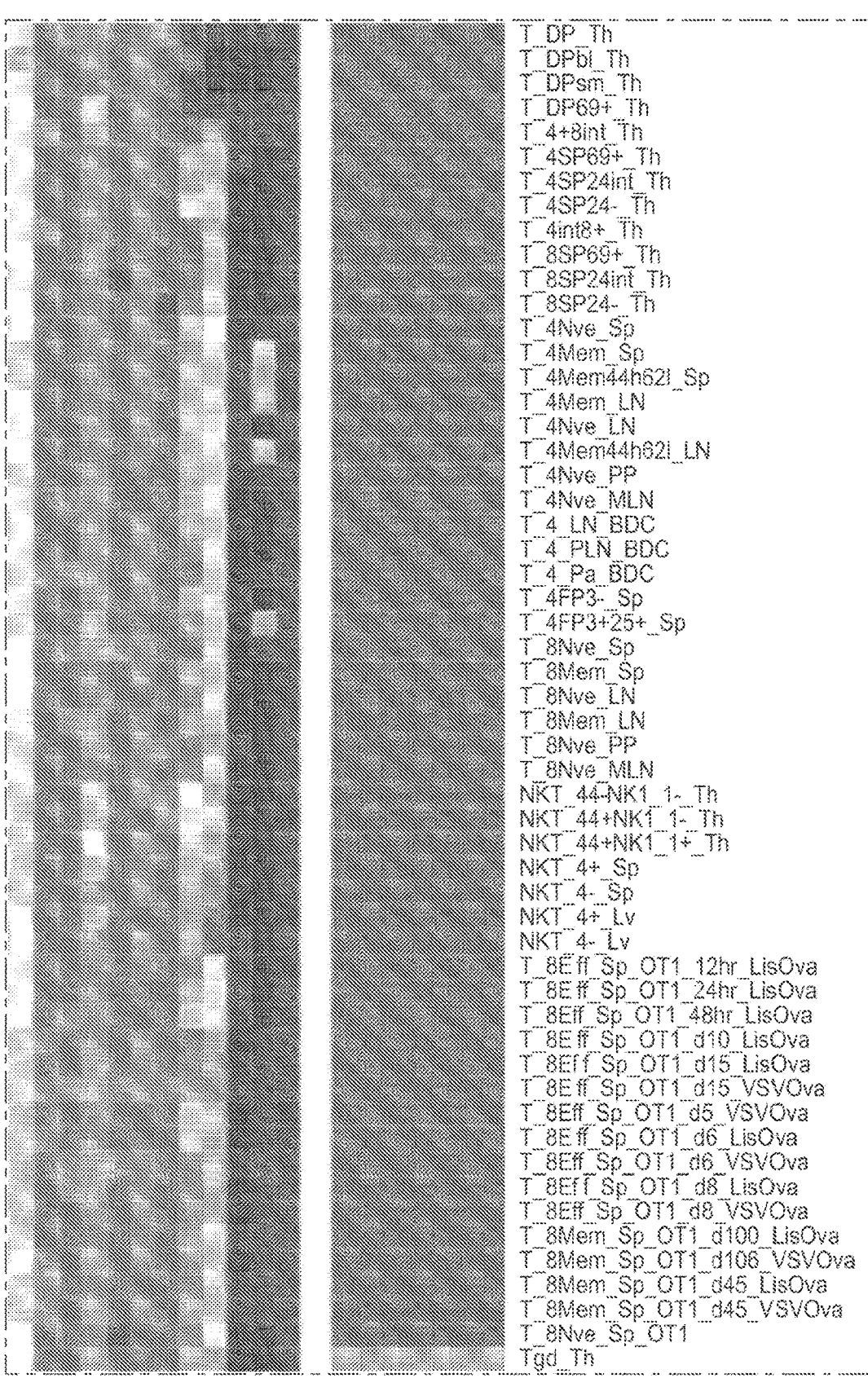

T_DP_Th
T_DPbl_Th
T_DPsm_Th
T_DP69+_Th
T_4+8int_Th
T_4SP69+_Th
T_4SP24int_Th
T_4SP24-_Th
T_4int8+_Th
T_8SP69+_Th
T_8SP24int_Th
T_8SP24-_Th
T_4Nve_Sp
T_4Mem_Sp
T_4Mem44h62l_Sp
T_4Mem_LN
T_4Nve_LN
T_4Mem44h62l_LN
T_4Nve_PP
T_4Nve_MLN
T_4_LN_BDC
T_4_PLN_BDC
T_4_Pa_BDC
T_4FP3-_Sp
T_4FP3+25+_Sp
T_8Nve_Sp
T_8Mem_Sp
T_8Nve_LN
T_8Mem_LN
T_8Nve_PP
T_8Nve_MLN
NKT_44-NK1_1-_Th
NKT_44+NK1_1-_Th
NKT_44+NK1_1+_Th
NKT_4+_Sp
NKT_4-_Sp
NKT_4+_Lv
NKT_4-_Lv
T_8Eff_Sp_OT1_12hr_LisOva
T_8Eff_Sp_OT1_24hr_LisOva
T_8Eff_Sp_OT1_48hr_LisOva
T_8Eff_Sp_OT1_d10_LisOva
T_8Eff_Sp_OT1_d15_LisOva
T_8Eff_Sp_OT1_d15_VSVOva
T_8Eff_Sp_OT1_d5_VSVOva
T_8Eff_Sp_OT1_d6_LisOva
T_8Eff_Sp_OT1_d6_VSVOva
T_8Eff_Sp_OT1_d8_LisOva
T_8Eff_Sp_OT1_d8_VSVOva
T_8Mem_Sp_OT1_d100_LisOva
T_8Mem_Sp_OT1_d106_VSVOva
T_8Mem_Sp_OT1_d45_LisOva
T_8Mem_Sp_OT1_d45_VSVOva
T_8Nve_Sp_OT1
Tgd_Th

FIG. 7F-2

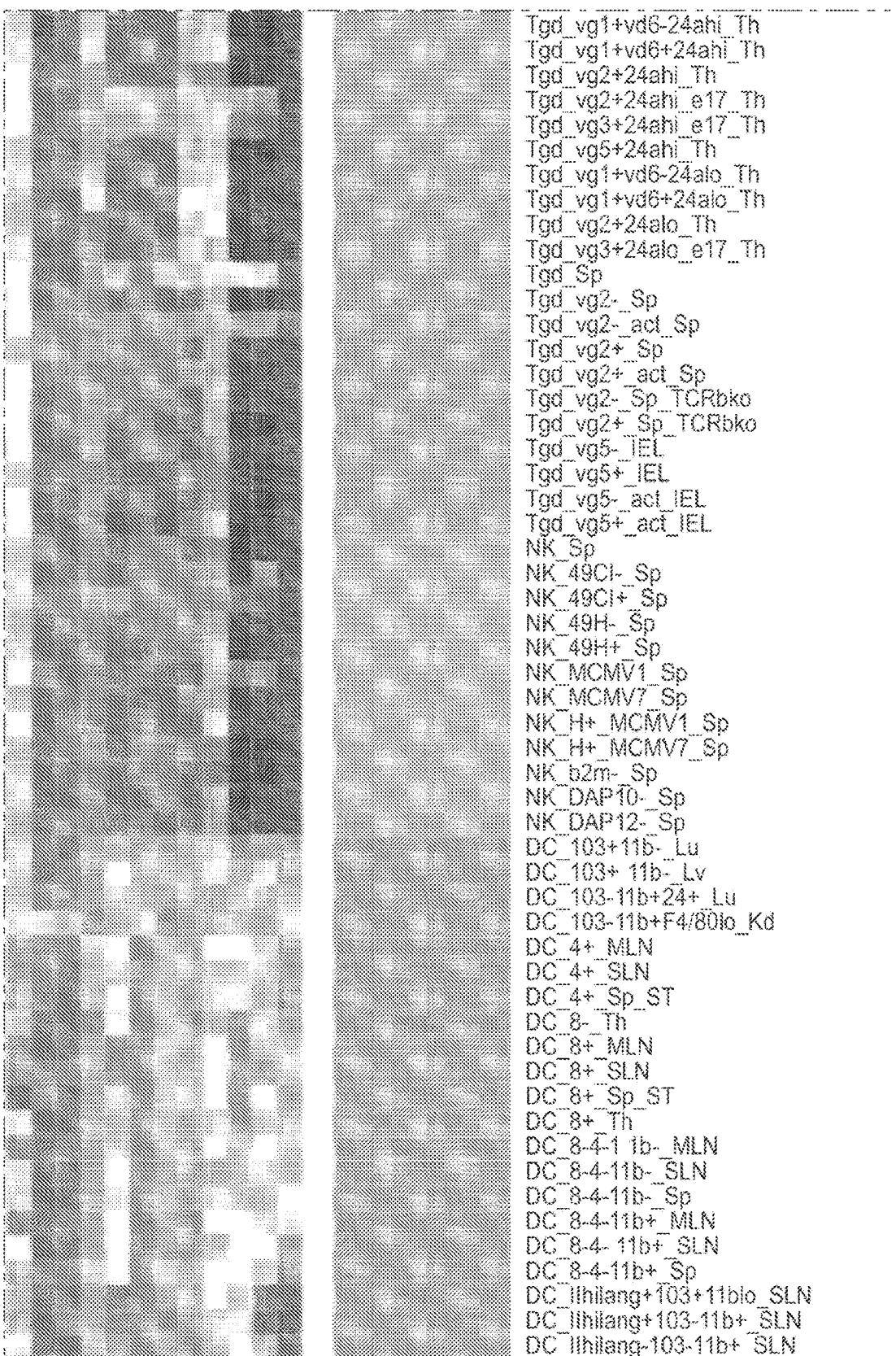

Tgd_vg1+vd6-24ahi_Th
Tgd_vg1+vd6+24ahi_Th
Tgd_vg2+24ahi_Th
Tgd_vg2+24ahi_e17_Th
Tgd_vg3+24ahi_e17_Th
Tgd_vg5+24ahi_Th
Tgd_vg1+vd6-24alo_Th
Tgd_vg1+vd6+24alo_Th
Tgd_vg2+24alo_Th
Tgd_vg3+24alo_e17_Th
Tgd_Sp
Tgd_vg2-_Sp
Tgd_vg2-_act_Sp
Tgd_vg2+_Sp
Tgd_vg2+_act_Sp
Tgd_vg2-_Sp_TCRbko
Tgd_vg2+_Sp_TCRbko
Tgd_vg5-_IEL
Tgd_vg5+_IEL
Tgd_vg5-_act_IEL
Tgd_vg5+_act_IEL
NK_Sp
NK_49CI-_Sp
NK_49CI+_Sp
NK_49H-_Sp
NK_49H+_Sp
NK_MCMV1_Sp
NK_MCMV7_Sp
NK_H+_MCMV1_Sp
NK_H+_MCMV7_Sp
NK_b2m-_Sp
NK_DAP10-_Sp
NK_DAP12-_Sp
DC_103+11b-_Lu
DC_103+11b-_Lv
DC_103-11b+24+_Lu
DC_103-11b+F4/80lo_Kd
DC_4+_MLN
DC_4+_SLN
DC_4+_Sp_ST
DC_8-_Th
DC_8+_MLN
DC_8+_SLN
DC_8+_Sp_ST
DC_8+_Th
DC_8-4-11b-_MLN
DC_8-4-11b-_SLN
DC_8-4-11b-_Sp
DC_8-4-11b+_MLN
DC_8-4-11b+_SLN
DC_8-4-11b+_Sp
DC_IIhilang+103+11blo_SLN
DC_IIhilang+103-11b+_SLN
DC_IIhilang-103-11b+_SLN

FIG. 7F-3

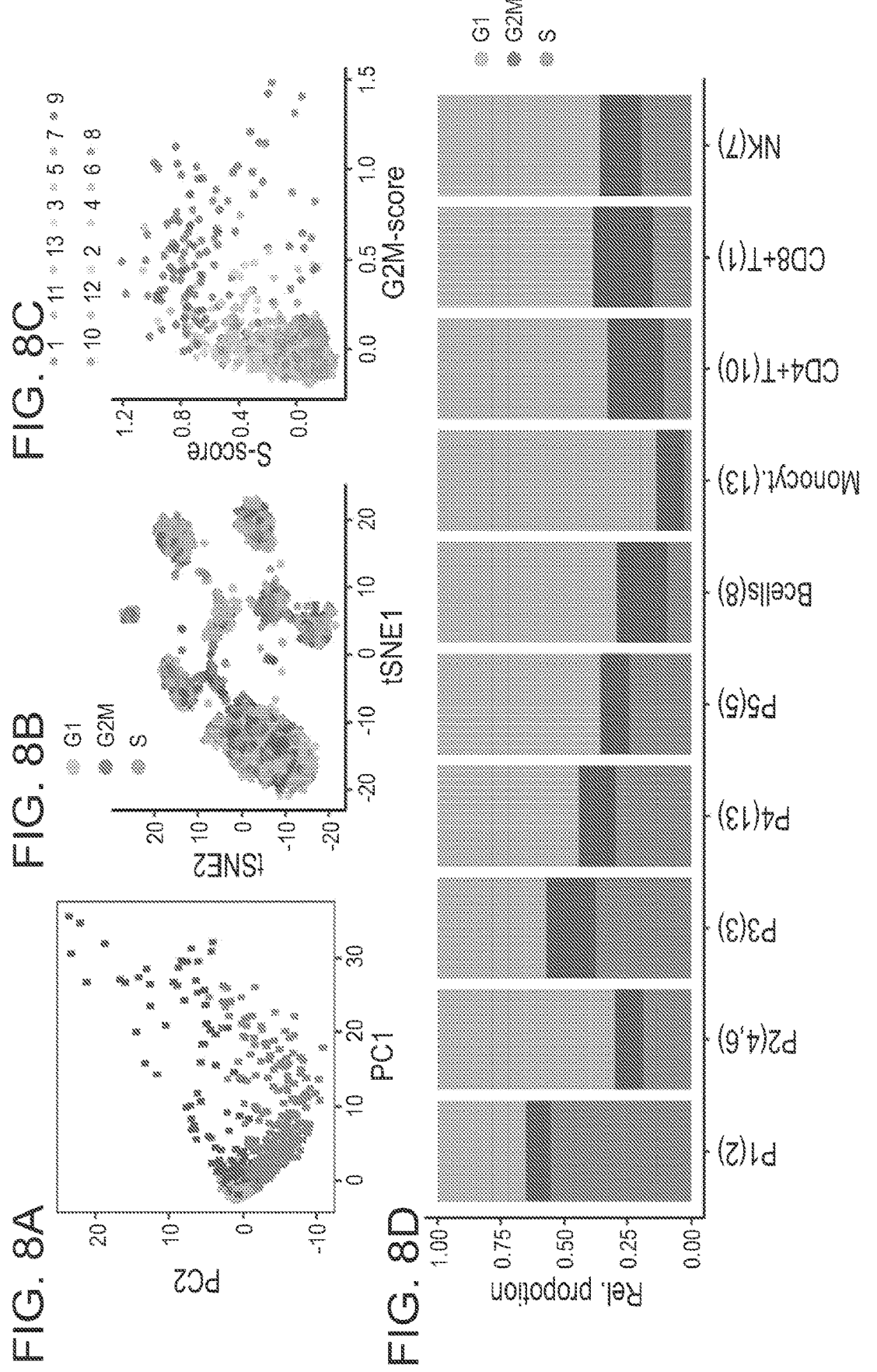

FIG. 9A
Healthy Donor 1    Healthy Donor 2    Healthy Donor 3   Healthy Donor 4
FIG. 9B
ETV6_p.R369Q      ETV6_p.R369W      NOTCH1_p.Q2391*
FIG. 9C
CSF3R_p.T618I     NOTCH1_p.F1592C     DNMT3A_p.Q402*
FIG. 9D
IL7R_p.I241N      GATA3_p.R276Q      NOTCH1_p.R1598P
FIG. 9E   NOTCH1_p.L1574P
FIG. 9F
JAK3_p.E958K      JAK1_p.R724H      NOTCH1_p.L1593P

Silhouette plot of (x = clusts, dist = diss)

Average silhouette width : 0.61

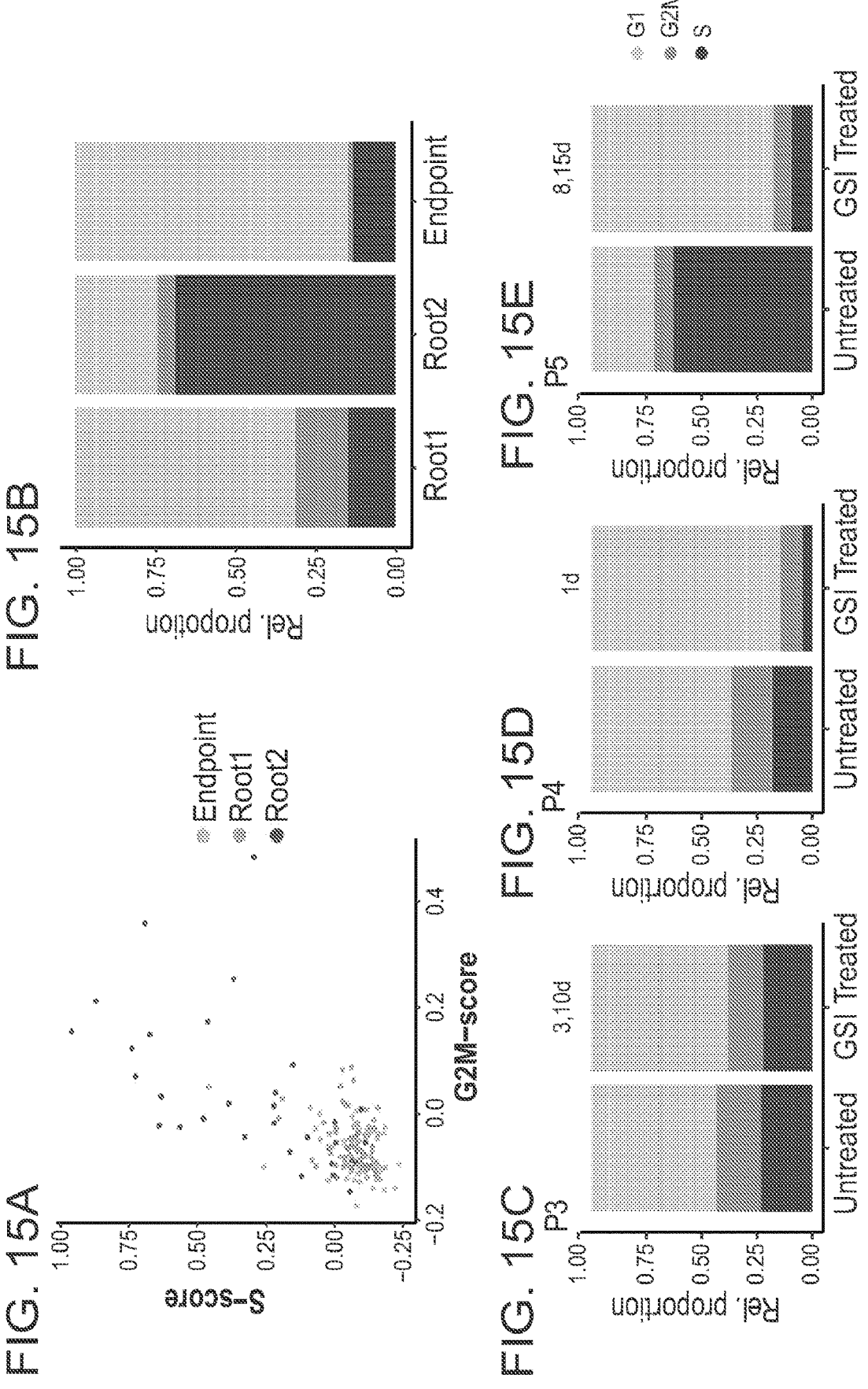

Subclusters
- cluster10
- cluster11
- cluster14
- cluster20
- cluster22
- cluster23
- cluster24
- cluster4
- cluster5
- cluster6
- cluster7
- cluster8

FIG. 17B

Flow sorting strategy for CD19+ B-cells, CD3+ T-cells and CD14+ monocytes

Cluster ·Root1 ·Root2

$R = -0.26$ , $p = 1.6e\text{-}06$

Cluster ·Root1 ·Root2

$R = 0.75$ , $p < 2.2e\text{-}16$

Cluster · Root1 · Root2

$R = 0.52$, $p = 2.2e\text{-}16$

Cluster · Root1 · Root2

$R = 0.68$, $p = 2.2e\text{-}16$

TARGETING GALECTIN-9 AS A THERAPEUTIC STRATEGY FOR T-CELL EXHAUSTION IN T-CELL ACUTE LYMPHOBLASTIC LEUKEMIA

RELATED APPLICATIONS

This application is a U.S. National Phase application, filed under 35 U.S.C. § 371, of International Application No. PCT/US2020/041570, filed Jul. 10, 2020, which claims the benefit of priority under 35 U.S.C. § 119 (e) to U.S. Provisional Application No. 62/872,987, filed on Jul. 11, 2019, each of which is incorporated herein by reference in its entirety.

GOVERNMENT LICENSE RIGHTS

This invention was made with government support under grant number K08 CA191091 and K08 CA191026 awarded by the National Institutes of Health. The government has certain rights in the invention.

SEQUENCE LISTING

The instant application contains a Sequence Listing which has been submitted electronically in ASCHII format and is hereby incorporated by reference in its entirety. Said ASCII copy, created on Jul. 10, 2020, is named 52095-620001WO_ST25.txt and is 8.08 KB bytes in size.

BACKGROUND OF THE INVENTION

T-cell acute lymphoblastic leukemia (T-ALL) is an aggressive malignancy associated with lymphoblast committed to T-cell lineage. Although there has been a progressive improvement in the treatment of pediatric cases with disease free survival (DFS) rate of 80%, adults have less favorable prognosis with DFS of only 25-50% (Pui and Evans, (2006), N. Engl. J. Med. 354:166-178). Various cytogenetic and molecular abnormalities that disrupt the normal thymocyte development can lead to T-ALL. Majority of T-ALL cases can be sub-classified based on the maturation status of blasts determined by factors that are specifically expressed during the early cortical, late cortical or mature T-cell developmental stages (Van Vlierberghe and Ferrando 2012). A particular sub-type of T-ALL termed "early T-cell precursor" (ETP), observed more predominantly in young adults, accounts for 15% of all T-ALL cases, and has been associated with a very high risk of treatment failure (Coustan-Smith et al., (2009), Lancet Oncol. 10: 147-156; Zhang et al., (2012), Nature 481:157-163)).

ETPs are multipotent blood progenitor cells that enter thymus from bone marrow. Using single cell assays, it has been observed that these precursor cells (DN1) can give rise to both T cells and myeloid cells including granulocytes and macrophages (Bell and Bhandoola, (2008), Nature 452:764-767; Wada et al., (2008), Nature 452:768-772; Schlenner et al., (2010), Immunity 32:426-436). Developmentally arrested ETP T-ALL is characterized by lack of expression of T-cell surface markers (CD1A, CD8) and aberrant expression of one or more myeloid and stem-cell markers (CD13, CD33, CD34 and CD117). Thus, ETP T-ALL shows unique genetic and transcriptional signatures that make ETP T-ALL distinct from other types of T-ALL (Haydu and Ferrando (2013), Curr. Opin. Hematol. 20: 369-373). Prior to the invention described herein, a better understanding of onco-genic programs and cellular pathways that lead to ETP T-ALL was required to design treatment strategies and improve the clinical outcome in this subset of patients.

SUMMARY OF THE INVENTION

The present invention is based upon the surprising discovery that early T-cell precursor acute lymphoblastic leukemic (ETP T-ALL) cells show ubiquitous expression of Galectin-9. As described herein, Galectin-9 has been implicated in causing T-cell exhaustion through interacting with its ligand, Tim-3. As described in detail below, endogenous T-cells in patients with T-cell acute lymphoblastic leukemia (T-ALL) demonstrated markers of T-cell exhaustion (T-cell receptor (TCR) oligoclonality, expression of Tim-3 and programmed cell death protein 1 (PD1)).

As described herein, supernatant of T-ALL cells can cause decreased T-cell effector function and T-cell exhaustion in activated polyclonal T cells, which can be reversed by neutralizing Galectin-9 with a neutralizing antibody. Accordingly, as described herein, blocking Galectin-9 is a therapeutic strategy for T-cell exhaustion in T-ALL, which is often refractory to conventional chemotherapy. Prior to the invention described herein, neither T-cell exhaustion, nor Galectin-9, as a cause for T-cell exhaustion, and its targeting, had been implicated in this disease or ALL, in general.

Provided herein are methods of treating a lymphoid malignancy, e.g., a lymphoma (non-Hodgkin lymphoma or Hodgkin lymphoma) a leukemia (acute lyphoblastic leukemia (ALL), acute myelogenous leukemia (AML), chronic lymphocytic leukemia (CLL), chronic myelogenous leukemia (CML), or acute monocytic leukemia (AMoL)), or a myeloma.

For example, provided are methods of treating T-ALL by identifying a subject, e.g., a human subject, in need thereof, e.g., a subject having or at risk of developing T-ALL; and administering to the subject a therapeutically effective amount of an inhibitor of Galectin-9, thereby treating T-ALL.

In some cases, the inhibitor of Galectin-9 comprises an anti-Galectin-9 antibody or antibody fragment, a small molecule inhibitor of Galectin-9, or a small interfering RNA (siRNA). For example, the anti-Galectin-9 antibody comprises a neutralizing anti-Galectin-9 antibody. In one aspect, the antibody or antibody fragment is partially humanized, fully humanized, or chimeric. Suitable anti-Galectin antibodies include monoclonal and polyclonal antibodies. An exemplary anti-Galectin-9 antibody comprises Galectin-9 monoclonal antibody, 9M1-3. Another suitable anti-Galectin-9 antibody comprises Galectin-9 monoclonal antibody, LYT-200. An additional anti-Galectin-9 antibody comprises Galectin-9 monoclonal antibody, D9R4A. Another suitable anti-Galectin-9 antibody comprises Galectin-9 monoclonal antibody, OT1D12.

In some cases, the T-ALL comprises early T-cell precursor acute lymphoblastic leukemia (ETP T-ALL).

Preferably, T cell effector function is increased and/or T cell exhaustion is decreased.

In one aspect, the method further comprises obtaining a test sample from the subject; and identifying malignant early T-cell precursor acute lymphoblastic leukemic cells in the test sample. Exemplary test samples include those obtained from a tumor tissue, a tumor microenvironment, a plasma sample, or a blood sample.

In some cases, the inhibitor of Galectin-9 comprises a small molecule inhibitor.

Preferably, tumor cell survival, tumor cell proliferation, or tumor metastasis is inhibited, e.g., by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%.

Optionally, tumor cell growth is reduced, e.g., by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%.

In some cases, the subject has relapsed or wherein the cancer is refractory to treatment.

Optionally, the method further comprises administering to the subject a chemotherapeutic agent, radiation therapy, cryotherapy, hormone therapy, or immunotherapy. Suitable chemotherapeutic agents include thalidomide, lenalidomide, ixazomib, bortezomib, carfilzomib, melphalan, vincristine, cyclophosphamide, doxorubicin, liposomal doxorubicin, rituximab, etoposide and bendamustine.

In one aspect, the chemotherapeutic agent is administered with a steroid. For example, the steroid comprises prednisone or dexamethasone.

In some cases, the method further comprises administering to the subject a combination chemotherapy agent. For example, the combination chemotherapy agent comprises hyper-CVAD, hyper-CVAD+nelarabine or augmented Berlin-Frankfurt-Münster (aBFM) regimen.

Optionally, the method further comprises administering a Notch inhibitor. Suitable Notch inhibitors include, e.g., a blocking anti-Notch antibody or a γ-secretase inhibitor (e.g., BMS-906024).

In some cases, the method also includes administering a phosphoinositide 3-kinase (PI3-K) inhibitor. Exemplary PI3-K inhibitors include BAY80-6946/Copanlisib, Duvelisib/IPI-145, and δ/γ CAL-101/idelalisib.

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term "about."

By "agent" is meant any small compound, antibody, nucleic acid molecule, or polypeptide, or fragments thereof.

By "alteration" is meant a change (increase or decrease) in the expression levels or activity of a gene or polypeptide as detected by standard art-known methods such as those described herein. As used herein, an alteration includes at least a 1% change in expression levels, e.g., at least a 2%, 3%, 4%, 5%, 6%, 7%, 8%, 9%, 10%, 20%, 30%, 40%, 50%, 60%, 70%, 80%, 90%, or 100% change in expression levels. For example, an alteration includes at least a 5%-10% change in expression levels, preferably a 25% change, more preferably a 40% change, and most preferably a 50% or greater change in expression levels.

The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

By "binding to" a molecule is meant having a physico-chemical affinity for that molecule.

By "control" or "reference" is meant a standard of comparison. In one aspect, as used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody, a protein) or a substance produced by a reporter construct (e.g, β-galactosidase or luciferase). Depending on the method used for detection, the amount and measurement of the change can vary. Determination of statistical significance is within the ability of those skilled in the art, e.g., the number of standard deviations from the mean that constitute a positive result.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to ameliorate the symptoms of a disease, e.g., ETP T-ALL, relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity, e.g., at least 80%, at least 85%, at least 90%, at least 95%, or at least 99% identity. Polynucleotides having "substantial identity" to an endogenous sequence are typically capable of hybridizing with at least one strand of a double-stranded nucleic acid molecule.

As used herein, "obtaining" as in "obtaining an agent" includes synthesizing, purchasing, or otherwise acquiring the agent.

Unless specifically stated or obvious from context, as used herein, the term "or" is understood to be inclusive. Unless specifically stated or obvious from context, as used herein, the terms "a", "an", and "the" are understood to be singular or plural.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier should be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

By "protein" or "polypeptide" or "peptide" is meant any chain of more than two natural or unnatural amino acids, regardless of post-translational modification (e.g., glycosylation or phosphorylation), constituting all or part of a naturally-occurring or non-naturally occurring polypeptide or peptide, as is described herein.

The term "prognosis," "staging," and "determination of aggressiveness" are defined herein as the prediction of the degree of severity of the neoplasia, e.g., T-All, and of its evolution as well as the prospect of recovery as anticipated from usual course of the disease. Once the aggressiveness has been determined, appropriate methods of treatments are chosen.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 10%, 25%, 50%, 75%, or 100%.

The term "sample" as used herein refers to a biological sample obtained for the purpose of evaluation in vitro.

Exemplary tissue samples for the methods described herein include tissue samples from ETP T-ALL tumors or the surrounding microenvironment (i.e., the stroma). With regard to the methods disclosed herein, the sample or patient sample preferably may comprise any body fluid or tissue. In some embodiments, the bodily fluid includes, but is not limited to, blood, plasma, serum, lymph, breast milk, saliva, mucous, semen, vaginal secretions, cellular extracts, inflammatory fluids, cerebrospinal fluid, feces, vitreous humor, or urine obtained from the subject. In some aspects, the sample is a composite panel of at least two of a blood sample, a plasma sample, a serum sample, and a urine sample. In exemplary aspects, the sample comprises blood or a fraction thereof (e.g., plasma or serum). Preferred samples are whole blood, serum, plasma, or urine. A sample can also be a partially purified fraction of a tissue or bodily fluid.

A reference sample can be a "normal" sample, from a donor not having the disease or condition fluid, or from a normal tissue in a subject having the disease or condition. A reference sample can also be from an untreated donor or cell culture not treated with an active agent (e.g., no treatment or administration of vehicle only). A reference sample can also be taken at a "zero time point" prior to contacting the cell or subject with the agent or therapeutic intervention to be tested or at the start of a prospective study.

By "specifically binds" is meant a compound or antibody that recognizes and binds a polypeptide of the invention, but which does not substantially recognize and bind other molecules in a sample, for example, a biological sample, which naturally includes a polypeptide of the invention.

By "selective inhibitor" is meant a compound or substrate that selectively binds a target protein to ultimately reduce or eliminate the protein's activity.

The term "subject" as used herein includes all members of the animal kingdom prone to suffering from the indicated disorder. In some aspects, the subject is a mammal, and in some aspects, the subject is a human. The methods are also applicable to companion animals such as dogs and cats as well as livestock such as cows, horses, sheep, goats, pigs, and other domesticated and wild animals.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from, e.g., ETP T-ALL is within the ability of those in the art. Subjects suffering from, and suspected of suffering from, a specific disease, condition, or syndrome are not necessarily two distinct groups.

As used herein, "susceptible to" or "prone to" or "predisposed to" or "at risk of developing" a specific disease or condition refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. It will be appreciated that, although not precluded, treating a disorder or condition does not require that the disorder, condition or symptoms associated therewith be completely eliminated.

In some cases, a composition of the invention is administered orally or systemically. Other modes of administration include rectal, topical, intraocular, buccal, intravaginal, intracisternal, intracerebroventricular, intratracheal, nasal, transdermal, within/on implants, or parenteral routes. The term "parenteral" includes subcutaneous, intrathecal, intravenous, intramuscular, intraperitoneal, or infusion. Intravenous or intramuscular routes are not particularly suitable for long-term therapy and prophylaxis. They could, however, be preferred in emergency situations. Compositions comprising a composition of the invention can be added to a physiological fluid, such as blood. Oral administration can be preferred for prophylactic treatment because of the convenience to the patient as well as the dosing schedule. Parenteral modalities (subcutaneous or intravenous) may be preferable for more acute illness, or for therapy in patients that are unable to tolerate enteral administration due to gastrointestinal intolerance, ileus, or other concomitants of critical illness. Inhaled therapy may be most appropriate for pulmonary vascular diseases (e.g., pulmonary hypertension).

Pharmaceutical compositions may be assembled into kits or pharmaceutical systems for use in arresting cell cycle in rapidly dividing cells, e.g., ETP T-ALL cells. Kits or pharmaceutical systems according to this aspect of the invention comprise a carrier means, such as a box, carton, tube, having in close confinement therein one or more container means, such as vials, tubes, ampoules, bottles, syringes, or bags. The kits or pharmaceutical systems of the invention may also comprise associated instructions for using the kit.

Any compositions or methods provided herein can be combined with one or more of any of the other compositions and methods provided herein.

Where applicable or not specifically disclaimed, any one of the embodiments described herein are contemplated to be able to combine with any other one or more embodiments, even though the embodiments are described under different aspects of the invention.

These and other embodiments are disclosed and/or encompassed by, the following Detailed Description.

BRIEF DESCRIPTION OF THE DRAWINGS

FIG. 1A is a schematic depicting the cohort, sample collection, processing and sorting of cells for single-cell transcriptional profiling using SMART-seq2 protocol. FIG. 1B is a plot showing that t-stochastic network embedding (t-SNE) of the processed single cell RNA-seq gene expression data revealed distinct patient-specific clusters along with heterogeneous clusters. FIG. 1C is a plot showing clusters were further analyzed using PAGODA2 to identify the cell type of individual cells. FIG. 1D is a plot showing correlation distance matrix (1-Pearson correlation coefficient) derived from normalized gene-expression values of individual malignant cells. The silhouette plot on top of the matrix depicts the uniqueness of each of the patient-specific malignant clusters. FIG. 1E is a heatmap showing expression of the top marker genes for each of the clusters containing normal cells. Marker gene analyses identify heterogenous clusters as CD4+ T-cells, CD8+ T-cells, NK-cells, B-cells and myeloid cells. FIG. 1F is a heat map showing that cells from normal donors are highlighted in the top and fall into normal cell clusters. Malignant clusters identified by calling of those pathogenic variants (SNV and CNVs) in single cells that were identified in individual patients by a clinical targeted exome sequencing (middle panel, Table 1). Expression of transcription factors (TFs) distinguishing malignant cells from non-malignant cells sequenced in this study (as inferred from random-forest model). *NFE2 was ranked lower when only untreated leukemic cells were used to build the model whereas *BCL11A was ranked higher.

FIG. 2A is a heatmap demonstrating expression of HSC, MPP, CMP, GMP and CLP signatures as defined by xcell in individual leukemic cells. FIG. 2B is a t-SNE plot showing all the malignant cells using genes involved in progenitor programs. Clusters are derived using the Louvain algorithm. FIG. 2C is a plot showing RNA-velocities projected on the t-SNE plot containing leukemic cells with root and endpoint cells highlighted. Distribution of these root (left) and endpoint cells (middle) across different Louvain clusters are depicted as stacked bar plot (right). FIG. 2D is a heatmap depicting the expression of marker genes in the identified root and endpoint cells. FIG. 2E is a violin plot depicting expression of key marker genes in root cells (top panel) and endpoint cells (bottom panel). GSEA plot depicting the enrichment of hematopoietic stem cell signature in the root cells (left), differentiating T-lymphocyte signature (middle) and interferon-gamma response (right) in the endpoint cells. FIG. 2F is t-SNE plot showing leukemic cells colored based on the predicted cell-cycle phase. FIG. 2G is a heatmap depicting clustered transcriptional regulons (predicted transcription factor activity based on target gene expression) in root and endpoint cells (see methods).

FIG. 3A-FIG. 3H are a set of plots and a heatmap showing that notch inhibition expands cells with PI3K signaling activity that coexist with Notch dependent cells and demonstrate opposing differentiation trajectories. FIG. 3A is a t-SNE plot showing leukemic cells colored based on GSI treatment. FIG. 3B is a heatmap depicting the relative activity of various signaling pathways as inferred by PROGENy in all the cells comprising the two root states. FIG. 3C is series of violin plots showing relative Notch activity upon GSI treatment inferred by average relative expression profile of defined Notch targets in a representative patient (P5). FIG. 3D is a scatter plot depicting the negative correlation between relative Notch activity (inferred by average relative expression of target genes) and PI3K activity in all leukemic cells. Cells are colored based on GSI treatment. FIG. 3E is a plot showing the projection of RNA velocity vectors onto PI3K-Notch activity captures two states depicting high PI3K and high Notch activity within the untreated leukemic cells. FIG. 3F is a plot showing that the cells belonging to two different root states are highlighted and fall into either high PI3K or high Notch activity clusters. FIG. 3G is a plot showing subclusters identified by monocle (see FIG. 15G) separate based on PI3K versus Notch activity. After GSI treatment cells with PI3K high activity persist without changing directionality by RNA velocity. FIG. 3H is a plot showing that endpoint cells are enriched at the interface of converging velocity trajectories.

FIG. 4A is a stacked barplot depicting percentage of clonal CD8+ T-cells observed in individuals as inferred from TCR group usage (n.d.=not determined; ND=normal donor). FIG. 4B is a plot showing the pseudotime trajectory inferred using unsupervised approach through monocle2. The cells on the trajectory are colored based on monocle states. FIG. 4C is a plot showing the pseudotime trajectory inferred using unsupervised approach through monocle 2. The cells on the trajectory are colored based on the source of CD8⁺ T-cells. FIG. 4D is a heatmap depicting expression of state-specific markers obtained through monocle 2. Canonical marker genes for naïve CD8⁺ T-cells, activation and exhaustion/dysfunction are annotated in the heatmap. FIG. 4E is a plot showing the projection of RNA velocity vectors on the CD8⁺ T-cell states 5 and 6 highlight a continuous trajectory. FIG. 4F is a boxplot depicting exhaustion score calculated for each CD8⁺ T-cells of all individuals from relative gene expression values of canonical naïve and exhaustion gene markers (see methods; green=unique TCR, orange=recurrent TCR, blue=n.d. (not determined).

FIG. 5A-5E are a series plots, bar graphs and photomicrographs showing HAVCR2-LGALS9 interactions and CD8⁺ T cell dysfunction in ETP T-ALL. FIG. 5A is a series of Violin plots depicting the expression of co-inhibitory receptors (on dysfunctional CD8⁺ T-cells, shown as open circles), and their interacting ligands (on malignant T-ALL cells, depicted as triangles). Colors represent malignant clusters based on PAGODA2. Each facet corresponds to the respective coinhibitory receptor-ligand interactions. FIG. 5B is a bar graph showing receptor-ligand interaction scores inferred from expression of receptor and ligand genes in the respective cell types point toward prominent HAVCR2-LGALS9 interaction (ligand on T-ALL cells, matching receptor on dysfunctional CD8⁺ T-cells). FIG. 5C is a series of photomicrographs showing immunohistochemistry (IHC) of LGALS9 and HAVCR2 on bone marrow from representative ETP-ALL patient (P2) demonstrates strong staining of LGALS9 on leukemic blasts and interspersed HAVCR2 staining on micro-environmental cells. FIG. 5D is a plot showing intracellular immunofluorescent staining of LGALS9 and isotype control in DND-41 T-ALL cell line. FIG. 5E is a bar graph showing the expression of T-cell dysfunction markers (HAVCR2, TIGIT) and effector cytokines (GZMB, IL-2, IFNγ on normal donor activated CD8+ T-cells cultured with T-ALL supernatant versus control media (*=p value<0.05, =p value<0.01, *=p value<0.001, averaged from 3 technical replicates, using two-sided t-test).

-FIG. 6F is a series of plots showing distribution of features in the unfiltered dataset—(i) library size per cell, (ii) number of genes detected in each cell, (iii) percentage of counts mapping to mitochondrial genes in each cell, and (iv) percentage of counts mapping to house-keeping genes in all cells sequenced. FIG. 6B is a scatter plot depicting the result of principal component analyses using the top two dimensions. The PCA was performed on these four features for all the 5077 cells. The outliers were detected using mvoutlier package and are highlighted in orange. FIG. 6C is a venn diagram depicting the overlap between the outliers detected by mvoutlier (blue) and manual cut-offs (red) using median absolute deviations (M.A.D's). FIG. 6D is a series of plots showing the distribution of the features after filtering out the cells detected to be outlier by both the methods. FIG. 6E is a scatter plot depicting the quality of data from the remaining 3562 cells through expression frequency and mean read counts per gene. FIG. 6F is a plot showing the density plot depicting the contribution of various technical factors contributing to the total variation observed in entire dataset.

FIG. 7A is a heatmap depicting the log-likelihood scores derived by comparison of scRNA-seq profile to the bulk RNA-seq profile obtained from purely sorted immune population. These bulk RNA-seq profile was obtained from BLUEPRINT consortium. The identity of the non-malignant clusters was further validated by confirming the expression of the specific marker genes from these clusters in all the immune cell-types from ImmGen consortium. FIG. 7B is a heatmap showing markers obtained for cluster 1 show specific expression in CD8+ T-cells in ImmGen dataset; FIG. 7C is a heatmap showing that cluster 7 shows specific expression in the NK cell population in ImmGen dataset. FIG. 7D is a heatmap showing that cluster 8 shows specific expression in the B-cell population. FIG. 7E is a heatmap showing that cluster 10 shows specific expression in CD4+ T-cell population. FIG. 7F is a heatmap showing that cluster 11 shows specific expression in the myeloid population from ImmGen dataset.

FIG. 8A-8D is a series of plots showing the effect of cell-cycle on clustering of scRNA-seq data. FIG. 8A is a PCA plot of the derived by considering all the genes involved in cell-cycle using SEURAT tool. FIG. 8B is a t-SNE plot of scRNA-seq profiles. Each dot represents a cell and is colored based on the cell-cycle phase predicted by SEURAT. FIG. 8C is a scatterplot depicting the G2M and S-score obtained for each of the cells. The cells are colored based on the clusters obtained from PAGODA2. FIG. 8D is a stacked bar plot depicting the relative distribution of different cell-cycle phases in each of the clusters. Notably the malignant clusters from all the five patients have more cells in S and G2M phase.

FIG. 9A-9F is a series of plots showing distribution of normal donor cells and pathogenic SNVs. FIG. 9A is a plot showing distribution of normal T-cells from four different normal donors. FIG. 9B is a plot showing the distribution of different pathogenic variants detected using rapid heme panel and confirmed through scRNA-seq profiling using mutect2 in P1. FIG. 9C is a plot showing the distribution of different pathogenic variants detected using rapid heme panel and confirmed through scRNA-seq profiling using mutect2 in P2. FIG. 9D is a plot showing the distribution of different pathogenic variants detected using rapid heme panel and confirmed through scRNA-seq profiling using mutect2 in P3. FIG. 9E is a plot showing the distribution of different pathogenic variants detected using rapid heme panel and confirmed through scRNA-seq profiling using mutect2 in P4. FIG. 9F is a plot showing the distribution of different pathogenic variants detected using rapid heme panel and confirmed through scRNA-seq profiling using mutect2 in P5.

FIG. 10A is a profile depicting the amplifications and deletion signals from all the patient cells using inferCNV. All the T-cells from normal donors were used as control. FIG. 10B is a Gaussian mixture model (GMM) fit to distinguish between malignant and non-malignant cells by using CON-ICSMAT algorithm. The model fit for five CNV events depicted in FIG. 1 is shown here.

FIG. 12A is a t-SNE plot colored based on the T-ALL classification obtained from the TARGET study. Each dot represents bulk-RNA seq profile from individual patient. FIG. 12B is the same t-SNE plot in FIG. 12A, colored based on the clusters derived from SC3 tool. FIG. 12C is a silhouette plot depicting the confidence of each of the clusters obtained. FIG. 12D, FIG. 12E, FIG. 12F, FIG. 12G, and FIG. 12H are a series of plots showing the data from single cell sequencing was collapsed for individual T-ALL patients. All the five patients in the study had around five 96-well SMART-seq2 plates sequenced. The sequencing reads from each of the plates were collapsed, hence five replicates were obtained for each patient. Each of these replicates were compared to average expression profile of individual T-ALL subtype cluster to obtain the log-likelihood score. All the patients showed high similarity to ETP T-ALL subtype with deregulated expression of LMO2-LYL 1. Only P3 showed high transcriptional similarity to TLX3 subtype of T-ALL in 3/5 replicates.

FIG. 13A is a plot depicting the relationship between the error and number of trees used by random forest model on malignant (green), non-malignant (red) and combined (black) by considering all the malignant and non¬malignant cells. The relative importance of each of the transcription factors in the model is depicted below. FIG. 13B is the same plot as FIG. 13A, generated by training the model only on the untreated cell population.

FIG. 14A is a plot showing relative fractions of root 1, root 2 and endpoint expression signatures after deconvolution using cibersort in bulk RNA-seq data from TARGET cohort. FIG. 14B is a plot showing relative fractions of root 1, root 2 and endpoint expression signatures in subtypes of T-ALL in TARGET cohort.

FIG. 15A-15H is a series of plots, bar graphs, and a heatmap showing GSI treatment and its effect on cell-cycle, Notch target genes and oncogenic signaling in leukemic cells. FIG. 15A is a Scatter plot depicting the G2M and S-phase scores for all the leukemic cells in the root 1, root 2 and endpoint states. FIG. 15B is a stacked barplot depicting the relative distribution of different phases of cell-cycle in the three states. FIG. 15C is a bar graph showing the change in relative distribution of cell-cycle phase upon treatment in P3. FIG. 15D is a bar graph showing the change in relative distribution of cell-cycle phase upon treatment in P4. FIG. 15E is a bar graph showing the change in relative distribution of cell-cycle phase upon treatment in P5. FIG. 15F is a heatmap depicting the downregulation of notch targets upon GSI treatment in P5. FIG. 15G is a plot showing subclusters identified in each of the patient-specific leukemic clusters using monocle2 are depicted on t-SNE. FIG. 15H is a violin plot depicting the PI3K activity score inferred by average relative expression of PI3K targets as inferred by PROGENy upon GSI treatment.

FIG. 16A is a graph showing data for DND-41: IC50=1.01 μM for Buparlisib, 0.132 μM for Buparlisib and 1 μM GSI. FIG. 16B is a graph showing data for HPB-ALL: IC50=0.34 μM for Buparlisib, 7.23e-006 μM for Buparlisib and 1 μM GSI. FIG. 16C is a graph showing data for KOPT-K1: IC50=1.16 μM for Buparlisib, 0.25 μM for Buparlisib and 1 μM GSI. FIG. 16D is a graph showing data for Jurkat: IC50=0.72 μM for Buparlisib, 0.423 μM for Buparlisib and 1 μM GSI. FIG. 16E is a graph showing data Loucy: IC50=0.65 μM for Buparlisib, 0.71 μM for Buparlisib and 1 μM GSI.

FIG. 17A-FIG. 17B is a series of plots showing inhibitory receptor-ligand interactions. FIG. 17A is an t-SNE plot depicting the expression of various inhibitory receptors and corresponding ligands on exhausted T-cells and T-ALL cells. FIG. 17B is a violin plot that depicts the expression of LGALS9 across various subsets of T-ALL from TARGET study.

FIG. 18A is a series of plots showing data for T-ALL cell lines, HPB-ALL, KOPT-K1, Loucy and MOLT-4. FIG. 18B is a series of plots showing data for B-ALL cell lines, NALM-6 and SEM. FIG. 18C is a series of plots showing data for AML cell lines, KG-1 and HL-60.

FIG. 20A is a series of box and whisker plots showing LGALS9 expression across all cancers profiled in TCGA (red=malignant, black=matched normal tissue). FIG. 20B is a line graph showing Kaplan-Meier estimates of overall survival of patients with high LGALS9 expression (upper quartile) versus low expression (lower quartile).

FIG. 24A is a correlation plot showing the relationship between the EGFR pathway and root 1 and root 2 leukemic cells. FIG. 24B is a correlation plot showing the relationship between the Hypoxia pathway and root 1 and root 2 leukemic cells. FIG. 24C is a correlation plot showing the relationship between the JAK STAT pathway and root 1 and root 2 leukemic cells. FIG. 24D is a correlation plot showing the relationship between the MAPK pathway and root 1 and root 2 leukemic cells. FIG. 24E is a correlation plot showing the relationship between the NFκB pathway and root 1 and root 2 leukemic cells. FIG. 24F is a correlation plot showing the relationship between the PI3K pathway and root 1 and root 2 leukemic cells. FIG. 24G is a correlation plot showing the relationship between the TGFb pathway and root 1 and root 2 leukemic cells. FIG. 24H is a correlation plot showing the relationship between the TNFa pathway and root 1 and root 2 leukemic cells. FIG. 24I is a correlation plot showing the relationship between the Trail pathway and root 1 and root 2 leukemic cells. FIG. 24J is a correlation plot showing the relationship between the VEGF pathway and root 1 and root 2 leukemic cells. FIG. 24K is a correlation plot showing the relationship between the p53 pathway and root 1 and root 2 leukemic cells.

DETAILED DESCRIPTION OF THE INVENTION

Figure 1A:
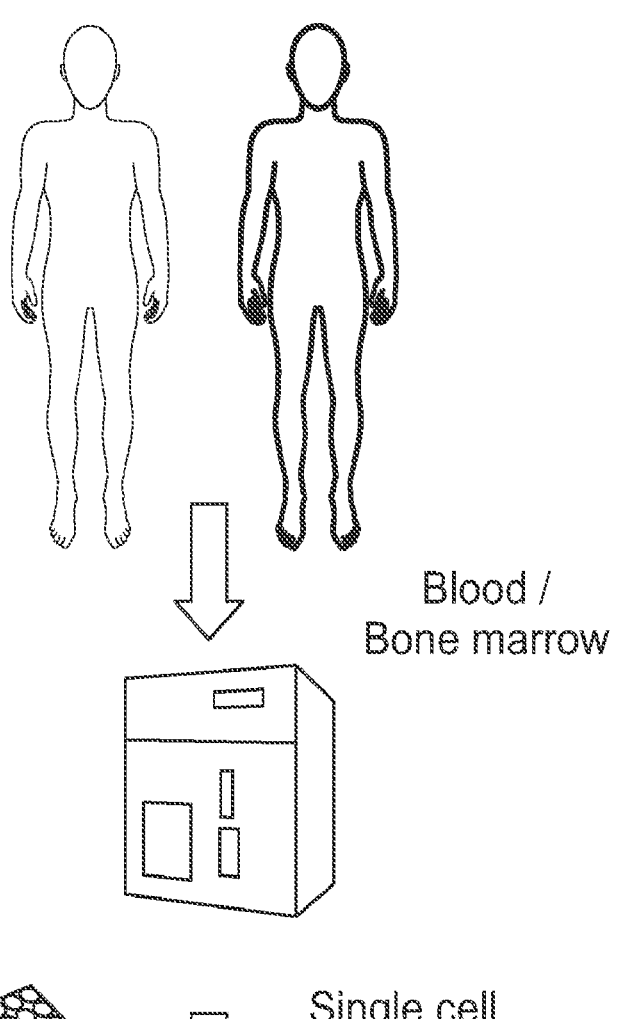
FIG. 1A-FIG. 1F are a set of plots and heatmaps and a schematic showing that ETP T-ALL cells have distinct transcriptional profile.
Figure 1A:
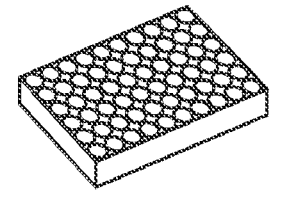

The present invention is based upon the surprising discovery that early T-cell precursor acute lymphoblastic leukemic (ETP T-ALL) cells show ubiquitous expression of Galectin-9 (LGALS9), and that immunomodulation of CD8+ T cell dysfunction is medidated by Galectin-9 expression on T-ALL cells. As described herein, Galectin-9 has been implicated in causing T-cell exhaustion through interacting with its ligand Tim-3. As described in detail below, endogenous T-cells in patients with T-cell acute lymphoblastic leukemia (T-ALL) demonstrated markers of T-cell exhaustion (T-cell receptor (TCR) oligoclonality, expression of Tim-3 and programmed cell death protein 1 (PD1)). As described in the examples that follow, supernatant of T-ALL cells can cause decreased T-cell effector function and T-cell exhaustion in activated polyclonal T cells, which can be reversed by neutralizing Galectin-9 with a neutralizing antibody. As described herein, blocking Galectin-9 is a therapeutic strategy for T-cell exhaustion in T-ALL, which is often refractory to conventional chemotherapy. Prior to the invention described herein, neither T-cell exhaustion, nor Galectin-9, as a cause for T-cell exhaustion, and its targeting, had been implicated in this disease or ALL in general.

Lineage plasticity has been invoked as a resistance mechanism in cancer (Neftel et al., 2019 Cell, 178(4):835-849 e821; Meacham et al., 2013 Nature, 501(7467):328-337; Beltran et al., 2019 Clin Cancer Res; McKenzie et al., 2019 Cell Stem Cell, 25(2):258-272 e259). Often, it is associated with increased stemness potential, which is permissive for dedifferentiation and use of non-lineage transcriptional circuits (Watson et al., 2015 Nat Rev Cancer, 15(12):701-711; Mu et al., 2017 Science, 355(6320):84-88). Several studies have employed single-cell sequencing to identify cells within tumor cell populations with enhanced plasticity (Venteicher et al., 2017 Science, 355(6332); Suva et al., 2014 Cell, 157(3):580-594; Suva et al., 2019 Mol Cell, 75(1):7-12). Despite their plasticity, these cells tend to adhere to the developmental hierarchies of the tissue of origin (Neftel et al., 2019 Cell, 178(4):835-849 e821; Filbin et al., 2018 Science, 360(6386):331-335; Anastas et al., 2019 Cancer Cell, 36(5):528-544 e510). Recent studies in acute myeloid leukemia (AML) have suggested that leukemic cells arrested at different developmental states that are dictated by driver genetic lesions (van Galen et al., 2019 Cell, 176(6):1265-1281.e1224; Potter et al., 2019 Leukemia, 33(5):1113-1123; Uckelmann et al., 2018 Cancer Cell, 34(3):355-357). However, prior to the invention described herein, it was unclear how functional heterogeneity and cellular plasticity of cancer cells shape interactions with the immune microenvironment and how developmental hierarchies relate to drug resistance, particularly in incurable lymphoid malignancies.

T-cell acute lymphoblastic leukemia (T-ALL) is an aggressive malignancy mainly affecting children and young adults. Although overall outcomes are good, roughly 20% of patients fail conventional therapy, and most of these patients die of relapsed/refractory disease. Various cytogenetic and molecular abnormalities that disrupt normal thymocyte development can lead to T-ALL and the majority of T-ALL cases can be sub-classified based on arrest at different thymocyte maturation stages (Belver et al., 2016 Nat Rev Cancer, 16(8):494-507) For example, ETP (early T-cell precursor) T-ALL shows unique genetic and transcriptional signatures suggesting a close relationship to myeloid precursors and myeloid malignancies (Haydu et al., 2013 Curr Opin Hematol, 20(4):369-373; Ntziachristos et al., 2012 Nat Med, 18(2):298-301; Zhang et al., 2012 Nature, 481(7380): 157-163). However, prior to the invention described herein, it was unclear if these signatures co-exist within individual ETP T-ALL cells or if they reflect discrete, heterogeneous cell states within the tumor cell population.

As described in detail below, the heterogeneity of ETP T-ALL was determined at single-cell resolution, using full-length single-cell RNA-sequencing, before and after targeted therapy with an inhibitor of NOTCH1, the major driving oncoprotein in T-ALL. A heterogeneous composition of malignant cell populations was identified with a deranged developmental hierarchy marked by the presence of two distinct stemness programs and ineffectual commitment to either lymphoid or myeloid lineage. The two stem-like states differ with regard to their cell-cycle status, transcriptional circuits and signaling dependencies (Notch and PI3K), and despite opposing differentiation trajectories converge onto a third, more mature cell state. Post-treatment cells had low Notch and high PI3K activity and likely account for the generally poor clinical response of T-ALL to Notch inhibition. As described in the Examples below, a broader analysis of cellular interactions in the leukemia ecosystem revealed that leukemic T-ALL blasts expressed the checkpoint ligand LGALS9 and were associated with dysfunctional CD8⁺ T-cells that express HAVCR2, the LGALS9 receptor, in the tumor microenvironment. Accordingly, targeting LGALS9 reverts T-cell exhaustion in these patients and provides a therapeutic approach to overcome T-ALL heterogeneity and lineage plasticity. Together, these findings lay a framework for rationally designed combination treatments in incurable hematopoietic malignancies.

As described in detail in the examples below, the cellular states that underlie treatment failures in hematopoietic cancers were defined. Using full-length scRNA-seq analyses of ETP T-ALL, a deranged developmental hierarchy was identified with co-existing stem-like and more mature states, ineffectual commitment to either lymphoid or myeloid lineage and immunomodulatory characteristics. Stem-like states show distinct transcriptional circuitries and differ with regards to cell cycle, epigenetic machinery and oncogenic dependencies. Notch pathway activation is the most prevalent oncogenic aberration in T-ALL including ETP T-ALL, yet Notch inhibition usually fail to control disease in vivo (Palomero et al., 2009 Clin Lymphoma Myeloma, 9 Suppl 3:S205-210; Knoechel et al., 2015 Cold Spring Harb Mol Case Stud, 1(1):a000539). Based on the results presented herein, Notch inhibition appears to be ineffectual because of pre-existing stem-like cells exhibiting a resistant state defined by high levels PI3K signaling and low Notch activity. This has important therapeutic implications for precision medicine as the results presented herein suggest that combination therapies targeting Notch and PI3K might be beneficial even in the absence of genetic events, if driven by transcriptional rewiring. However, the results presented herein also caution that in this scenario combined inhibition of Notch and PI3K may not be enough to completely eliminate all cancer cells due to co-existence of multiple transcriptional states in individual cancer cells, which provide a route to escape. Rather, the results suggest that integrating precision medicine with checkpoint blockade may provide efficacy for targeting cancer cell populations that survive otherwise effective therapeutic targeting.

Lineage plasticity and stemness have been implicated in drug resistance in cancer and single-cell sequencing studies have highlighted how cancer cells relate to and maintain their respective tissue's developmental hierarchy in solid tumors (Venteicher et al., 2017 Science, 355(6332); Suva et al., 2014 Cell, 157(3):580-594; Suva et al., 2019 Mol Cell, 75(1):7-12). A recent study in AML demonstrated that while leukemic cells take on different developmental states based on their genetic drivers, they follow the developmental hierarchy of hematopoiesis (van Galen et al., 2019 Cell, 176(6):1265-1281.e1224). Remarkably, as described in detail below, in ETP T-ALL, a deranged developmental hierarchy was found. Identification of hematopoietic stem, myeloid and lymphoid progenitor signatures was present in almost all individual cells. Differentiation trajectories within the leukemic population identified two co-existing stem-like states that differed with regards to cell-cycle as well as Notch and PI3K activity.

Closer exploration of T-ALL cells within their immune microenvironment demonstrated an unexpected role of immune evasion in T-ALL. Targeting a dysfunctional microenvironment with checkpoint blockade has gained a lot of attention in several cancers, including lymphoma (Pardoll et al., 2012 Nat Rev Cancer, 12(4):252-264; Topalian et al., 2016 Nat Rev Cancer, 16(5):275-287; Alencar et al., 2019 Nat Rev Clin Oncol, 16(10):599-60). The results presented herein demonstrate a role for HAVCR2-LGALS9 interactions in causing CD8$^+$ T-cell dysfunction, which provide a therapeutic strategy to restore T-cell function, and thereby generate an effective host immune response in T-ALL.

Prior to the invention described herein, most studies investigating the utility of checkpoint blockade have focused on PD1 blockade. Interestingly, the results presented herein suggest that HAVCR2-LGALS9 interactions as the most prominent interaction between leukemic and microenvironmental cells, independent of their developmental states. Furthermore, the results presented herein suggest that checkpoint blockade may provide efficacy for targeting cancer cell populations that survive otherwise effective therapeutic targeting, including stem-like cellular states. Thus, this may overcome the therapeutic dilemma caused by lineage plasticity that often limits the success of precision medicine approaches.

The results presented herein indicate that stem-like states in T-ALL are non-uniform and differ in their epigenetic and oncogenic dependencies and cycling potential. Although these states are associated with a considerable degree of lineage infidelity, the differentiation routes that each individual cancer cell takes do not appear to be arbitrary, but follow convergent trajectories. Therapeutic targeting based on cellular states therefore, rather than genetic variants, may limit the options of molecular escape for each cancer cell. Auspiciously, immune-modulatory programs in T-ALL cells appear to transcend individual stem-like and differentiation states, providing attractive opportunities for combination of specific targeting of signaling pathways with checkpoint blockade or other immunotherapy approaches. Thus, as described herein, combination therapies that target defined cellular states combined with immunotherapeutic approaches produce more effective treatment concepts for relapsed and refractory hematopoietic cancers.

As described in detail in the Examples that follow, lineage plasticity and stemness have been invoked as the cause of therapy resistance in cancer, as these flexible states allow cancer cells to de-differentiate and alter their dependencies. As set forth in the Examples below, such resistance mechanisms were investigated in relapsed T-cell acute lymphoblastic leukemia, an example of a treatment-refractory malignancy, by full-length single-cell RNA sequencing of malignant and microenvironmental cells. Two highly distinct stem-like states that critically differ in their cell-cycle and signaling dependencies were identified. Fast-cycling stem-like leukemia cells demonstrate Notch activation and are effectively eliminated in patients by Notch inhibition, while slow cycling stem-like cells are Notch-independent but rather rely on PI3K signaling, likely explaining the poor efficacy of Notch inhibition in this disease. Remarkably, as described in the Examples that follow, both stem-like states can differentiate into a more mature leukemia state with prominent immune-modulatory functions, including high expression of the LGALS9 checkpoint molecule. These cells promote an immunosuppressive leukemia ecosystem with clonal accumulation of dysfunctional CD8$^+$ T cells that express HAVCR2, the cognate receptor for LGALS9. Described herein is the identification of complex interactions between signaling programs, cellular plasticity and immune programs that underlie refractory T-ALL and illustrates the multi-dimensionality of tumor heterogeneity. As described herein, combination therapies targeting diverse oncogenic states and the immune ecosystem eliminate tumor cells that escape treatment through co-existing transcriptional programs.

Lymphoid Malignancies

Lymphoid malignancies are cancers that originate from lymphocytes. Lymphoid tissues can be divided into two types: (a) the central or primary tissues (bone marrow and thymus), in which lymphoid precursor cells mature to a stage at which they can express antigen receptors, and (b) the peripheral or secondary lymphoid tissues (lymph nodes, spleen, and mucosa-associated lymphoid tissues), in which antigen-specific responses occur. These structures enable the development of the immunoglobulin receptor-expressing B cell lineage, including naive, germinal center, memory B cells, and plasma cells, as well as the T cell receptor-expressing T cell lineage, including helper, cytotoxic, and regulatory T cell subpopulations.

Although present in non-lymphoid tumors, chromosomal translocations represent the hallmark of lymphoid malignancies, and these translocations often represent a major pathogenetic determinant. The analysis of these genetic alterations has led to the identification of many classical proto-oncogenes, with general importance extending far beyond lymphoid biology, including the pleiotropic transcription factor gene MYC and the antiapoptotic gene BCL2.

Exemplary lymphoid malignancies include lymphomas (non-Hodgkin lymphoma or Hodgkin lymphoma), leukemias (acute lyphoblastic leukemia (ALL), acute myelogenous leukemia (AML), chronic lymphocytic leukemia (CLL), chronic myelogenous leukemia (CML), or acute monocytic leukemia (AMoL), myelomas, and lymphocytic leukemias.

T-ALL

T-cell acute lymphoblastic leukemia (T-ALL) is an aggressive malignant neoplasm of the bone marrow. It accounts for ~20% of all cases of acute lymphoblastic leukemia (ALL) and is somewhat more common in adults than children, although the incidence diminishes with older age. T-ALL affects the lymphoid-cell-producing stem cells, in particular, T lymphocytes, as opposed to acute lympho-blastic leukemia (ALL), which commonly affects B lymphocytes.

Several characteristic genetic changes lead to the creation of a leukemic lymphoblast. These changes include chromosomal translocations, intrachromosomal rearrangements, changes in the number of chromosomes in leukemic cells, and additional mutations in individual genes. An example of this includes the translocation of C-MYC, a gene that encodes a transcription factor that leads to increased cell division, next to the immunoglobulin heavy- or light-chain gene enhancers, leading to increased C-MYC expression and increased cell division. Other large changes in chromosomal structure include the merger of chromosomal pairs, which lead to the transcription of new fusion proteins. Examples of this include the ETV6-RUNX1 fusion gene that combines two factors that promote blood cell development and the BCR-ABL1 fusion gene of the Philadelphia chromosome. BCR-ABL1 encodes an always-activated tyrosine kinase that causes frequent cell division. These mutations produce a cell that divides more often, even in the absence of growth factors. In T-cell ALL, LYL1, TAL1, TLX1, and TLX3 rearrangements can occur.

The most common signs and symptoms of T-ALL are caused by the bone marrow being unable to produce enough normal blood cells. General symptoms can include anemia, weakness, tiredness, shortness of breath, light-headedness, palpitations, frequent and severe infections, fever, malaise, sweats, purpura, nosebleeds, bleeding gums, and bruising. T-ALL often causes swollen lymph nodes in the middle part of the chest (mediastinum) which may affect breathing or the circulation, as well as hyperleukocytosis with extramedullary involvement of lymph nodes and other organs, including frequent central nervous system infiltration and the presence of a mediastinal mass, arising from the thymus.

T-ALL can only be diagnosed through laboratory tests, such as lumbar puncture, X-rays, ultrasound, or MRI Scans, but is most often diagnosed through a simple blood count. A large number of white blood cells and lymphoblasts in the circulating blood can be indicative of an ALL prognosis because a higher count usually is a characteristic of a rapid production of lymphoid cells in the marrow. While white blood cell counts at initial presentation can vary significantly, circulating lymphoblast cells are seen on peripheral blood smears in the majority of cases. A bone marrow biopsy provides conclusive proof of T-ALL, typically with >20% of all cells being leukemic lymphoblasts. A lumbar puncture (also known as a spinal tap) can determine whether the spinal column and brain have been invaded. Usually, a chest x-ray and scan will be taken to look for swollen lymph nodes, or other affected sites.

Acute leukemia is often curable with standard treatments, in younger and/or fitter patients. Older or less fit patients will usually have a good initial response to treatment but the condition will most often relapse. Standard treatments include chemotherapy, radiation therapy, immunotherapy, and stem cell transplant. Stem cell transplantation is usually performed for patients who do not respond well to chemotherapy.

Chemotherapy is the initial treatment of choice, and most people with ALL receive a combination of medications. There are no surgical options because of the body-wide distribution of the malignant cells. In general, cytotoxic chemotherapy for ALL combines multiple antileukemic drugs tailored to each person. Chemotherapy for ALL consists of three phases: remission induction, intensification, and maintenance therapy.

| Phase | Agents |
| --- | --- |
| Remission Induction | Combination of: steroids - prednisolone or dexamethasone vincristine asparaginase (better tolerance in people in pediatric care) daunorubicin (used in Adult ALL) Central nervous system prophylaxis can be achieved via: cranio-spinal irradiation cytarabine + methotrexate or liposomal cytarabine |
| Consolidation/ Intensification | Typical protocols use the following given as blocks (varies from 1-3 blocks depending on person's risk category) in different multi-drug combinations: vincristine cyclophosphamide cytarabine daunorubicin etoposide thioguanine mercaptopurine Central nervous system relapse is treated with intrathecal administration of hydrocortisone, methotrexate, and cytarabine. |
| Maintenance Therapy | Typical protocol would include: daily oral mercaptopurine weekly oral methotrexate monthly 5-day course of intravenous vincristine and oral corticosteroids |

Improved outcomes for adolescents and young adults with acute lymphoblastic leukemia (ALL) resulted from treatment with pediatric-based ALL regimens, such as the Augmented Berlin-Frankfurt-Münster (ABFM) regimen and hyper-fractionated cyclophosphamide, vincristine, Adriamycin and dexamethasone (hyper-CVAD) hyper-CVAD or hyper-CVAD with nelarabine in AYA patients. For example, in one study (Rytting et al., 2016 American Journal of Hematology, 91(8)) the complete remission (CR) rate was 93% with ABFM and 98% with hyper-CVAD. The 5-year complete remission duration (CRD) were 53% and 55% respectively (p=0.98). The 5-year overall survival (OS) rates were 60% and 60%, respectively. The MRD status on Day 29 and Day 84 of therapy were predictive of long-term outcomes on both ABFM and hyper-CVAD. Severe regimen toxicities with ABFM included hepatotoxicity in 41%, pancreatitis in 11%, osteonecrosis in 9%, and thrombosis in 19%. Myelosuppression-associated complications were most significant with hyper-CVAD. ABFM and hyper-CVAD resulted in similar efficacy outcomes, but were associated with different toxicity profiles, asparaginase-related with ABFM and myelosuppression-related with hyper-CVAD.

ETP T-ALL

Early T-cell precursor (ETP) acute lymphoblastic leukemia/lymphoma (ALL/LBL) is a recently-recognized high-risk T lymphoblastic leukemia/lymphoma (T-ALL/LBL) subgroup. It comprises 5-15% of all T-ALL and is associated with a poor prognosis. It is derived from thymic cells at the early T-cell precursor (ETP) differentiation stage. ETPs are recent immigrants from the bone marrow (BM) to the thymus, derived from hematopoietic stem cells, which retain a certain level of multilineage pluripotency. ETP cells share similarities with hematopoietic stem cells and myeloid progenitor cells.

In the World Health Organization (WHO) classification, ETP-ALL/LBL falls within the early T-ALL/LBL category. ETP ALL has been reported in 11% to 12% of childhood T-ALL/LBL and in 7.4% of adult T-ALL/LBL. ETP-ALL is currently defined by a distinctive phenotype characterized by a lack of expression of the T-lineage cell surface markers CD1a and CD8, weak or absent expression of CD5 and aberrant expression of one or more myeloid or stem cell markers. ETP-ALL/LBL is also characterized by a distinct molecular profile with a lower incidence of NOTCH1 mutations and frequent presence of FLT3 and DNMT3A mutations. Importantly, ETP-ALL/LBL is associated with a significantly worse outcome in children and young adults compared with other T-ALL/LBL subtypes.

The clinical characteristics were similar between ETP-ALL and classical T-ALL with regard to gender, hemoglobin concentration, and central nervous system involvement. However, ETP-ALL patients presented with a lower white blood cell (WBC) count, lower frequency of the mediastinal mass and higher age (10 years or older) at presentation when compared to those with classical T-ALL.

Patients with ETP-ALL show a poor initial response to standard intensive chemotherapies. Combination chemotherapy has been the cornerstone of T-ALL/LBL treatment. Yet, despite an overall complete response (CR) rate of 90% to 95%, approximately one-third of patients experience disease relapse, and the 5-year overall survival (OS) rate for adults is approximately 50% to 55%.

Galectin-9 (LGALS9)

Galectin-9 was originally isolated from mouse embryonic kidney as a 36 kDa beta-galactoside lectin protein protein. Human galectin-9 is encoded by the LGALS9 gene. The expression of galectin-9 has been detected on various hematological malignancies, such as chronic lymphocytic leukemia (CLL), myelodysplastic syndromes (MDS), Hodgkin and Non-Hodgkin lymphomas, acute myeloid leukemia (AML) or solid tumors, such as lung cancer, breast cancer, and hepatocellular carcinoma.

An exemplary Galectin-9 amino acid sequence is provided at NCBI Accession No. XP_016880112, version XP_016880112.1, incorporated herein by reference and set forth below (SEQ ID NO: 1):

```
  1 mafsgsqapy lspavpfsgt iqgglqdglq itvngtvlss sgtrfavnfq tgfsgndiaf 61 hfnprfedgg yvvcntrqng swgpeerkth mpfqkgmpfd lcflvqssdf kvmvngilfv 121 qyfhrvpfhr vdtisvngsv qlsyisfqnp rtvpvqpafs tvpfsqpvcf pprprgrrqk 181 tqtvihtvqs apgqmfstpa ippmmyphpa ypmpfittil gglypsksil lsgtvlpsaq 241 rfhinlcsgn hiafhlnprf denavvrntq idnswgseer slprkmpfvr gqsfsvwilc
```

-continued
```
301 eahclkvavd gqhlfeyyhr lrnlptinrl evggdiqlth vqt
```

An exemplary Galectin-9 nucleic acid sequence is provided at NCBI Accession No XM_017024623, version XM_017024623.2, incorporated herein by reference and set forth below (SEQ ID NO: 2):

```
  1    1 ttctatttct ttgttaagtc gttccctcta caaaggactt cctagtgggt gtgaaaggca 61 gcggtggcca cagaggcggc ggagagatgg ccttcagcgg ttcccaggct ccctacctga 121 gtccagctgt ccccttttct gggactattc aaggaggtct ccaggacgga cttcagatca 181 ctgtcaatgg gaccgttctc agctccagtg gaaccaggtt tgctgtgaac tttcagactg 241 gcttcagtgg aaatgacatt gccttccact tcaaccctcg gtttgaagat ggagggtacg 301 tggtgtgcaa cacgaggcag aacggaagct gggggcccga ggagaggaag acacacatgc 361 ctttccagaa ggggatgccc tttgacctct gcttcctggt gcagagctca gatttcaagg 421 tgatggtgaa cgggatcctc ttcgtgcagt acttccaccg cgtgcccttc caccgtgtgg 481 acaccatctc cgtcaatggc tctgtgcagc tgtcctacat cagcttccag aaccccgca 541 cagtccctgt tcagcctgcc ttctccacgg tgccgttctc ccagcctgtc tgtttcccac 601 ccaggcccag ggggcgcaga caaaaaaccc agacagtcat ccacacagtg cagagcgccc 661 ctgacagat gttctctact cccgccatcc cacctatgat gtacccccac cccgcctatc 721 cgatgccttt catcaccacc attctgggag ggctgtaccc atccaagtcc atcctcctgt 781 caggcactgt cctgcccagt gctcagaggt tccacatcaa cctgtgctct gggaaccaca 841 tcgccttcca cctgaacccc cgttttgatg agaatgctgt ggtccgcaac acccagatcg 901 acaactcctg ggggtctgag gagcgaagtc tgccccgaaa aatgcccttc gtccgtggcc 961 agagcttctc agtgtggatc ttgtgtgaag ctcactgcct caaggtggcc gtggatggtc
```

-continued

```
1021 agcacctgtt tgaatactac catcgcctga ggaacctgcc caccatcaac agactggaag 1081 tggggggcga catccagctg acccatgtgc agacataggc ggcttcctgg ccctggggcc 1141 gggggctggg gtgtggggca gtctgggtcc tctcatcatc cccacttccc aggcccagcc 1201 tttccaaccc tgcctgggat ctgggcttta atgcagaggc catgtccttg tctggtcctg 1261 cttctggcta cagccaccct ggaacggaga aggcagctga cggggattgc cttcctcagc 1321 cgcagcagca cctggggctc cagctgctgg aatcctacca tcccaggagg caggcacagc 1381 cagggagagg ggaggagtgg gcagtgaaga tgaagcccca tgctcagtcc cctcccatcc 1441 cccacgcagc tccaccccag tcccaagcca ccagctgtct gctcctggtg ggaggtggcc 1501 tcctcagccc ctcctctctg acctttaacc tcactctcac cttgcaccgt gcaccaaccc 1561 ttcacccctc ctggaaagca ggcctgatgg cttcccactg gcctccacca cctgaccaga 1621 gtgttctctt cagaggactg gctcctttcc cagtgtcctt aaaataaaga aatgaaaatg 1681 cttgttggca cattca
```

Galectin-9 Neutralizing Antibodies

Galectin 9 Monoclonal Antibody, 9M1-3, (ThermoFisher, Cat #16-9116-85; Biolegend, Cat #348907) is an exemplary neutralizing antibody of Galectin-9. Another suitable anti-Galectin-9 antibody comprises Galectin-9 monoclonal antibody, LYT-200 (PureTech)._Additional anti-Galectin-9 antibodies include Galectin-9 monoclonal antibodies, D9R4A and OT1D12. Galectin-9 polyclonal antibodies are also suitable for use in the methods described herein.

Notch Receptor Inhibitors

The Notch receptor is a single pass trans-membrane protein evolutionarily conserved. It contains an extracellular domain, a transmembrane domain, and an intracellular domain (NIC). Notch was first identified as an oncogene in T-cell acute lymphoblastic leukemia (T-ALL). As such, many therapeutic avenues aim to inhibit its activity.

A first class of Notch receptor inhibitors are neutralizing antibodies against Notch 1, 2 and 3. Two classes of blocking anti-Notch antibodies have been developed. One is directed to the extracellular negative regulator region (NRR) of Notch, blocking the conformational change that allows the ADAM protease cleavage. A second class consists of ligand-competitors directed against the EGF-repeat region of Notch receptors, blocking the ligand binding domain (LBD). An exemplary list of these antibodies includes, but is not limited to, OMP-59R5 (OncoMed), a humanized mAb that blocks Notch 2 and Notch 3 signaling, Anti-D114 (Invitrogen, Thermofisher), OMP-21M18 (OncoMed), and A5226A (EMD Millipore).

A second class of Notch receptor inhibitors includes decoys, which are soluble forms of the extracellular domain of Notch receptors or Notch ligands. Soluble decoys compete with their endogenous cell surface-bound counterparts and abrogate Notch signaling due to the lack of a transmembrane region necessary for receptor activation. A Notch1 decoy that acts as a ligand-dependent Notch antagonist blocks Notch signaling in endothelial cells, affecting tumor neoangiogenesis and growth. It also reduces Notch1 activity and interferes with Dll1, Dll4 and Jagged1 activities, acting as a pan-ligand inhibitor. An exemplary list of decoys includes $N1_{10-24}$, and $N_{11-13}$.

A third class of Notch receptor inhibitors include γ-secretase inhibitors because the activation of Notch depends largely on γ-secretase activity. Non-selective γ-secretase inhibitors (GSIs), often referred to as "Notch inhibitors" in oncology are widely assumed to be equivalent in terms of biological activity and have cytostatic or cytotoxic activities in various cancer cells. GSIs are in clinical trials in a variety of indications. Several chemical classes of GSIs have been developed. Most of them are competitive inhibitors of the catalytic activity of presenilins. An exemplary list of GSIs includes, but it not limited to, LY411,575 (Eli Lily), MK-0752 (Merck), GSI MRK-003 (the parent compound of clinical agent MK-0752; Merck), GSI RO4929097 (Roche), GSI PF-03084014 (Pfizer); and BMS-708163 (Bristol-Myers Squibb). BMS-906024, a Notch inhibitor, is also a γ-secretase inhibitor (GSI).

The fourth class of Notch receptor inhibitors include peptides that work by blocking the transcriptional nuclear complex formed by Notch, CSL and coactivators. A example of an inhibitory peptide includes MAML1, which forms a transcriptionally inert complex with Notch1 and CSL to inhibit the growth of transformed T-ALL cell lines, as well as the synthetic, cell-permeable, stabilized α-helical, hydrocarbon-stapled peptide SAHM1 that was generated from MAML1.

The last class of Notch receptor inhibitors include dietary derived compounds. A list of exemplary natural compounds include isoflavone genistein, sulforaphane, quercetin, curcumin, and resveratrol.

PI3K Inhibitors

Phosphatidylinositol-3-kinase (PI3K)/AKT/mammalian target of rapamycin (mTOR) signaling is one of the most important intracellular pathways, which can be considered as a master regulator for cancer. PI3K pathway is deregulated through a variety of mechanisms, including loss or inactivation of the tumor suppressor PTEN, mutation or amplification of PI3K, as well as activation of tyrosine kinase growth factor receptors or oncogenes upstream of PI3K. Therefore, inhibition of PI3K is an attractive therapeutic direction in the treatment of cancer.

PI3K inhibitors are subdivided into dual PI3K/mTOR inhibitors, pan-PI3K inhibitors and isoform-specific inhibitors. An exemplary list of Dual PI3K/mTOR inhibitors in Phase I trials includes GSK458/Omipalisib (GlaxoSmithKline) and P7170 (Piramal) SB2343/VS-5584 (Verastem); in Phase II trials includes BEZ235/Dactolisib (Novartis), GDC-0084 (Novogen), GDC-0980/Apitolisib (Genentech), LY3023414 (Eli Lilly), PQR309/Bimiralisib, (PIQUR Therapeutics), XL765/Voxtalisib (Sanofi), and SF-1126 (SignalRx); and in Phase III trials includes PF-05212384/gedatolisib/PKI-587 (Pfizer).

An exemplary list of Pan-PI3K inhibitor in Phase I trials includes CH5132799 (TohokuNiproPharm); in Phase II trials includes XL147/Pilaralisib (Sanofi) and ZSTK474 (Zenyaku Kogyo); and in Phase III trials includes BKM-120/Buparlisib (Novartis).

An exemplary list of Isoform-specific PI3K inhibitors in Phase I trials includes AZD8186 (AstraZeneca) β/δ, KA2237 (Karus Therapeutics) β/δ, GS-9820/CAL-120 (Gilead) β/δ, ME401/PWT-143 (MEI Pharma) δ; in Phase II trials includes AMG 319 (Amgen) δ, GSK2636771 (GlaxoSmithKline) β, INCB050465/Parsaclisib (Incyte) δ, Serabelisib/INK-1117 (Takeda) α, Umbralisib/TGR-1202 (TG Therapeutics) δ, and RP6530/Tenalisib (Rhizen Pharmaceuticals) δ/γ, and in Phase III trials includes GDC-0032/Taselisib, (Genentech) α/δ/γ, and BYL719/Alpelisib (Novartis) α.

An exemplary list of other types of PI3K inhibitors in Phase II includes CUDC-907/Fimepinostat (Curis) and in Phase III Rigosertib/ON-01910 (Onconova Therapeutics).

An exemplary FDA approved Pan-PI3K inhibitor includes BAY80-6946/Copanlisib (Bayer).

A list of Isoform-specific PI3K inhibitors includes Duvelisib/IPI-145 (Infinity) and δ/γ CAL-101/idelalisib (Gilead) δ, both of which are FDA-approved.

World Health Organization Criteria

The WHO Criteria for evaluating the effectiveness of anti-cancer agents on tumor shrinkage, developed in the 1970s by the International Union Against Cancer and the World Health Organization, represented the first generally agreed specific criteria for the codification of tumor response evaluation. These criteria were first published in 1981 (Miller et al., 1981 Clin Cancer Res., 47(1): 207-14, incorporated herein by reference). WHO Criteria proposed >50% tumour shrinkage for a Partial Response and >25% tumour increase for Progressive Disease.

Response Evaluation Criteria in Solid Tumors (RECIST)

RECIST is a set of published rules that define when tumors in cancer patients improve ("respond"), stay the same ("stabilize"), or worsen ("progress") during treatment (Eisenhauer et al., 2009 European Journal of Cncer, 45: 228-247, incorporated herein by reference). Only patients with measureably disease at baseline should be included in protocols where objective tumor response is the primary endpoint.

The response criteria for evaluation of target lesions are as follows:

Complete Response (CR): Disappearance of all target lesions.

Partial Response (PR): At least a 30% decrease in the sum of the longest diameter (LD) of target lesions, taking as reference the baseline sum LD.

Stable Disease (SD): Neither sufficient shrinkage to qualify for PR nor sufficient increase to qualify for PD, taking as reference the smallest sum LD since the treatment started.

Progressive Disease (PD): At least a 20% increase in the sum of the LD of target lesions, taking as reference the smallest sum LD recorded since the treatment started or the appearance of one or more new lesions.

The response criteria for evaluation of non-target lesions are as follows:

Complete Response (CR): Disappearance of all non-target lesions and normalization of tumor marker level.

Incomplete Response/Stable Disease (SD): Persistence of one or more non-target lesion(s) or/and maintenance of tumor marker level above the normal limits.

Progressive Disease (PD): Appearance of one or more new lesions and/or unequivocal progression of existing non-target lesions.

The response criteria for evaluation of best overall response are as follows. The best overall response is the best response recorded from the start of the treatment until disease progression/recurrence (taking as reference for PD the smallest measurements recorded since the treatment started). In general, the patient's best response assignment will depend on the achievement of both measurement and confirmation criteria.

Patients with a global deterioration of health status requiring discontinuation of treatment without objective evidence of disease progression at that time should be classified as having "symptomatic deterioration". Every effort should be made to document the objective progression even after discontinuation of treatment.

In some circumstances, it may be difficult to distinguish residual disease from normal tissue. When the evaluation of complete response depends on this determination, it is recommended that the residual lesion be investigated (fine needle aspirate/biopsy) to confirm the complete response status.

Immune-Related Response Criteria

The immune-related response criteria (irRC) is a set of published rules that define when tumors in cancer patients improve ("respond"), stay the same ("stabilize"), or worsen ("progress") during treatment, where the compound being evaluated is an immuno-oncology drug. The Immune-Related Response Criteria, first published in 2009 (Wolchok et al., 2009 Clin Cancer Res, 15(23):7412, incorporated herein by reference), arose out of observations that immuno-oncology drugs would fail in clinical trials that measured responses using the WHO or RECIST Criteria, because these criteria could not account for the time gap in many patients between initial treatment and the apparent action of the immune system to reduce the tumor burden. The key driver in the development of the irRC was the observation that, in studies of various cancer therapies derived from the immune system such as cytokines and monoclonal antibodies, the looked-for Complete and Partial Responses as well as Stable Disease only occurred after an increase in tumor burden that the conventional RECIST Criteria would have dubbed "Progressive Disease". RECIST failed to take account of the delay between dosing and an observed anti-tumour T cell response, so that otherwise 'successful' drugs—that is, drugs which ultimately prolonged life—failed in clinical trials.

The irRC are based on the WHO Criteria; however, the measurement of tumor burden and the assessment of immune-related response have been modified as set forth below.

Measurement of Tumor Burden

In the irRC, tumor burden is measured by combining 'index' lesions with new lesions. Ordinarily, tumor burden would be measured with a limited number of 'index' lesions (that is, the largest identifiable lesions) at baseline, with new lesions identified at subsequent timepoints counting as 'Progressive Disease'. In the irRC, by contrast, new lesions are a change in tumor burden. The irRC retained the bidirectional measurement of lesions that had originally been laid down in the WHO Criteria.

Assessment of Immune-Related Response

In the irRC, an immune-related Complete Response (irCR) is the disappearance of all lesions, measured or unmeasured, and no new lesions; an immune-related Partial Response (irPR) is a 50% drop in tumor burden from baseline as defined by the irRC; and immune-related Progressive Disease (irPD) is a 25% increase in tumor burden from the lowest level recorded. Everything else is considered immune-related Stable Disease (irSD). Even if tumor burden is rising, the immune system is likely to "kick in" some months after first dosing and lead to an eventual decline in tumor burden for many patients. The 25% threshold accounts for this apparent delay.

Gene Expression Profiling

In general, methods of gene expression profiling may be divided into two large groups: methods based on hybridization analysis of polynucleotides and methods based on sequencing of polynucleotides. Methods known in the art for the quantification of mRNA expression in a sample include northern blotting and in situ hybridization, RNAse protection assays, RNA-seq, and reverse transcription polymerase chain reaction (RT-PCR). Alternatively, antibodies are employed that recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). For example, RT-PCR is used to compare mRNA levels in different sample populations, in normal and tumor tissues, with or without drug treatment, to characterize patterns of gene expression, to discriminate between closely related mRNAs, and/or to analyze RNA structure.

In some cases, a first step in gene expression profiling by RT-PCR is the reverse transcription of the RNA template into cDNA, followed by amplification in a PCR reaction. For example, extracted RNA is reverse-transcribed using a GeneAmp RNA PCR kit (Perkin Elmer, Calif., USA), following the manufacturer's instructions. The cDNA is then used as template in a subsequent PCR amplification and quantitative analysis using, for example, a TaqMan RTM (Life Technologies, Inc., Grand Island, N.Y.) assay.

Microarrays

Differential gene expression can also be identified, or confirmed using a microarray technique. In these methods, polynucleotide sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of mRNA typically is total RNA isolated from human tumors or tumor cell lines and corresponding normal tissues or cell lines. Thus, RNA is isolated from a variety of primary tumors or tumor cell lines. If the source of mRNA is a primary tumor, mRNA is extracted from frozen or archived tissue samples.

In the microarray technique, PCR-amplified inserts of cDNA clones are applied to a substrate in a dense array. The microarrayed genes, immobilized on the microchip, are suitable for hybridization under stringent conditions.

In some cases, fluorescently labeled cDNA probes are generated through incorporation of fluorescent nucleotides by reverse transcription of RNA extracted from tissues of interest (e.g., leukemia tissue). Labeled cDNA probes applied to the chip hybridize with specificity to loci of DNA on the array. After washing to remove non-specifically bound probes, the chip is scanned by confocal laser microscopy or by another detection method, such as a charge-coupled device (CCD) camera. Quantification of hybridization of each arrayed element allows for assessment of corresponding mRNA abundance.

In some configurations, dual color fluorescence is used. With dual color fluorescence, separately labeled cDNA probes generated from two sources of RNA are hybridized pairwise to the array. The relative abundance of the transcripts from the two sources corresponding to each specified gene is thus determined simultaneously. In various configurations, the miniaturized scale of the hybridization can afford a convenient and rapid evaluation of the expression pattern for large numbers of genes. In various configurations, such methods can have sensitivity required to detect rare transcripts, which are expressed at fewer than 1000, fewer than 100, or fewer than 10 copies per cell. In various configurations, such methods can detect at least approximately two-fold differences in expression levels (Schena et al., Proc. Natl. Acad. Sci. USA 93(2): 106-149 (1996)). In various configurations, microarray analysis is performed by commercially available equipment, following manufacturer's protocols, such as by using the Affymetrix GenChip technology, or Incyte's microarray technology.

RNA-Seq

RNA sequencing (RNA-seq), also called whole transcriptome shotgun sequencing (WTSS), uses next-generation sequencing (NGS) to reveal the presence and quantity of RNA in a biological sample at a given moment in time.

RNA-Seq is used to analyze the continually changing cellular transcriptome. See, e.g., Wang et al., 2009 Nat Rev Genet, 10(1): 57-63, incorporated herein by reference. Specifically, RNA-Seq facilitates the ability to look at alternative gene spliced transcripts, post-transcriptional modifications, gene fusion, mutations/SNPs and changes in gene expression. In addition to mRNA transcripts, RNA-Seq can look at different populations of RNA to include total RNA, small RNA, such as miRNA, tRNA, and ribosomal profiling. RNA-Seq can also be used to determine exon/intron boundaries and verify or amend previously annotated 5' and 3' gene boundaries.

Prior to RNA-Seq, gene expression studies were done with hybridization-based microarrays. Issues with microarrays include cross-hybridization artifacts, poor quantification of lowly and highly expressed genes, and needing to know the sequence of interest. Because of these technical issues, transcriptomics transitioned to sequencing-based methods. These progressed from Sanger sequencing of Expressed Sequence Tag libraries, to chemical tag-based methods (e.g., serial analysis of gene expression), and finally to the current technology, NGS of cDNA (notably RNA-Seq).

Pharmaceutical Therapeutics

For therapeutic uses, the agents (e.g., a Galectin-9 inhibitor or neutralizing antibody) described herein may be administered systemically, for example, formulated in a pharmaceutically-acceptable buffer such as physiological saline. Preferable routes of administration include, for example, subcutaneous, intravenous, interperitoneal, intramuscular, or intradermal injections that provide continuous, sustained levels of the drug in the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the agents to be administered varies depending upon the manner of administration, the age and body weight of the patient, and with the clinical symptoms of (e.g., ETP T-ALL). Generally, amounts will be in the range of those used for other agents used in the treatment of other diseases associated T-ALL (e.g., ETP T-ALL), although in certain instances lower amounts will be needed because of the increased specificity of the agents. For example, an agent is administered at a dosage that is cytotoxic to a neoplastic cell.

Formulation of Pharmaceutical Compositions

Human dosage amounts can initially be determined by extrapolating from the amount of the agent used in animal models, as a skilled artisan recognizes it is routine in the art to modify the dosage for humans compared to animal models. In certain embodiments it is envisioned that the dosage may vary from between about 1 μg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other cases, this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other aspects, it is envisaged that doses may be in the range of about 5 mg compound/Kg body to about 20 mg compound/Kg body. In other embodiments, the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

In some cases, the agent of the invention is administered at a dose that is lower than the human equivalent dosage (HED) of the no observed adverse effect level (NOAEL) over a period of three months, four months, six months, nine months, 1 year, 2 years, 3 years, 4 years or more. The NOAEL, as determined in animal studies, is useful in determining the maximum recommended starting dose for human clinical trials. For instance, the NOAELs can be extrapolated to determine human equivalent dosages. Typically, such extrapolations between species are conducted based on the doses that are normalized to body surface area (i.e., mg/m$^2$). In specific embodiments, the NOAELs are determined in mice, hamsters, rats, ferrets, guinea pigs, rabbits, dogs, primates, primates (monkeys, marmosets, squirrel monkeys, baboons), micropigs or minipigs. For a discussion on the use of NOAELs and their extrapolation to determine human equivalent doses, see Guidance for Industry Estimating the Maximum Safe Starting Dose in Initial Clinical Trials for Therapeutics in Adult Healthy Volunteers, U.S. Department of Health and Human Services Food and Drug Administration Center for Drug Evaluation and Research (CDER), Pharmacology and Toxicology, July 2005, incorporated herein by reference.

The amount of an agent of the invention used in the prophylactic and/or therapeutic regimens which will be effective in the treatment of ETP T-ALL can be based on the currently prescribed dosage of the agent as well as assessed by methods disclosed herein and known in the art. The frequency and dosage will vary also according to factors specific for each patient depending on the specific agent administered, the severity of the cancerous condition, the route of administration, as well as age, body, weight, response, and the past medical history of the patient. For example, the dosage of an agent of the invention which will be effective in the treatment of cancer can be determined by administering the agent to an animal model such as, e.g., the animal models disclosed herein or known to those skilled in the art. In addition, in vitro assays may optionally be employed to help identify optimal dosage ranges.

In some aspects, the prophylactic and/or therapeutic regimens comprise titrating the dosages administered to the patient so as to achieve a specified measure of therapeutic efficacy. Such measures include a reduction in the cancer cell population in the patient.

In certain cases, the dosage of the agent of the invention in the prophylactic and/or therapeutic regimen is adjusted so as to achieve a reduction in the number or amount of cancer cells found in a test specimen extracted from a patient after undergoing the prophylactic and/or therapeutic regimen, as compared with a reference sample. Here, the reference sample is a specimen extracted from the patient undergoing therapy, wherein the specimen is extracted from the patient at an earlier time point. In one aspect, the reference sample is a specimen extracted from the same patient, prior to receiving the prophylactic and/or therapeutic regimen. For example, the number or amount of cancer cells in the test specimen is at least 2%, 5%, 10%, 15%, 20%, 30%, 40%, 50%, 60%, 70%, 80%, 90%, 95% or 99% lower than in the reference sample.

In some cases, the dosage of the agent of the invention in the prophylactic and/or therapeutic regimen is adjusted so as to achieve a number or amount of cancer cells that falls within a predetermined reference range. In these embodiments, the number or amount of cancer cells in a test specimen is compared with a predetermined reference range.

In other embodiments, the dosage of the agent of the invention in prophylactic and/or therapeutic regimen is adjusted so as to achieve a reduction in the number or amount of cancer cells found in a test specimen extracted from a patient after undergoing the prophylactic and/or therapeutic regimen, as compared with a reference sample, wherein the reference sample is a specimen is extracted from a healthy, noncancer-afflicted patient. For example, the number or amount of cancer cells in the test specimen is at least within 60%, 50%, 40%, 30%, 20%, 15%, 10%, 5%, or 2% of the number or amount of cancer cells in the reference sample.

In treating certain human patients having solid tumors, extracting multiple tissue specimens from a suspected tumor site may prove impracticable. In these cases, the dosage of the agent of the invention in the prophylactic and/or therapeutic regimen for a human patient is extrapolated from doses in animal models that are effective to reduce the cancer population in those animal models. In the animal models, the prophylactic and/or therapeutic regimens are adjusted so as to achieve a reduction in the number or amount of cancer cells found in a test specimen extracted from an animal after undergoing the prophylactic and/or therapeutic regimen, as compared with a reference sample. The reference sample can be a specimen extracted from the same animal, prior to receiving the prophylactic and/or therapeutic regimen. In specific embodiments, the number or amount of cancer cells in the test specimen is at least 2%, 5%, 10%, 15%, 20%, 30%, 40%, 50% or 60% lower than in the reference sample. The doses effective in reducing the number or amount of cancer cells in the animals can be normalized to body surface area (e.g., mg/m$^2$) to provide an equivalent human dose.

The prophylactic and/or therapeutic regimens disclosed herein comprise administration of an agent of the invention or pharmaceutical compositions thereof to the patient in a single dose or in multiple doses (e.g., 1, 2, 3, 4, 5, 6, 7, 8, 10, 15, 20, or more doses).

In one aspect, the prophylactic and/or therapeutic regimens comprise administration of the agent of the invention or pharmaceutical compositions thereof in multiple doses.

When administered in multiple doses, the agent or pharmaceutical compositions are administered with a frequency and in an amount sufficient to treat the condition. For example, the frequency of administration ranges from once a day up to about once every eight weeks. In another example, the frequency of administration ranges from about once a week up to about once every six weeks. In another example, the frequency of administration ranges from about once every three weeks up to about once every four weeks.

Generally, the dosage of an agent of the invention administered to a subject to treat cancer is in the range of 0.01 to 500 mg/kg, e.g., in the range of 0.1 mg/kg to 100 mg/kg, of the subject's body weight. For example, the dosage administered to a subject is in the range of 0.1 mg/kg to 50 mg/kg, or 1 mg/kg to 50 mg/kg, of the subject's body weight, more preferably in the range of 0.1 mg/kg to 25 mg/kg, or 1 mg/kg to 25 mg/kg, of the patient's body weight. In another example, the dosage of an agent of the invention administered to a subject to treat cancer in a patient is 500 mg/kg or less, preferably 250 mg/kg or less, 100 mg/kg or less, 95 mg/kg or less, 90 mg/kg or less, 85 mg/kg or less, 80 mg/kg or less, 75 mg/kg or less, 70 mg/kg or less, 65 mg/kg or less, 60 mg/kg or less, 55 mg/kg or less, 50 mg/kg or less, 45 mg/kg or less, 40 mg/kg or less, 35 mg/kg or less, 30 mg/kg or less, 25 mg/kg or less, 20 mg/kg or less, 15 mg/kg or less, 10 mg/kg or less, 5 mg/kg or less, 2.5 mg/kg or less, 2 mg/kg or less, 1.5 mg/kg or less, or 1 mg/kg or less of a patient's body weight.

In another example, the dosage of an agent of the invention administered to a subject to treat cancer in a patient is a unit dose of 0.1 to 50 mg, 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

In another example, the dosage of an agent of the invention administered to a subject to treat cancer in a patient is in the range of 0.01 to 10 g/m$^2$, and more typically, in the range of 0.1 g/m$^2$ to 7.5 g/m$^2$, of the subject's body weight. For example, the dosage administered to a subject is in the range of 0.5 g/m$^2$ to 5 g/m$^2$, or 1 g/m$^2$ to 5 g/m$^2$ of the subject's body's surface area.

In another example, the prophylactic and/or therapeutic regimen comprises administering to a patient one or more doses of an effective amount of an agent of the invention, wherein the dose of an effective amount achieves a plasma level of at least 0.1 μg/mL, at least 0.5 μg/mL, at least 1 μg/mL, at least 2 μg/mL, at least 5 μg/mL, at least 6 μg/mL, at least 10 μg/mL, at least 15 μg/mL, at least 20 μg/mL, at least 25 μg/mL, at least 50 μg/mL, at least 100 μg/mL, at least 125 μg/mL, at least 150 μg/mL, at least 175 μg/mL, at least 200 μg/mL, at least 225 μg/mL, at least 250 μg/mL, at least 275 μg/mL, at least 300 μg/mL, at least 325 μg/mL, at least 350 μg/mL, at least 375 μg/mL, or at least 400 μg/mL of the agent of the invention.

In another example, the prophylactic and/or therapeutic regimen comprises administering to a patient a plurality of doses of an effective amount of an agent of the invention, wherein the plurality of doses maintains a plasma level of at least 0.1 μg/mL, at least 0.5 μg/mL, at least 1 μg/mL, at least 2 μg/mL, at least 5 μg/mL, at least 6 μg/mL, at least 10 μg/mL, at least 15 μg/mL, at least 20 μg/mL, at least 25 μg/mL, at least 50 μg/mL, at least 100 μg/mL, at least 125 μg/mL, at least 150 μg/mL, at least 175 μg/mL, at least 200

μg/mL, at least 225 μg/mL, at least 250 μg/mL, at least 275 μg/mL, at least 300 μg/mL, at least 325 μg/mL, at least 350 μg/mL, at least 375 μg/mL, or at least 400 μg/mL of the agent of the invention for at least 1 day, 1 month, 2 months, 3 months, 4 months, 5 months, 6 months, 7 months, 8 months, 9 months, 10 months, 11 months, 12 months, 15 months, 18 months, 24 months or 36 months.

Combination Therapy

In one example, the agents are administered in combination therapy, i.e., combined with other agents, e.g., therapeutic agents, that are useful for treating pathological conditions or disorders, such as various forms of cancer. The term "in combination" in this context means that the agents are given substantially contemporaneously, either simultaneously or sequentially. If given sequentially, at the onset of administration of the second compound, the first of the two compounds is in some cases still detectable at effective concentrations at the site of treatment.

The administration of a compound or a combination of compounds for the treatment of a neoplasia may be by any suitable means that results in a concentration of the therapeutic that, combined with other components, is effective in ameliorating, reducing, or stabilizing a neoplasia. The agent may be contained in any appropriate amount in any suitable carrier substance, and is generally present in an amount of 1-95% by weight of the total weight of the composition. The agent may be provided in a dosage form that is suitable for parenteral (e.g., subcutaneously, intravenously, intramuscularly, or intraperitoneally) administration route. The agent may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Accordingly, in some examples, the prophylactic and/or therapeutic regimen comprises administration of an agent of the invention in combination with one or more additional anticancer therapeutics. In one example, the dosages of the one or more additional anticancer therapeutics used in the combination therapy is lower than those which have been or are currently being used to treat cancer. The recommended dosages of the one or more additional anticancer therapeutics currently used for the treatment of cancer can be obtained from any reference in the art including, but not limited to, Hardman et al., eds., Goodman & Gilman's The Pharmacological Basis Of Basis Of Therapeutics, 10th ed., McGraw-Hill, New York, 2001; Physician's Desk Reference (60.sup.th ed., 2006), which is incorporated herein by reference in its entirety.

In some embodiments, the agent of the invention may be used in combination with one or more additional anticancer therapeutics. Examples of anticancer therapeutics include thalidomide, lenalidomide, ixazomib, bortezomib, carfilzomib, melphalan, vincristine, cyclophosphamide, doxorubicin, liposomal doxorubicin, or bendamustine.

In some embodiments, the anticancer therapeutics may be co-administered with prednisone or dexamethasone.

In some embodiments, the prophylactic and/or therapeutic regimen comprises administration of an agent of the invention in combination with a combination chemotherapy agent (e.g., Hyper-CVAD (course A: cyclophosphamide, vincristine, doxorubicin (Adriamycin®), and dexamethasone; course B: methotrexate and cytarabine), hyper-CVAD+ nelarabine, augmented Berlin-Frankfurt-Münster (aBFM) regimen).

The agent of the invention and the one or more additional anticancer therapeutics can be administered separately, simultaneously, or sequentially. In various aspects, the agent of the invention and the additional anticancer therapeutic are administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, 96 hours apart, 120 hours part, or 168 hours apart. In another example, two or more anticancer therapeutics are administered within the same patient visit.

In certain aspects, the agent of the invention and the additional anticancer therapeutic are cyclically administered. Cycling therapy involves the administration of one anticancer therapeutic for a period of time, followed by the administration of a second anticancer therapeutic for a period of time and repeating this sequential administration, i.e., the cycle, in order to reduce the development of resistance to one or both of the agents, to avoid or reduce the side effects of one or both of the agents, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to the agent, to avoid or reduce the side effects of one of the agent, and/or to improve the efficacy of the agent.

In another example, the agents are administered concurrently to a subject in separate compositions. The combination the agents of the invention may be administered to a subject by the same or different routes of administration.

When an agent of the invention and the additional anticancer therapeutic are administered to a subject concurrently, the term "concurrently" is not limited to the administration of the agent at exactly the same time, but rather, it is meant that they are administered to a subject in a sequence and within a time interval such that they can act together (e.g., synergistically to provide an increased benefit than if they were administered otherwise). For example, the agents may be administered at the same time or sequentially in any order at different points in time; however, if not administered at the same time, they should be administered sufficiently close in time so as to provide the desired therapeutic effect, preferably in a synergistic fashion. The combination of the agents can be administered separately, in any appropriate form and by any suitable route. When the components of the combination the agents are not administered in the same pharmaceutical composition, it is understood that they can be administered in any order to a subject in need thereof. For example, an agent of the invention can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the additional anticancer therapeutic, to a subject in need thereof. In various aspects, the agents are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one example, the agents are administered within the same office visit. In another example, the combination the agents of the invention are administered at 1 minute to 24 hours apart.

Release of Pharmaceutical Compositions

Pharmaceutical compositions according to the invention may be formulated to release the agents substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that target a neoplasia by using carriers or chemical derivatives to deliver the agent to a particular cell type (e.g., neoplastic cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the agent. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the agent that reduces or ameliorates a neoplasia, the composition may include suitable parenterally acceptable carriers and/or excipients. The agent may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active antineoplastic therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug may be incorporated in biocompatible carriers, liposomes, nanoparticles, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Kits or Pharmaceutical Systems

The present compositions may be assembled into kits or pharmaceutical systems for use in ameliorating a neoplasia. Kits or pharmaceutical systems according to this aspect of the invention comprise a carrier means, such as a box, carton, tube or the like, having in close confinement therein one or more container means, such as vials, tubes, ampoules, or bottles. The kits or pharmaceutical systems of the invention may also comprise associated instructions for using the agent of the invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Materials and Methods to Identify that Co-Existing Stem-Like States and Immune Evasion Programs Underlie T-ALL Pathogenesis and Drug Resistance The following materials and methods were utilized to generate the results described herein.

Primary Samples

Banked blood or bone marrow samples from patients with relapsed/refractory ETP T-ALL (see Table 1) were used in this study. All patients provided informed consent and were enrolled on a phase I clinical trial (NCT01363817) with the γ-secretase inhibitor (GSI) BMS-906024, a Notch inhibitor. Ayala Pharmaceuticals is investigating AL101 (BMS-906024) in a Phase II open-label, single-arm, multicenter study in ACC patients harboring known NOTCH1-4 activating mutations (ACCURACY; NCT03691207). Normal donor blood was obtained from Research Blood Components, LLC; and mononuclear cells (PBMCs) were isolated using Ficoll-Paque PLUS from GE Healthcare.

TABLE 1

| | | | | Allele Frequencies | | | | Days post treatment |
| Patient | Gender | Age (y) | Rapid Heme Panel Results | (%) | Cytogenetics | Immunophenotype | Source | |
|---|---|---|---|---|---|---|---|---|
| | | | Clinical patient information and tumor characteristics (immunophenotype, cytogenetics, and targeted DNA-sequencing results) | | | | | |
| P1 | Female | 44 | ETV6 NM_001987 c.1105C > T p.R369W | 42.1 | 46, XX, inv(3)(p2 | CD45(dim), CD34, | Blood | 0 |
| | | | ETV6 NM_001987 c.1106G > A p.R369Q | 44.9 | ?5q2?5), add(4) | CD56, CD7, CD5 | | |

TABLE 1-continued

Clinical patient information and tumor characteristics (immunophenotype,
cytogenetics, and targeted DNA-sequencing results)

| Patient | Gender | Age (y) | Rapid Heme Panel Results | Allele Frequencies (%) | Cytogenetics | Immunophenotype | Source | Days post treatment |
|---------|--------|---------|--------------------------|------------------------|--------------|-----------------|--------|--------------------|
| | | | NOTCH1 NM_017617 c.7171C > T p.Q2391* | 51.2 | (q21), −6, | (subset), CD33, | | |
| | | | RUNX1 NM_001754 c.750_750insGG p.R251fs* | 29.4 | add(19)(q13.1), | CD117 (subset), | | |
| | | | TP53 NM_000546 c.1119delA p.K374fs* | 55 | +21, +der(?)t(6;?) | CD15 (subset) | | |
| | | | WT1 NM_024426 c.1109_1100 | 39.1 | (p21;?), +mar | | | |
| | | | 5GTCGCACATCCTGCA > TCGGAC | | [cp17]//46, XY | | | |
| | | | p.R367_370DVRRsplice | | [3] | | | |
| P2 | Male | 53 | NOTCH1, chr9, c4775T > G, p.F1592C | 64.9 | 46, XY, | CD45(dim), CD34 | Blood | 0 |
| | | | PTPN11, chr12, c.8541 > C, p.F285S | 40 | karyotype with | (84%), CD3 | | |
| | | | DNMT3A, chr2, c.1204C > T, p.Q402* | 99.3 | del(7p13) | (Cytoplamic, 90%), | | |
| | | | | | | CD5 (75%), CD7 | | |
| | | | | | | (86%), CD33 (87%), | | |
| | | | | | | and TdT (dim, 58%) | | |
| P3 | Male | 18 | GATA3 NM_001002295 c.830G > A p.R277Q | 46.2 | 46, XY, add(1) | CD45(dim), CD2, | Blood | 0, 3, 10 |
| | | | IL7R NM_002185 c.722T > A p.I241N | 50.2 | (q42)[13]/46, XY | CD3 (cytoplasmic), | | |
| | | | JAK1 NM_002227 c.2108C > A p.S703I | 68.8. | [7] | CD7, CD13 | | |
| | | | NOTCH1 NM_017617 c.4793C > G p.R1598P | 50 | | | | |
| | | | NOTCH1 NM_017617 | 50 | | | | |
| | | | c.7399_7399insATGGAGAAATCC p.S2467fs* | | | | | |
| P4 | Female | 27 | NOTCH1 NM_017617 c.47211 > C p.L1574P | 47.8 | 45, X,- | CD45(dim), CD34, | Blood | 0, 1 |
| | | | | | X, del(1)(p13p2 | TDT, CD7, CD33, | | |
| | | | | | 2), add(5)(p15), | CD117, | | |
| | | | | | del(5)(q22q31), | myeloperoxidase | | |
| | | | | | der(6)del(6)(p11 | (small subset) | | |
| | | | | | p21)del(6)(q13q | | | |
| | | | | | 21), add(9)(p13) | | | |
| | | | | | ,- | | | |
| | | | | | 11, del(11)(q23), | | | |
| | | | | | del(12)(p13), del | | | |
| | | | | | (13)(q12q22)+ | | | |
| P5 | Male | 39 | DNMT3A NM_175629 c.19871 > C p.S663P | 6.2 | 46, XY, del(12)(p | CD45(dim), HLA-DR | Bone | 0, 8, 15 |
| | | | JAK1 NM_002227 c.2171G > A p.R724H | 44.7 | 11.2)[9]/46, XY | (variable), CD117 | marrow | |
| | | | JAK3 NM_000215 c.2872G > A p.E958K | 35.9 | [Cp11] | (dim), CD56, | (d0)/ | |
| | | | NOTCH1 NM_017617 c.4778T > C p.L1593P | 75 | | CD5, CD7, | Blood | |
| | | | | | | cytoplasmic CD3 | (d8, 15) | |

Tumor Cell Lines

The leukemia cell lines (all verified by STR profiling) DND-41, KOPT-K1, HPB-ALL, Loucy, MOLT-4, NALM-6, SEM, KG-1 and HL-60 were obtained from ATCC or DSMZ, and were cultured in RPMI 1640 with 10% of heat-inactivated fetal bovine serum, 1% penicillin/streptomycin (Invitrogen).

T-Cell Activation and Functional Assays

T-cells were isolated using Easy Sep Human T-cell Enrichment kit (StemCell Technologies), activated and expanded with Dynabeads Human T-activator CD3/CD28 (ThermoFisher Scientific) in X-VIVO 15 (Lonza) with 5% of human AB serum, and 50 U/mL IL-2 (Miltenyi Biotech). For T-cell exhaustion functional assays, activated CD8' T-cells were cultured in X-VIVO 15 media or in supernatant media of DND-41 cell line, with 50 U/mL IL-2. For HAVCR2-LSGAL9 pathway blocking experiments, activated CD8+ T-cells were cultured in X-VIVO 15 media or in supernatant media of DND-41 T-ALL supplemented with anti-human Galectin-9 10 μg/mL (Thermo Fisher Scientific) or recombinant Galectin-9 2.5 μg/mL (R&D systems) for 72 hours.

In Vitro Inhibitor and Cell Proliferation Assays

Buparlisib (Selleckchem) and GSI (Santa Cruz Biotechnology, Inc) were prepared in DMSO (Sigma-Aldrich). Cell proliferation assays were measured by CellTiter-Glo Luminescent Cell viability assay (Promega), after a period of seven days. IC50 values were calculated by fitting the dose-response curves to a three-parameter sigmoid dose-response model using GraphPad. Error bars reflect standard deviation.

Flow Cytometry

T-ALL samples were stained for CD45 FITC (Thermo Fisher Scientific), T-cells for CD3 PerCP-Cy5.5 (Thermo Fisher Scientific), monocytes for CD14 APC-Cy7 (BD Biosciences), B-cells for CD19 PE (BioLegend). Cells were stained with DAPI (1 μg/mL, Sigma-Aldrich) to exclude dead cells. Single-cells were sorted into 96-well plates containing TCL buffer (Qiagen) using a Sony SH800 sorter (Figures S16, S17). For intracellular flow staining of LGALS9, cells were fixed and permeabilized (BD Cytofix/Cytoperm Fixation/Permeabilization kit) (Figure S18). Following permeabilization, cells were stained with anti-Galectin-9-APC (BioLegend) or matching isotype control Mouse IgG1, κ (Thermo Fisher Scientific); and analyzed on BD LSRFortessa flow cytometer (BD) using FlowJo software v10.

Immunohistochemistry Staining for LGALS9 and HAVCR2

All immunohistochemistry staining (IHC) was performed on the Leica Bond automated staining platform. Anti-HAVCR2 (Cell Signaling Technology), was run at 1:100 dilution and anti-LGALS9 (BioLegend), was run at 1:50 dilution using the Leica Biosystems Refine Detection Kit with citrate antigen retrieval.

Quantitative Real-Time PCR

RNA was isolated using RNeasy Mini Kit (Qiagen), followed by reverse transcription with SuperScript III Reverse Transcriptase (ThermoFisher Scientific). Gene expression was quantified by quantitative real-time PCR using Power SYBR Green PCR Master Mix (Applied Biosystems, Vial instrument). Primer sequences are listed in Table 2. Three technical replicates were used in each assay, error bars represent±standard deviation.

TABLE 2

Primer sequences used for qRT-PCR

| Primer Name | Primer Sequence | SEQ ID NO |
|---|---|---|
| HAVCR F | 5'-CTGCTGCTACTACTTACAAGGTC-3' | 3 |
| HAVCR2 R | 5'-GCAGGGCAGATAGGCATTCT-3' | 4 |
| TIGIT F | 5'-GGAATGATGACAGGCACAATAGA-3' | 5 |
| TIGIT R | 5'-CCATCAGGGTAGGTGTGATAGA-3' | 6 |
| GZMB F | 5'-TACCATTGAGTTGTGCGTGGG-3' | 7 |
| GZMB R | 5'-GCCATTGTTTCGTCCATAGGAGA-3' | 8 |
| IL-2 F | 5'-AACTCCTGTCTTGCATTGCAC-3' | 9 |
| IL-2 R | 5'-GCTCCAGTTGTAGCTGTGTTT-3' | 10 |
| INF-gamma F | 5'-GTAGCGGATAATGGAACTCTTT-3' | 11 |
| INF-gamma R | 5'-TTTCGAAGTCATCTCGTTTCTT-3' | 12 |
| GAPDH F | 5'-AATCCCATCACCATCTTCCA-3' | 13 |
| GAPDH R | 5'-TGGGACTCCACGACGTACTCA-3' | 14 |

Single-Cell RNA-Seq Library Preparation

Full-length single-cell RNA-seq libraries were prepared using the SMART-seq2 protocol (Picelli et al., 2014 Nat Protoc, 9(1):171-181). cDNA was fragmented using Nextera XT (Illumina) and amplified with indexed Nextera PCR primers. Products were quantified using a Bioanalyzer High Sensitivity DNA Kit. Pooled libraries were sequenced on a NextSeq 500 (Illumina) with an average sequencing depth of 0.5-1 million reads per cell.

Computational and Statistical Analyses

Processing and quality filtering of scRNA-seq data was carried out using trimmomatic[21], STAR (Dobin et al., 2013 Bioinformatics, 29(1):15-21), HTSeq (Anders et al., 2015 Bioinformatics, 31(2):166-169) and RSEM (Li et al., 2011 BMC Bioinformatics, 12:323). Clustering of single-cell profiles and marker gene analyses were performed using PAGODA2 (Fan et al., 2016 Nature methods, 13(3):241-244), monocole2 (Trapnell et al., 2014 Nat Biotechnol, 32(4):381-386), SEURAT (Butler et al., 2018 Nature Biotechnology, 36(5):411-420) and RNA velocity (La et al., 2018 Nature, 560(7719):494-498). Single nucleotide variant and copy number analyses were performed with mutect2 (Cibulskis et al., 2013 Nat Biotechnol, 31(3):213-219), InferCNV (Patel et al., 2014 Science, 344(6190):1396-1401; Tirosh et al., 2016 Science, 352(6282):189-196) and CON-ICSmat (Muller et al., 2018 Bioinformatics, 34(18):3217-3219). Single-cell profiles were compared with cell types from ImmGen (Heng et al., 2008 Nat Immunol, 9(10):1091-1094) and BLUEPRINT (using a log-likelihood model. Transcriptional regulon and signaling pathway activities were analyzed with SCENIC (Fernandez et al., 2016 Cell Syst, 3(5):491-495 e495) and PROGENy (Schubert et al., 2018 Nat Commun, 9(1):20). Further details of the analysis are set forth below.

Processing of scRNA-Seq Data

Following sequencing reads were trimmed using trimmomatic and aligned to the hg19 version of the genome using STAR aligner with following parameters '—twopassMode Basic—alignIntronMax 100000—alignMatesGapMax 100000—alignSJDBoverhangMin 10—alignSJstitchMismatchNmax 5-1 5 5' (Dobin et al., 2013 Bioinformatics, 29(1):15-21; Bolger et al., 2014 Bioinformatics, 30(15): 2114-2120) Raw counts and normalized TPM values were obtained from the aligned bam file using HTSeq and RSEM, respectively (Anders et al., 2015 Bioinformatics, 31(2):166-169; Li et al., 2011 BMC Bioinformatics, 12:323).

Quality Filtering of scRNA-Seq Data

Figures 6A, 6B:
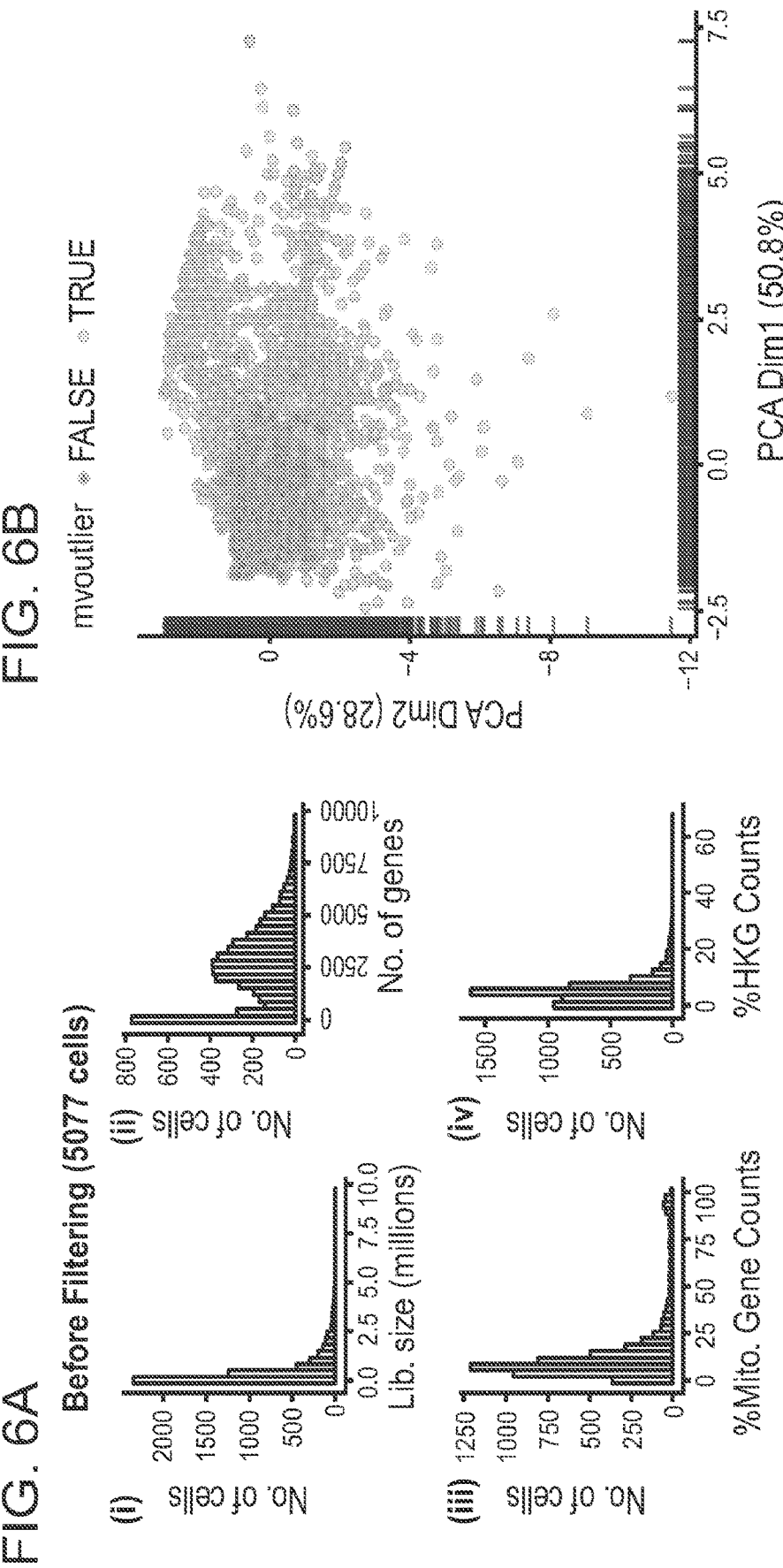
FIG. 6A-6F is series of plots and a venn diagram showing quality filtering of scRNA-seq dataset. Specifically, FIG. 6A
Figures 6C, 6D:
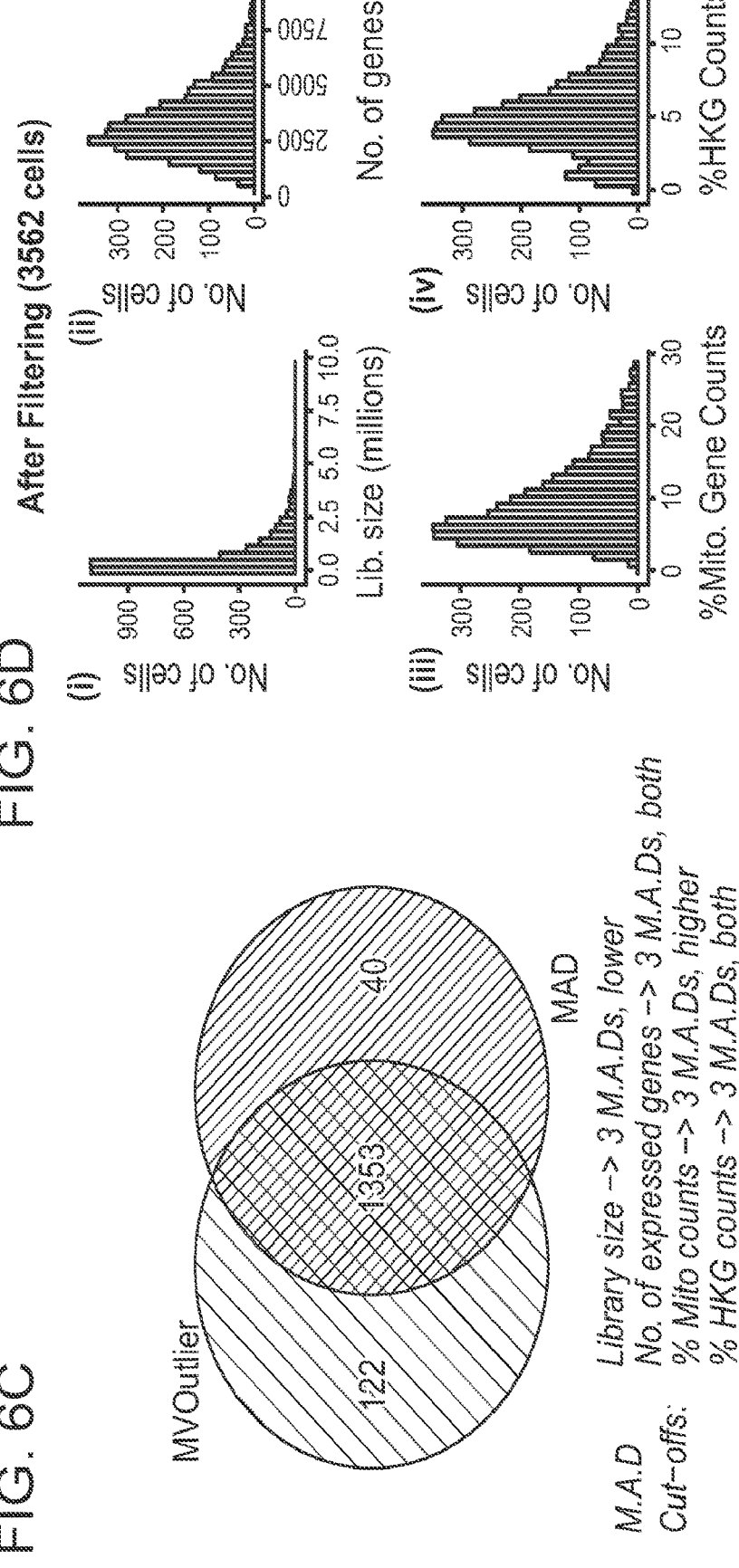
Figures 6E, 6F:
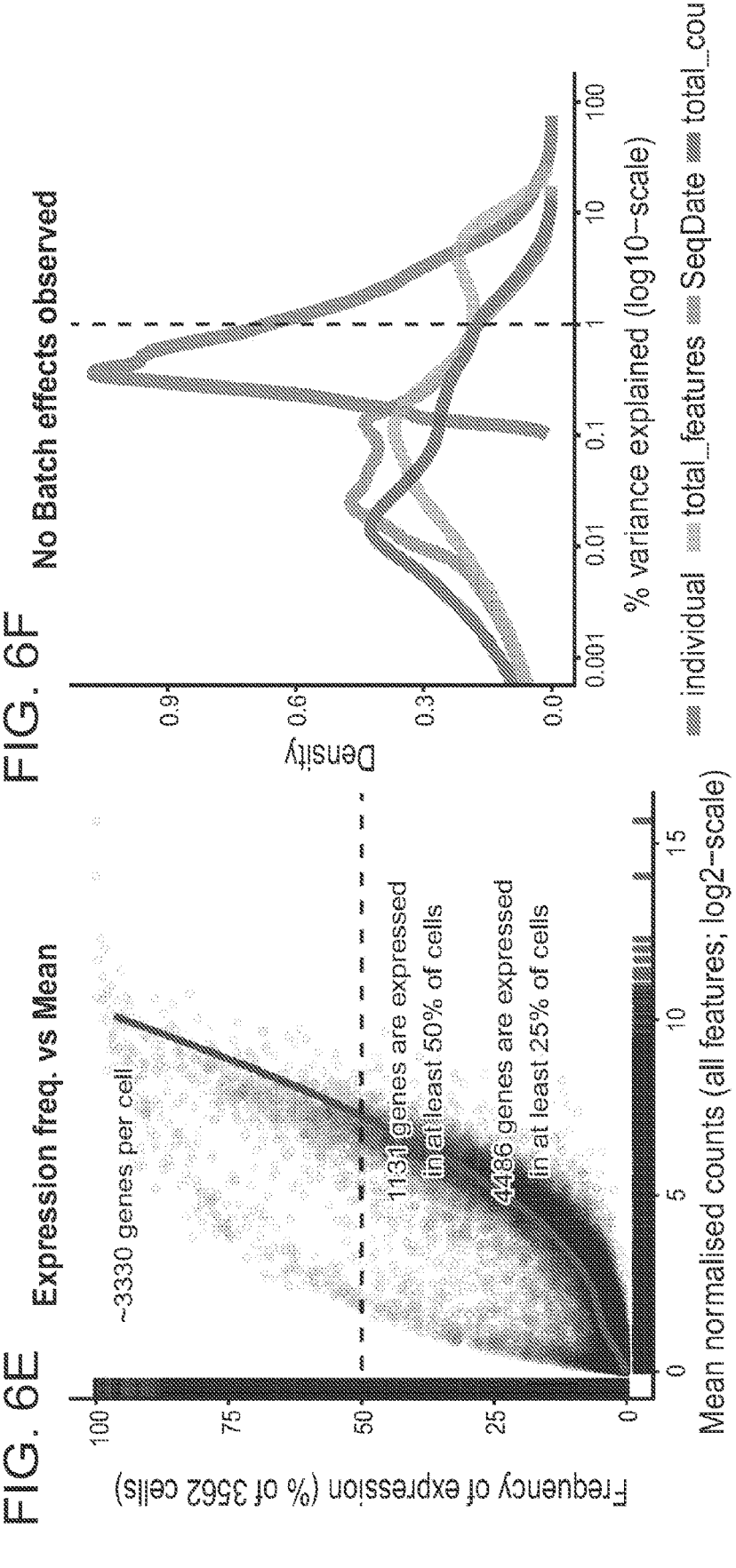
Figure 7A:
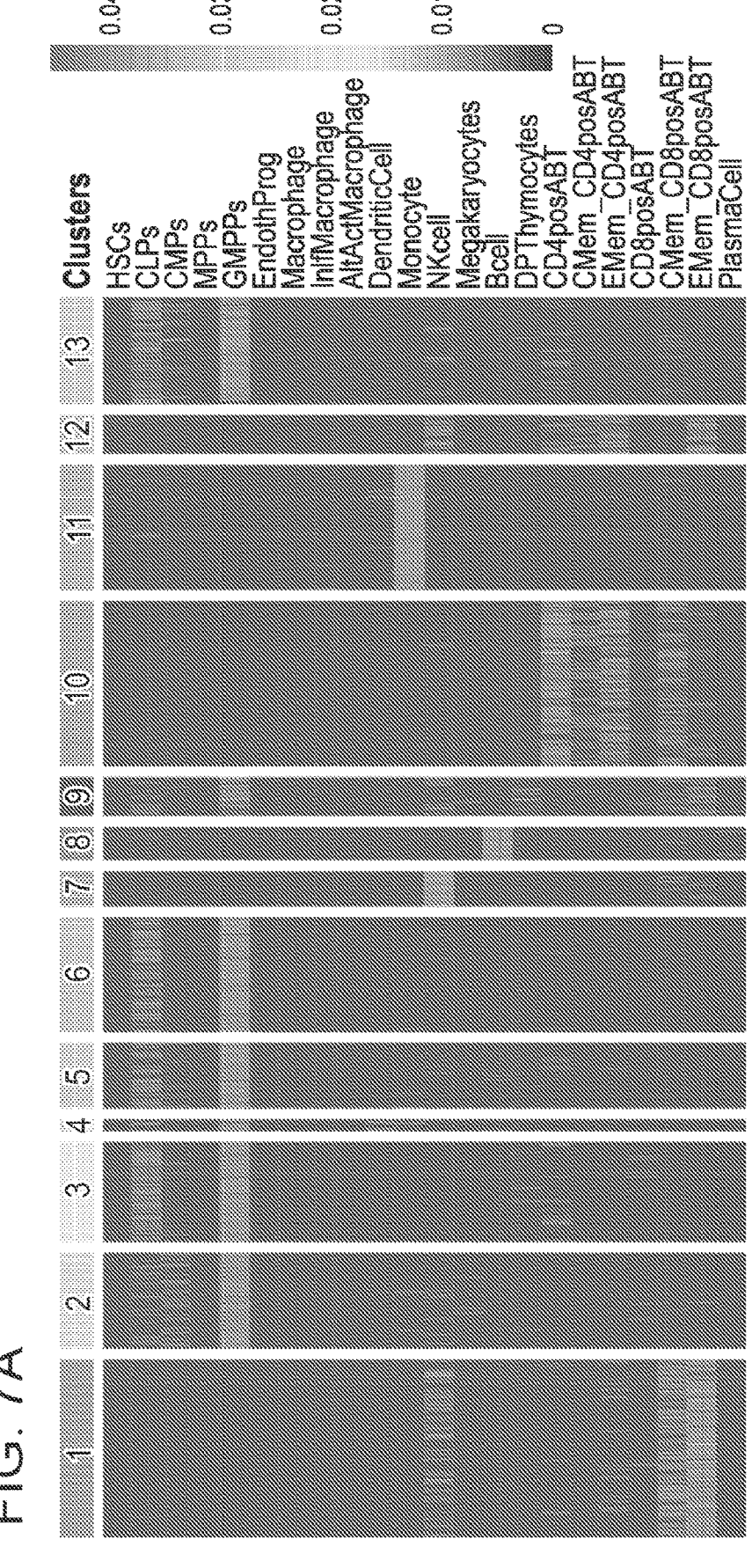
FIG. 7A-7F is a series of heatmaps confirming the identity of non-malignant immune cell clusters.
Figures 1, 7B:
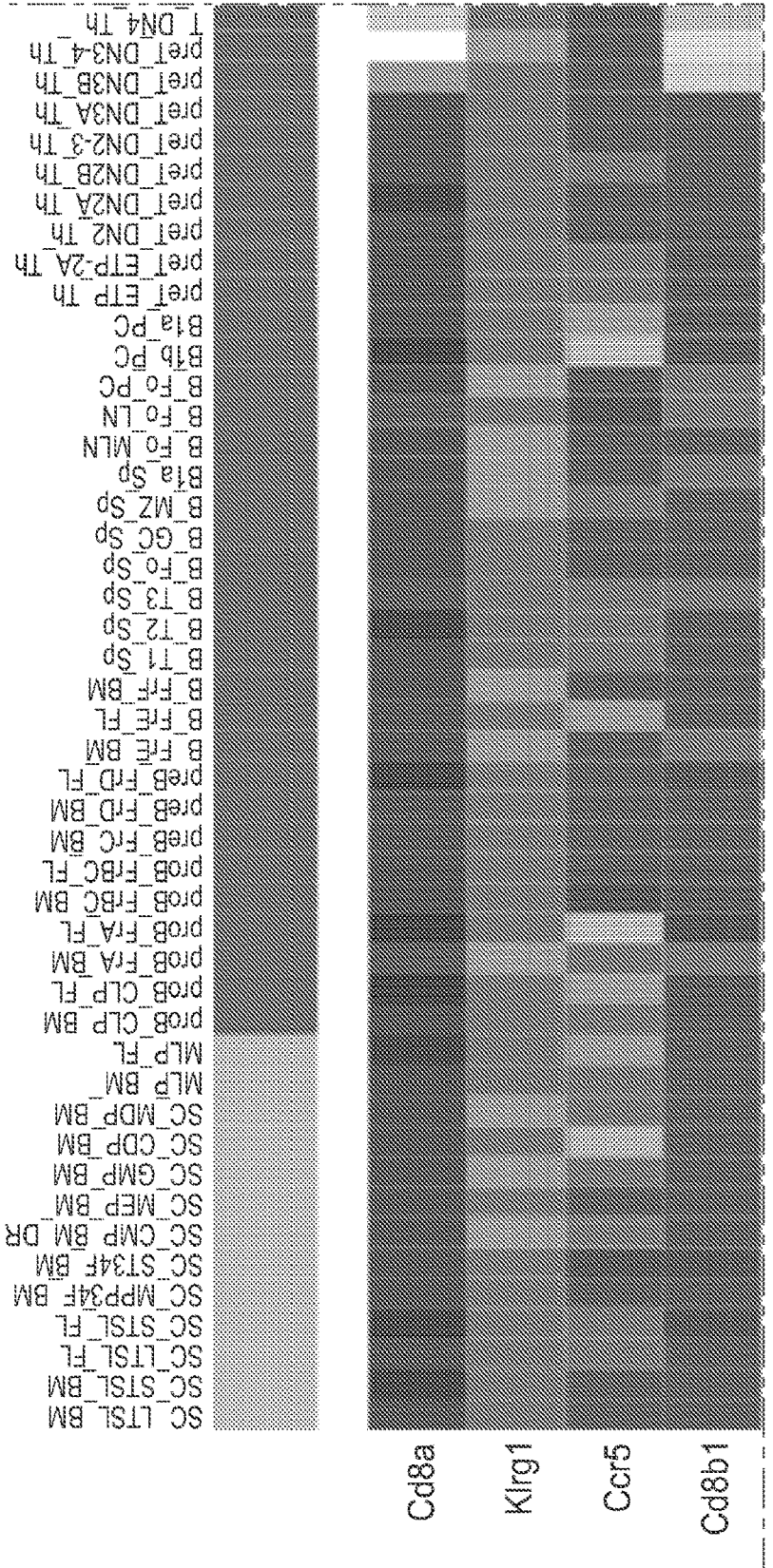
Figures 2, 7B:
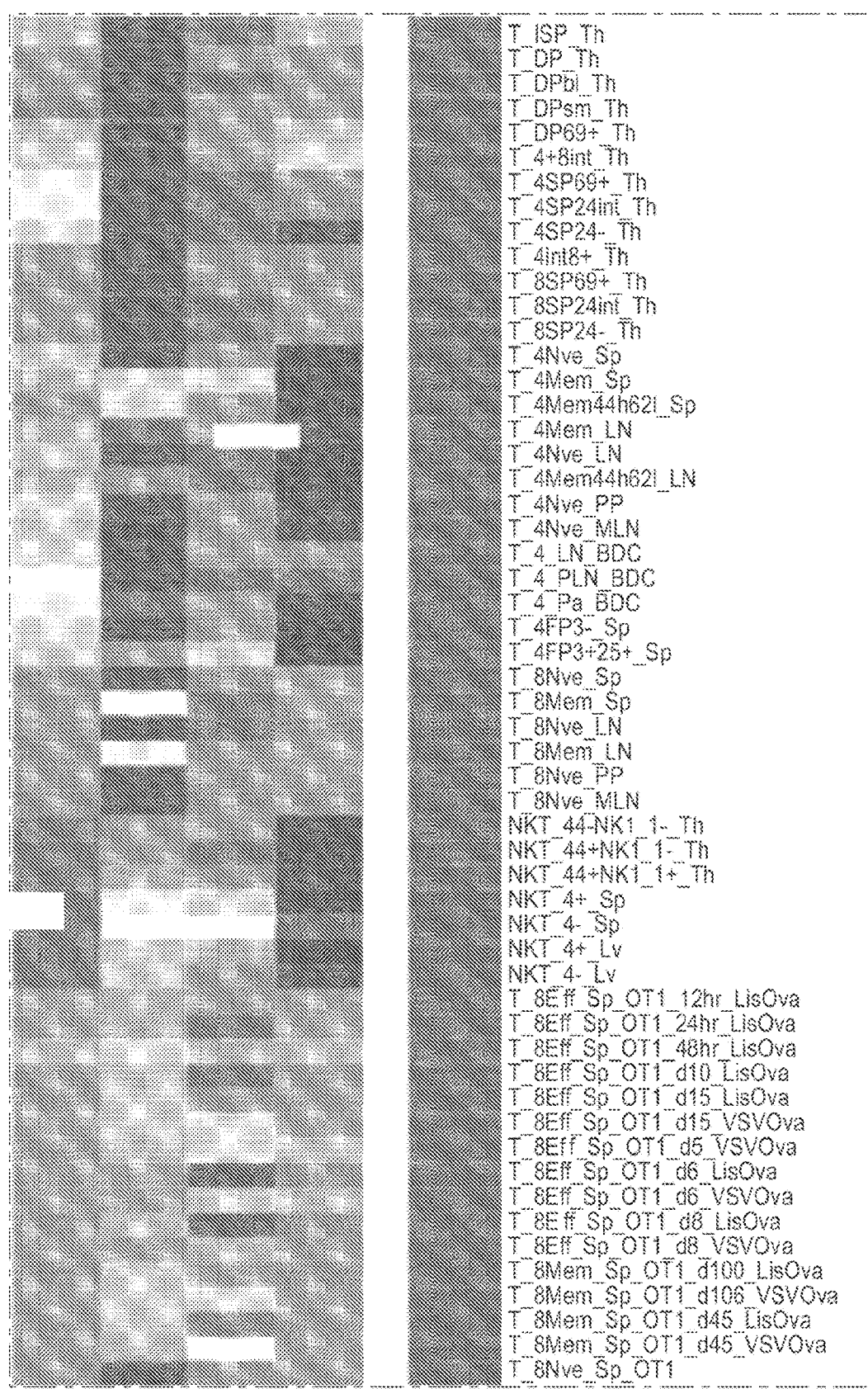
Figures 3, 7B:
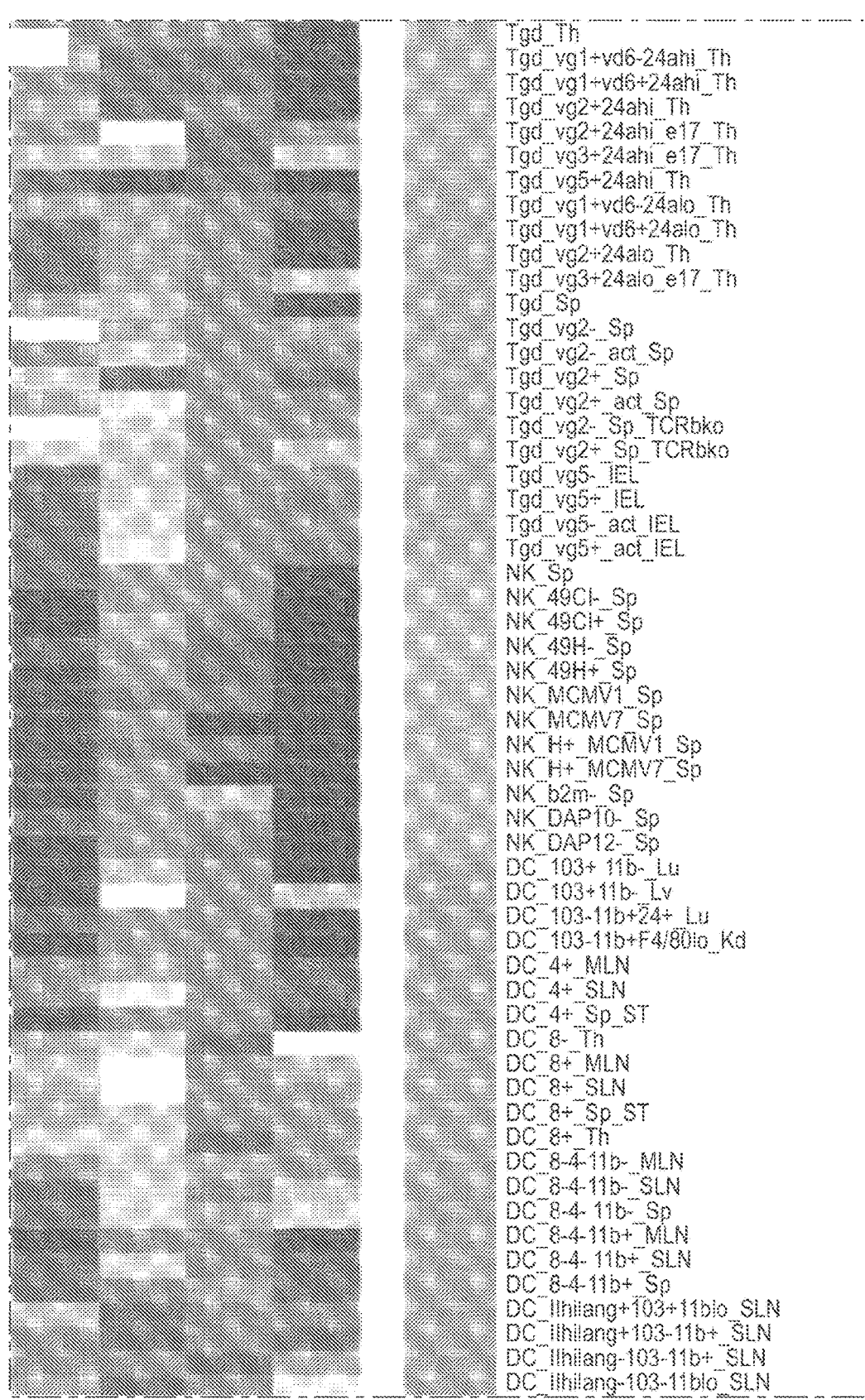
Figures 5, 7B:
Figures 6, 7B:
Figures 7, 7B:
Figures 7, 7B, 8:
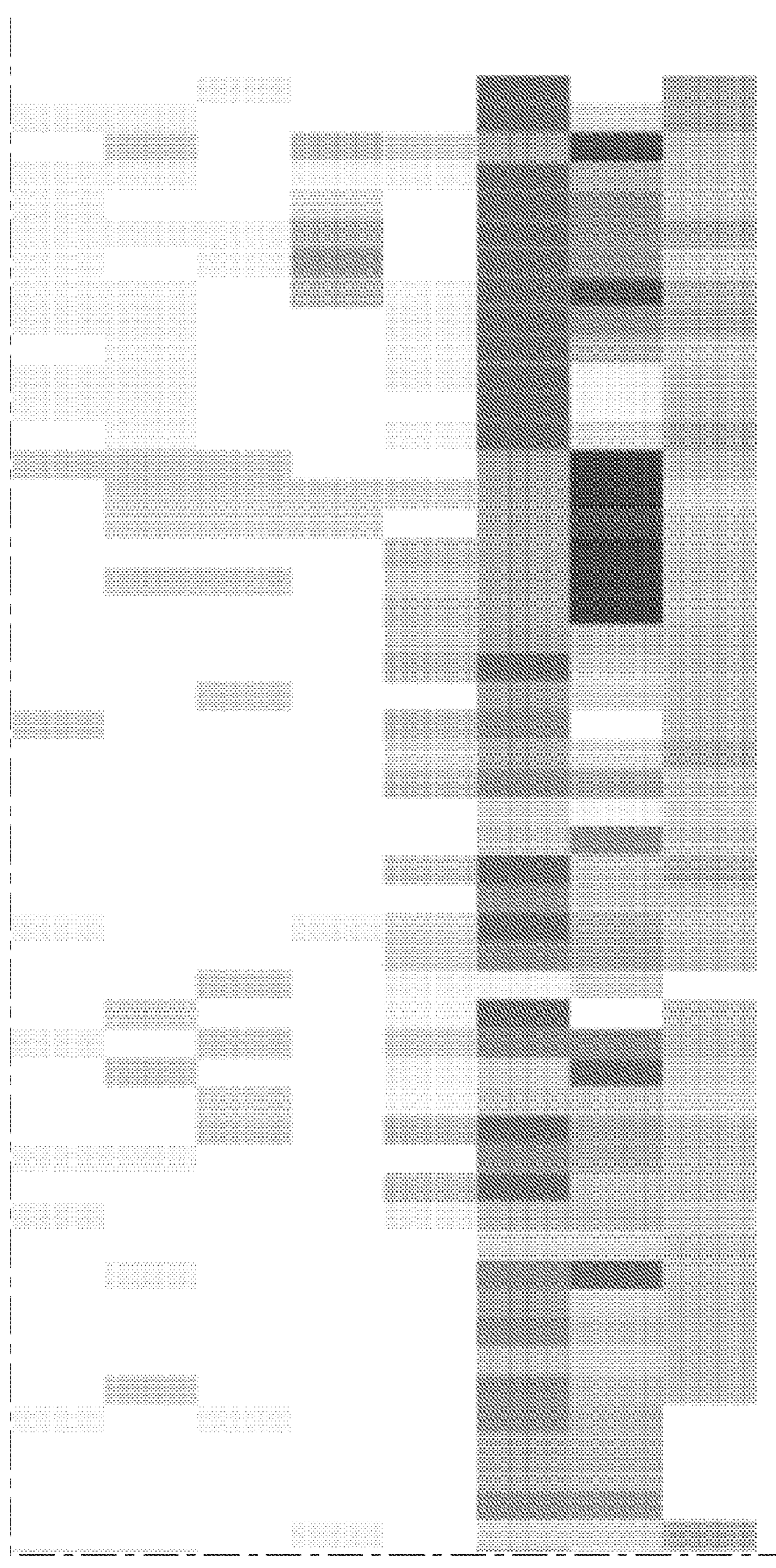
Figures 3, 7C:
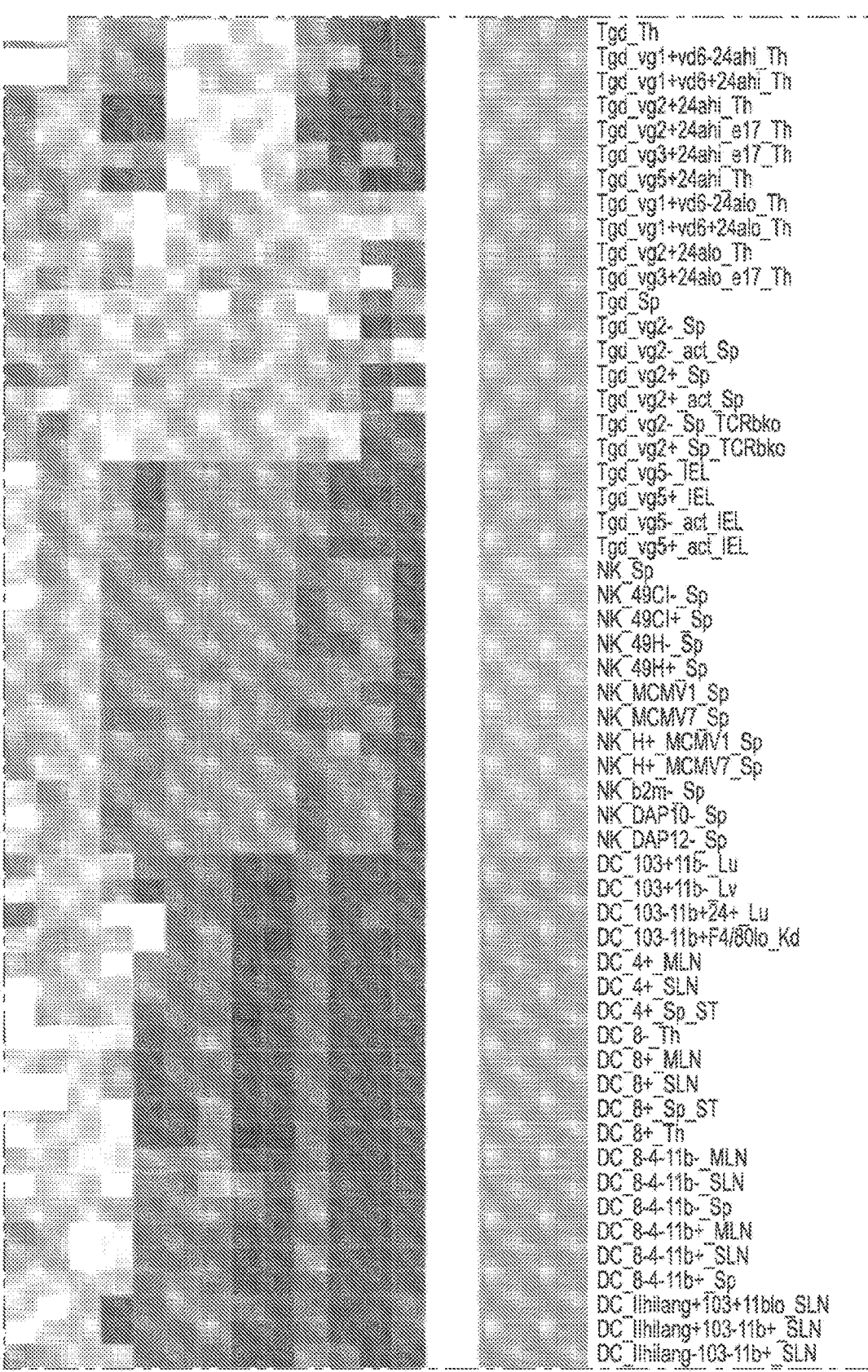
Figures 4, 7C:
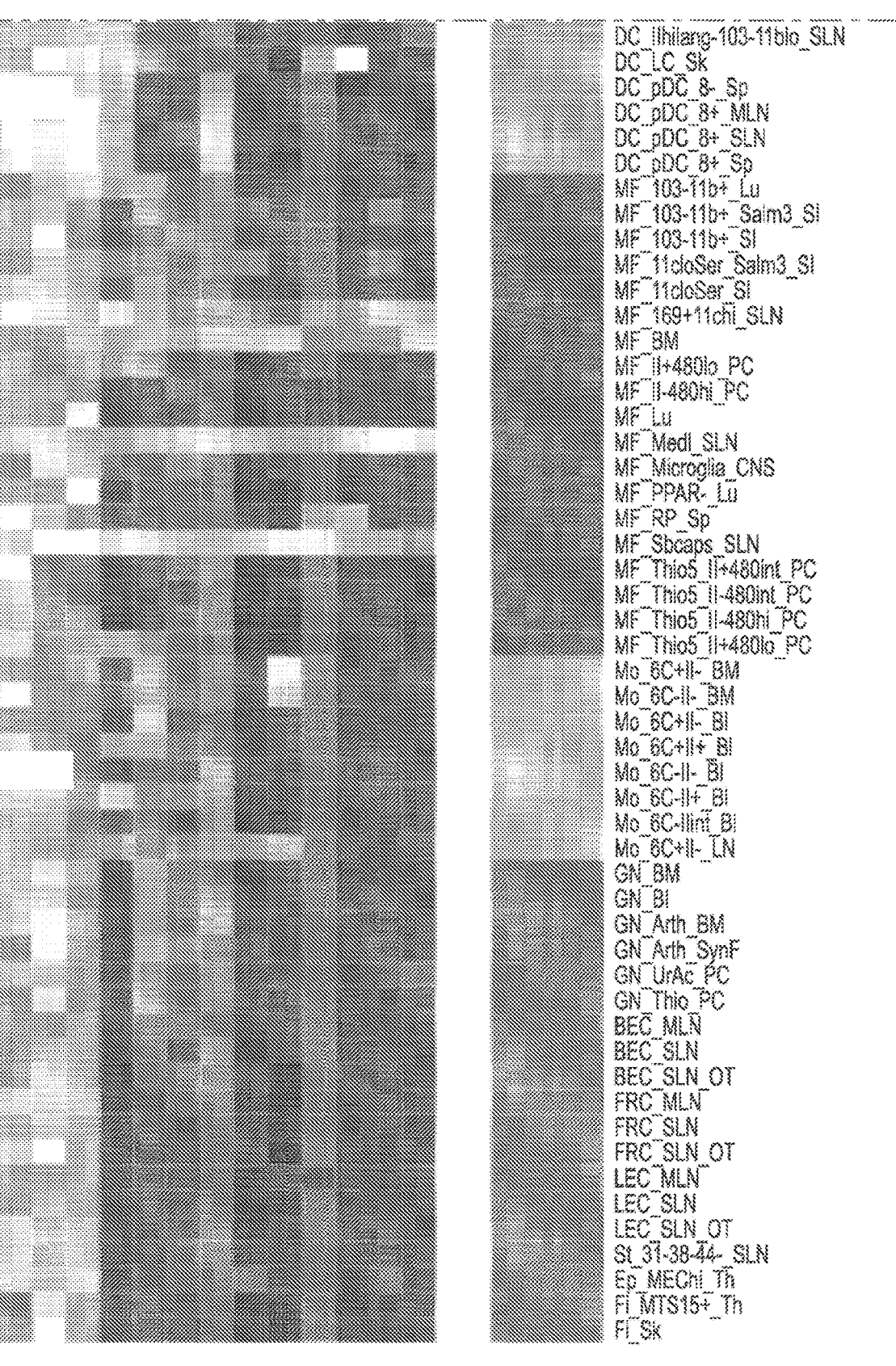
Figures 5, 7C:
Figures 6, 7C:
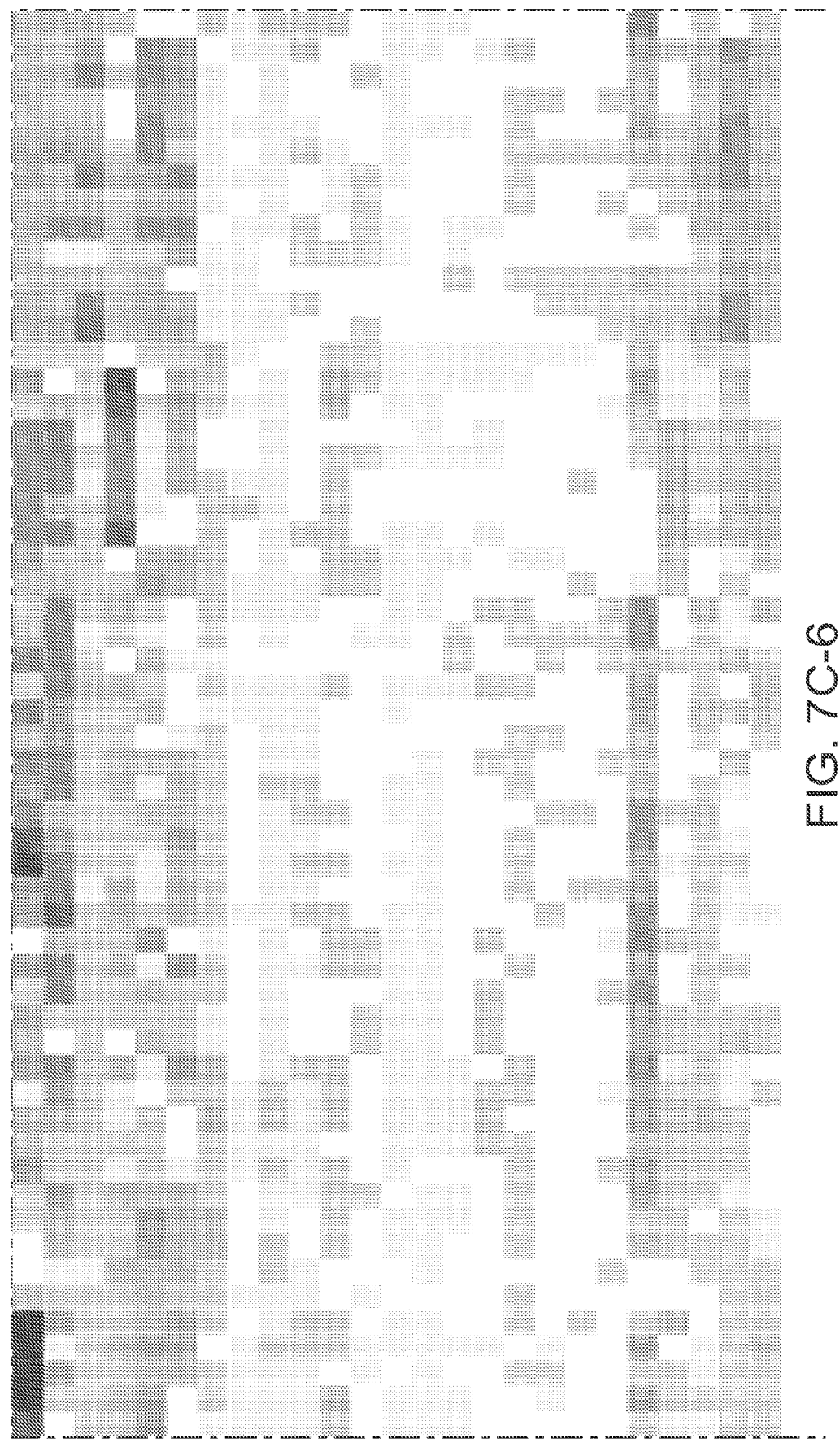
Figures 7, 7C:
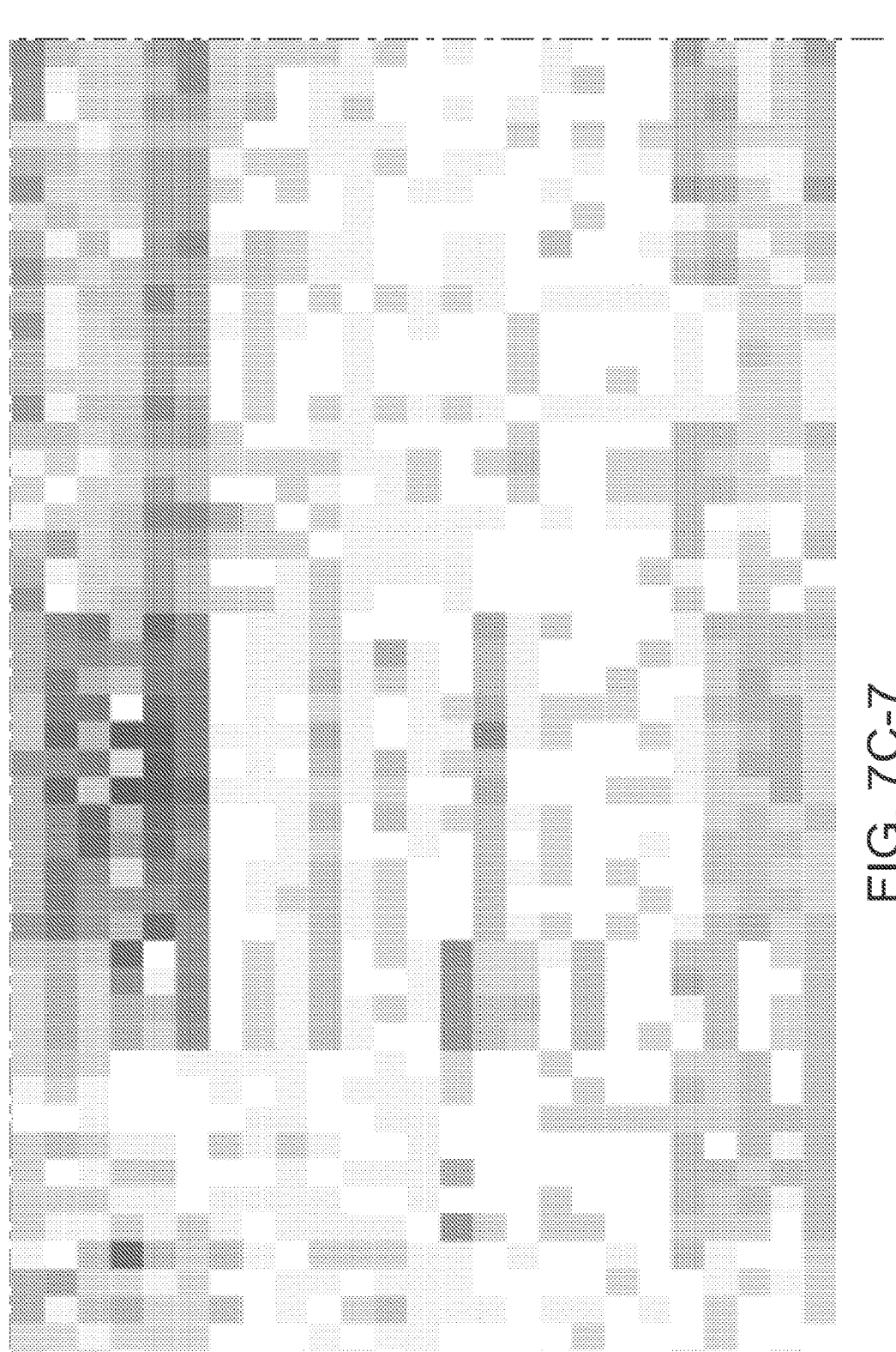
Figures 7, 7C, 8:
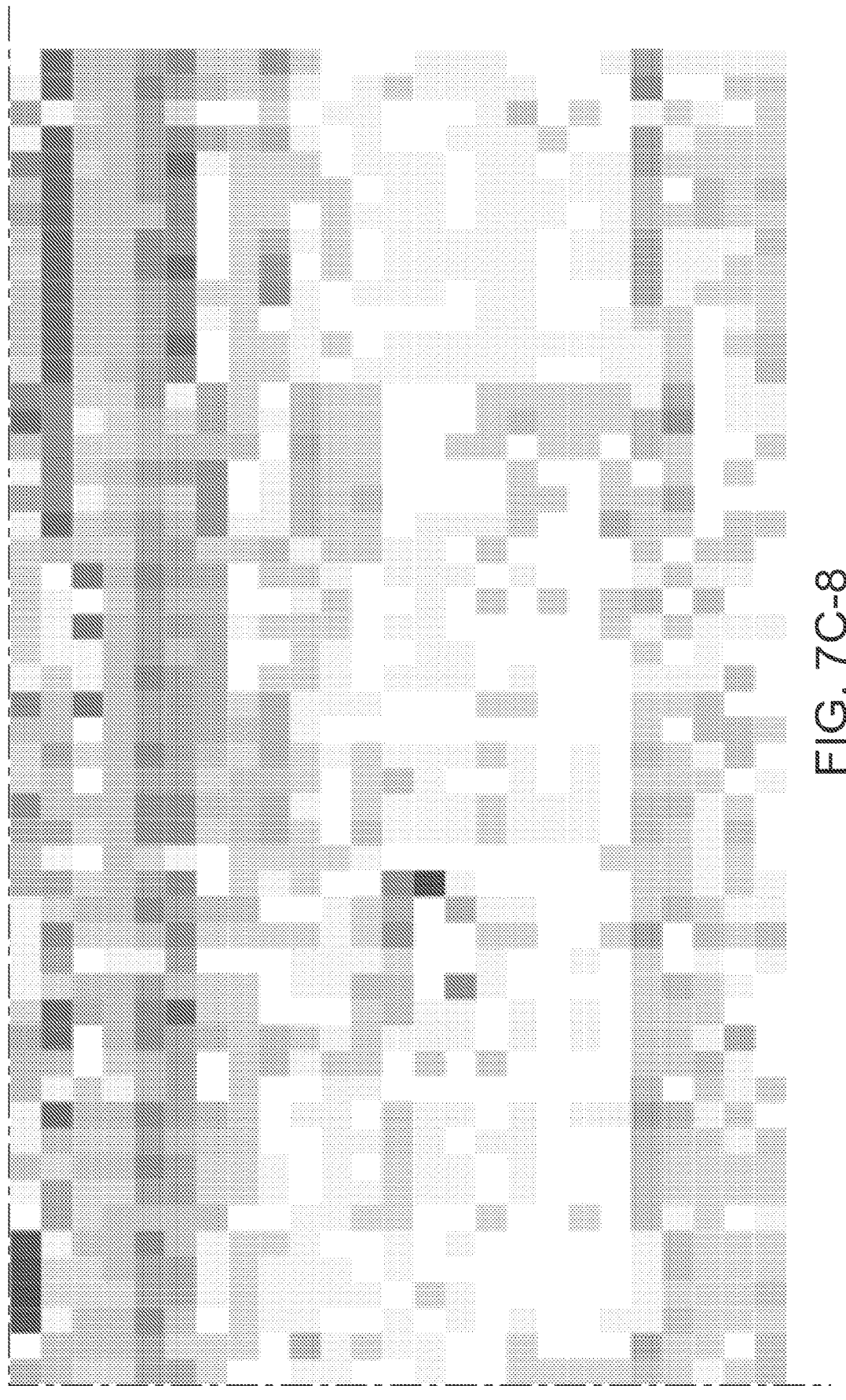
Figures 3, 7D:
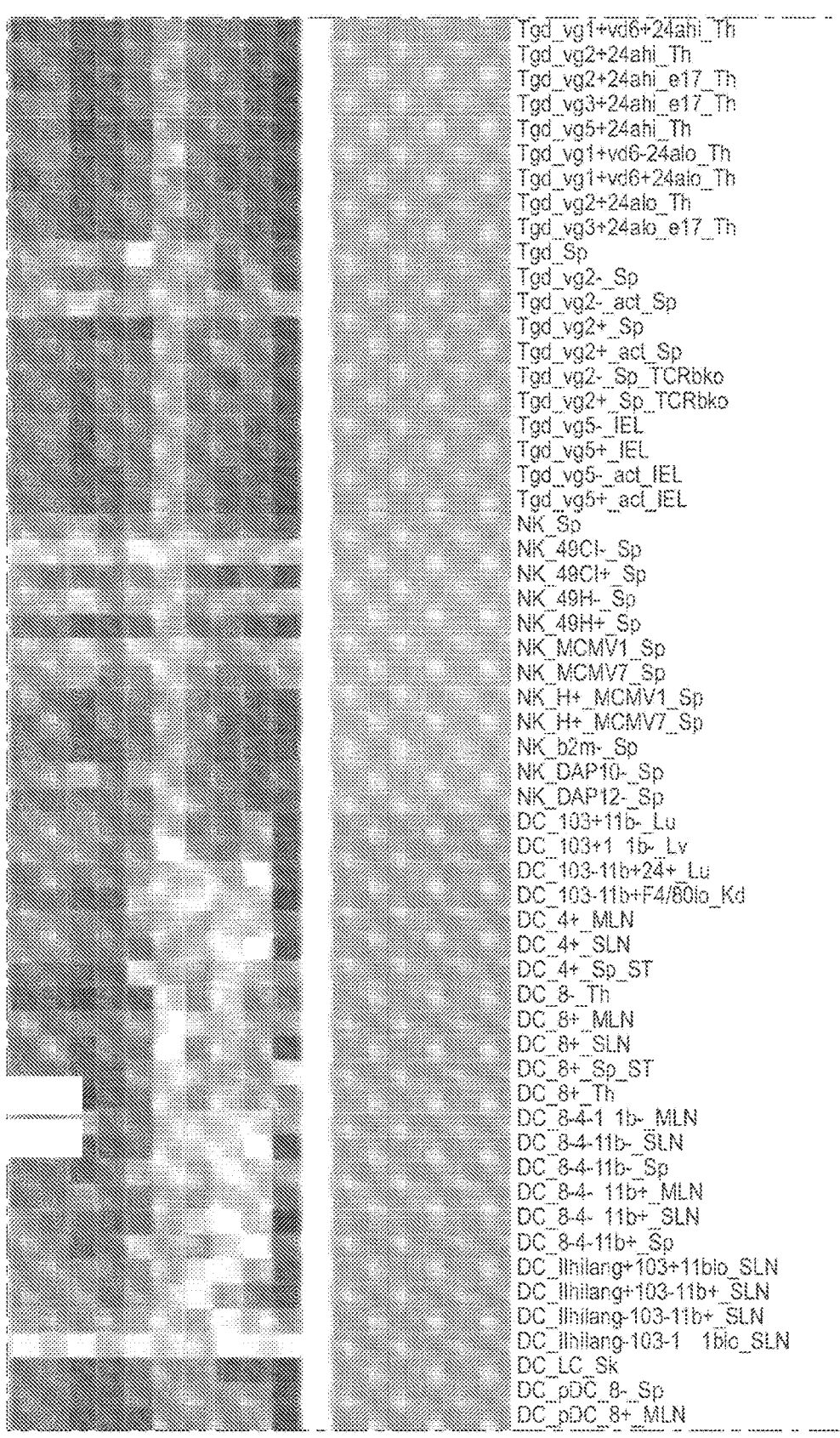
Figures 4, 7D:
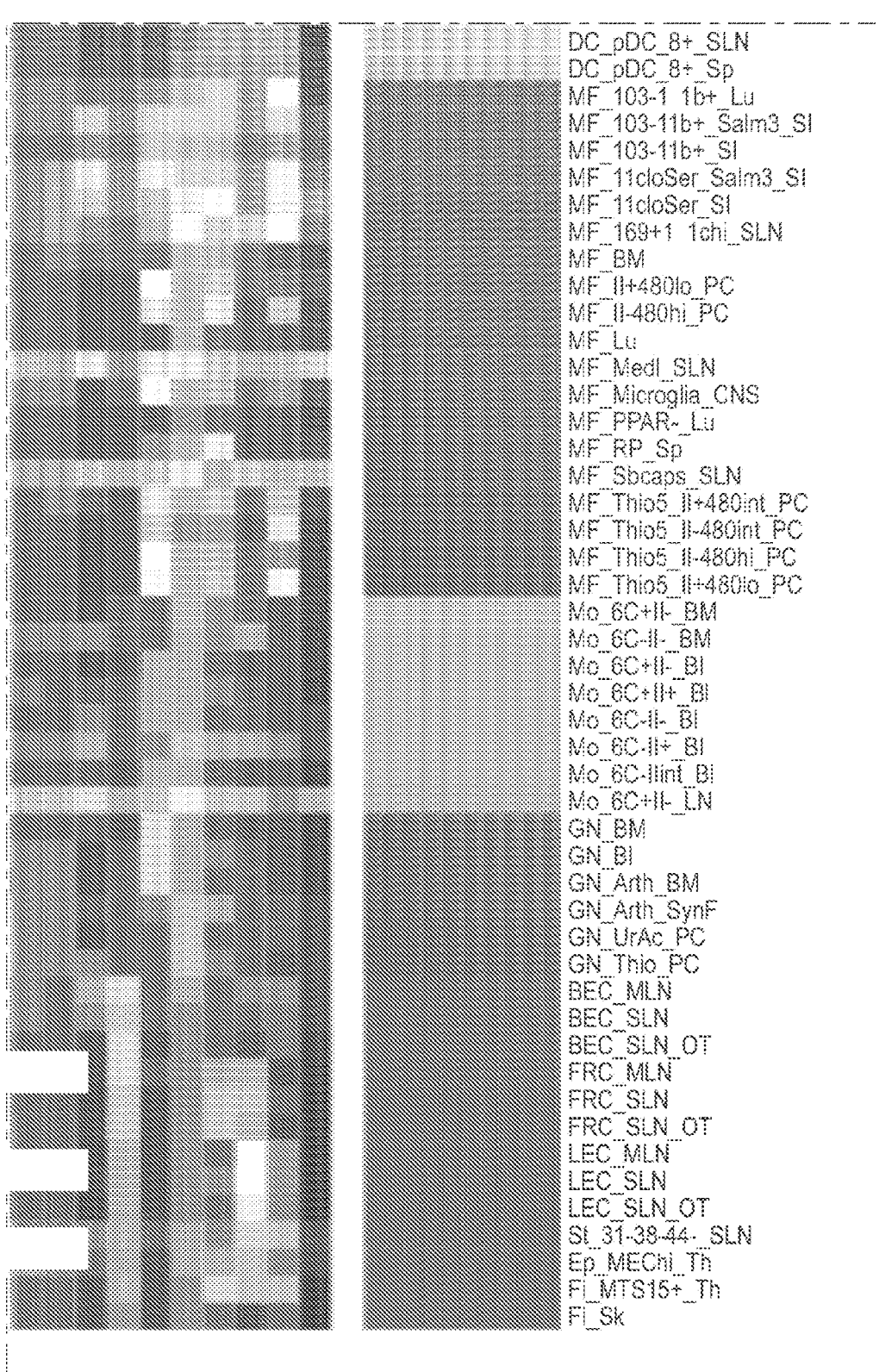
Figures 5, 7D:
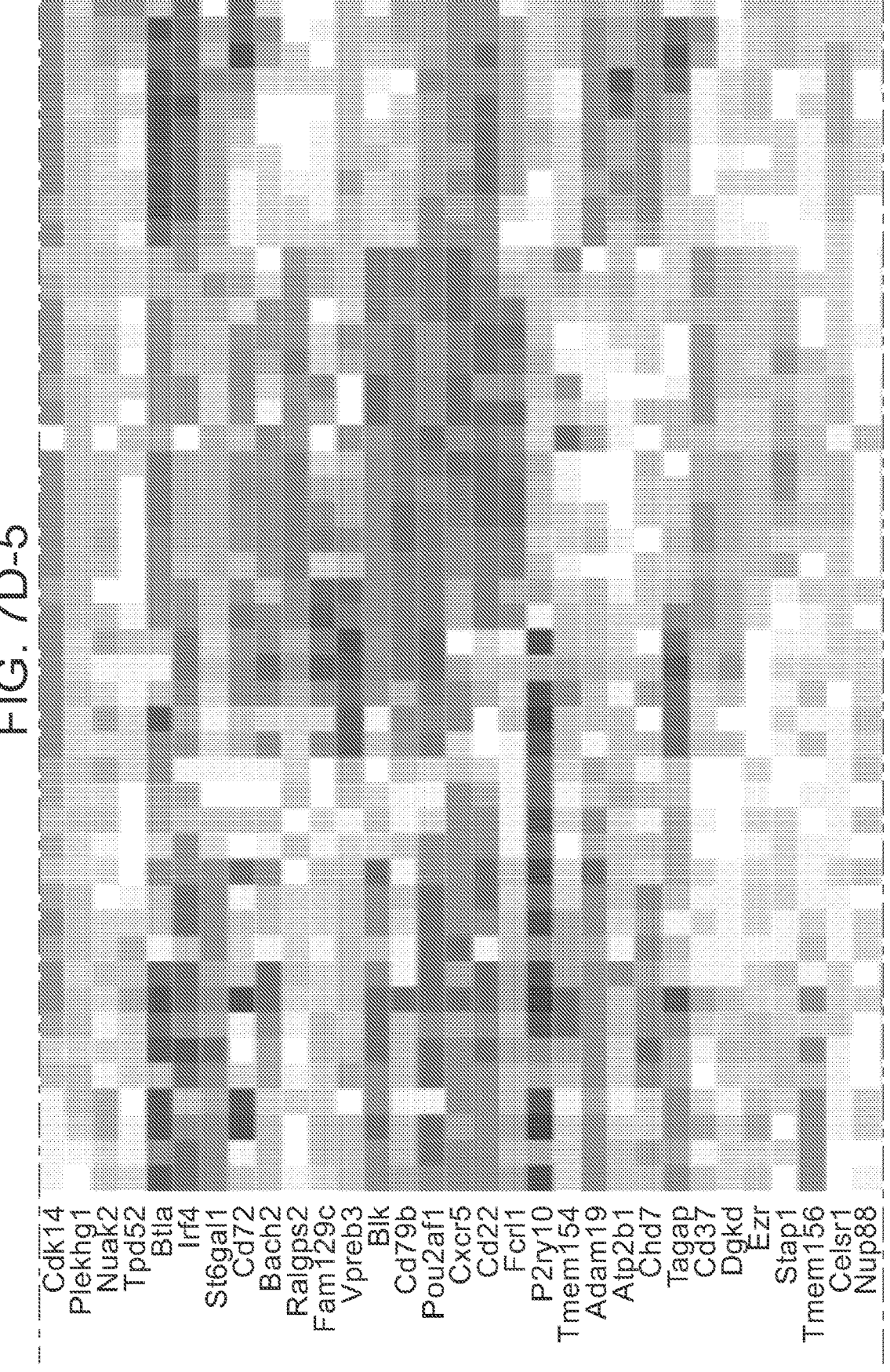
Figures 6, 7D:
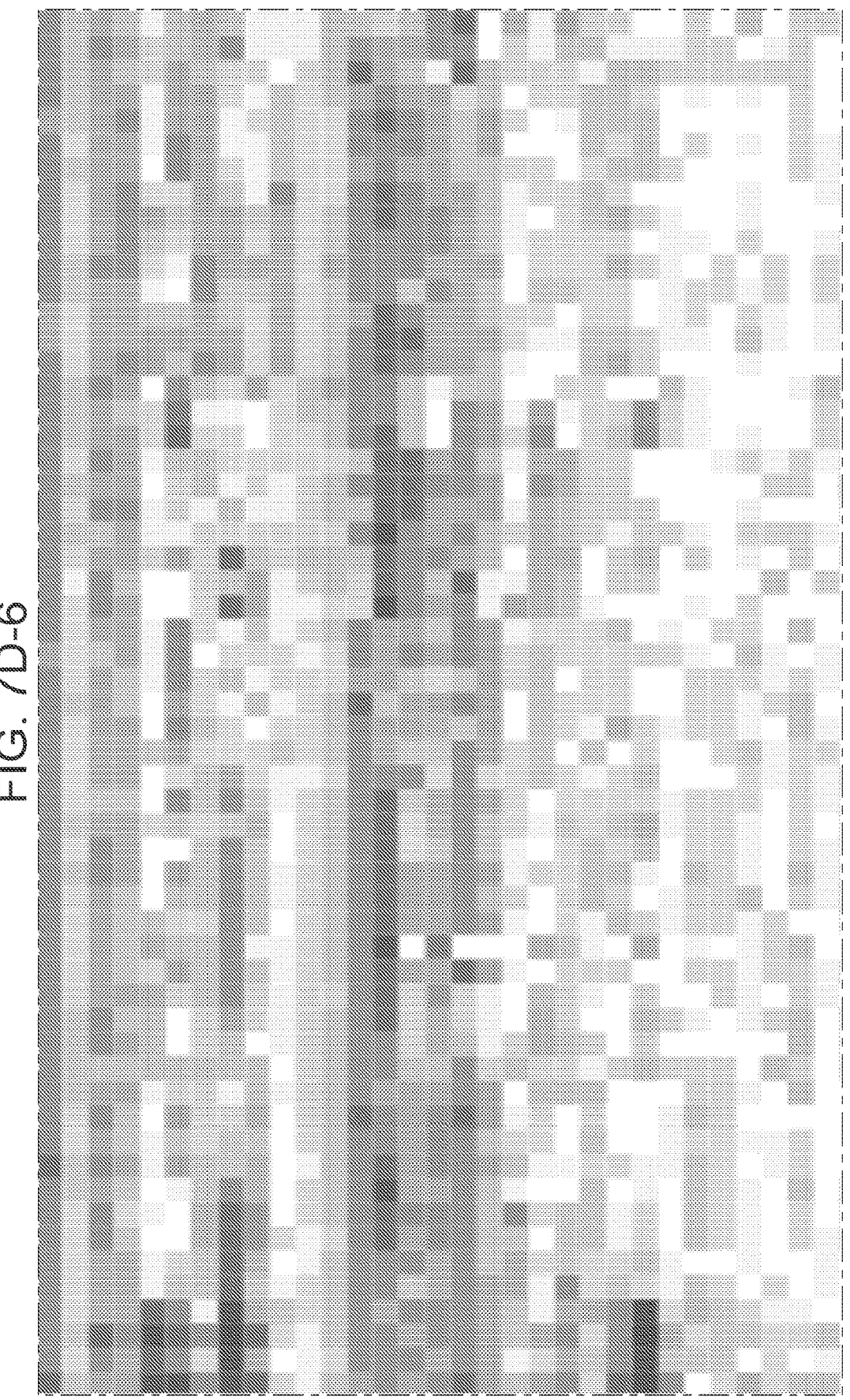
Figures 7, 7D:
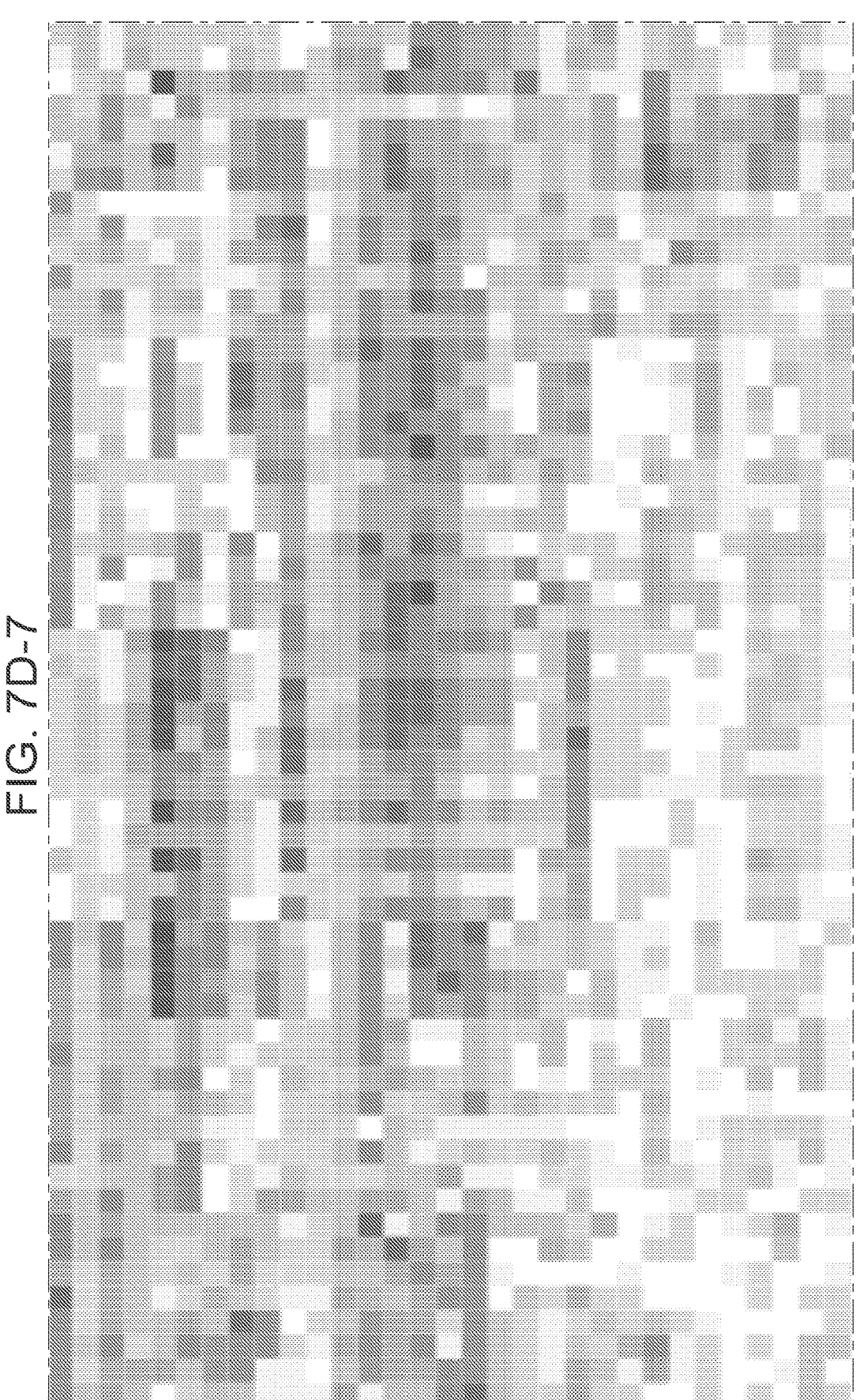
Figures 7, 7D, 8:
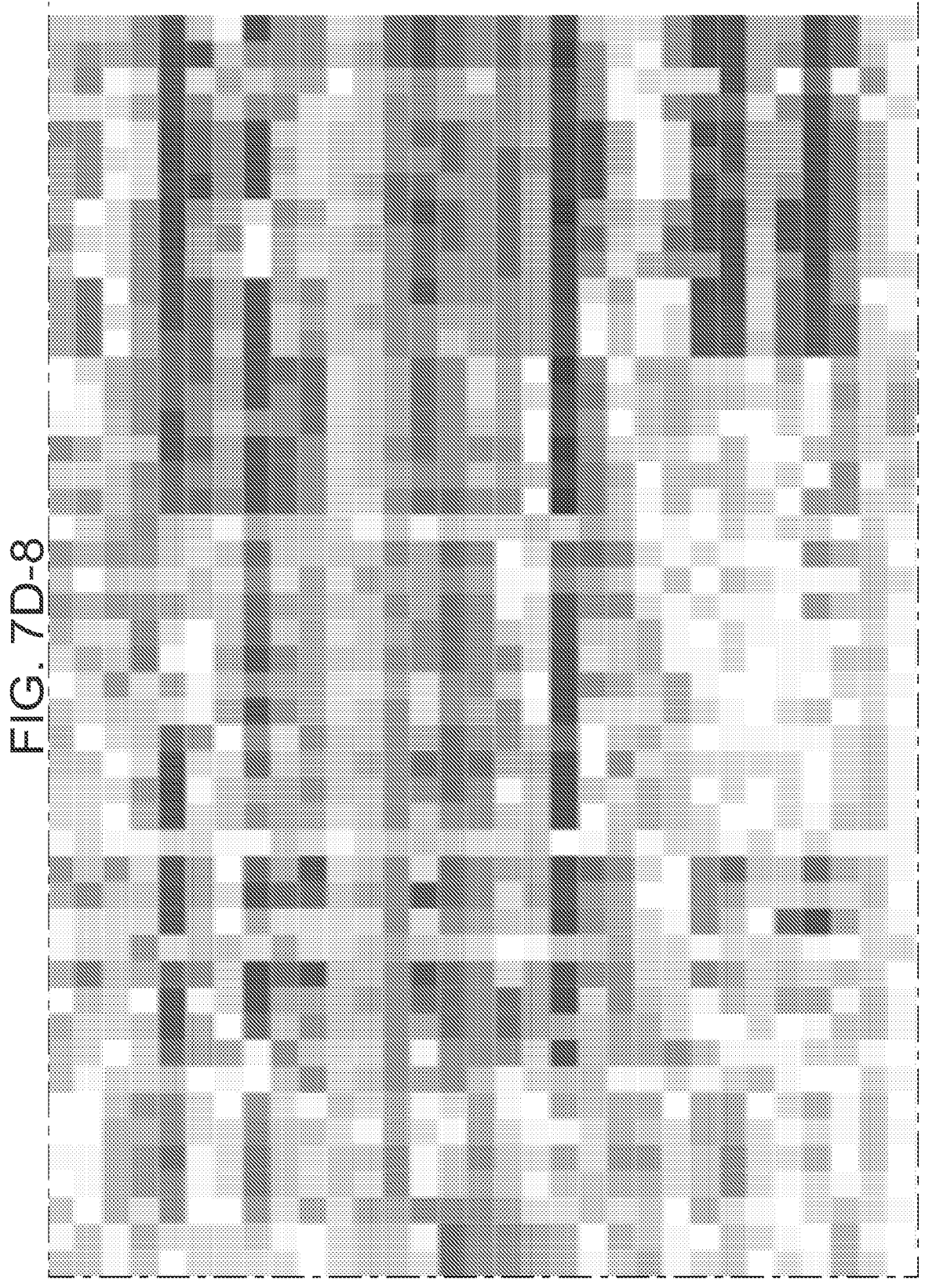
Figures 7, 7D, 8, 9:
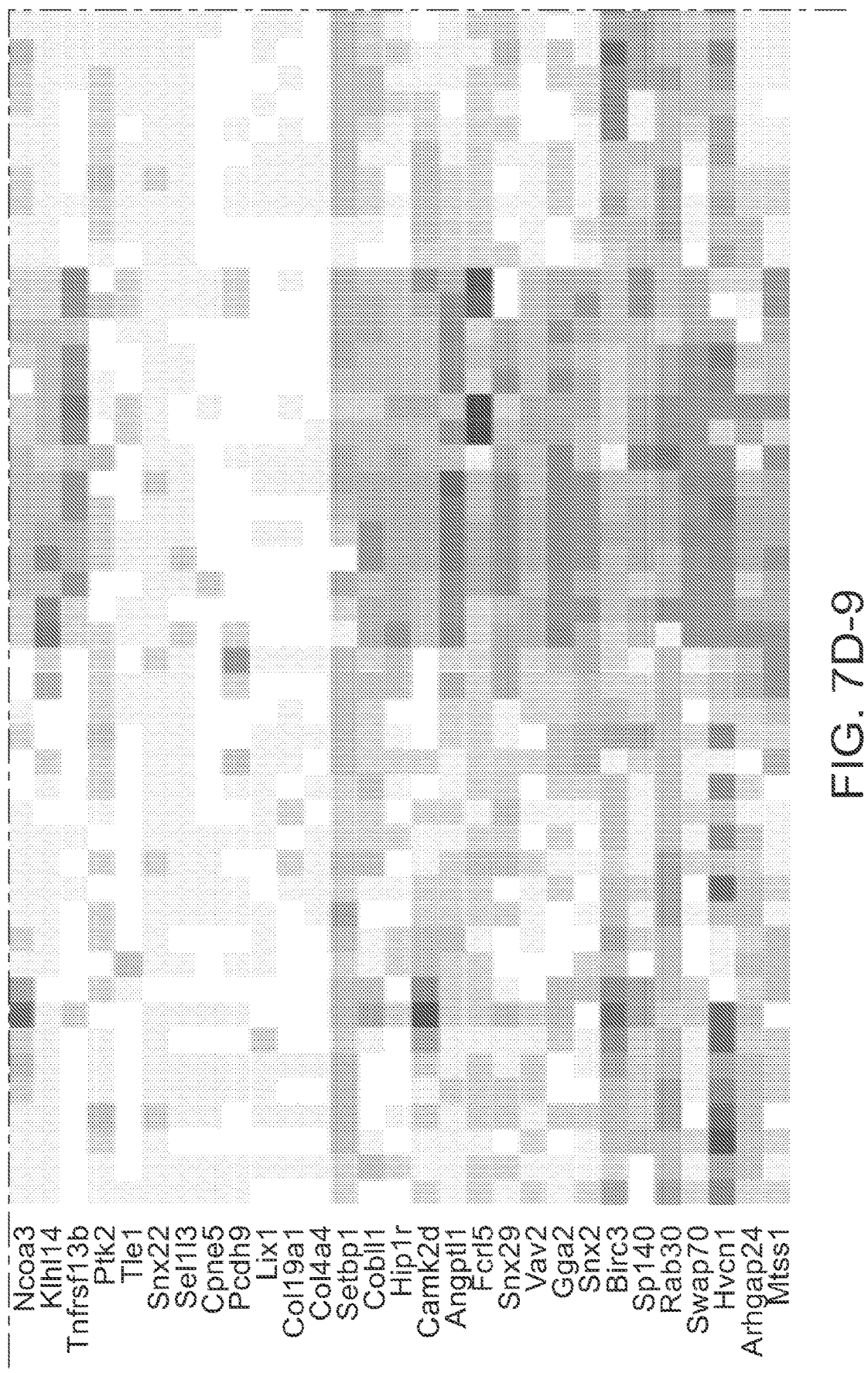
Figures 7, 7D, 8, 9, 10:
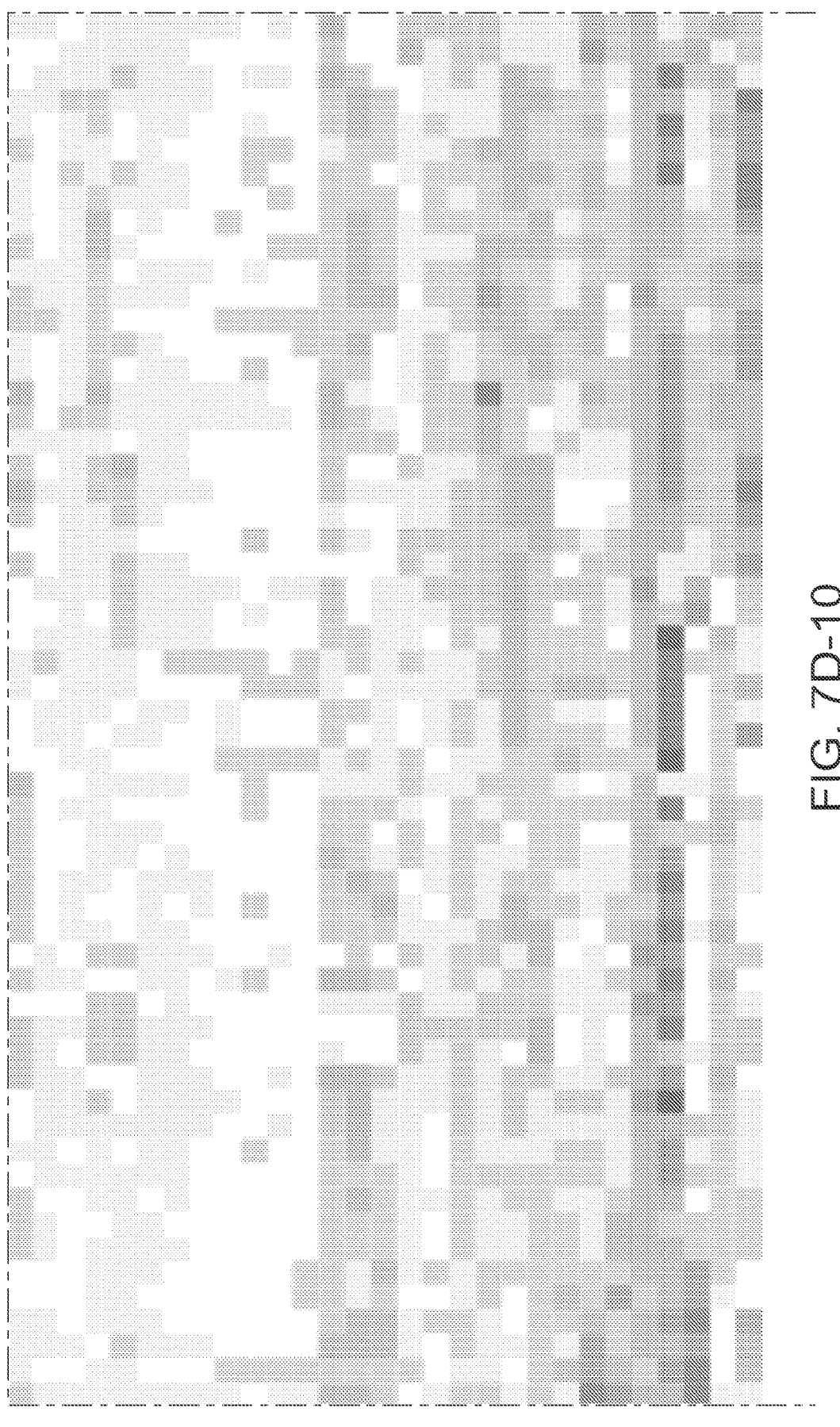
Figures 7, 7D, 8, 9, 10, 11:
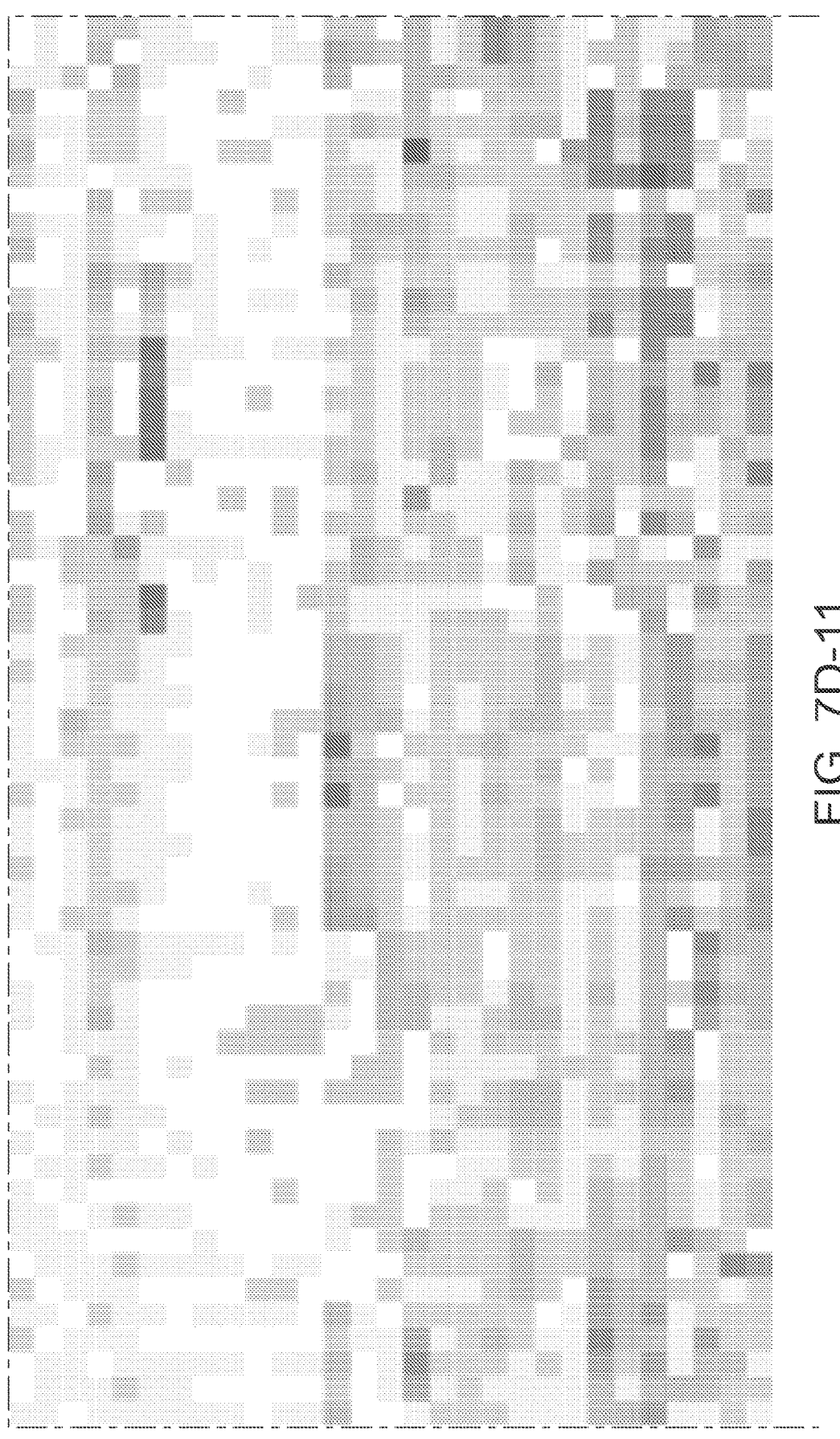
FIG. 11 is a plot showing T-ALL specific transcription factors. Specifically, shown is a t-SNE plot depicting the expression of various transcription factors known to be generally deregulated in T-ALL. All the five tumors show expression of LMO2 and LYL1 transcription factors. A subset of tumors also expresses TAL1 and HOX transcription factors.
Figures 7, 7D, 8, 9, 10, 11, 12:
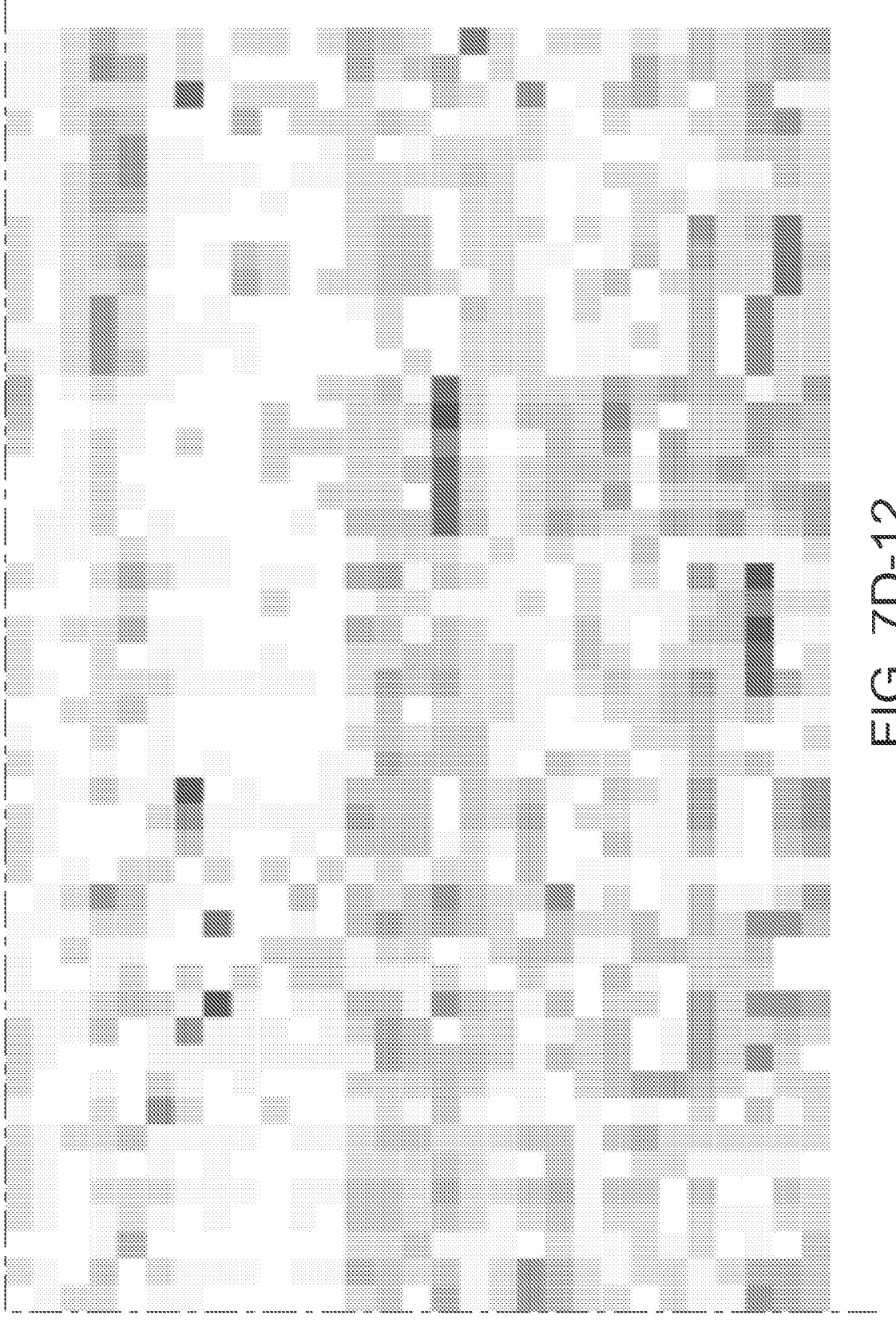
Figures 1, 7E:
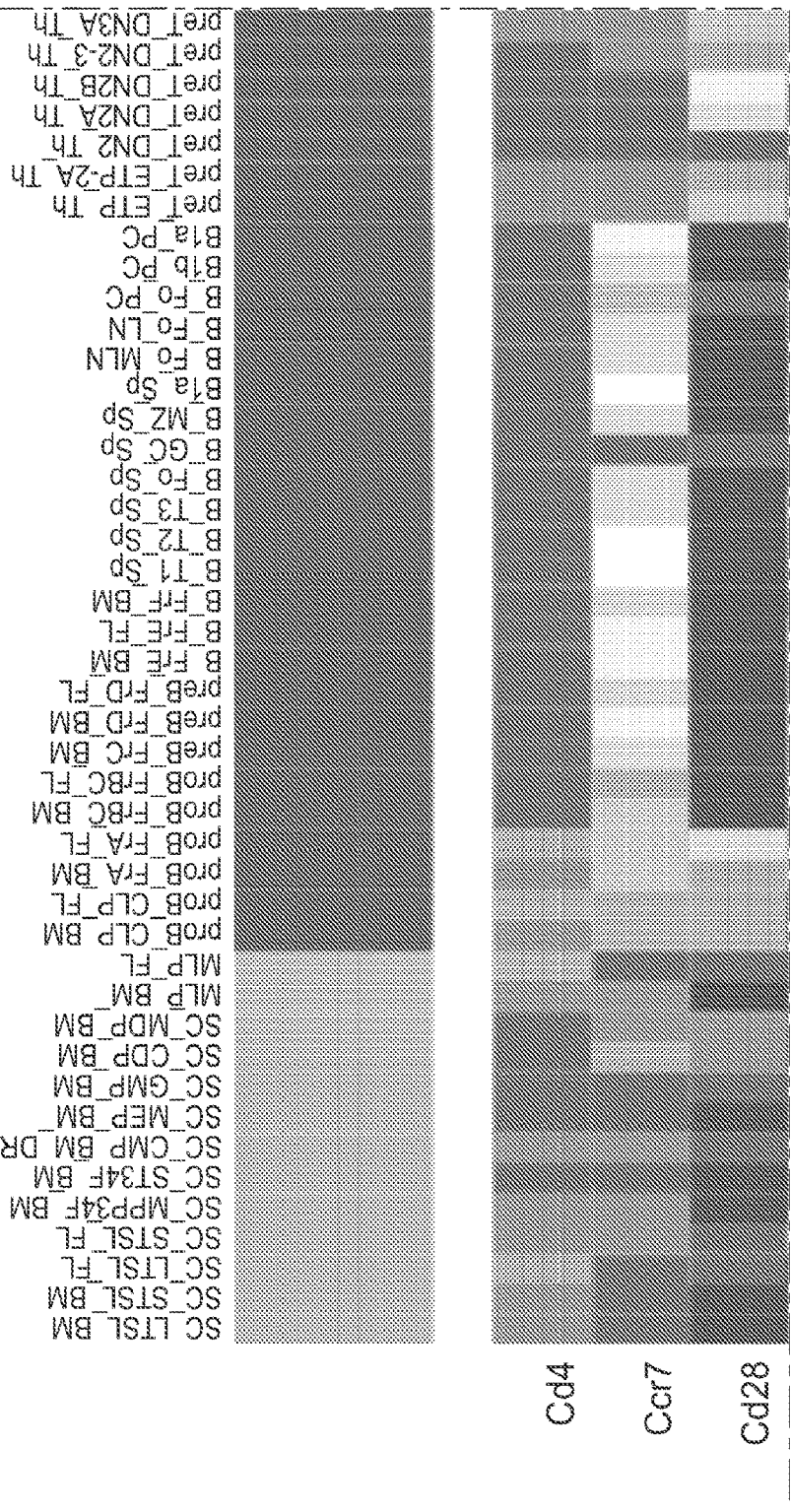
Figures 5, 7E:
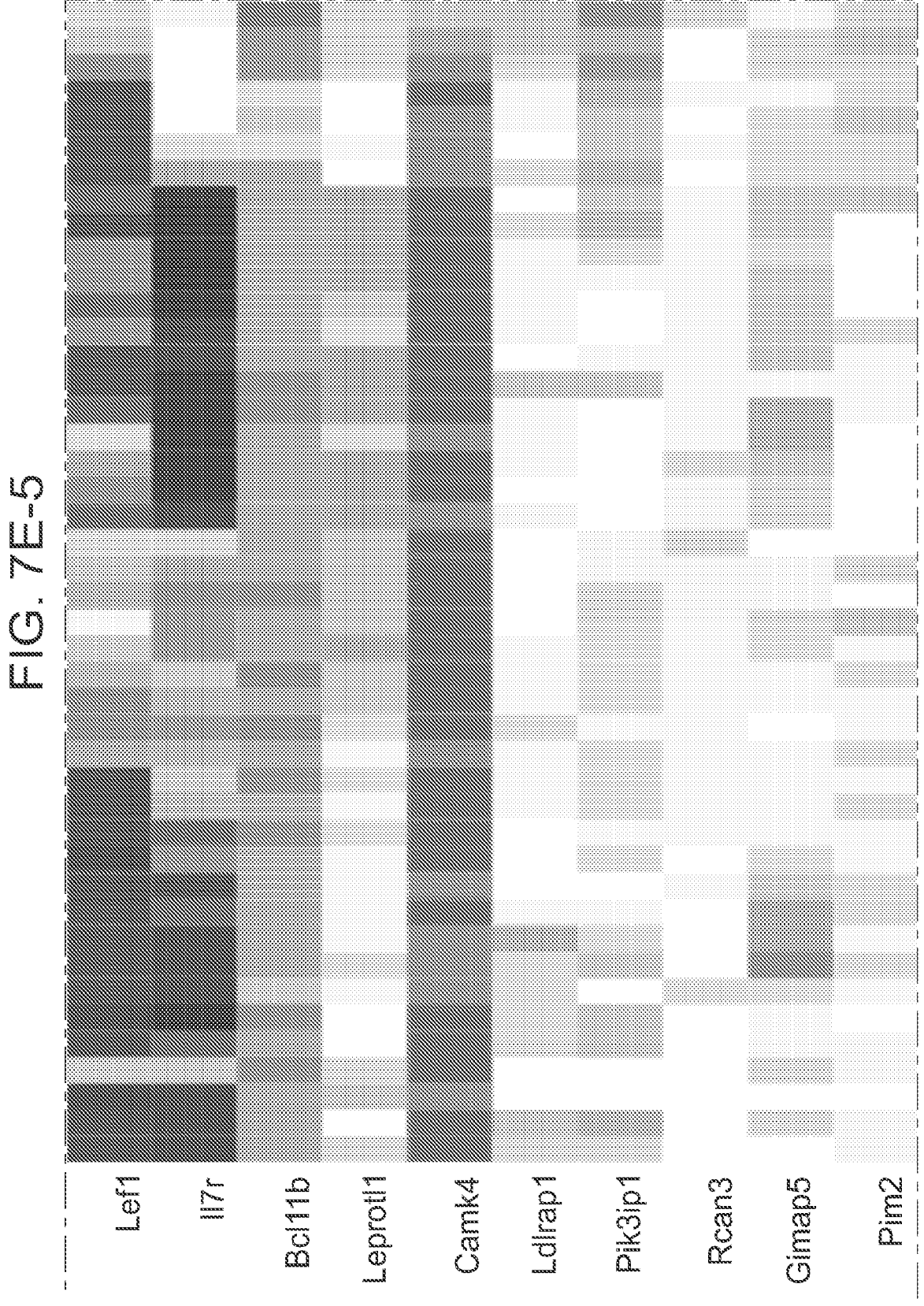
Figures 6, 7E:
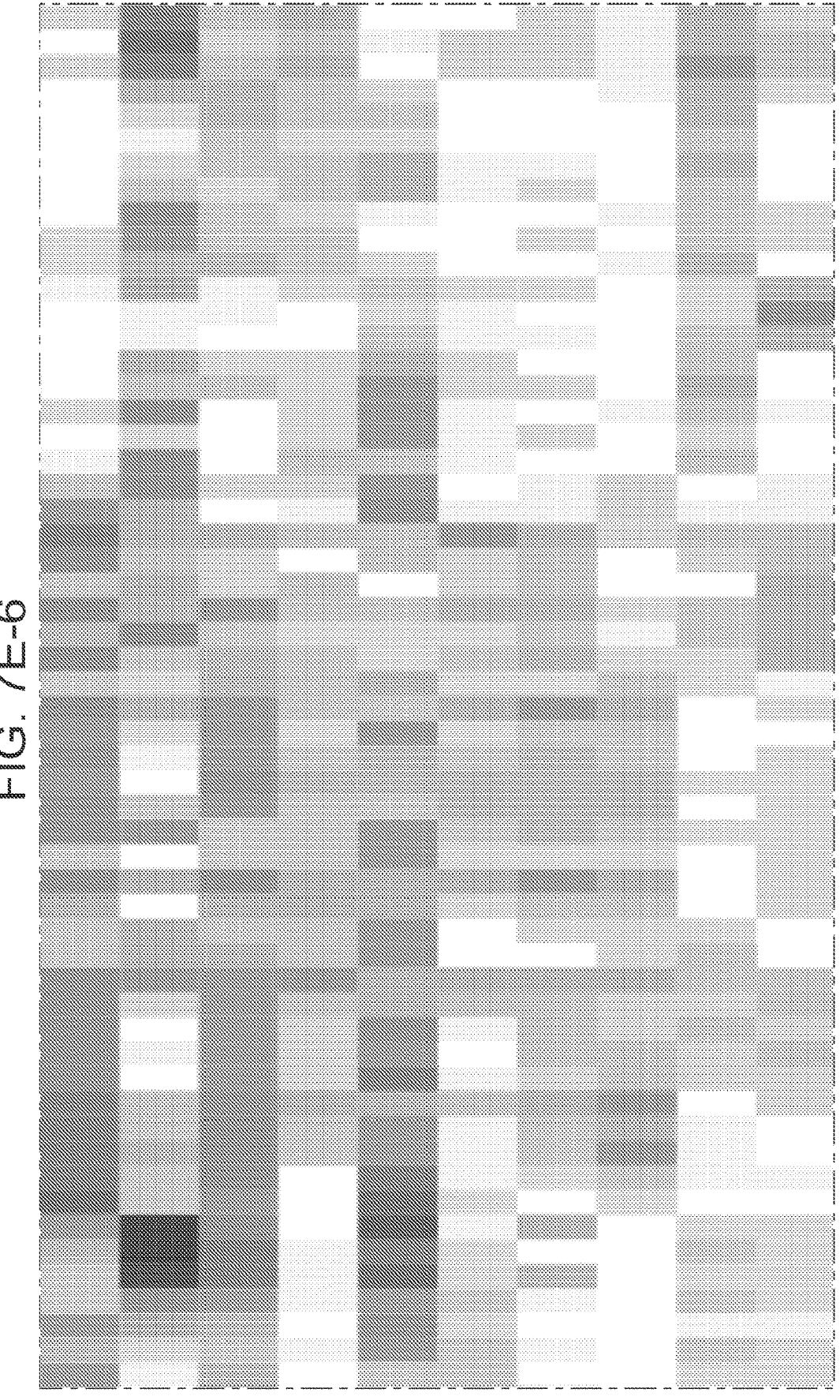
Figures 7, 7E:
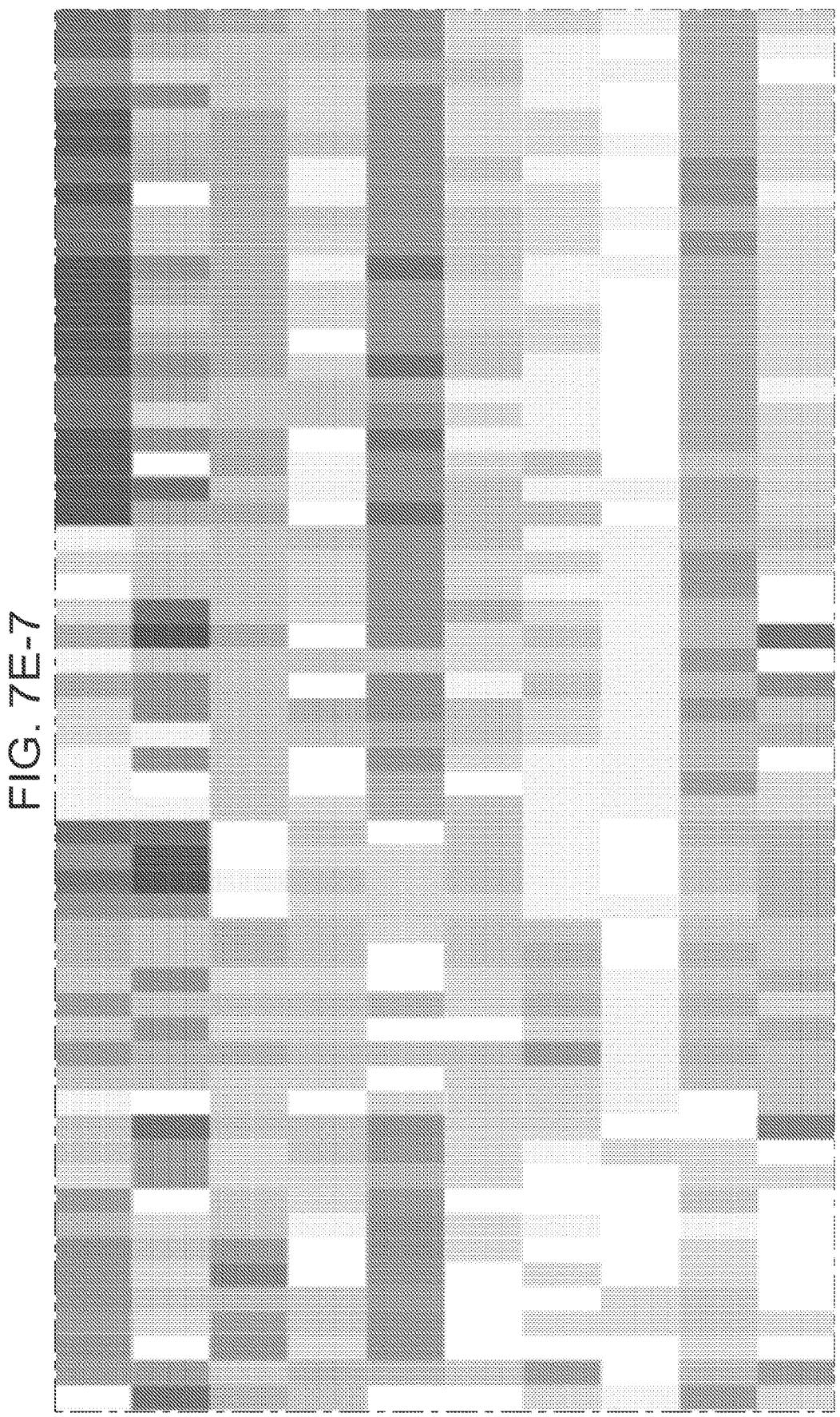
Figures 7, 7E, 8:
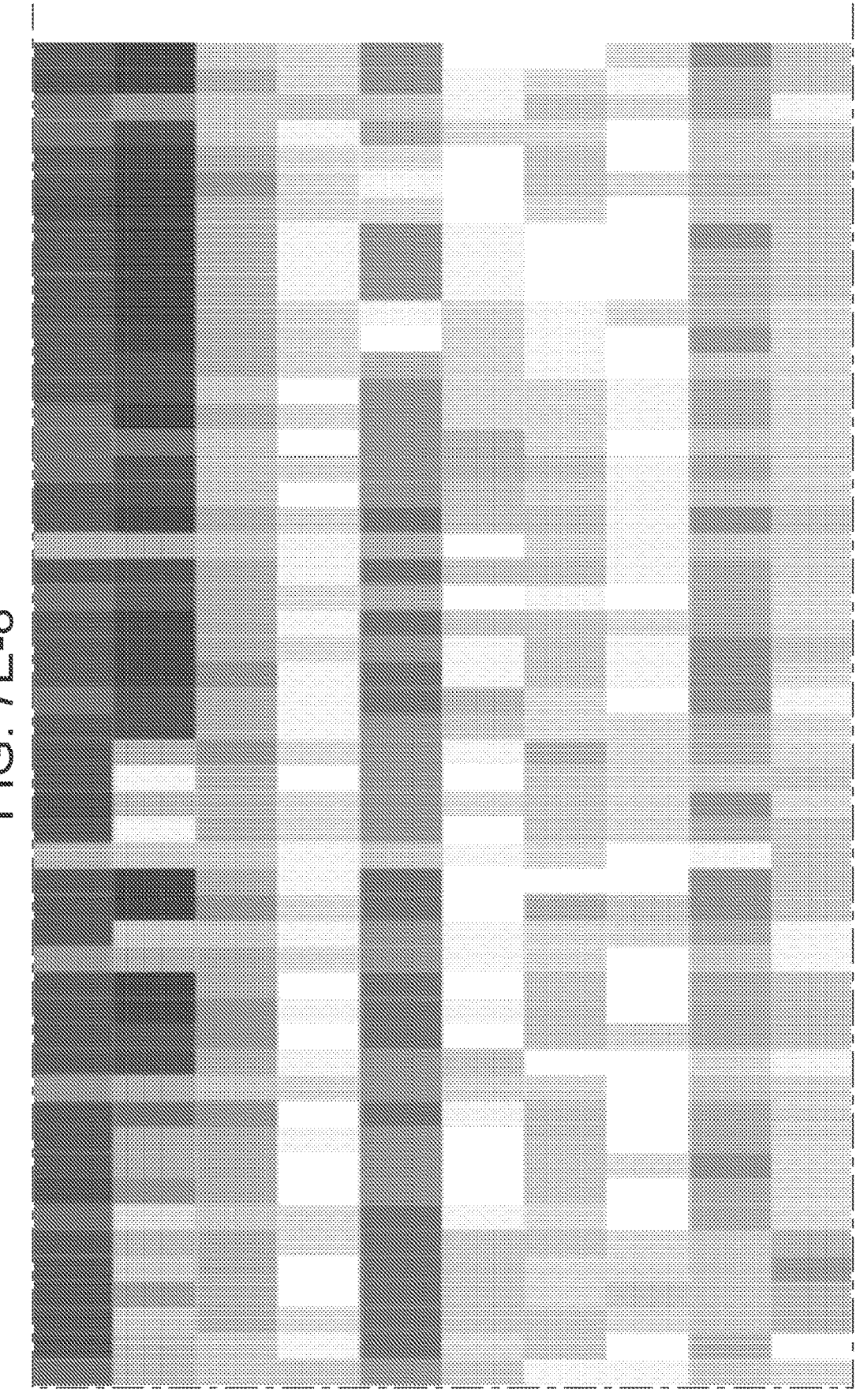
Figures 7, 7E, 8, 9:
Figures 7, 7E, 8, 9, 10:
Figures 7, 7E, 8, 9, 10, 11:
Figures 7, 7E, 8, 9, 10, 11, 12:
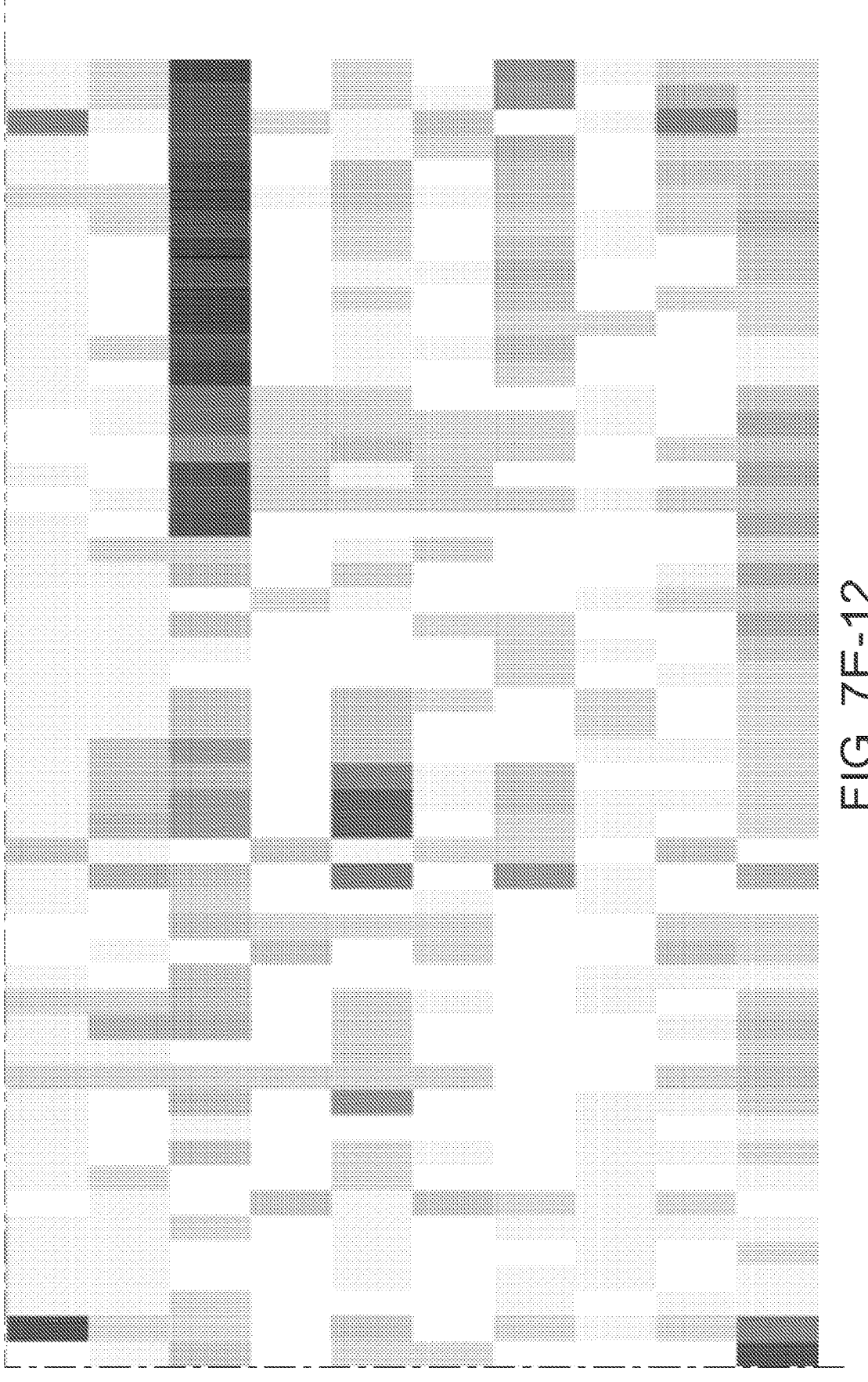
Figures 4, 7F:
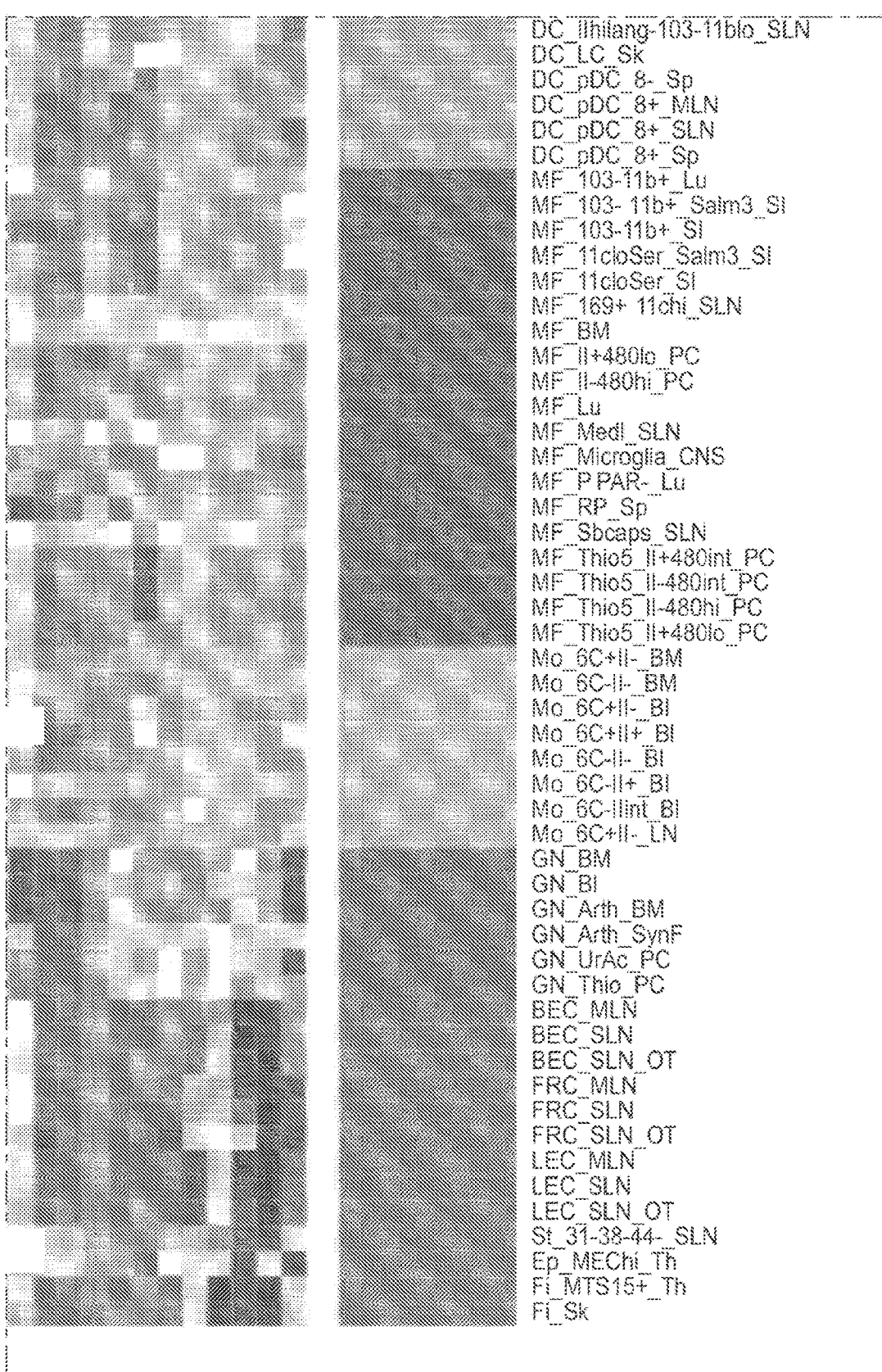
Figures 5, 7F:
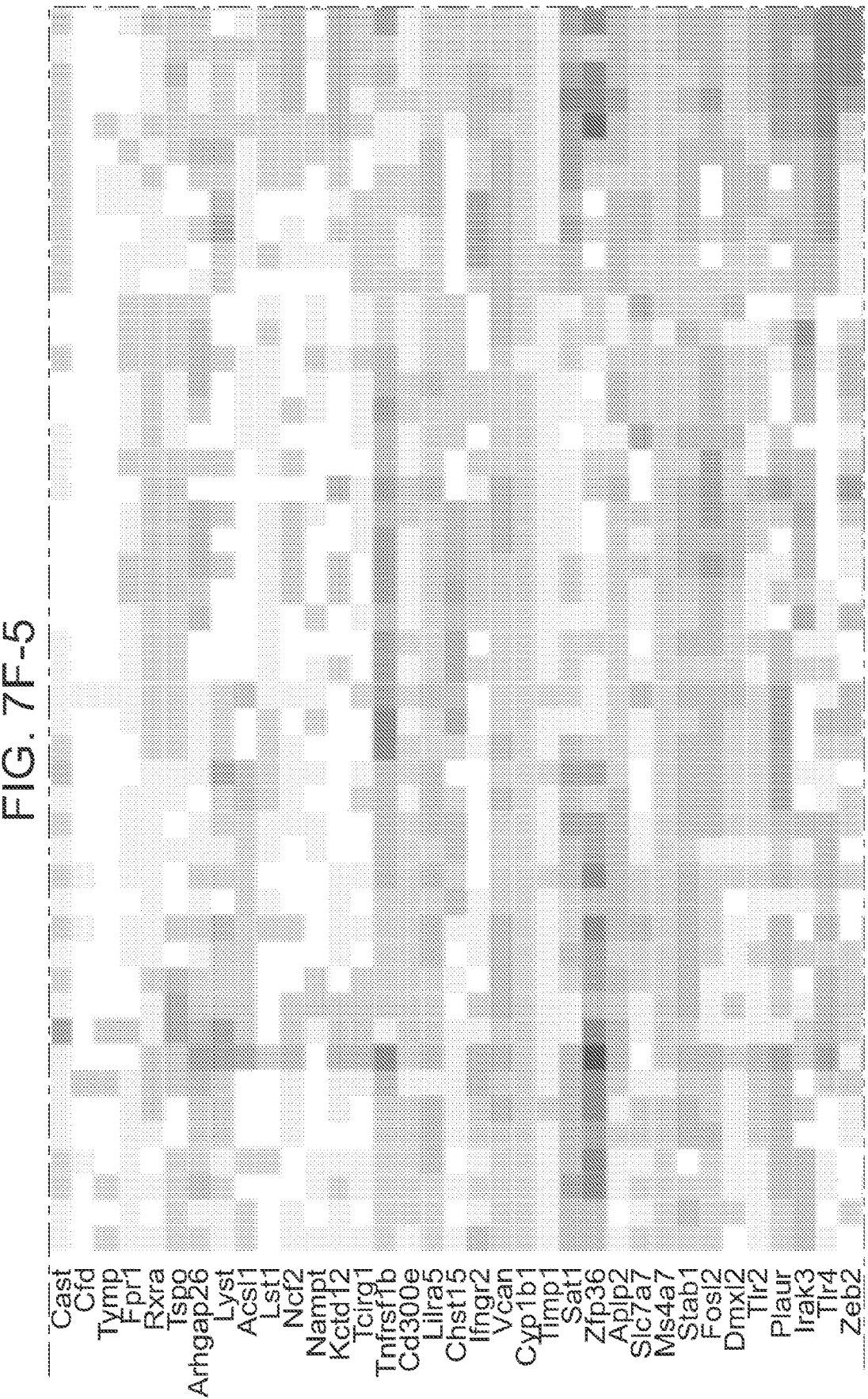
Figures 6, 7F:
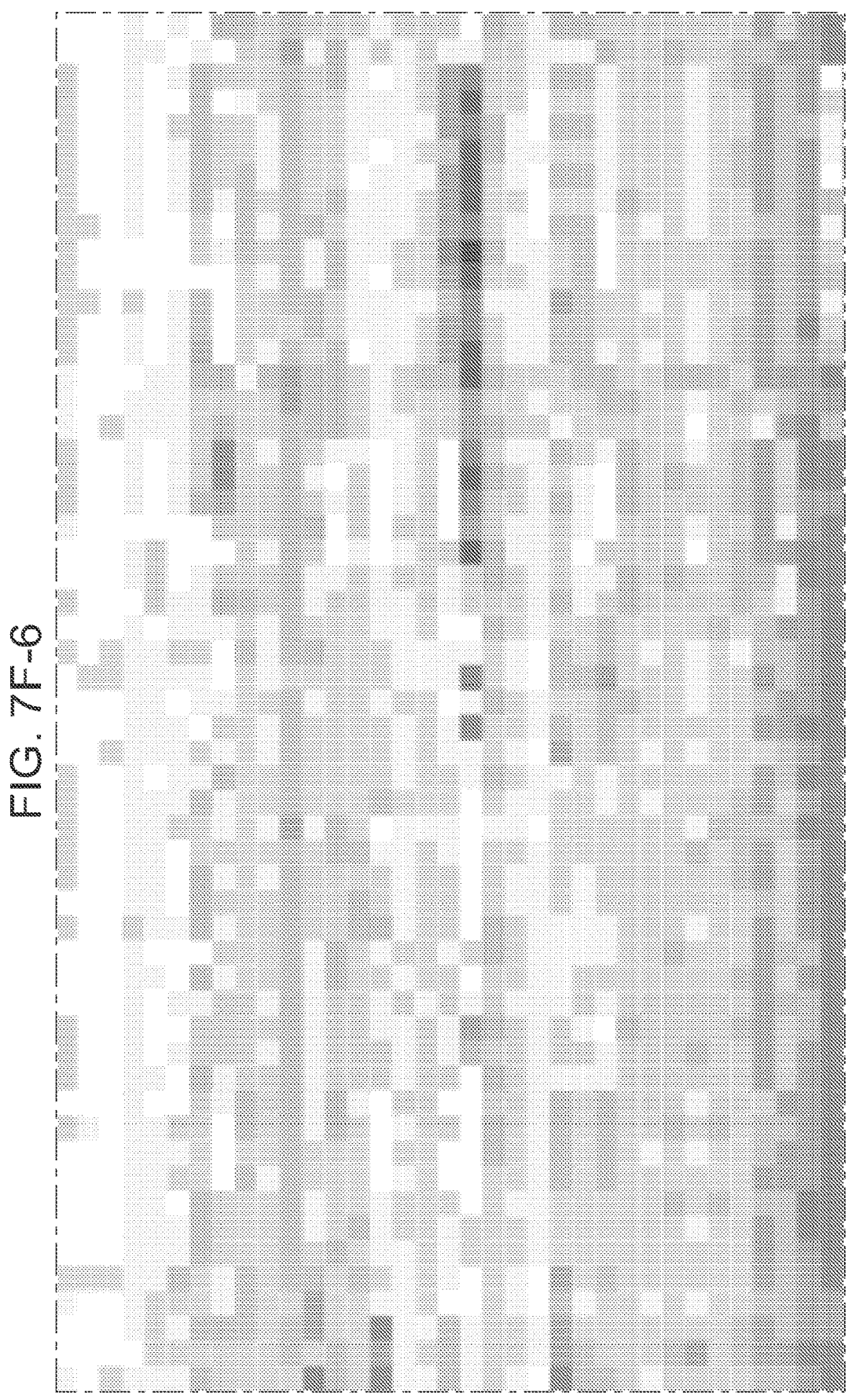
Figures 7, 7F:
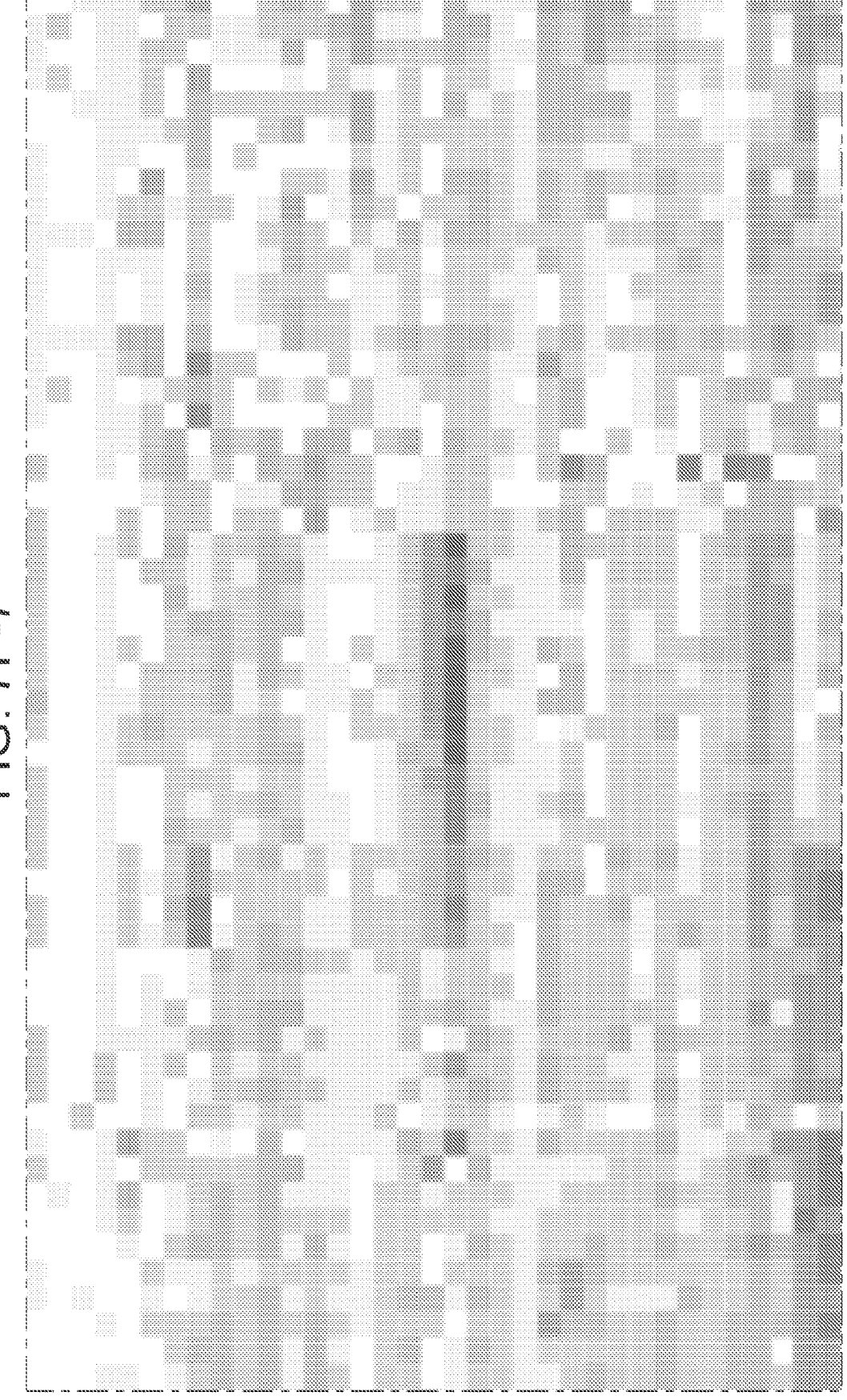
Figures 7, 7F, 8:
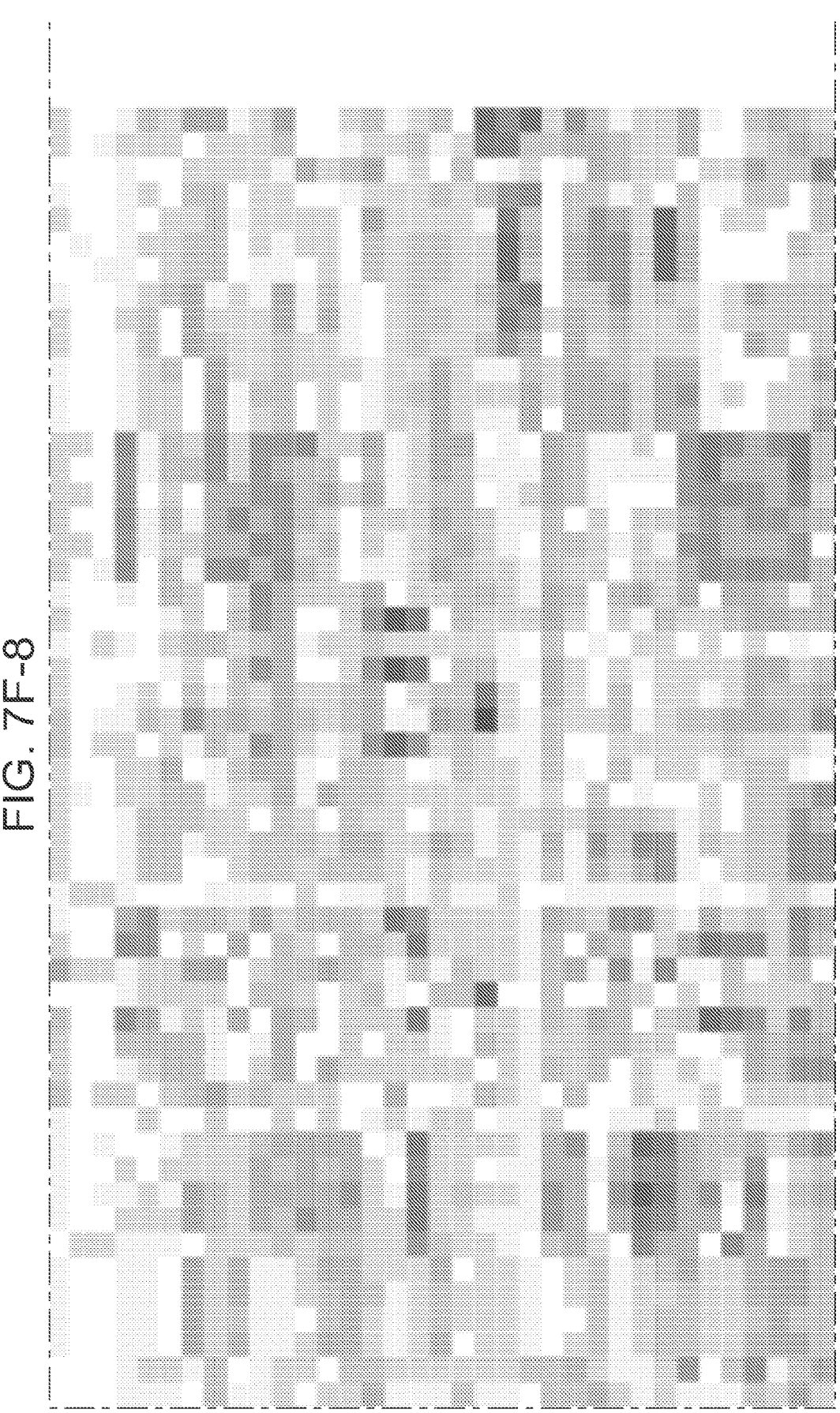
Figures 7, 7F, 8, 9:
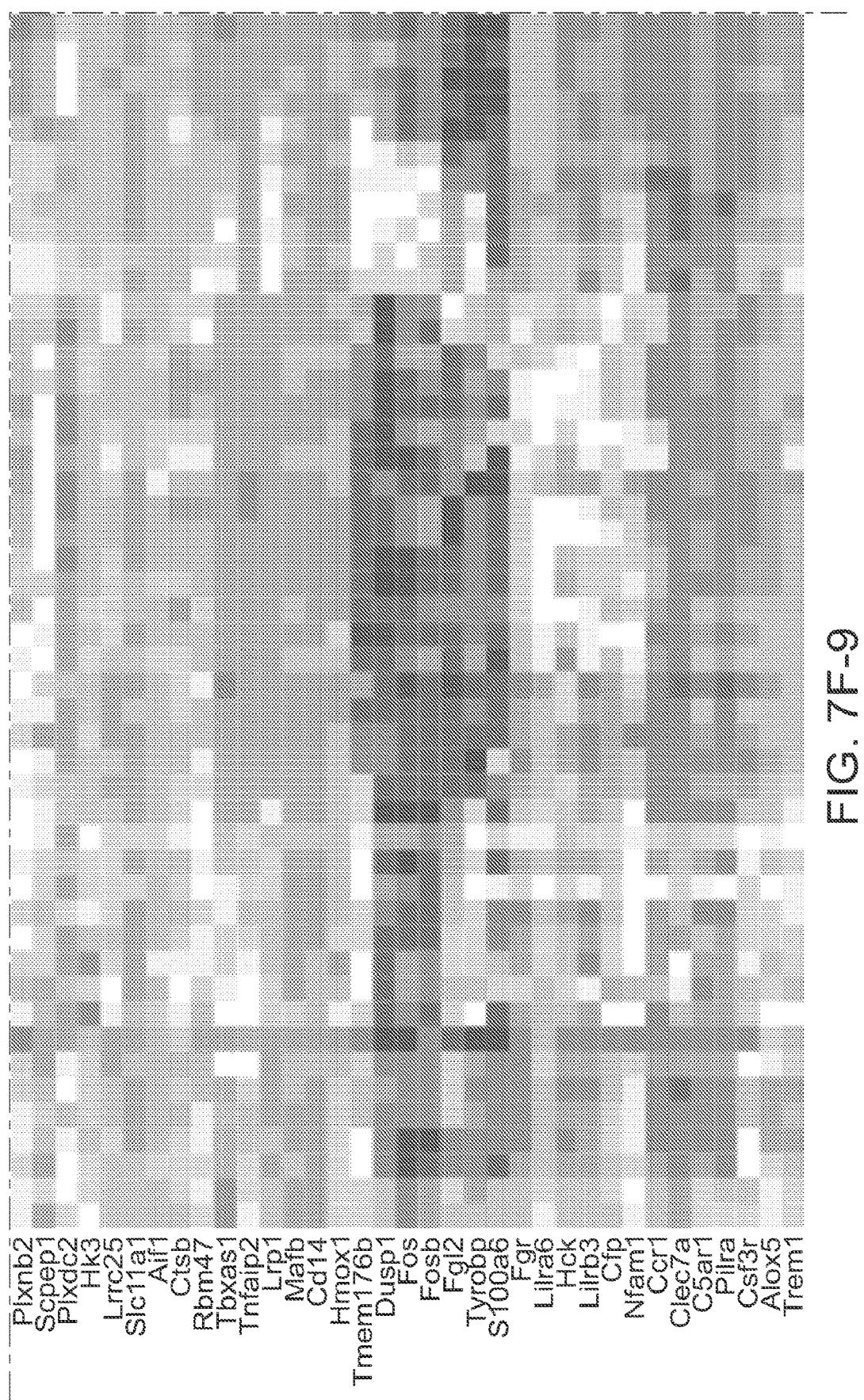
Figures 7, 7F, 8, 9, 10:
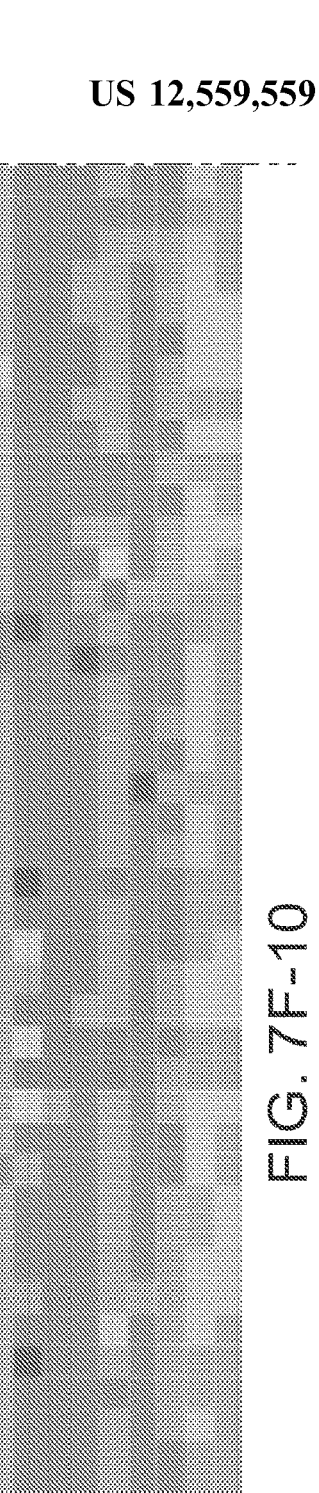
Figures 7, 7F, 8, 9, 10, 11:
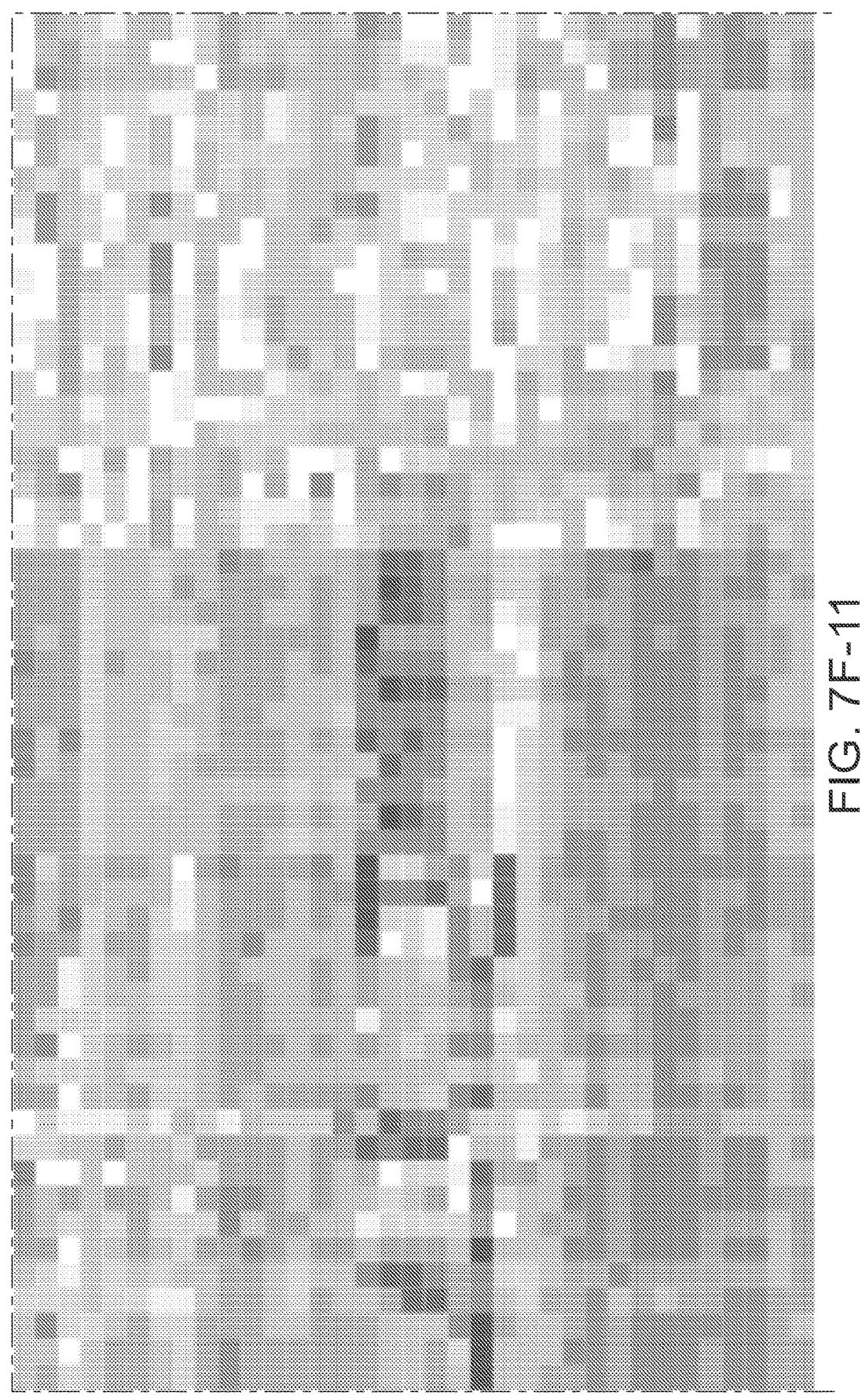
Figures 7, 7F, 8, 9, 10, 11, 12:
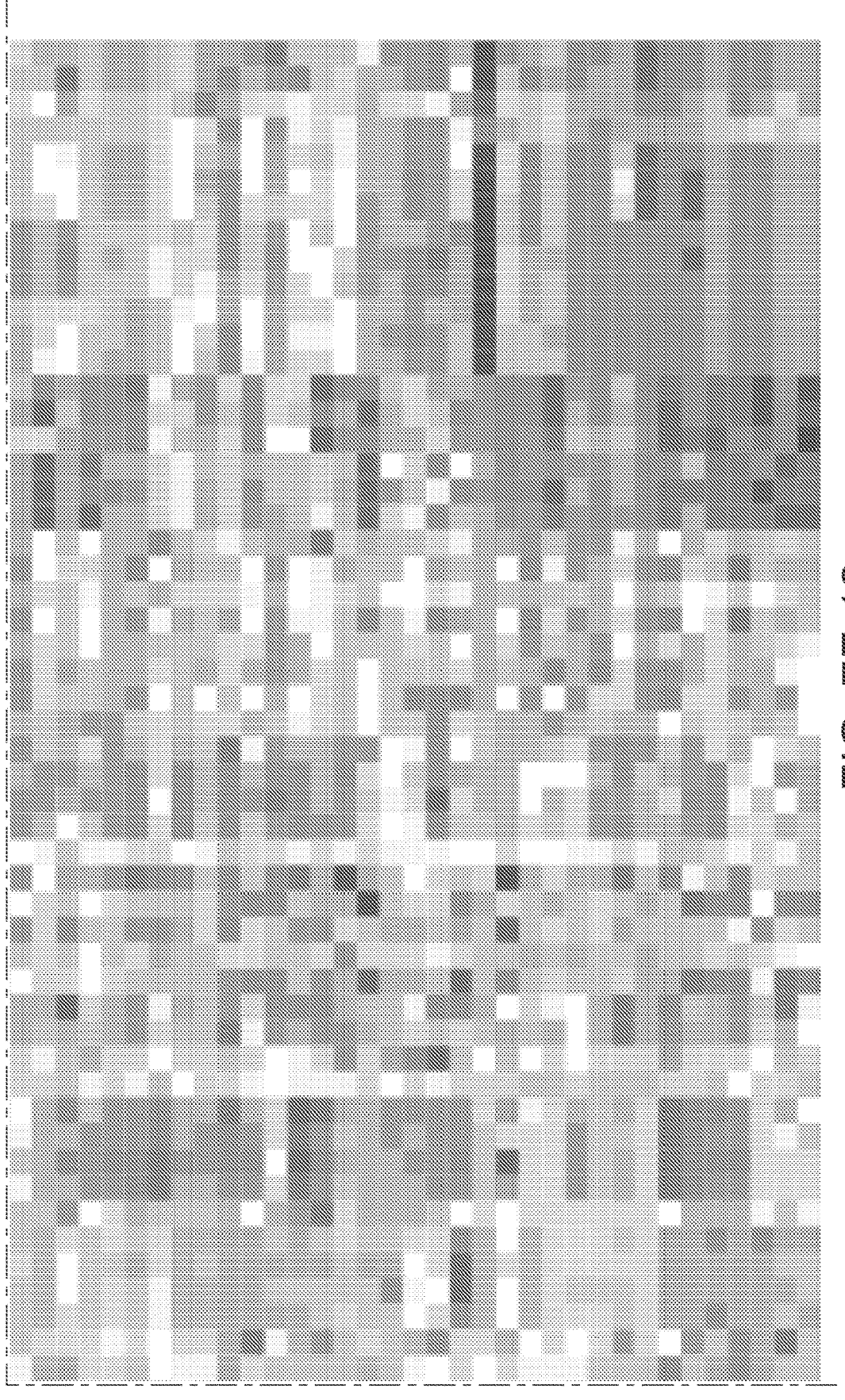
Figure 10A:
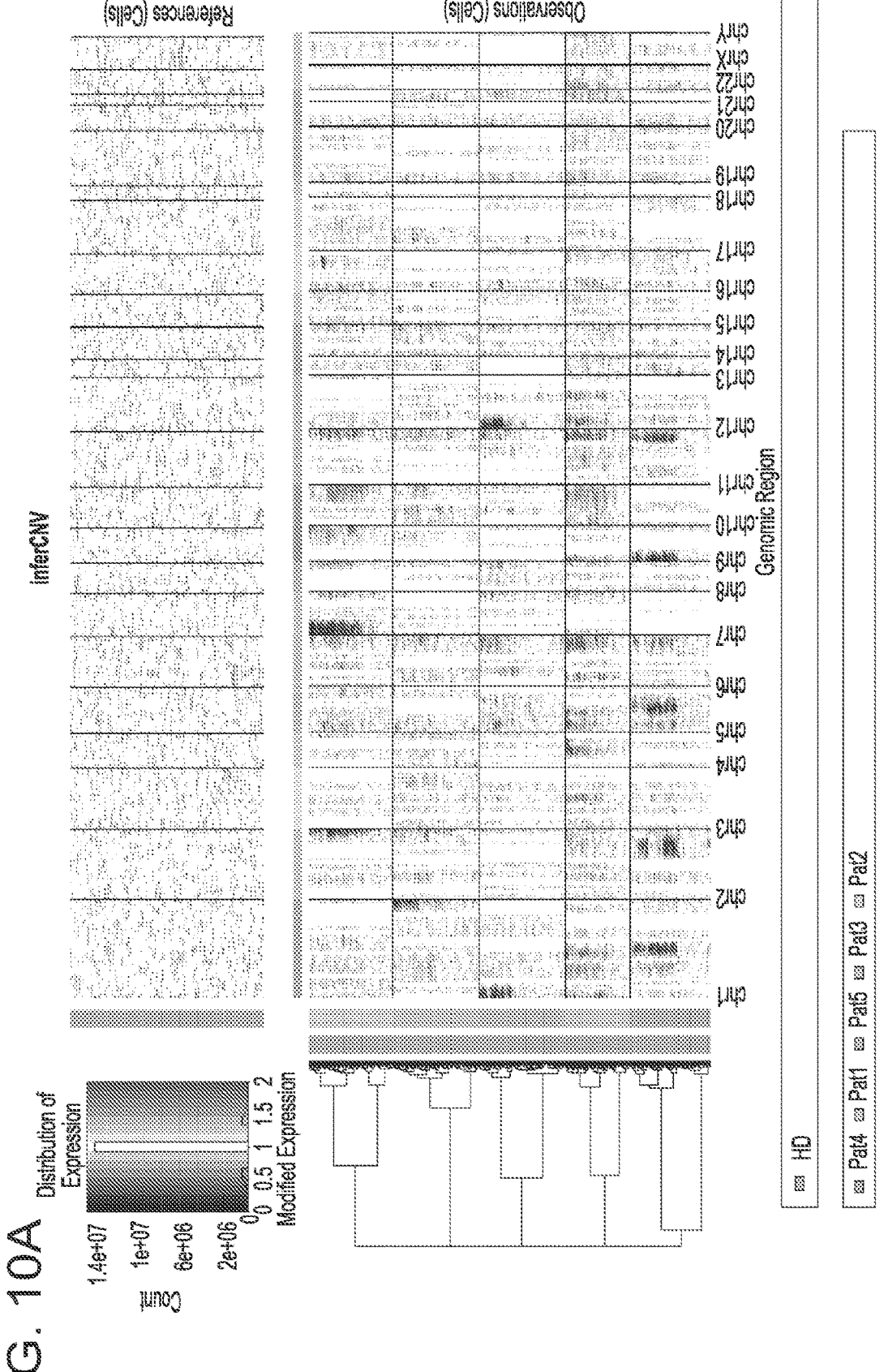
FIG. 10A-FIG. 10B is a series of graphs showing copy number variation (CNV) profile from scRNA-seq data.
Figure 10B:
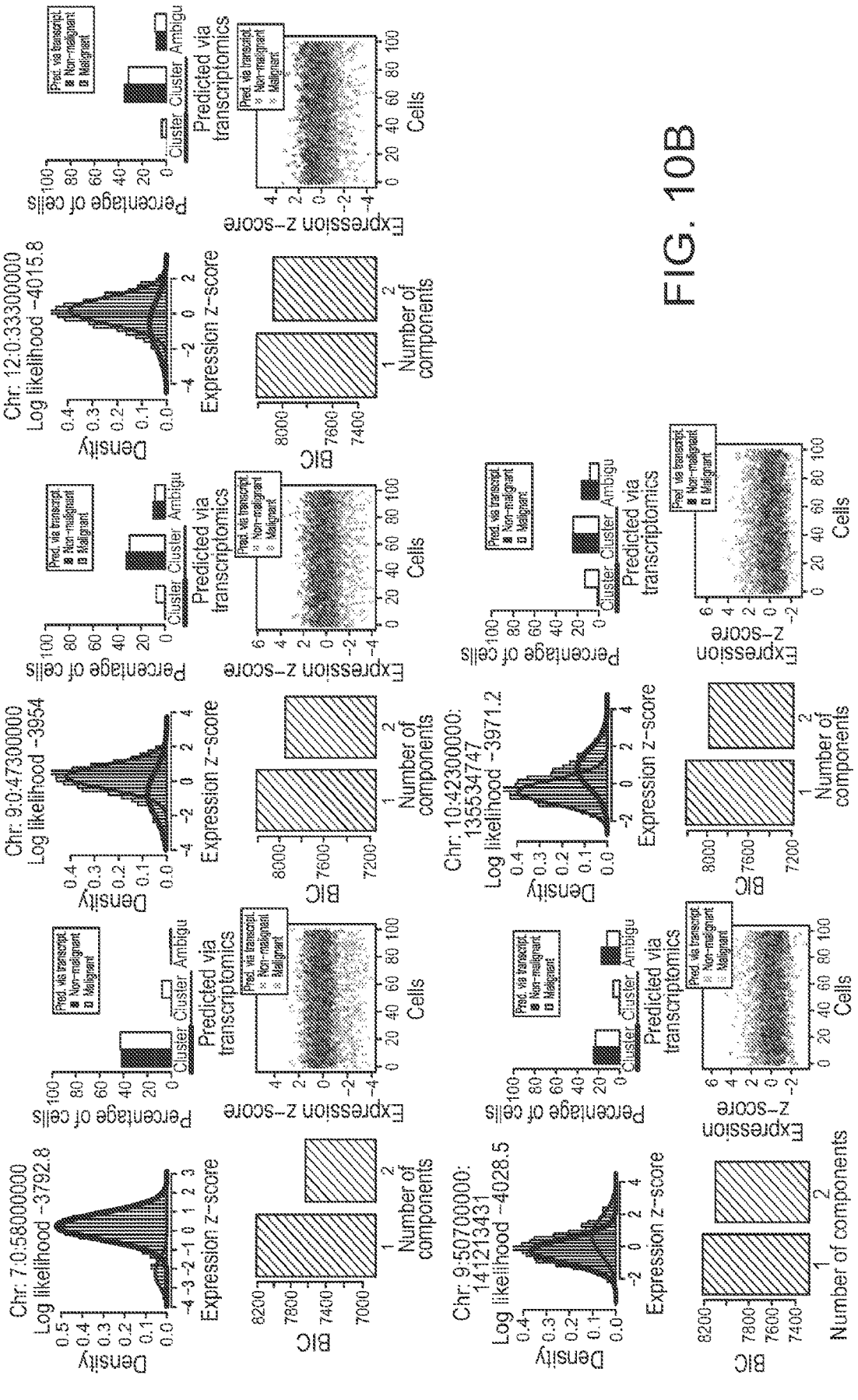
Figure 11:
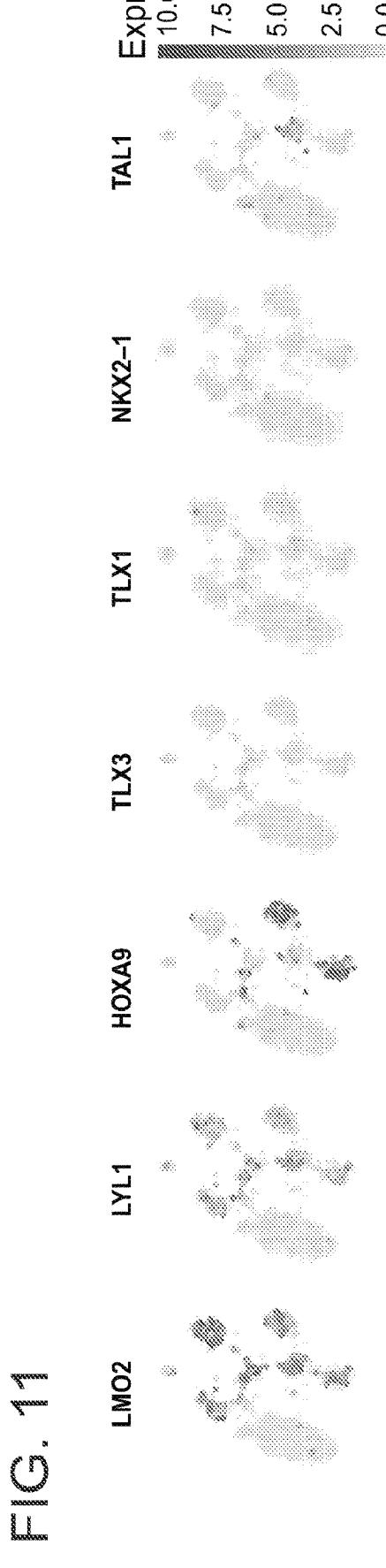
Figure 12B:
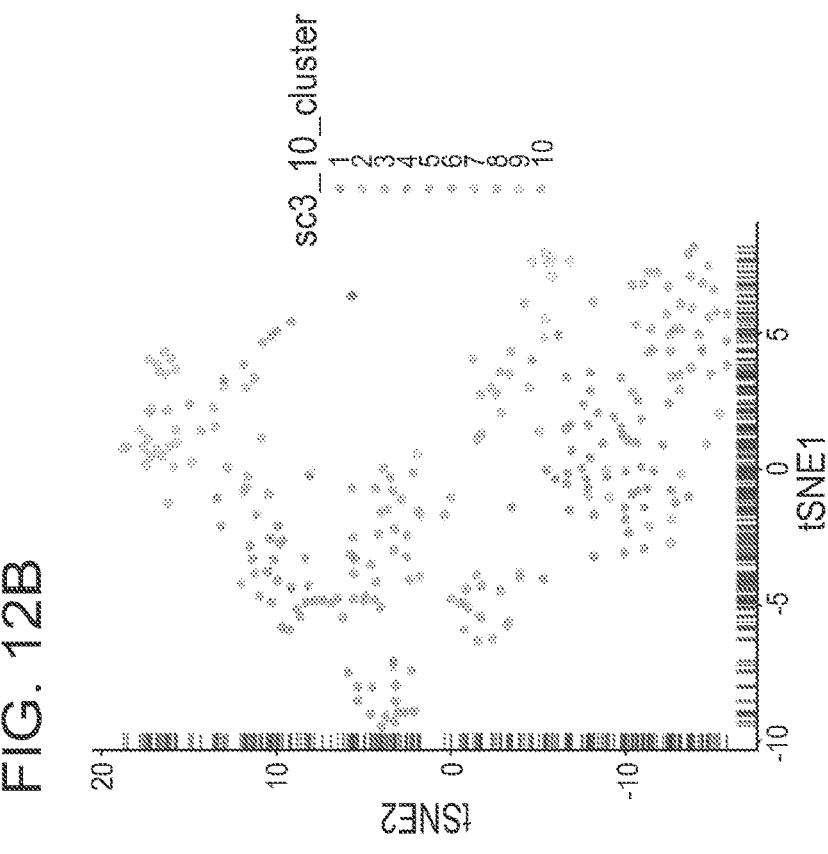
FIG. 12A-12H is a series of plots showing comparison to TARGET study.
Figure 12A:
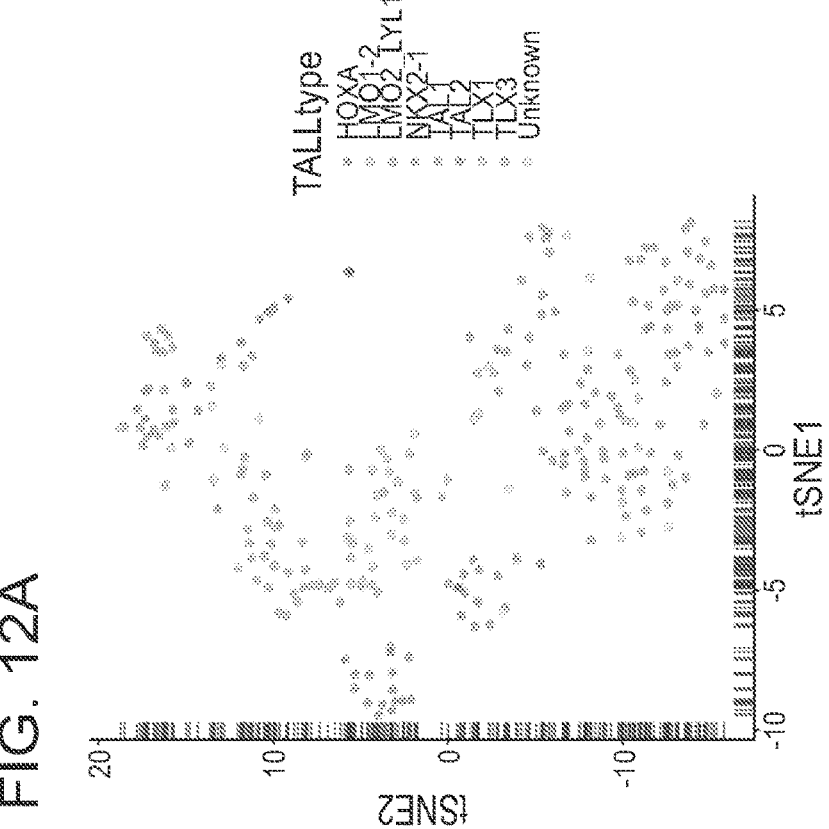
Figure 12C:
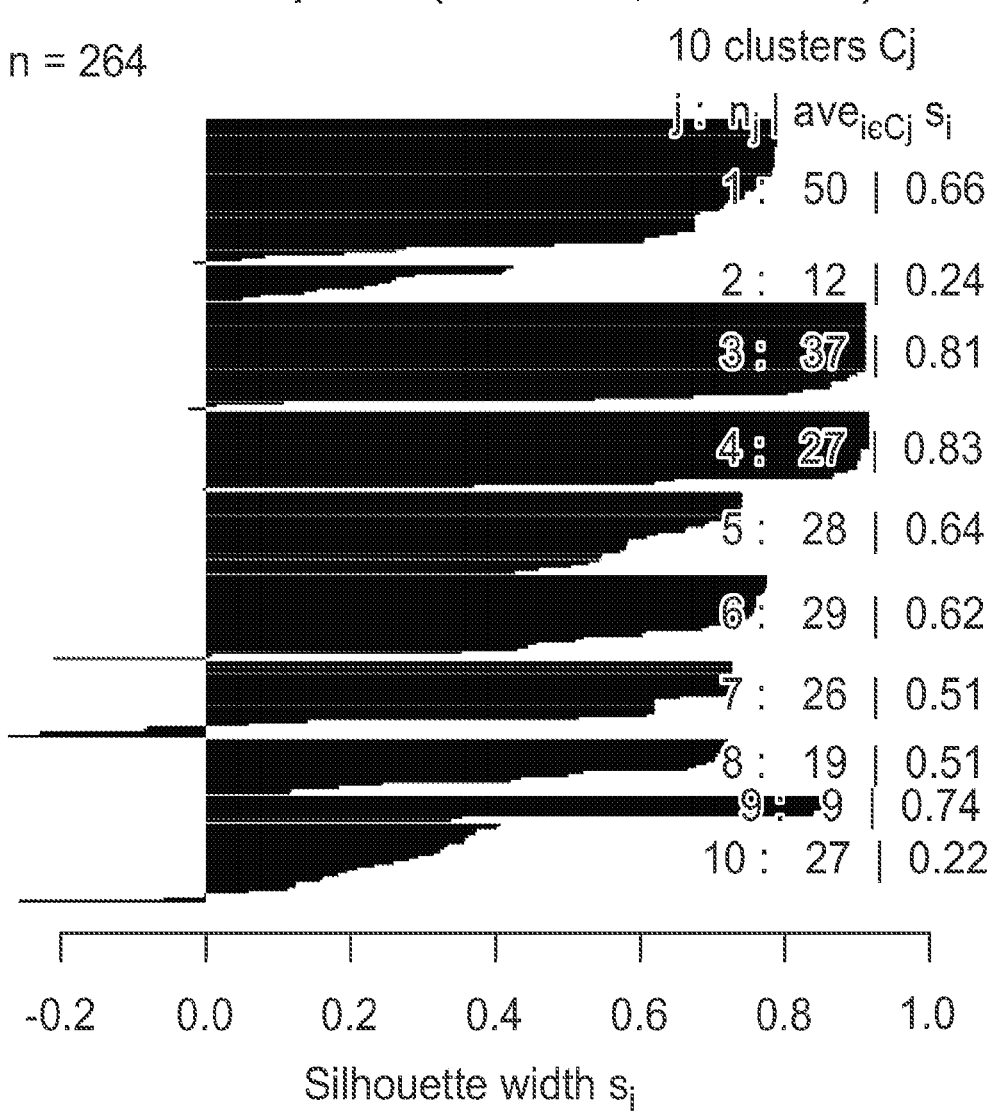
Figure 12D:
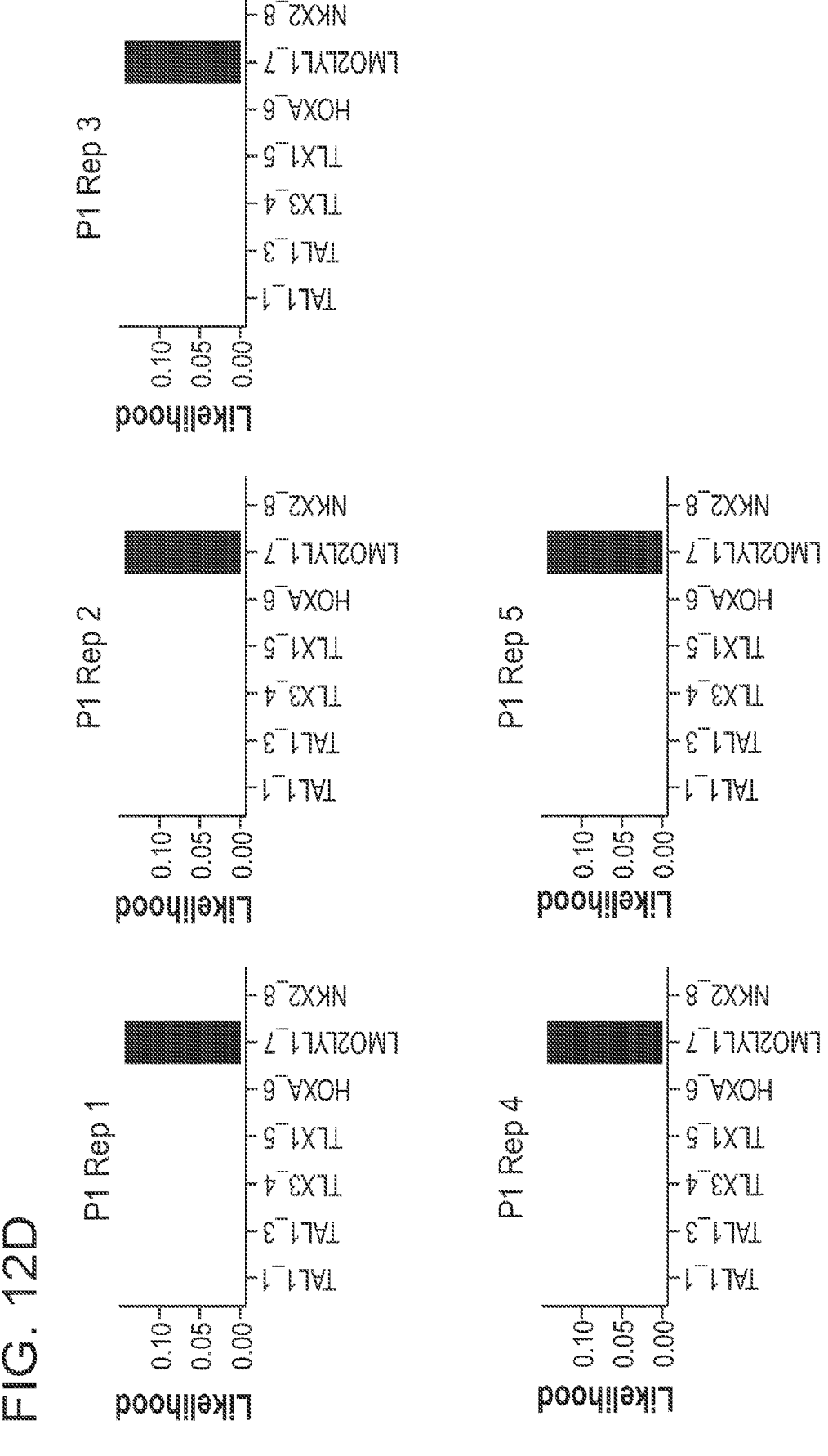
Figure 12E:
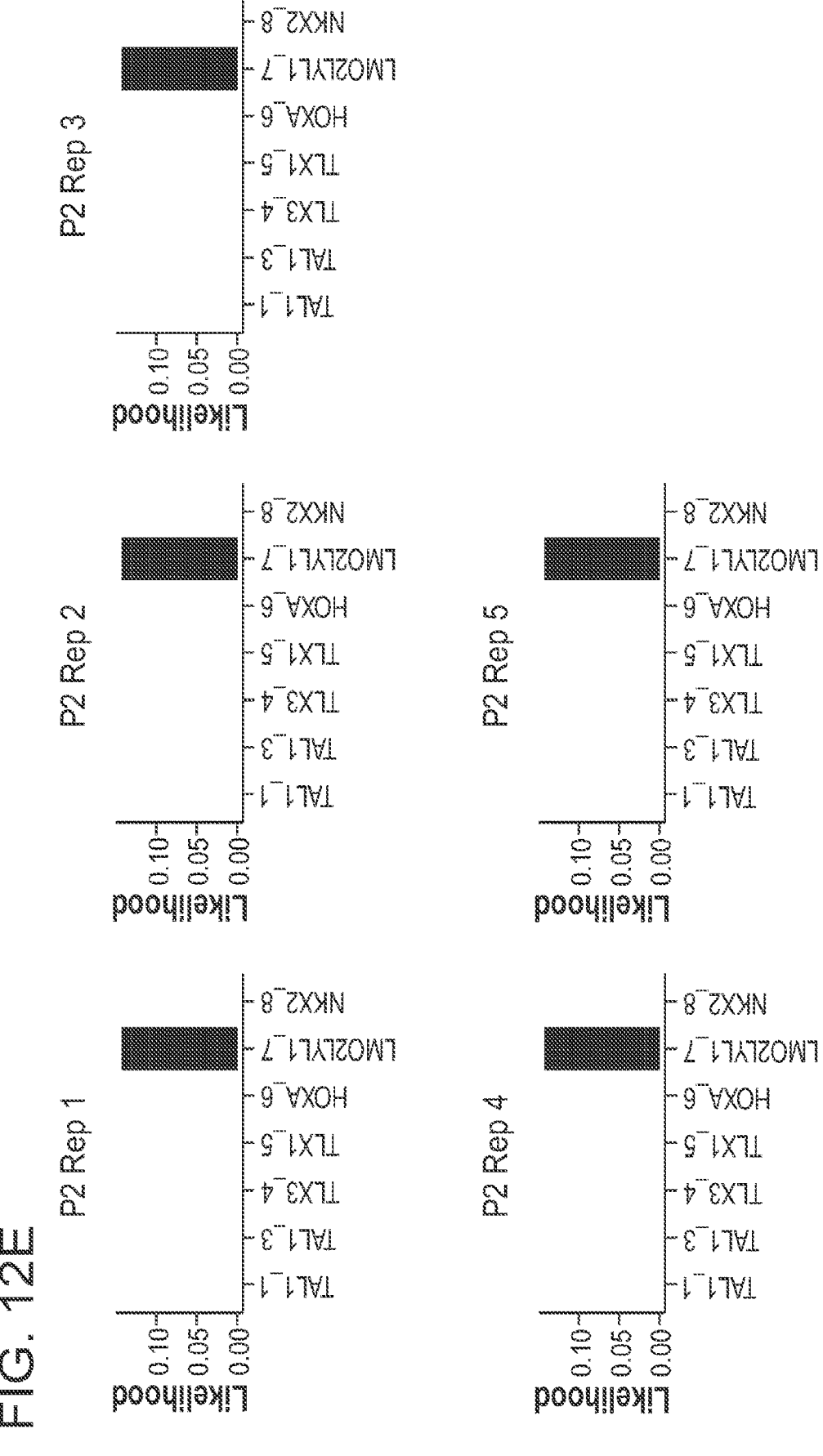
Figure 12F:
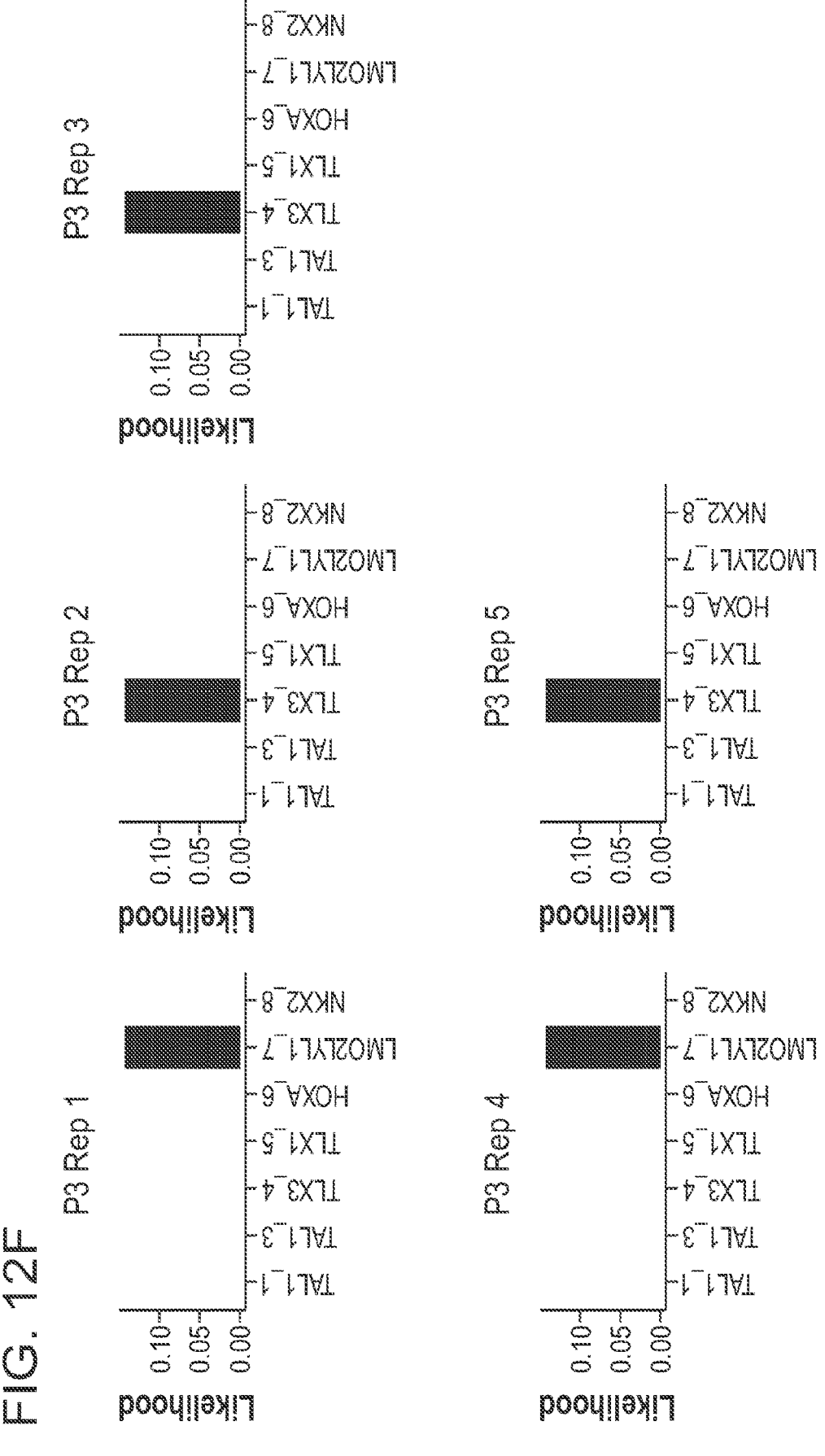
Figure 12G:
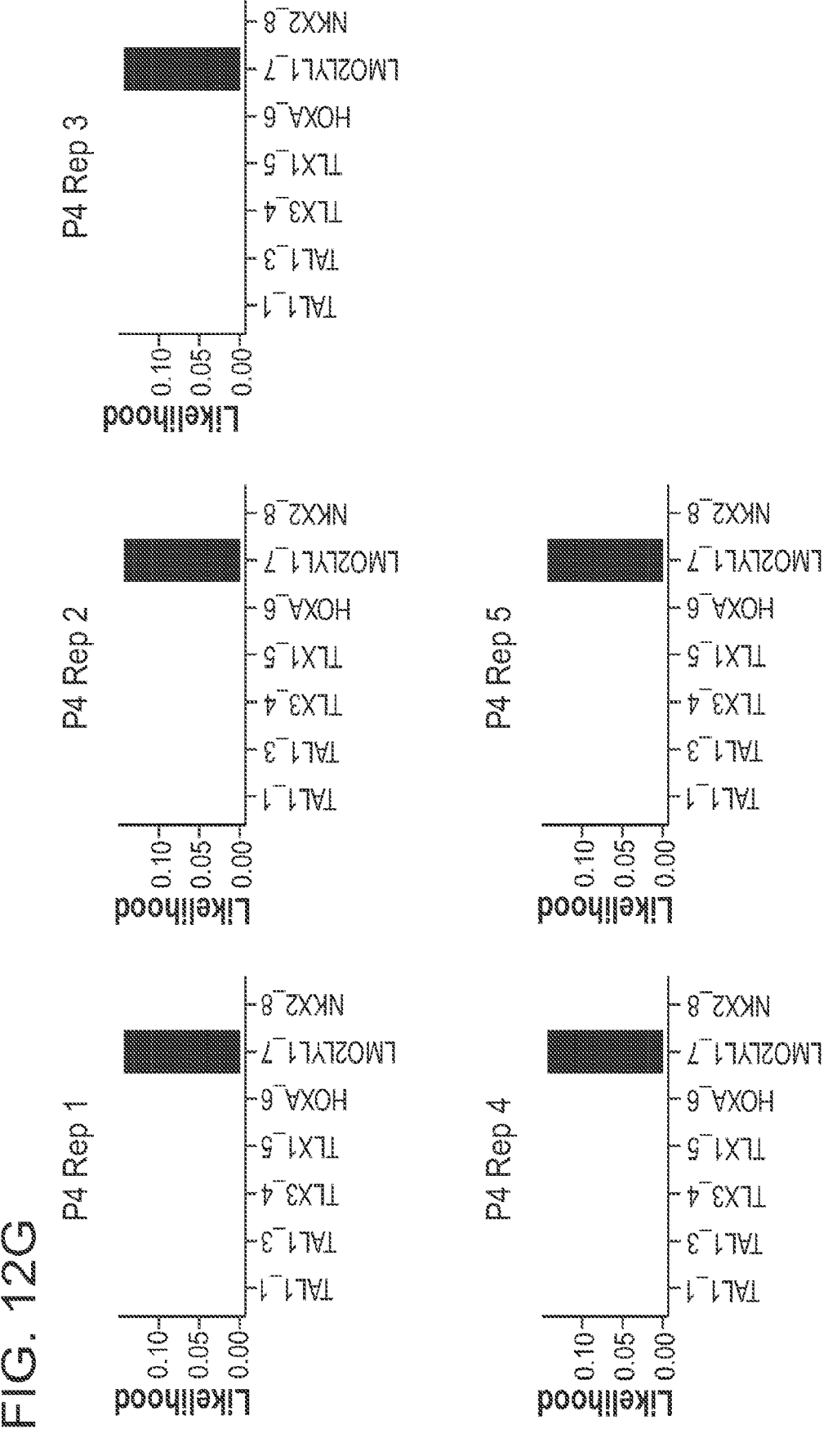
Figure 12H:
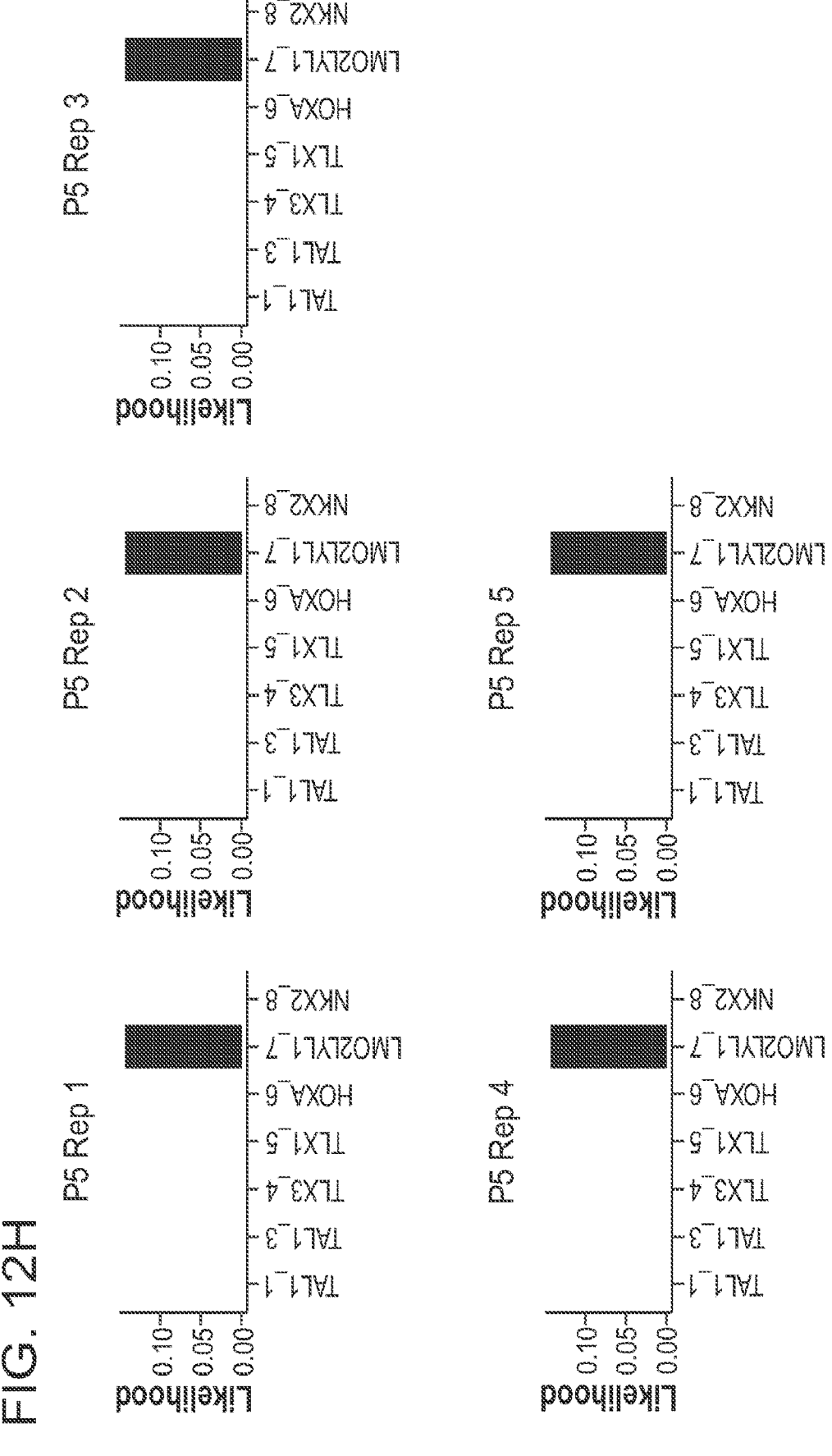

In order to filter out low quality cells from the dataset, four different parameters were used—i) library size, ii) number of genes detected, iii) percentage of reads mapping to mitochondrial genes, and iv) percentage of reads mapping to house-keeping genes (FIG. 6A). The cells in the distribution that were beyond three median absolute deviations (M.A.D's) were flagged as low quality cells. Poor quality cells were also identified without any predefined cut-offs using the R package 'mvoutlier' (FIG. 6B). Cells that were detected as outliers by both MAD-based cutoffs and mvoutlier predictions were filtered out from the dataset (FIG. 6C). This resulted in retention of 3562 high-quality cells for further downstream analyses (FIG. 6D). On average around 3330 genes were detected in these cells (FIG. 6E). The variance in the dataset was also used to systematically investigate the contribution of various technical factors and batch effect(s). The proportion of variance explained by the variables such as—individual patients, total number of genes detected, sequencing run and library size were found to be low (FIG. 6F).

Clustering of scRNA-Seq Profiles and Identification of Cell-Types

Clustering of high-quality cells was performed using PAGODA2 (Fan et al., 2016 Nature methods 13(3):241-244). Around 13 clusters were found using multilevel graph-based clustering algorithm within PAGODA2. In order to rule out the possibility of clusters being purely driven by cell-cycle, each individual cell was analyzed for expression of G1, G2M and S phase markers to predict the cell-cycle phase using Seurat2 (Butler et al., 2018 Nat Biotechnol 36(5):411-420). The observed clusters did not show high concordance with the cell-cycle stages as indicated by low adjusted-rand index, thus ruling out the possibility of cell-cycle being a major contributor to differences between clusters. The marker genes for each of the clusters were determined using findMarker function in the scran package (Lun et al., 2016 F1000Res, 5:2122). Using the information of the marker genes, the individual clusters consisting of normal cells were manually annotated to be either CD4+ T-cells, CD8+ T-cells, NK cells, myeloid or B-cells (FIG. 1A-FIG. 1F).

Identification of Pathogenic Variants from scRNA-Seq Data

The workflow for detecting SNVs was adapted from GATK best practices (Van der Auwera et al., 2013 Curr Protoc Bioinformatics, 43:11 10 11-33). In brief, the aligned reads in BAM format were sorted, duplicate reads were flagged, read filters applied, (SplitNCigarReads, GATK 4.0), local realignment performed to minimize the number of mismatching bases across all reads (RealignerTargetCreator and IndelRealigner, GATK 4.0), base scores were recalibrated (BaseRecalibrator, GATK 4.0), and finally mutect2 (Cibulskis et al., 2013 Nat Biotechnol 31(3):213-219) was used for variant calling.

Detection of Copy Number Variations from scRNA-Seq and Cytogenetics

The copy number variants were inferred from the scRNA-seq data using two different method—InferCNV (Patel et al., 2014 Science 344(6190):1396-1401; Tirosh I et al., Science, 352(6282): 189-196) (github.com/broadinstitute/inferCNV) and CONICSmat (Muller et al., 2018 Bioinformatics, 34(18):3217-3219) (github.com/diazlab/CONICS). T-cells from the normal donors were used as controls for both methods. The detected CNVs were compared to the cytogenetics report obtained as clinical routine (Table 1).

The signals for copy-number variations through infer-CNV could detect duplication of chr21 that was in agreement for P1 and del7p for P2. The deletion of 1p, 4q, 6q and 11q could be reliably identified for P4 and del12p was specifically predicted for P5. No strong signals for copy number variations could be identified from scRNA-seq for P3. In addition to these, we also could capture additional copy number signals that were not reported by cytogenetics such as amp10q; del4q for P1, amp9q for P2, del9p for P4.

Comparison to Bulk RNA-Seq from ImmGen and BLUE-PRINT Datasets

The expression data from the purely sorted bulk populations of immune cells from the ImmGen and BLUEPRINT datasets was used to define the identity of cell types. A multinomial log-likelihood model reported (Zemmour et al., 2018 Nature Immunology, 19(3):291) to determine the probability of each cell belonging to a particular cell type was used. The bulk RNA-seq gene expression matrix was used to provide prior probabilities (probability to express gene i in cell-type j=$p_{ij}$), and for each cell c the likelihood of it belonging to cell-type j ($L_{cj}$) was calculated. For normalization, the log posterior probabilities were summed to one during calculation.

$$L_{cj} = \sum_i c_i \times \log(p_{ij})$$

Evaluating Relative Importance of Transcription Factors Using Random-Forest Model A random-forest model was employed in order to evaluate the relative importance of transcription factors in distinguishing between malignant and non-malignant cells. The relative expression of all the transcription factors from the transcription factor database (Hu et al., 2019 Nucleic Acids Res, 47(D1):D33-D38) (Animal TFDB) were used as features. The cells belonging to patient-specific clusters, having specific enrichment for pathogenic variants and copy-number aberrations were defined as malignant. A random-forest classifier (Liaw et al., 2001 Classification and Regression by Random Forest, Vol. 23) was built in R using this definition of malignant and non-malignant as labels. Around 70% of the data was used to build the model. The optimum parameters—mtry (39) and ntrees (400) for random forest were determined using tuneRF function. The best model had the OOB estimate of error rate at 2.65% with 0.049 and 0.005% class error rate. The relative importance of transcription factors in classification was evaluated using varImpPlot function. The process was repeated by both including and excluding the GSI treated cells.

Determining the Co-Existing/Mutually Exclusive Signatures in Malignant Cells

The signatures for the hematopoietic stem cells (HSCs), multipotent-progenitors (MPP), common lymphoid progenitors (CLP), common myeloid progenitor (CMP) and granulocyte-macrophage progenitors (GMP) were derived from previously published literature comprising bulk RNA-seq studies on purely sorted immune populations (Aran et al., 2017 Genome Biol, 18(1):220; Fernandez et al., 2016 Cell Syst, 3(5):491-495 e495) The genes in each of these signatures were scored using AUCell package (Aibar et al., 2014 Nat Methods, 14(11): 1083-1086).

Characterization of Heterogeneity at Single Cell Resolution

Monocle2 was employed to discover the subclusters within each of the patient-specific T-ALL cells clusters using only the raw counts from single cells (Trapnell et al., 2014 Nat Biotechnol, 32(4):381-386). The clusters derived using this approach for P2 and P4 overlapped with the clusters derived from graph-based infomap clustering algorithm applied on RNA velocity (La Manno et al., 2018 Nature, 560(7719):494-498). Finally, a perturbation-response based score for assessing the signaling activity in each cell (Schubert et al., 2018 Nat Commun, 9(1):20) was also used to characterize the heterogeneous clusters.

Defining TCR-Usage in CD8[+] T-Cells

A TCR usage group was defined to be based on a previously reported study (Tirosh et al., Science, 352(6282): 189-196) that considers the frequency of the read counts aligned to the V and the J locus of the alpha and the beta chains ($V_\alpha$, $J_\alpha$, $V_\beta$ and $J_\beta$. The sequences of different alleles for TCRs were downloaded from the IMGT database and aligned using ncbi-magicblast (Boratyn et al., 2019 BMC Bioinformatics, 20(1):405). Each cell was assigned V and J allele for alpha and beta TCR chain based on the number of reads uniquely aligned. Two cells were considered to belong to same clonotype if three of the four alleles overlapped.

Exhaustion Score and Receptor-Ligand Interaction Scores

T-cell exhaustion, naïve and cytotoxic scores were calculated by average relative expression of key marker genes from the literature (Tirosh et al., Science, 352(6282):189-196). The exhaustion score was defined as difference between average relative expression of exhaustion markers—PDCD1, TIGIT, LAGS, HAVCR2, CTLA4 and naïve markers—CCR7, TCF7, LEF1 and SELL. The cytotoxic score was defined as difference between average relative expression of cytotoxic markers—NKG7, CCL4, CST7, PRF1, GZMA, GZAB, IFNG, CCL3 and naïve markers. The co-inhibitory ligand and receptor pairs that could potentially result in exhaustion were derived from reviewed literature (Chen et al., 2013 Nat Rev Immunol, 13(4):227-242). The ligand-receptor pairs were scored based on their expression levels as described (Kumar et al., 2018 Cell Rep, 25(6): 1458-1468 e1454).

Example 2

ETP T-ALL Cells Express Transcription Factors Associated with Normal B-Lymphoid and Myeloid Progenitors In order to fully define ETP T-ALL heterogeneity on the single-cell level, a full-length transcriptome analysis of 5,077 malignant and normal immune cells (T-cells, B-cells and monocytes) was performed from bone marrow or blood from four healthy donors and five patients with relapsed/refractory ETP T-ALL, diagnosed by immunophenotyping for ETP T-ALL, all with NOTCH1 gain-of-function mutations. These patients were treated with the γ-secretase inhibitor (GSI), and pre- and post-treatment samples were processed for this study. Patient information and tumor characteristics are summarized in Table 1.

Figures 1B, 1C:
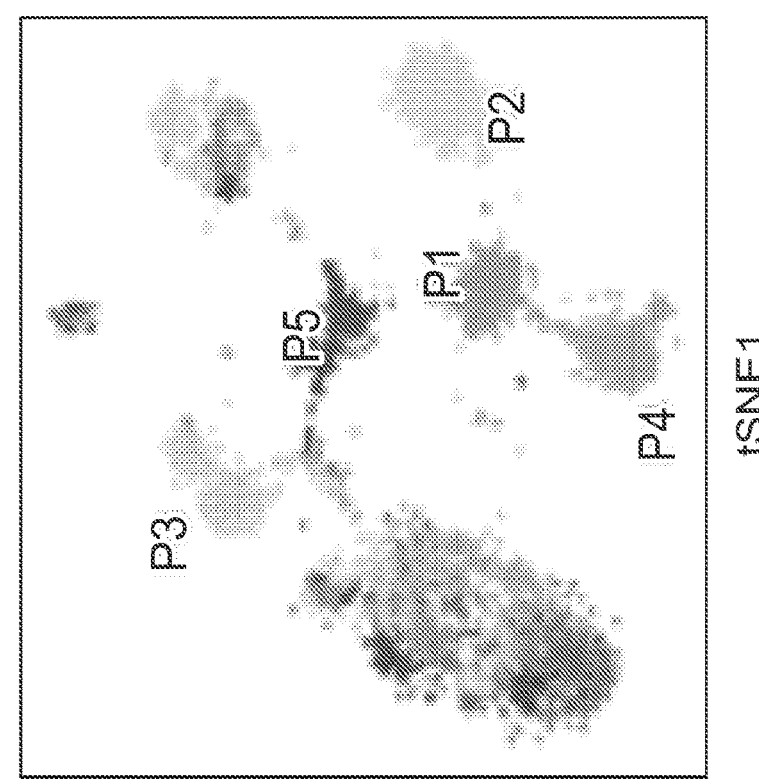
Figure 1D:
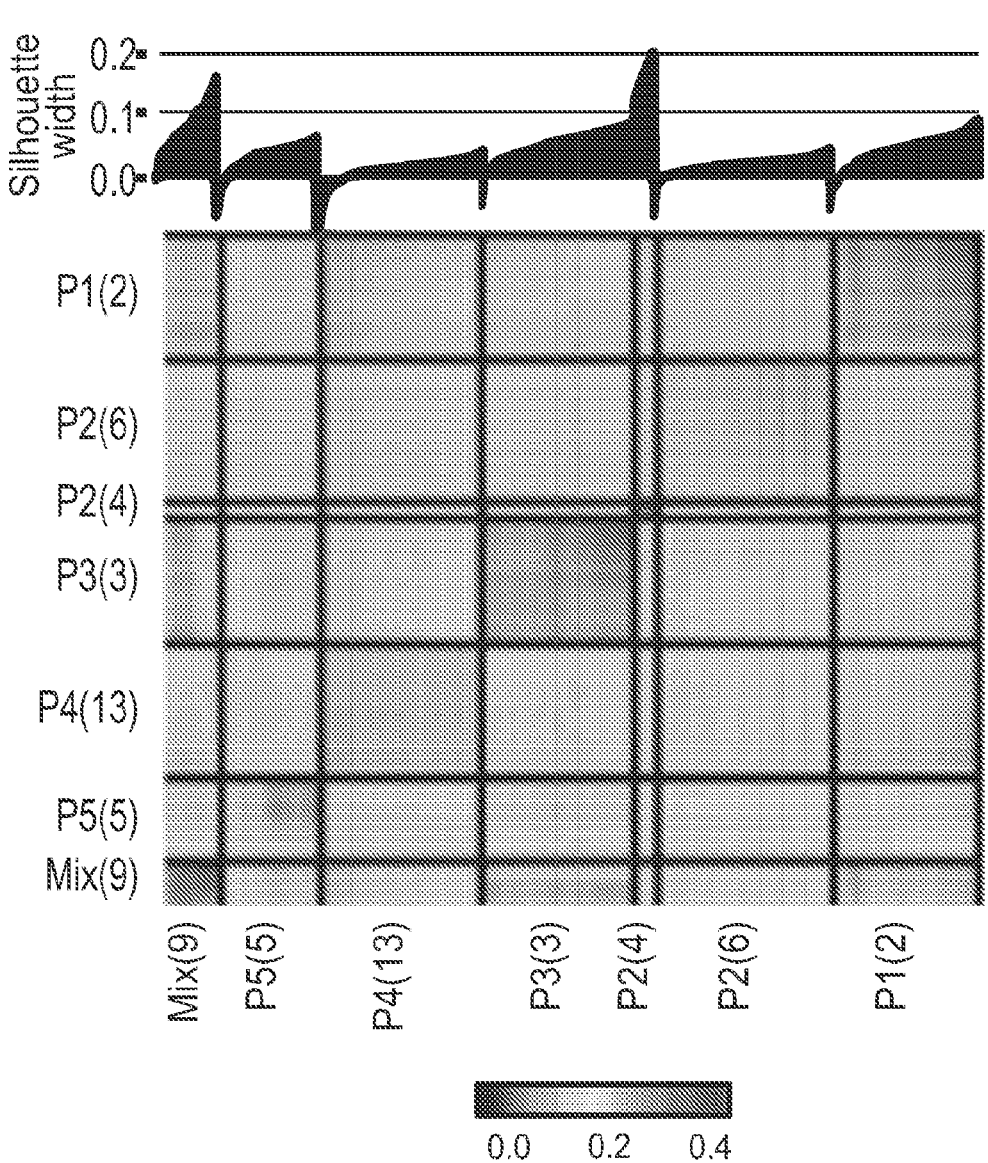
Figure 1E:
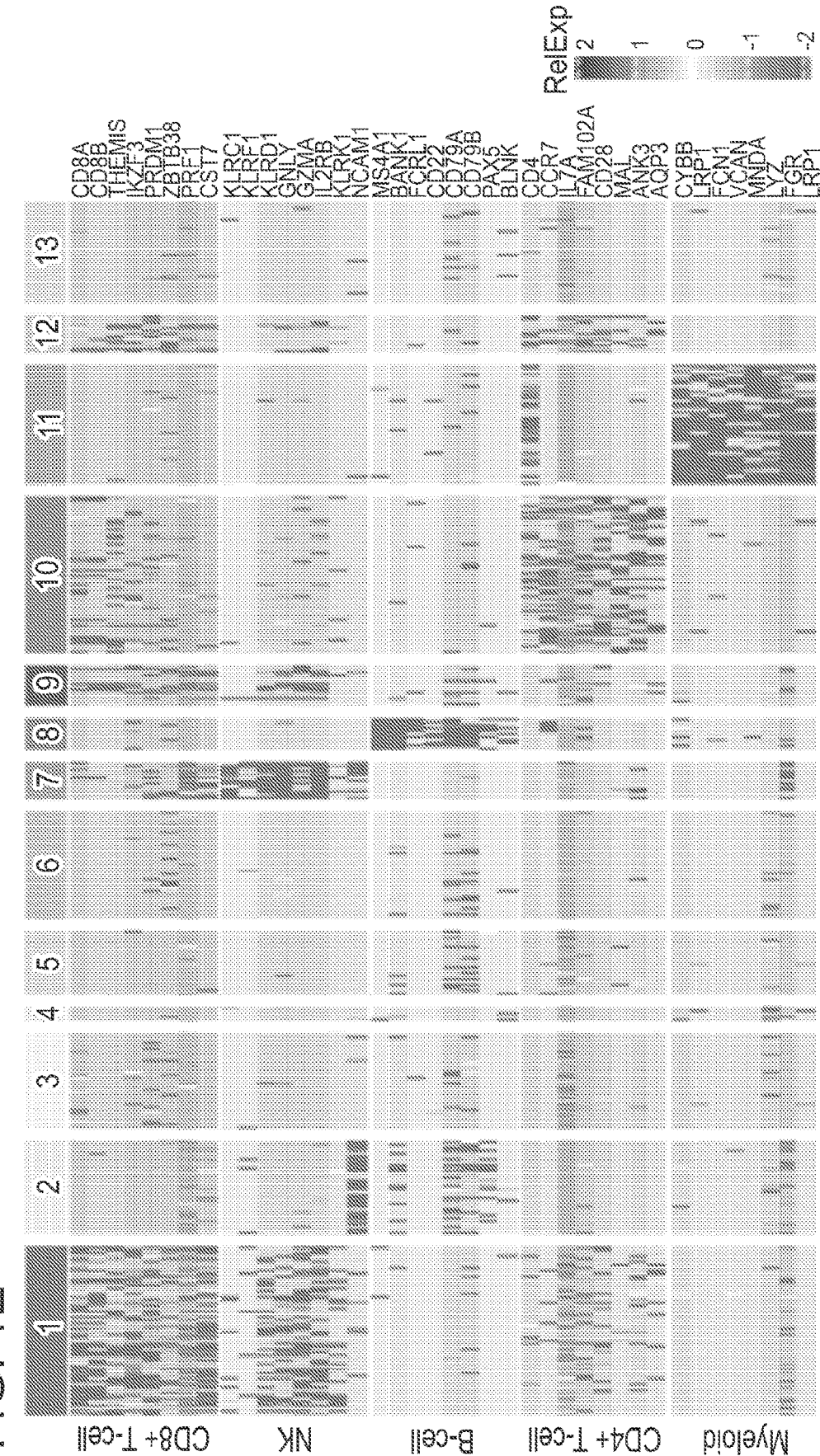

Leukemia cells were enriched by sorting on CD45$^{low}$ expressing blasts and also collected T-cells, B-cells, and monocytes by sorting on appropriate surface markers (FIG. 1A). After several scRNA-seq quality control filtering steps (Example 1 and FIG. 6A-FIG. 6F), a PAGODA2 clustering and t-Stochastic Neighbor Embedding (t-SNE) visualization was performed (Fan et al., 2016 Nature methods, 13(3):241-244), which revealed 13 distinct cell clusters (FIG. 1B-FIG. 1C). Five clusters (cluster 1, 7, 8, 10 and 11) were common to different patients and normal donors, whereas the remaining clusters were specific for individual ETP T-ALL patients and showed high intrapatient correlation (FIG. 1A, FIG. 1C, and FIG. 1D). Comparisons of these single-cell profiles to two independent expression datasets of immune cell populations (BLUEPRINT (Fernandez et al., 2016 Cell Syst, 3(5):491-495 e495) and ImmGen (Heng et al., 2008 Nat Immunol, 9(10):1091-1094) consortia) showed that clusters 10, 1, 7, 8 and 11 represent CD4$^+$ T-cells, CD8$^+$ T-cells, NK-cells, B-cells and myeloid cells, respectively (FIG. 7A-FIG. 7F). This classification was also confirmed by differential expression of well-established lineage markers (FIG. 1E). With the exception of cluster9, which contained a mixture of cells from different patients, cell-cycle did not drive clustering of the cells (FIG. 8A-FIG. 8D).

Figure 1F:
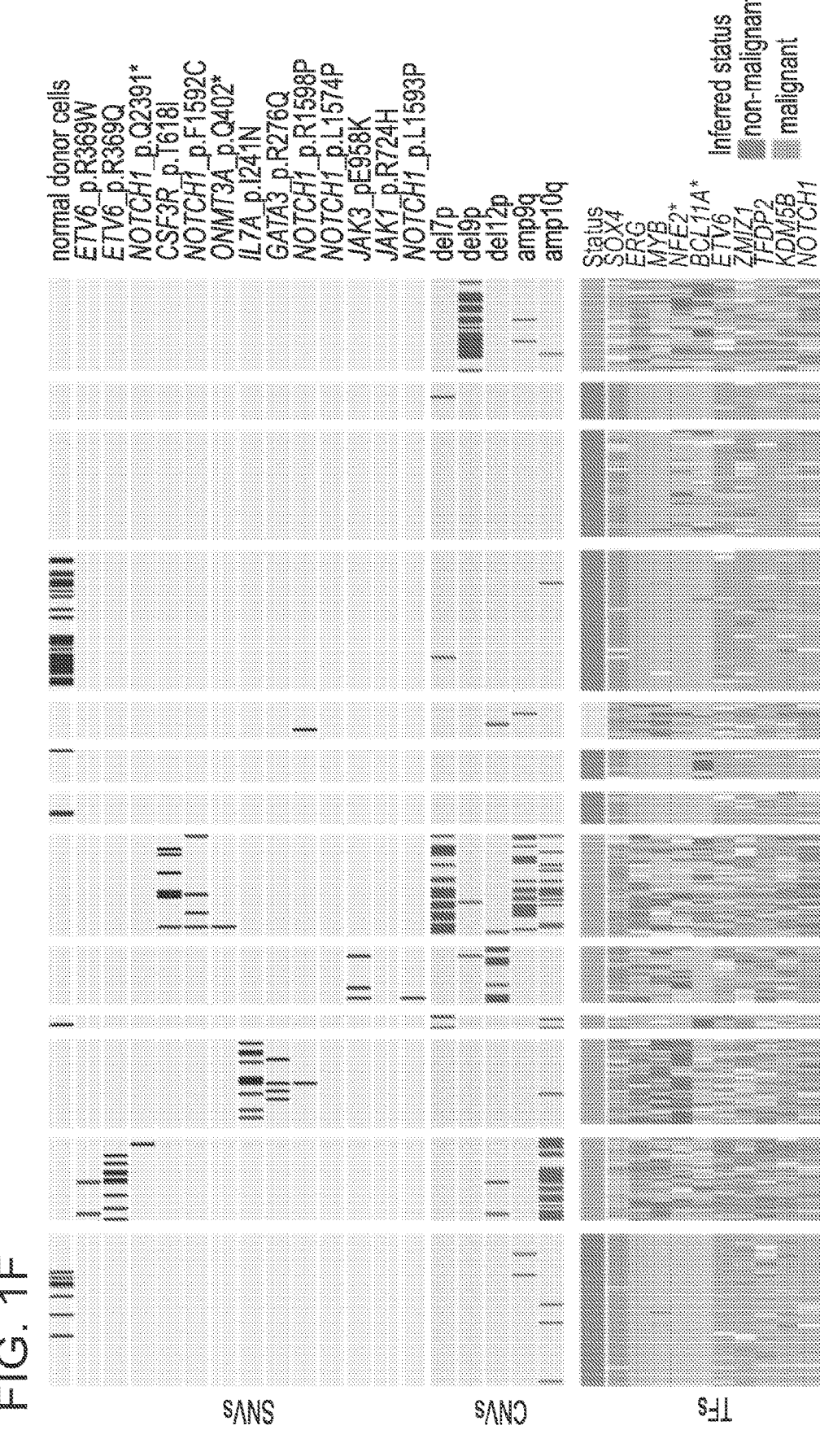
Figure 13A:
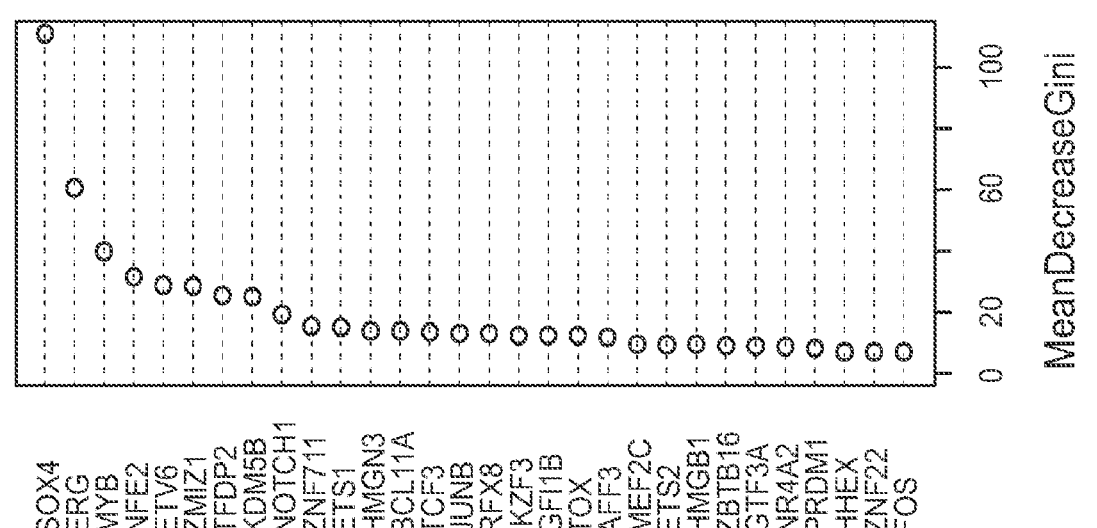
FIG. 13A-13B is a series of plots showing Random Forest Model trained on transcription factors.
Figure 13A:
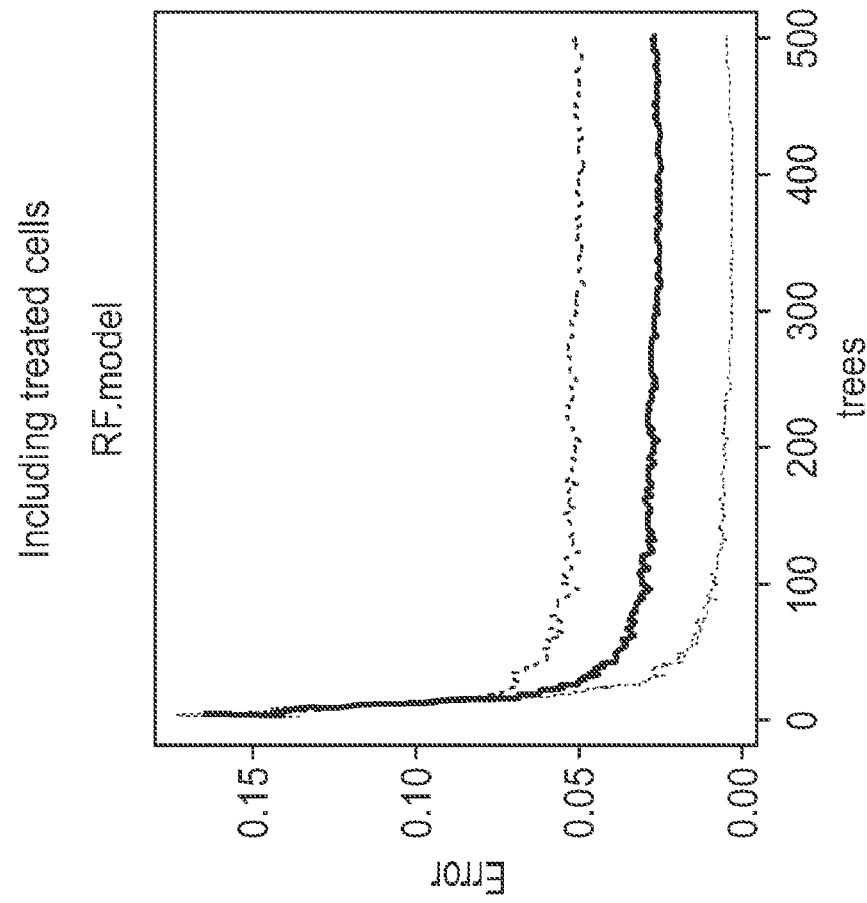
Figure 13B:
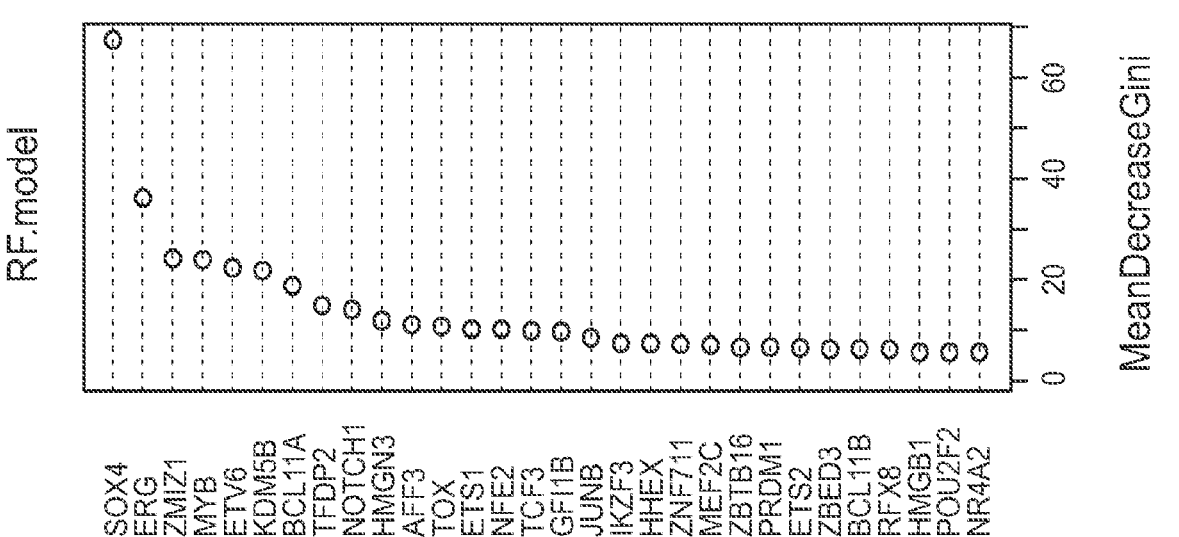
Figure 13B:
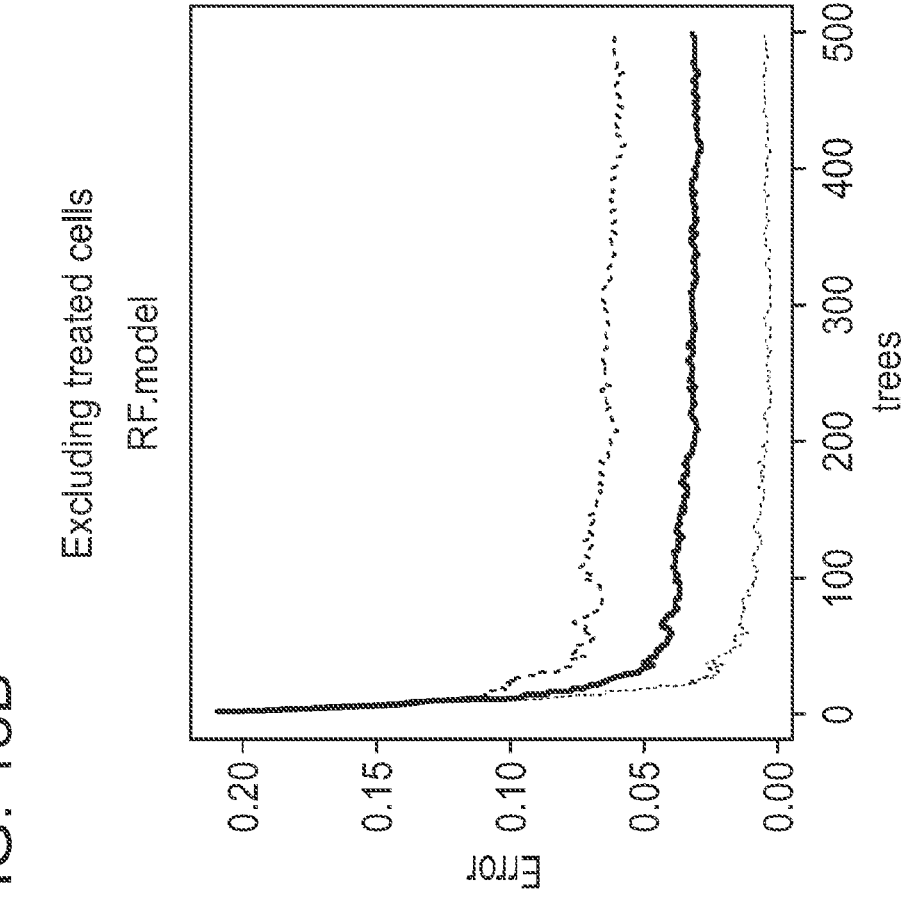

Since clusters 2, 3, 4, 5, 6, and 13 were specific to ETP T-ALL patients and not being seen in normal donors (FIG. 1B and FIG. 1C), it was hypothesized that these were malignant cells. Complementary approaches were employed to definitively distinguish malignant and non-malignant cells (FIG. 1F). First, mutect2 was used to look for tumor-specific pathogenic single nucleotide variants (SNVs) that were identified previously by targeted DNA-sequencing of bulk tumor cells as part of routine clinical work-up, and inferred copy number variants (CNVs) from all single-cells using inferCNV (Cibulskis et al., 2013 Nat Biotechnol, 31(3):213-219; Tirosh et al., 2016 Science, 352(6282):189-196; Kluk et al., 2016, J Mol Diagn, 18(4):507-515). SNVs and CNVs agreed well with clinical sequencing results and when combined were specific to the presumed malignant cell clusters (FIG. 1F, FIG. 9A-FIG. 9F, FIG. 10A-FIG. 10B; Table 1). Next, the presumed malignant clusters were examined for expression of key transcription factors with known roles in T-ALL (Liu et al., 2017 Nat Genet, 49(8):1211-1218; Aster et al., 2017 Annu Rev Pathol, 12:245-275). ETP T-ALL commonly exhibits deregulation of LMO2/LYL1, which is expressed in all of the presumed malignant clusters (FIG. II). The scRNA-seq profiles were compared to a cohort of 216 T-ALLs from the National Cancer Institute TARGET study. This revealed that the malignant clusters most closely resemble the ETP subset with deregulated LMO2/LYL1 (FIG. 12A-FIG. 12D). Lastly, a random forest model was employed to rank transcriptional regulators that differentiate malignant and non-malignant clusters (FIG. 1F, FIG. 13A-FIG. 13B). This identified several transcription factors with known function in T-ALL, i.e. NOTCH1, MYB, ERG, ETV6, ZMIZ (Weng et al., 2004 Science, 306(5694):269-271; Lahortiga et al., 2007 Nat Genet, 39(5):593-595; Thoms et al., 2011 Blood, 117(26):7079-7089; Van et al., 2011 J Exp Med, 208(13):2571-2579; Pinnell et al., 2015 Immunity, 43(5):870-883; Rakowski et al., 2013 Cancer Res, 73(2):930-941; Zhang et al., 2016 Nat Genet, (12):1481-1489; De Bie et al., 2018 Leukemia, 32(6):1358-1369). In addition, several transcriptional regulators that are master regulators of other hematopoietic lineages or malignancies were identified (TFDP2, erythroid lineage (Chen et al., 2014 Exp Hematol, (6):464-476 e465); KDM5B, dysregulated in AML and B-ALL (Wang et al., 2016 J Biol Chem, 291(8):4004-40180). SOX4 expression was the strongest predictor of malignant cells. SOX4 is aberrantly expressed in myeloid leukemias and has been implicated in B-ALL, but not T-ALL pathogenesis (Ramezani-Rad et al., 2013 Blood, 121(1):148-155). Thus, in addition to known transcriptional regulators in T-ALL, all five ETP-ALLs demonstrate expression of transcriptional regulators of other hematopoietic lineages, consistent with lineage infidelity.

Example 3

Figure 2A:
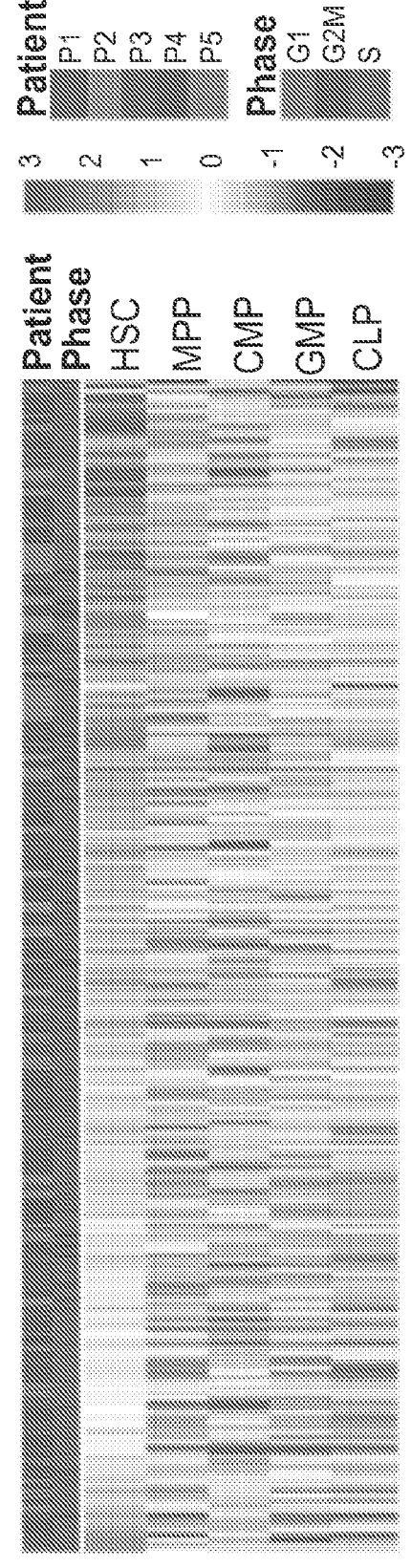
FIG. 2A-FIG. 2G are a set of plots and heatmaps showing that functional heterogeneity in ETP T-ALL reveals deranged developmental hierarchy with co-existing stem-like states and ineffectual lineage commitment.
Figure 2B:
Figure 2C:
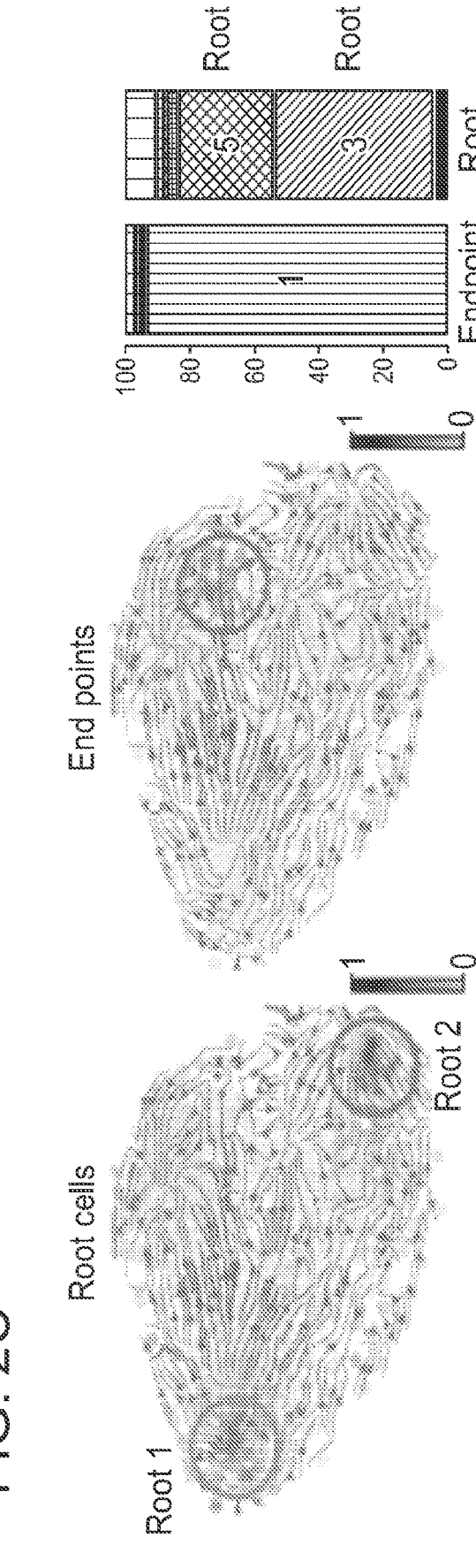
Figure 2D:
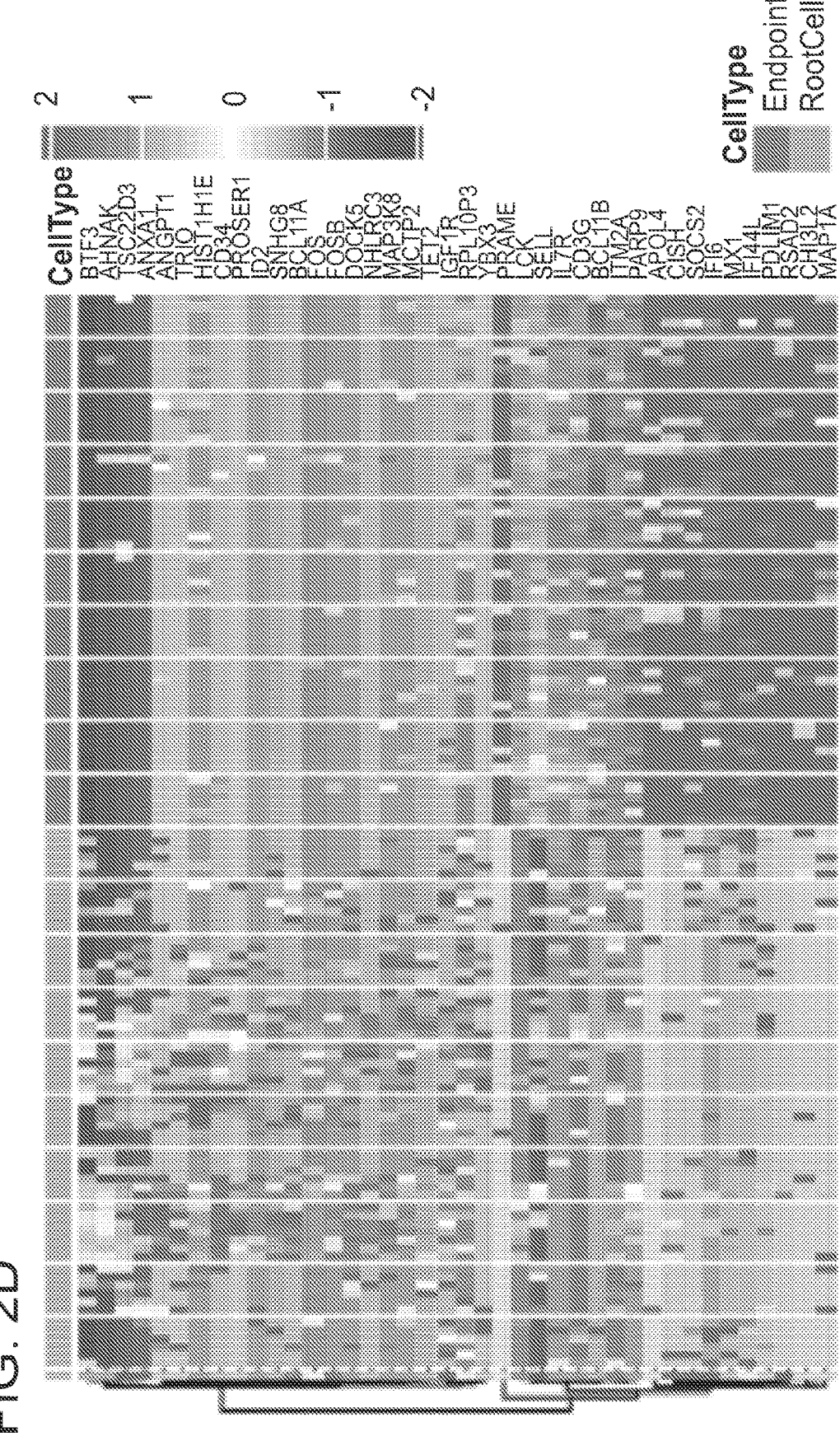
Figure 2E:
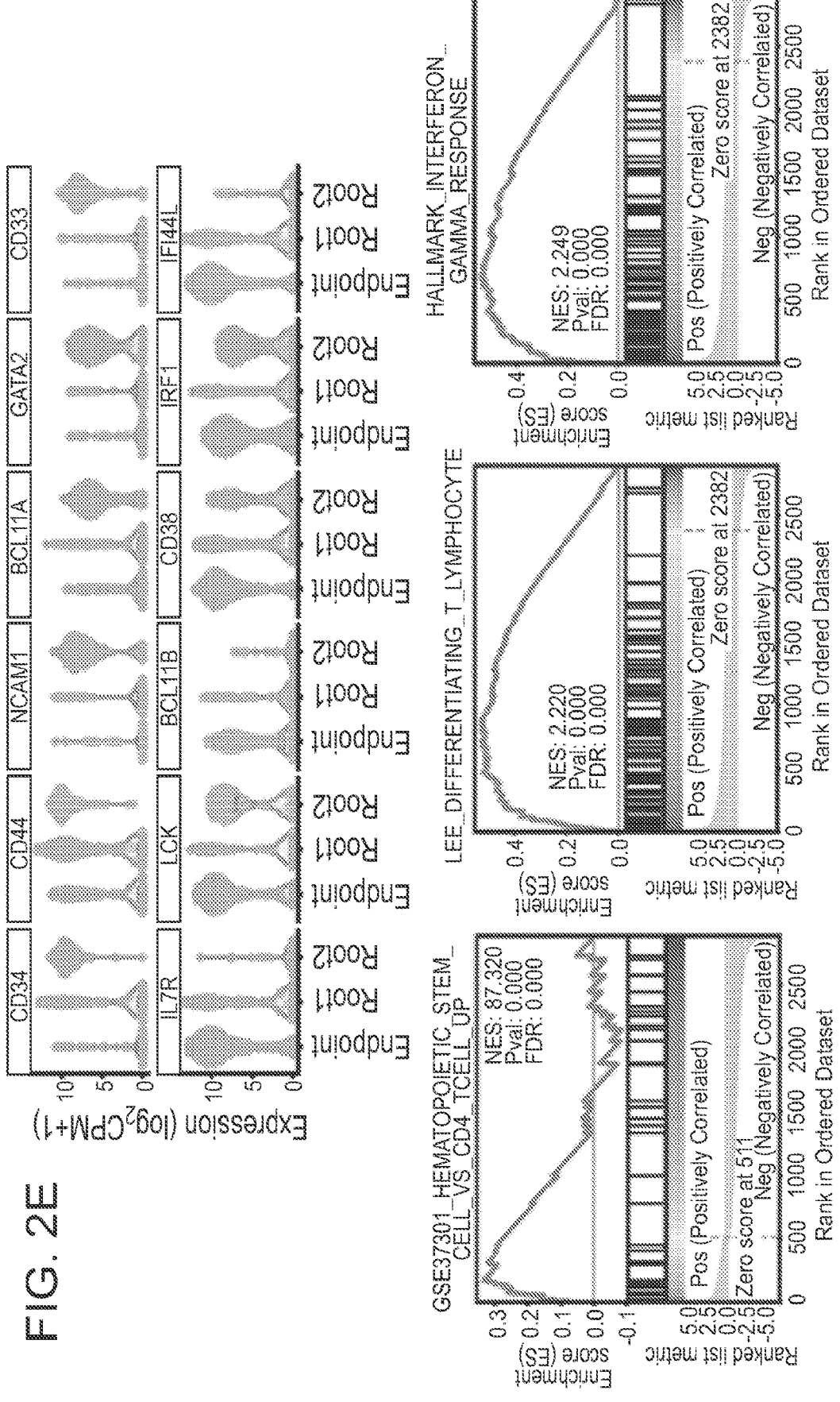

ETP T-ALL Exhibits Deranged Developmental Hierarchy with Ineffectual Lineage Commitment and Co-Existing Stem-Like States To further explore lineage infidelity within single-cells, expression of HSC (hematopoietic stem cell) and MPP (multipotent progenitor) signatures, as well as CMP (common myeloid progenitor), GMP (granulocyte-monocyte progenitor) and CLP (common lymphoid progenitor) early lineage commitment signatures, as defined by the BLUEPRINT consortium, was looked for in ETP T-ALL cells. This analysis revealed aberrant co-expression of multiple developmental signatures in almost all ETP T-ALL cells, with only a small fraction of cells demonstrating the complete absence of CLP or HSC signatures (FIG. 2A). While there is strong data for the existence of cancer stem cells in some solid tumors and AML, leukemia stem cells in ALL are much less studied (Park et al., 2019 Cell Stem Cell, 24(1):153-165 e157; Beck et al., 2013 Nat Rev Cancer, 13(10):727-738; Shlush et al., 2017 Nature, 547(7661):104-108). It was hypothesized that despite the co-expression of stem cell and lineage markers in almost all cells studied, there might be a subpopulation of cells with more robust stem-like features. To this end, t-SNE was used to cluster all leukemic cells based on expression of genes associated with hematopoietic stem and progenitor cell programs (FIG. 2B). RNA velocity was employed to identify cells along a trajectory of maturation based on the levels of unspliced/spliced transcripts (La et al., 2018 Nature, 560(7719):494-498). Velocity projections onto t-SNE dimensions revealed two immature root states and a single endpoint state (FIG. 2C). These states fall into distinct unsupervised clusters, suggesting that they are governed by discrete transcriptional circuits (FIG. 2C). Both root states are enriched for genes frequently associated with hematopoietic stem cells such as CD34, CD44, NCAM1, BCL11A, and GATA2 (Civin et al., 1984 J Immunol, 133(1):157-165; Cao et al., 2016 Haematologica, 101 (1):26-37; Luc et al., 2016 Cell Rep, 16(12):3181-3194; Katsumura et al., 2018 Proc Natl Acad Sci USA, 115(43):E10109-E10118; Sasca et al., 2019 Blood, 133(21):2305-2319; Wang et al., 2007 Haematologica, 92(3):300-307) (FIG. 2D, FIG. 2E). In contrast, the endpoint state is characterized by expression of genes associated with T-cell differentiation such as IL7R, LCK, BCL11B and CD38 (Carrette et al., 2012 Semin Immunol, 24(3):209-217; Palacios et al., 2004 Oncogene, 23(48):7990-8000; Hosokawa et al., 2018 Nat Immunol, 19(12):1427-1440; Munoz et al., 2003 J Biol Chem, 278(50):50791-50802), which are typically expressed at low levels in stem cells (FIG. 2D and FIG. 2E). Endpoint cells also demonstrate strong enrichment of signatures of immune modulation, marked by expression of IRF1, IFITM3, and IFI441 (FIG. 2D and FIG. 2E).

Figures 2F, 2G:
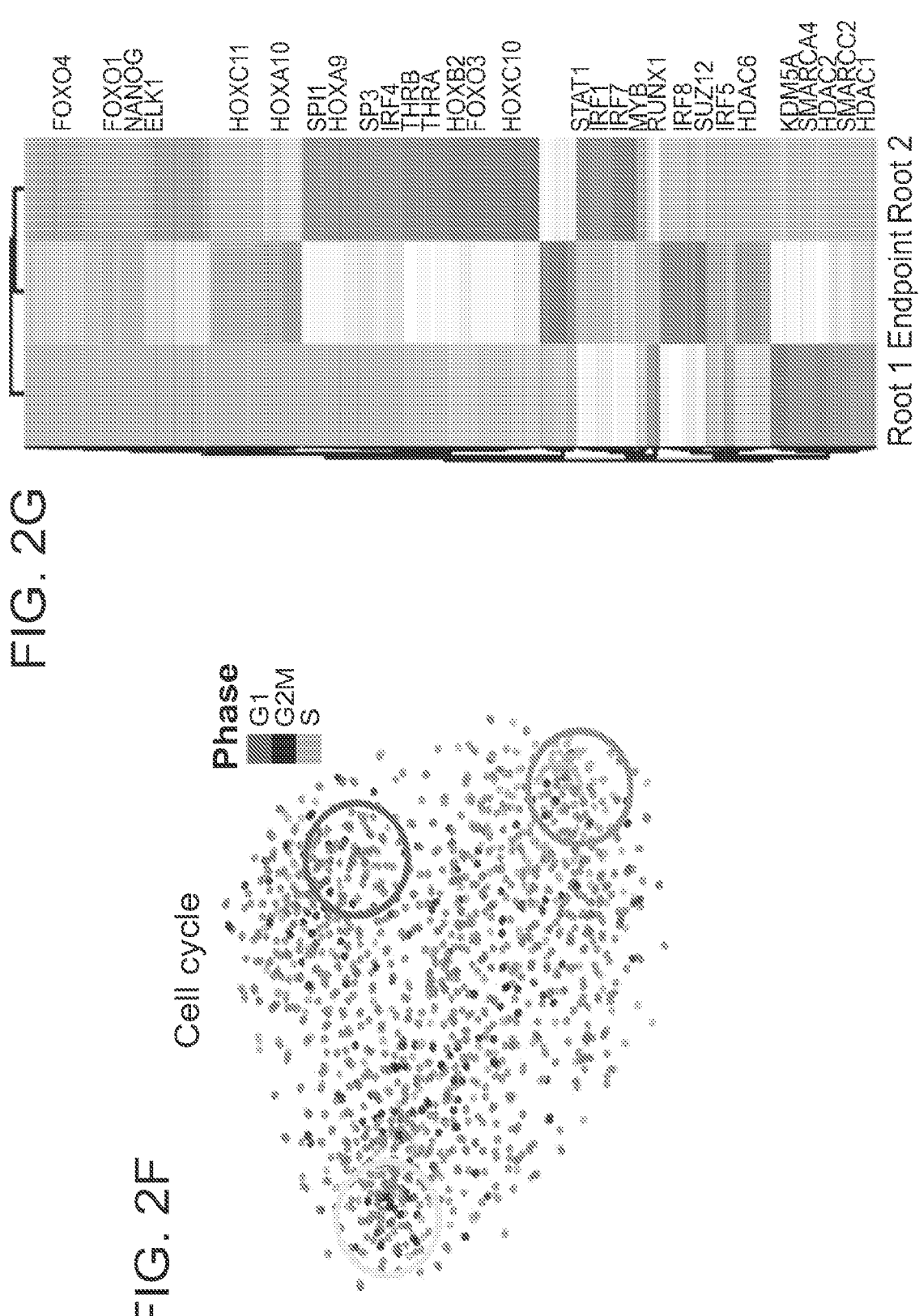

Next, the differences in the two root states were examined. Cell-cycle analysis demonstrated that cells in root1 are not cycling, whereas root2 cells are enriched for cells in S phase (FIG. 2F). It was reasoned that if these root states reflect distinct stem-like states, there should be distinct transcriptional regulators that drive each of these states. To this end, the most prominent transcriptional regulons were identified (transcription factor and its target genes) for each of the two root states using scenic (FIG. 2G). Non-cycling root1 cells were enriched for transcriptional regulators involved in stemness (NANOG, SP1, SP3), HOX genes, as well as AKT/MAPK signaling (FOXO1, THRA). In contrast, cycling root 2 cells are characterized by activity of several chromatin remodelers, including HDACs, SWI/SNF complex, and EZH2, as well as genes associated with glucocorticoid signaling. Of note, cells that did not belong to any of the two root states expressed transcriptional regulons driving immune modulation, including genes in the interferon pathway. Thus, ETP T-ALL cells not only demonstrate deranged developmental states with ineffectual lineage commitment, but also show two co-existing stem-like states that differ in their cell-cycle and transcriptional dependencies.

Figure 14A:
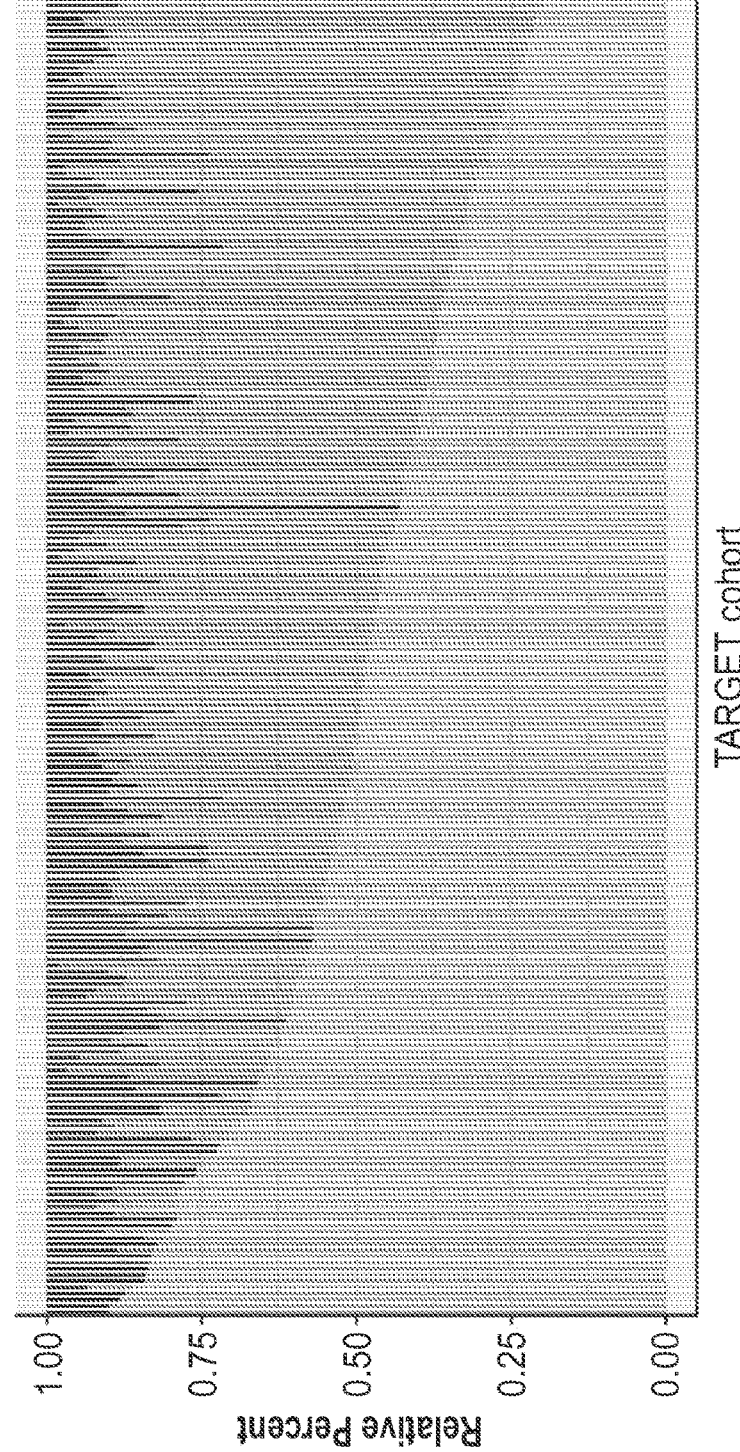
FIG. 14A-14B is a series of plots showing deconvolution of root and endpoint signatures in bulk RNA-seq data.
Figure 14B:
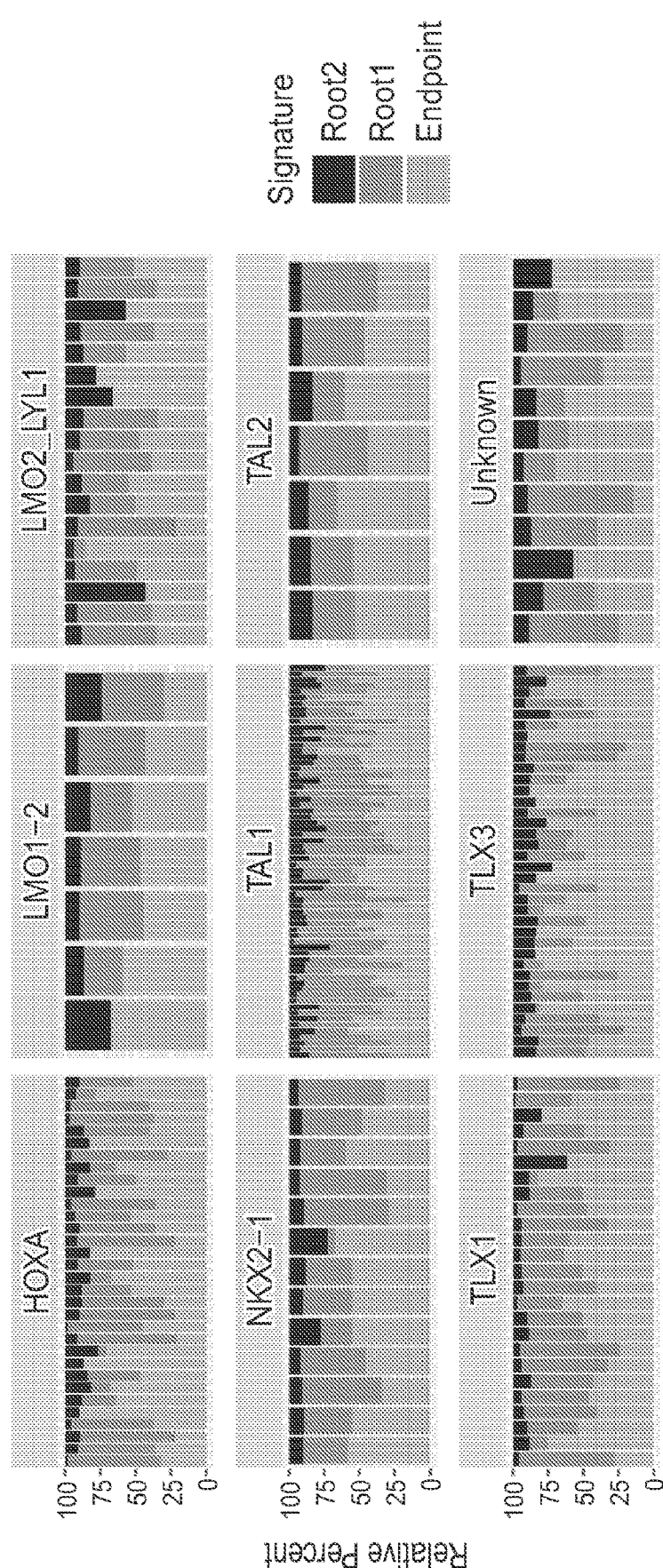
Figure 15F:
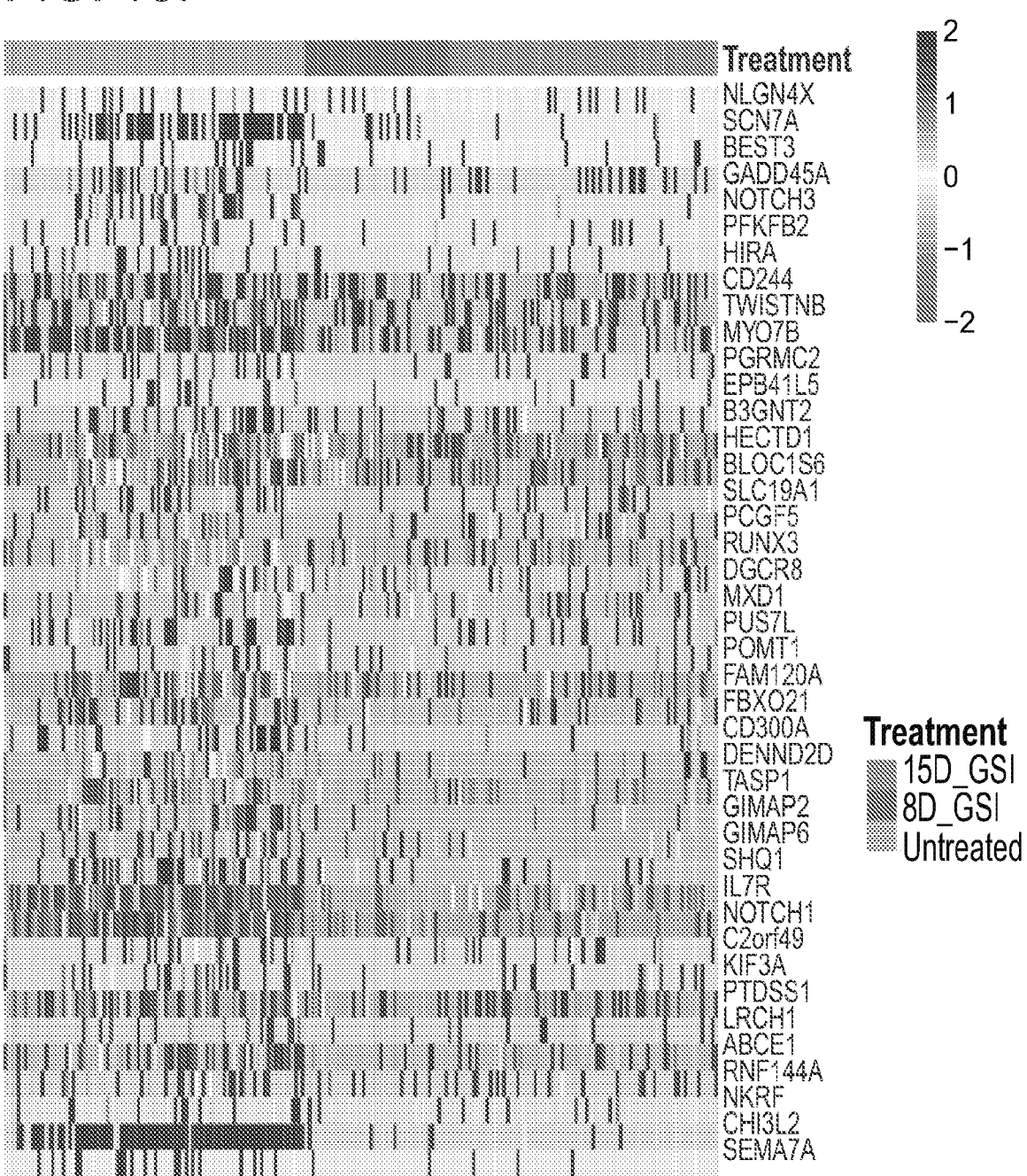
Figure 15G:
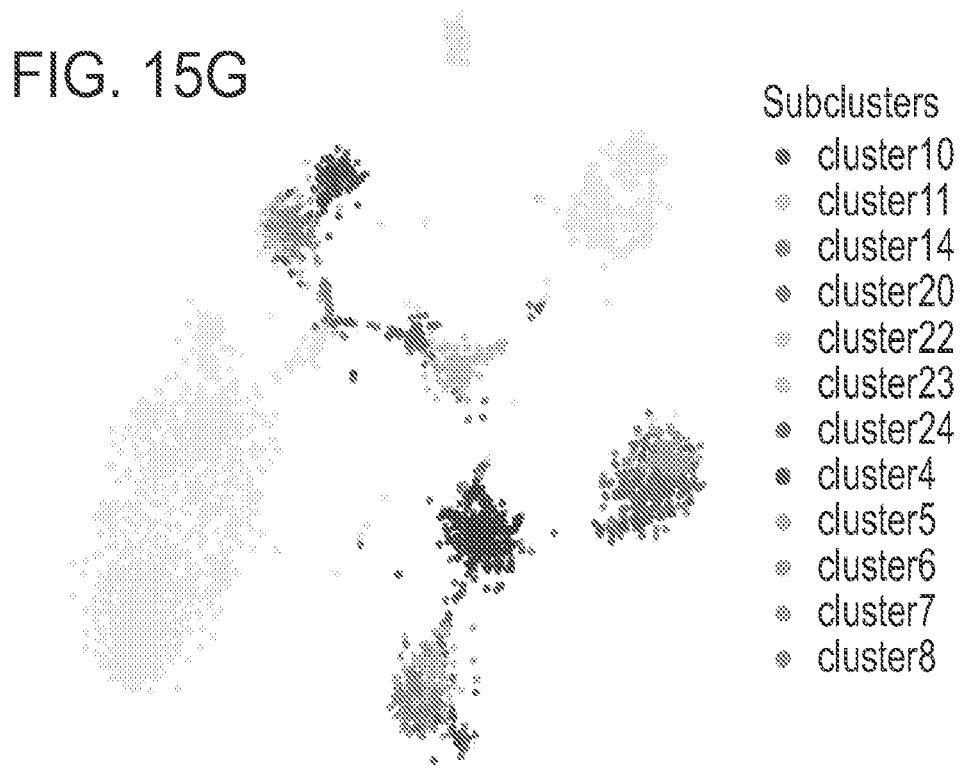
Figure 15H:
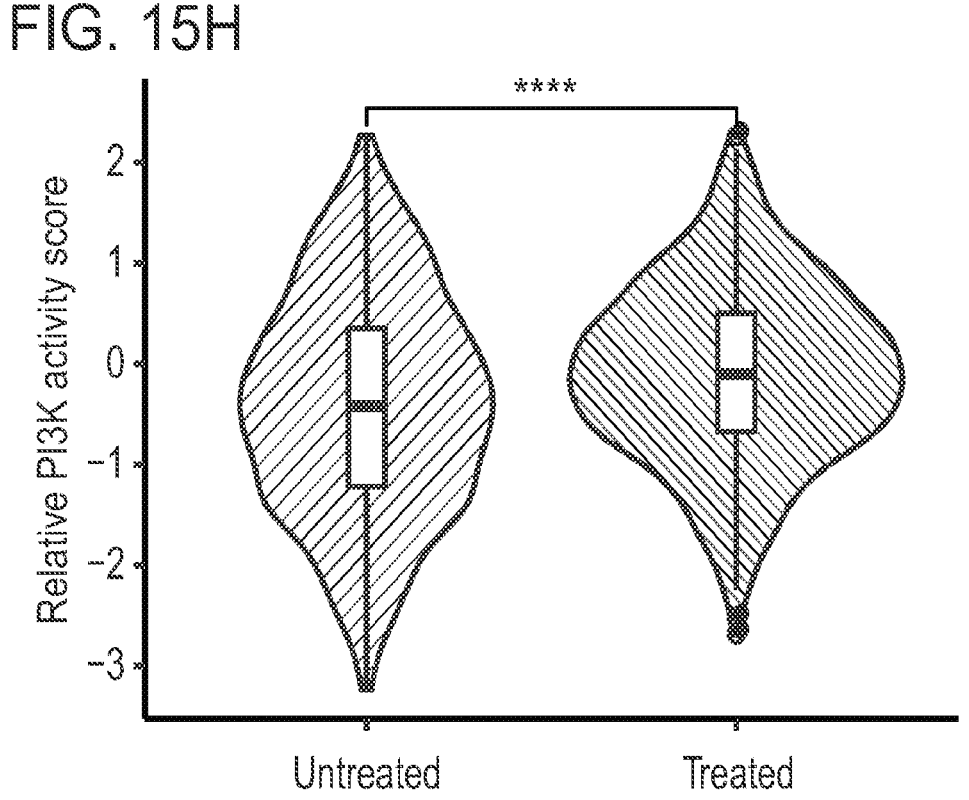
Figures 16A, 16B:
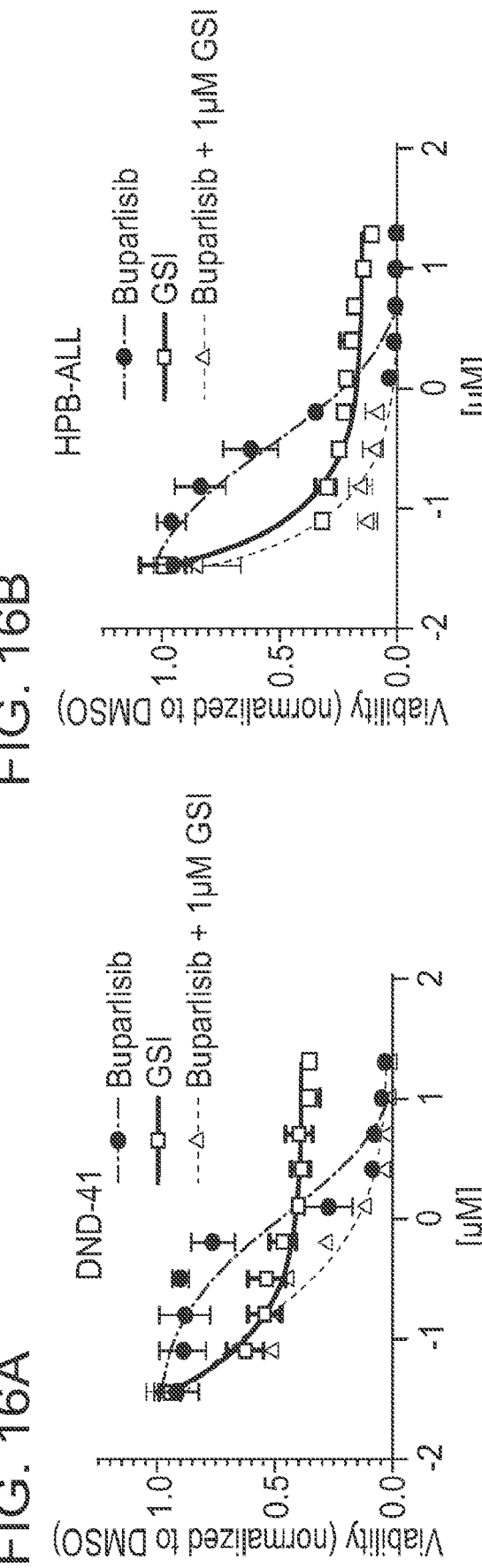
FIG. 16A-16E is a series of graphs showing inhibition of T-ALL proliferation by PI3K inhibitor is increased when combined with GSI. DND-41, HPB-ALL, KOPT-K1, Jurkat and Loucy T-ALL cell lines were treated with Buparlisib, GSI, Buparlisib with 1 μM of GSI or DMSO for 7 days. Dose response curves of cell viability normalized to DMSO are shown (datapoints are derived from 3 replicates each, error bars show standard deviation).
Figures 16C, 16D, 16E:
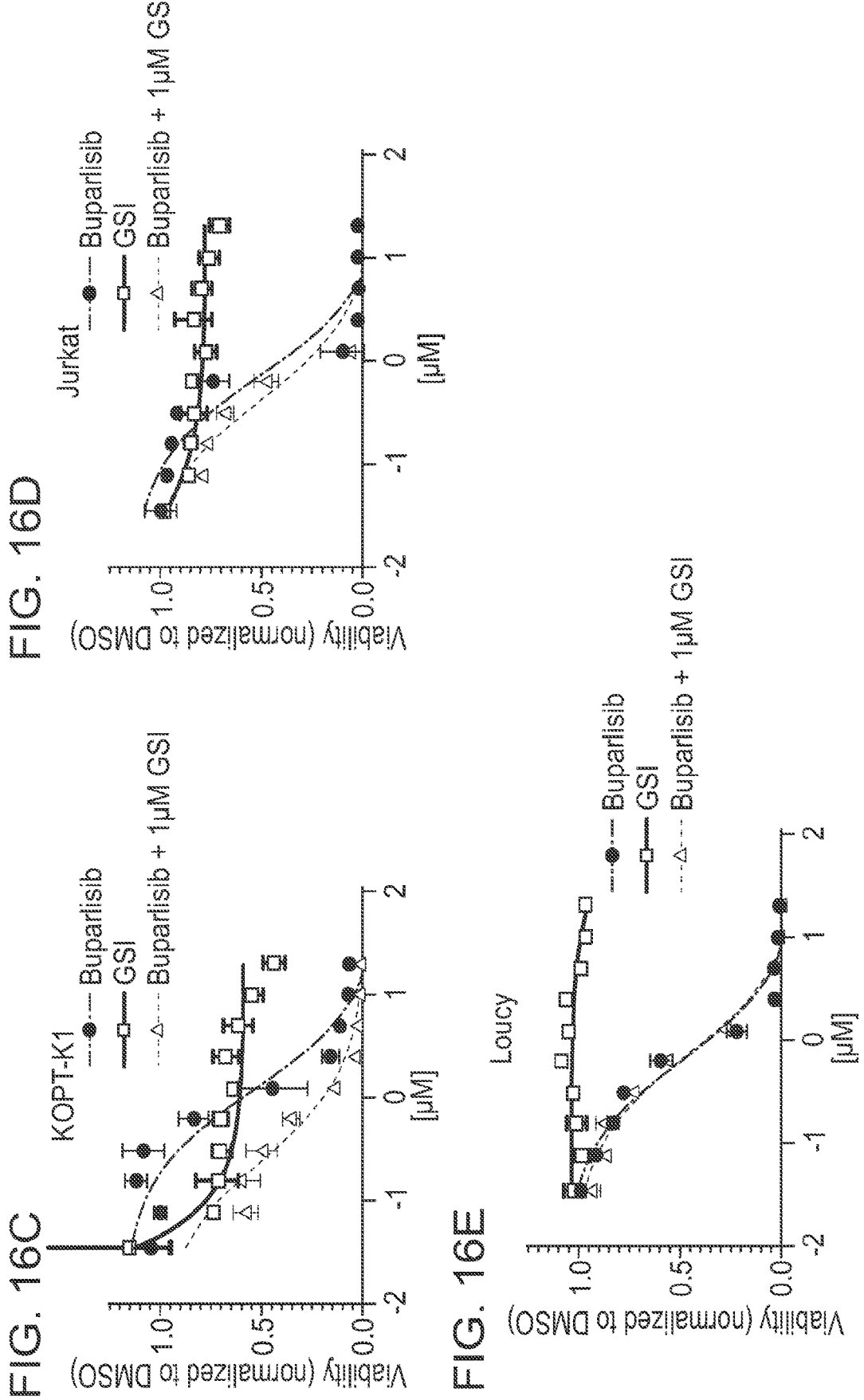

Lastly, it was validated whether distinct stem-like states are coexisting with more mature cells in a larger dataset of T-ALL. Markers were compiled for each of the three states from the differential gene expression analyses. CIBERSORT was employed (Newman et al., 2015 Nat Methods, 12(5): 453-457) to deconvolute bulk RNA-Seq data from 216 T-ALL patients from the TARGET dataset. This analysis demonstrated that co-existing stem-like states can be detected in the majority of T-ALLs, most prominently in the more immature subtypes (FIG. 14A-FIG. 14B).

Example 4

Figures 3A, 3B:
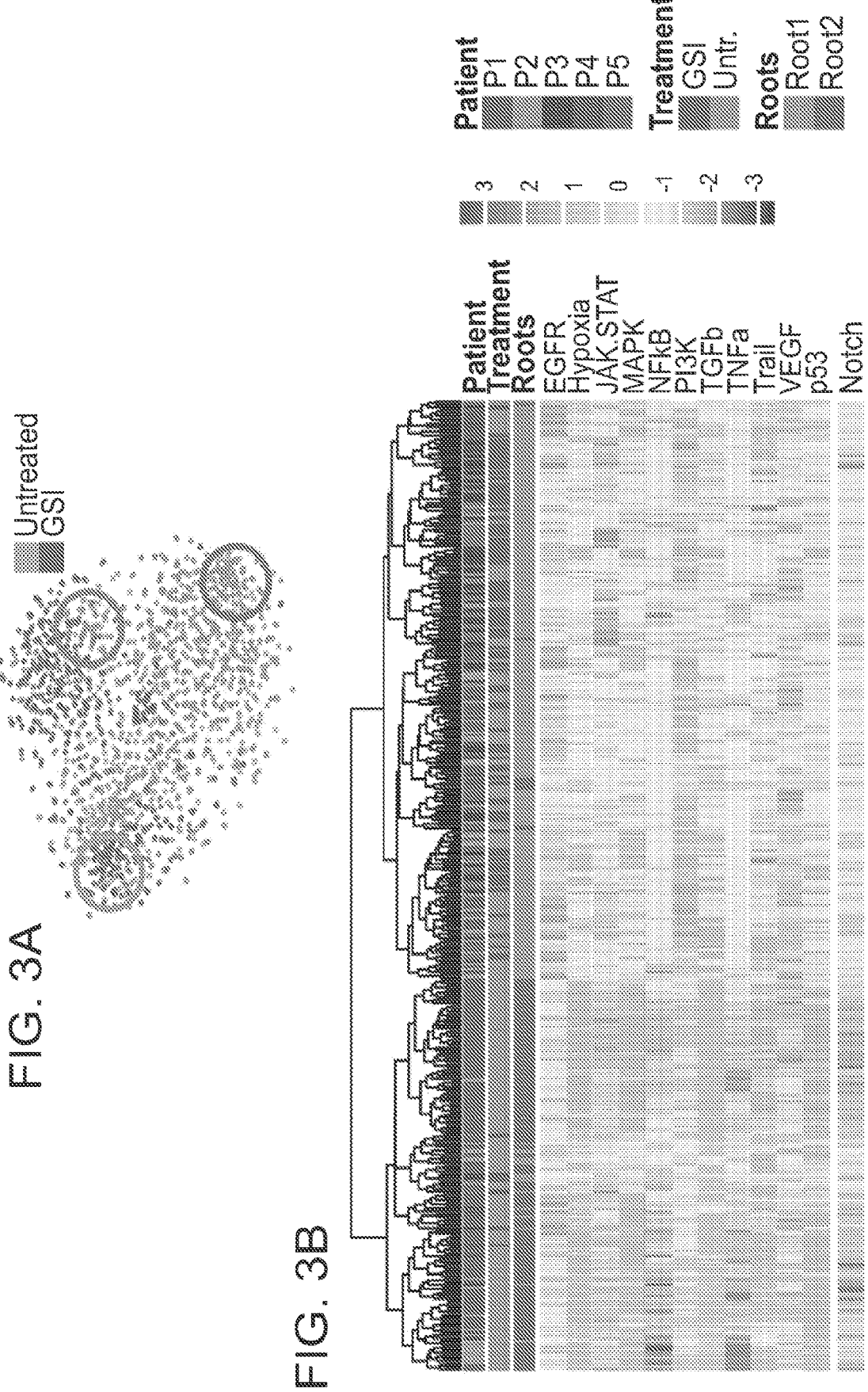
Figures 3C, 3D:
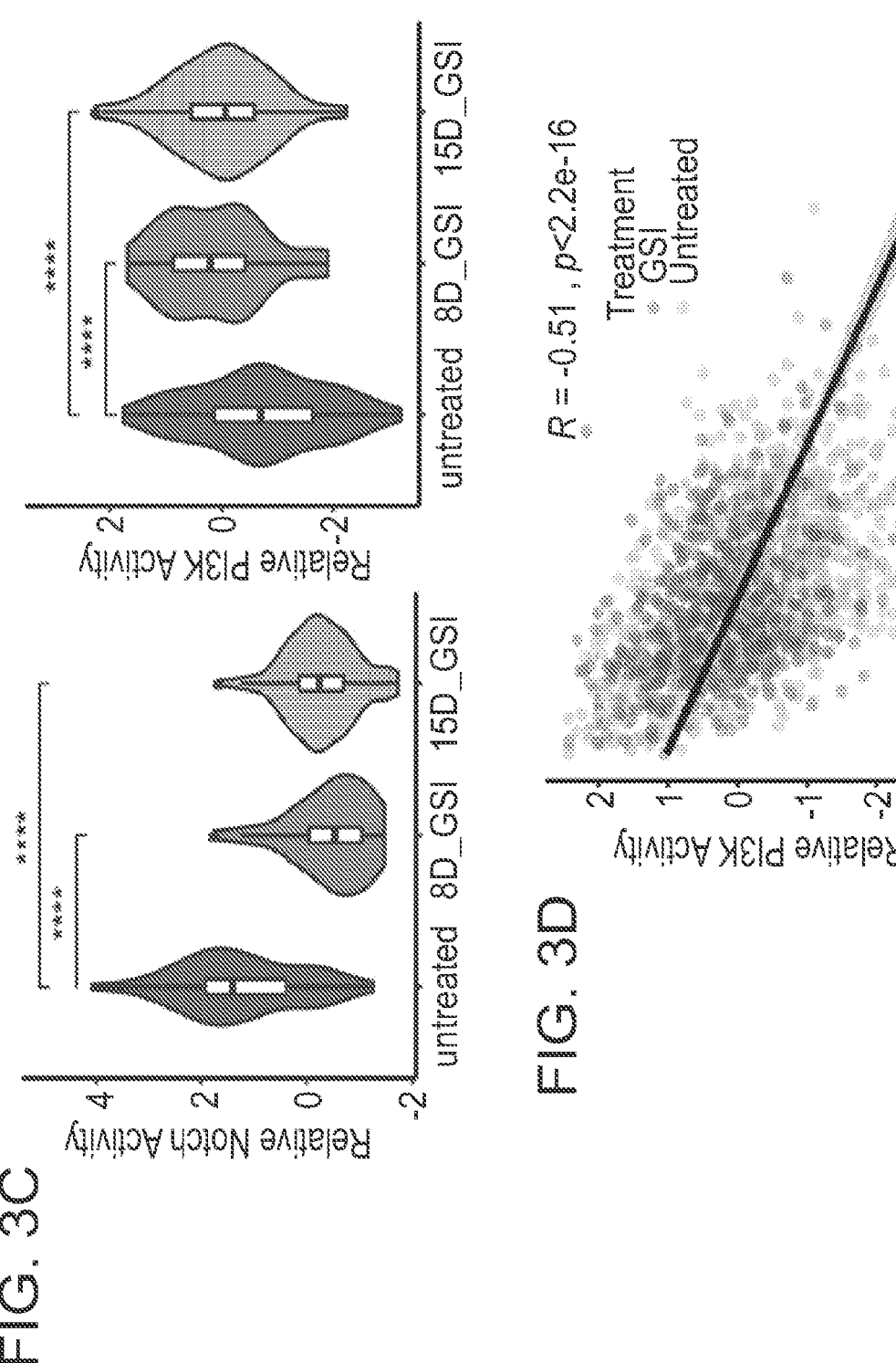

Stem-Like States are Characterized by Opposing Oncogenic Signaling Through Notch or PI3K The effects of Notch inhibition were next explored. Monotherapy directed at Notch with GSI infrequently induces complete remissions in T-ALL patients (Knoechel et al., 2014 Nat Genet, 46(4):364-370; Palomero et al., 2009 Clin Lymphoma Myeloma, 9 Suppl 3:S205-210; Knoechel et al., 2015 Cold Spring Harb Mol Case Stud, 1(1):a000539; Yashiro-Ohtani et al., 2014 Proc Natl Acad Sci USA., 111(46):E4946-4953; Cullion et al., 2009 Blood, 113(24): 6172-6181; Real et al., 2009 Nat Med, 15(1):50-58), suggesting that pre-existing GSI-resistant tumor cells are present in most cases. Cell cycle arrest and downregulation of Notch target genes was first confirmed in ETP T-ALL patients treated with GSI (FIG. 15A-FIG. 15H). It was hypothesized that persistence of a stem-like population might be the reason for the limited effects of Notch inhibitors in patients with relapsed/refractory Notch-mutant T-ALL. Indeed, while Notch inhibition abolishes the cycling stem-like root cells (root2), non-cycling root cells (root1) persist in the face of treatment with a Notch inhibitor (FIG. 3A).

Figures 24A, 24B:
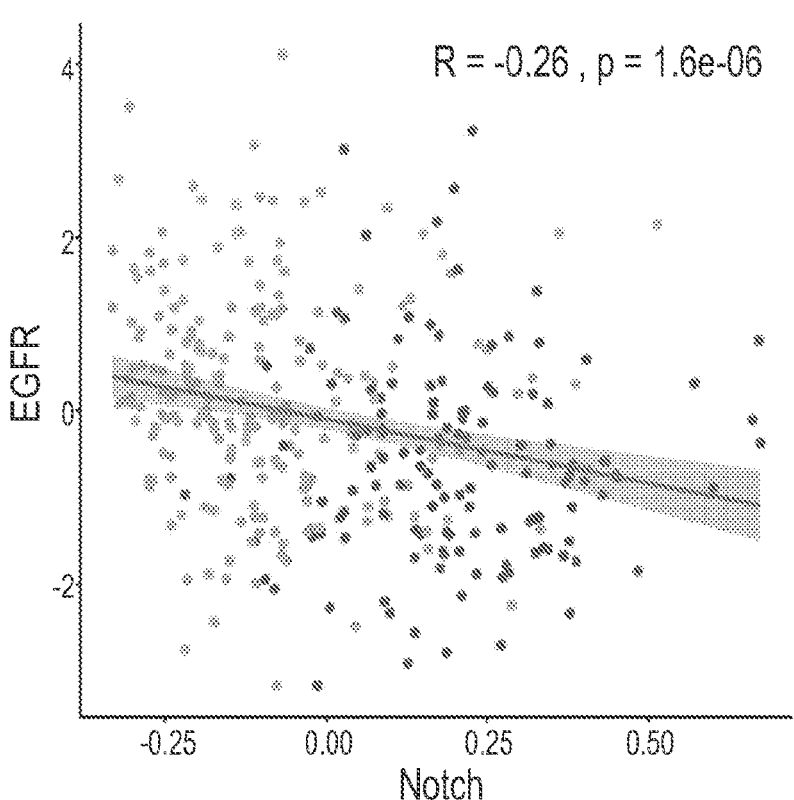
FIG. 24A-24K is a series of correlation plots of different oncogenic signaling pathway between root 1 and root 2 leukemic cells.
Figure 24C:
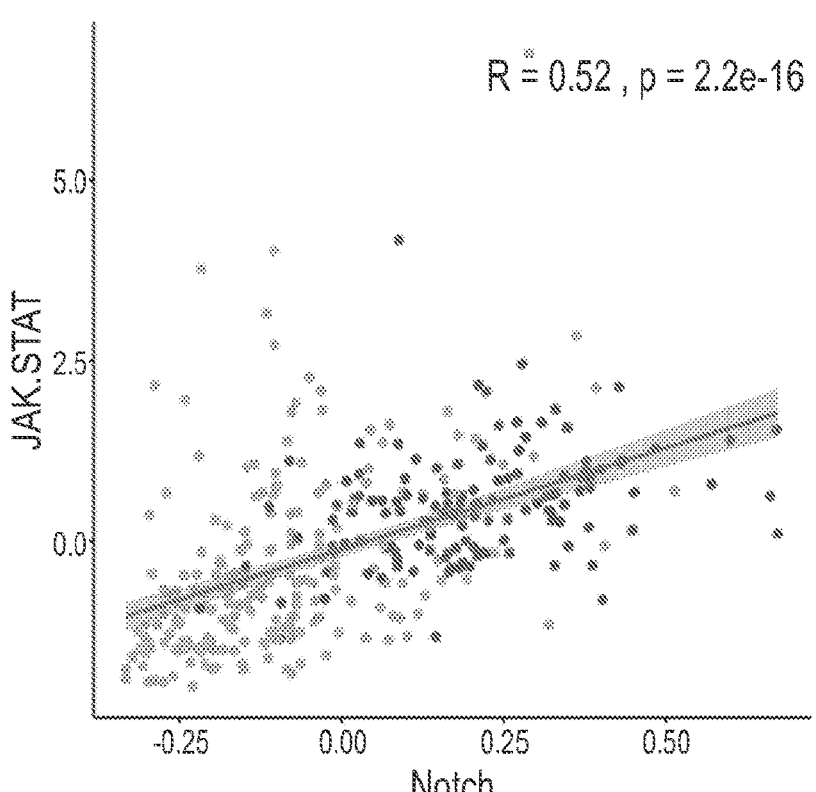
Figure 24D:
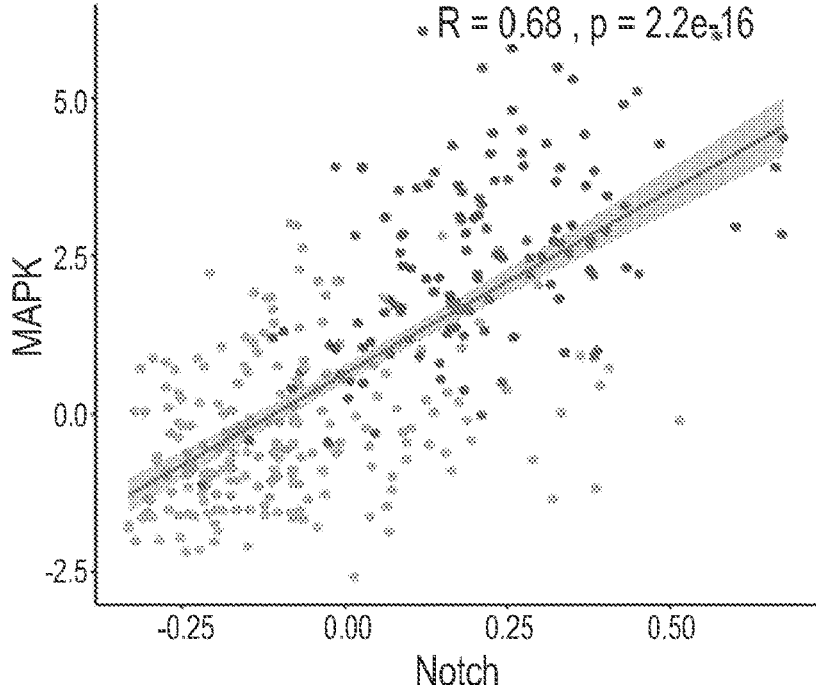
Figure 24E:
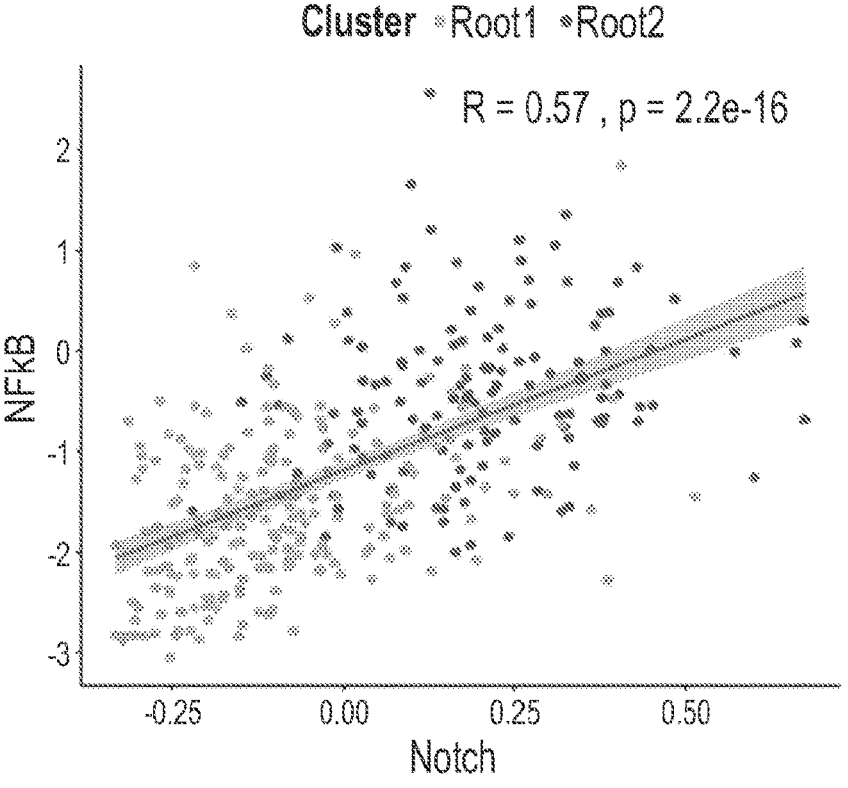
Figure 24F:
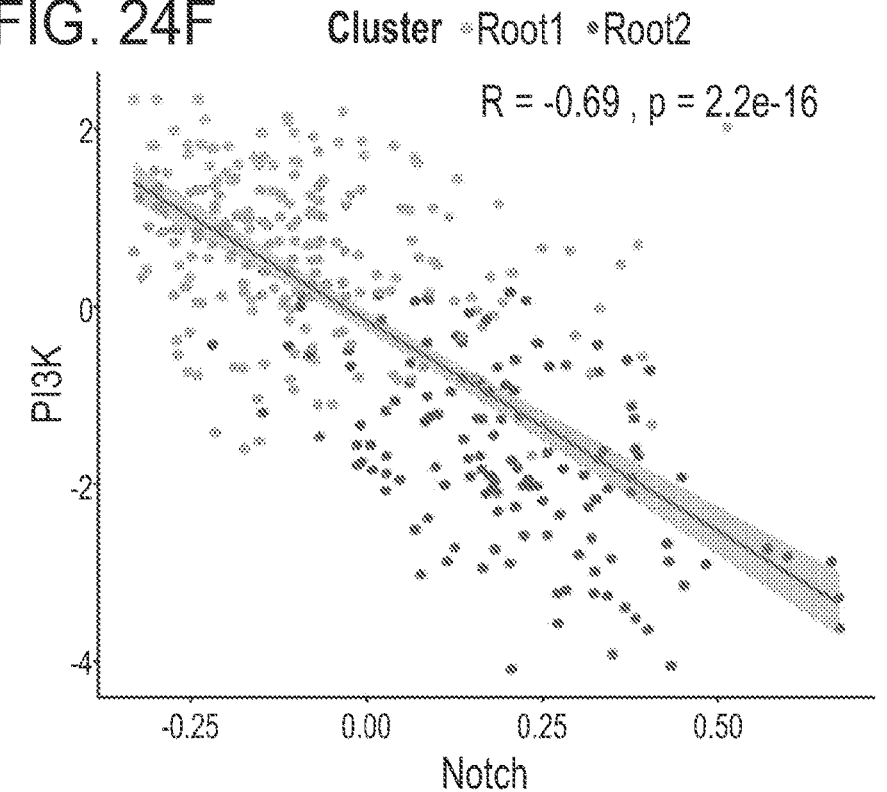
Figure 24G:
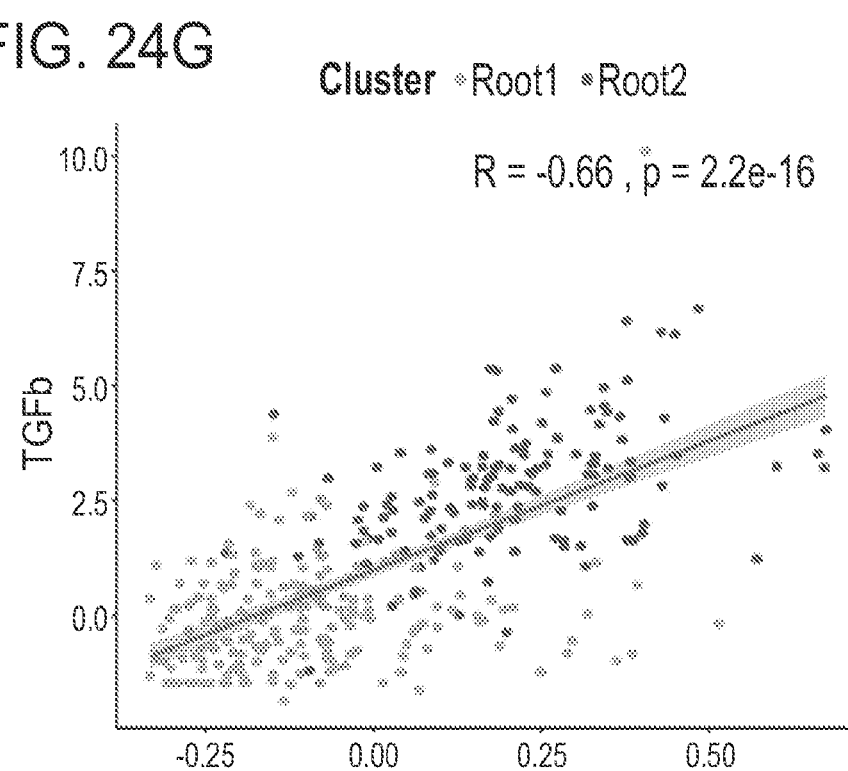
Figure 24H:
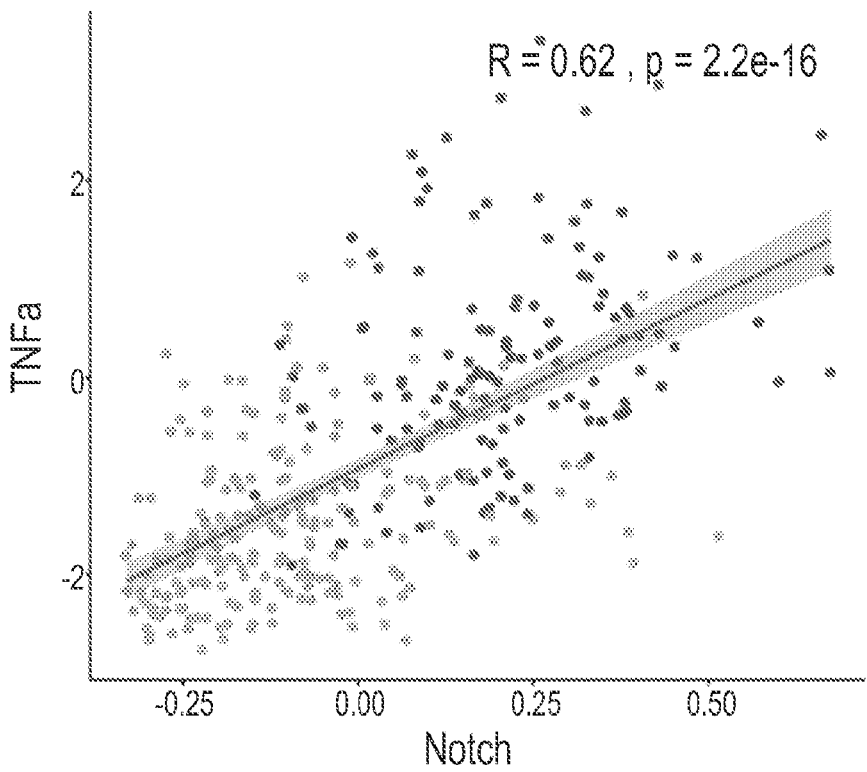
Figure 24I:
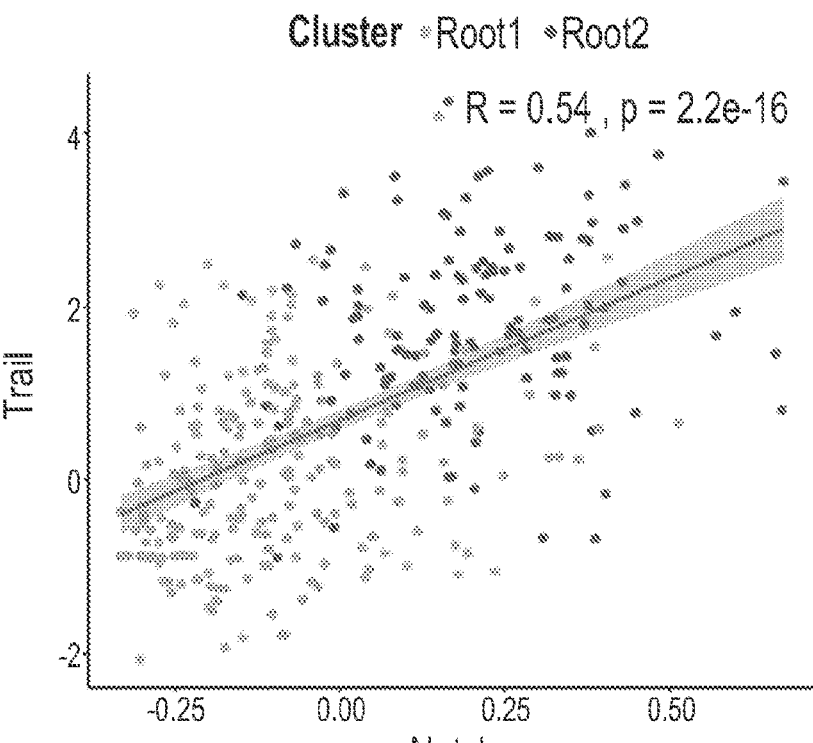
Figure 24J:
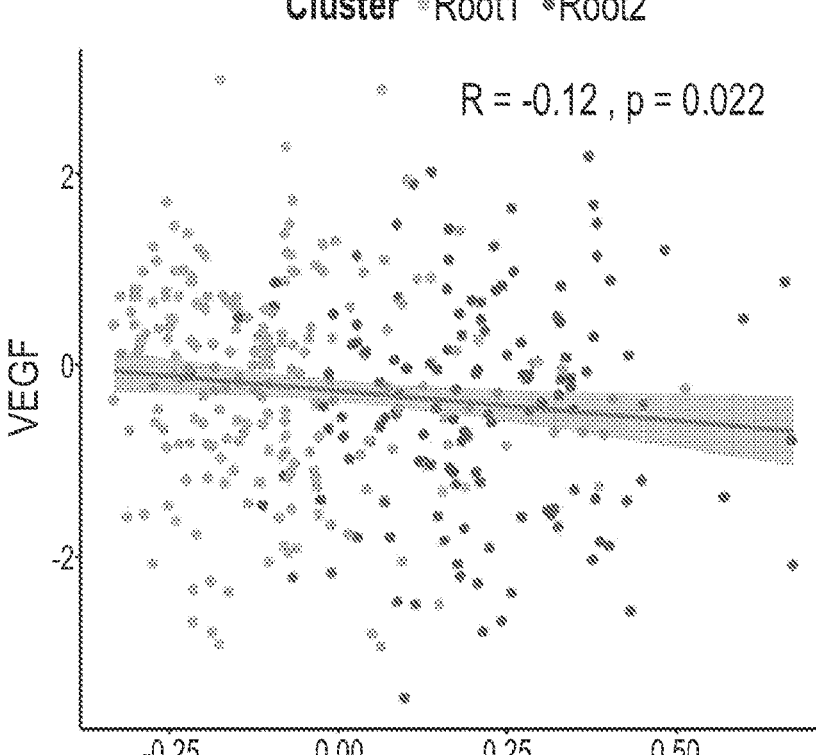
Figure 24K:
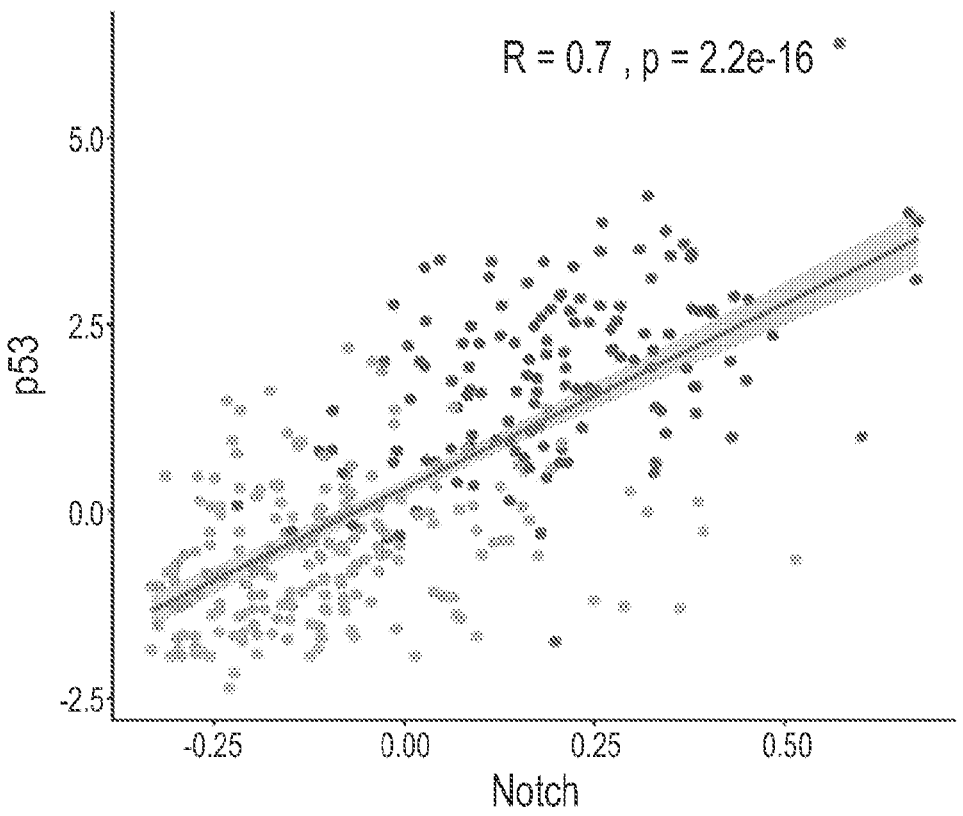

The dependencies of the non-cycling root cells was next investigated, which must involve pathways that are independent of Notch. To address this question, it was predicted the activity of signaling pathways from well-validated perturbation experiments using PROGENy (Schubert et al., 2018 Nat Commun, 9(1):20). Surprisingly, this analysis demonstrated PI3K as the pathway that is most anti-correlated with Notch signaling, as the PI3K signature is strongly enriched in non-cycling stem-like cells and virtually absent in the cycling stem-like cells (FIG. 3B, Table 3, FIG. 24A-24B).

TABLE 3

| Correlation scores of signaling pathways inferred by PROGENy with Notch activity in root 1 versus root 2 leukemic cells | | |
| --- | --- | --- |
| | Correlation | p-value |
| PI3K-Notch | −0.69 | p < 2.2e−16 |
| VEGF-Notch | −0.12 | 0.022 |
| EGFR-Notch | −0.26 | 1.60E−06 |
| Hypoxia-Notch | 0.75 | p < 2.2e−16 |
| MAPK-Notch | 0.68 | p < 2.2e−16 |
| p53-Notch | 0.7 | p < 2.2e−16 |
| TGFb-Notch | 0.66 | p < 2.2e−16 |
| JAK/STAT-Notch | 0.52 | p < 2.2e−16 |
| TNFa-Notch | 0.62 | p < 2.2e−16 |
| NFkB-Notch | 0.57 | p < 2.2e−16 |
| Trail-Notch | 0.54 | p < 2.2e−16 |

PI3K pathway activating mutations have been shown to be a genetic mechanism of Notch resistance in murine models (Dail et al., 2014 Nature, 513(7519):512-516; Palomero et al., 2007 Nat Med, 13(10):1203-1210), however, prior to the invention described herein, it was unclear how transcriptional rewiring contributes to Notch- and PI3K-dependencies. GSI treatment led to enrichment of cells with high PI3K signaling activity compared to untreated cells (FIG. 3C-FIG. 3D, FIG. 14A-FIG. 14B) PI3K-active versus Notch-active cells clustered separately by monocle2 (Trapnell et al., 2014 Nat Biotechnol, 32(4): 381-386) suggesting that they have distinct transcriptional states (FIG. 3E, FIG. 14A-FIG. 14B). Further analysis of the transcriptional dynamics of these subclusters, revealed two states with either high Notch activity or high PI3K activity with antagonistic differentiation trajectories by RNA velocity that both point toward a shared state with intermediate PI3K and Notch activity (FIG. 3E). Stem-like cells fall into either Notch-active or PI3K-active populations (FIG. 3F, correlation coefficient R=−0.7, p=2.2e-16), whereas endpoint state cells are enriched at the interface with no correlation between Notch and PI3K activity (FIG. 3H, R=−0.28, p=1.2e-07). With treatment, the subclusters with high PI3K activity dominate, but without any change in their differentiation trajectory towards the intermediate end-point state at the interface (FIG. 3G). Combined targeting of Notch and PI3K signaling may thus specifically target both stem-like states but might be less effective on more mature leukemic cells.

Example 5

Figures 4A, 4B, 4C:
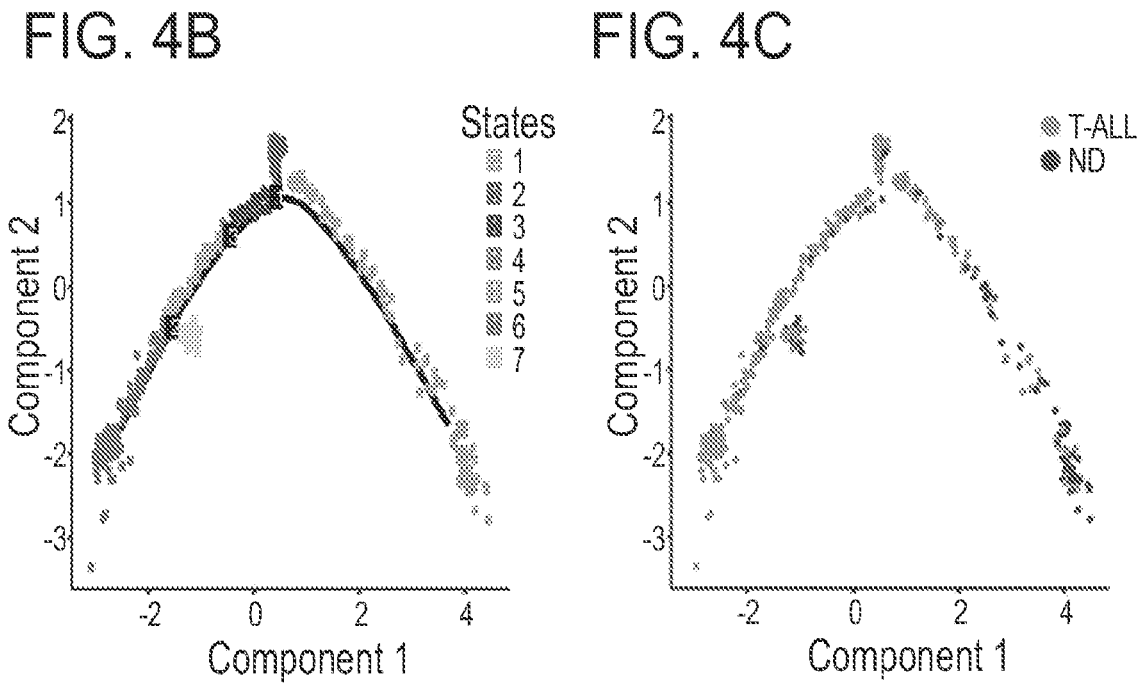
FIG. 4A-FIG. 4F are set of plots and a heatmap showing that CD8+ T cell dysfunction in ETP T-ALL.
Figure 4D:
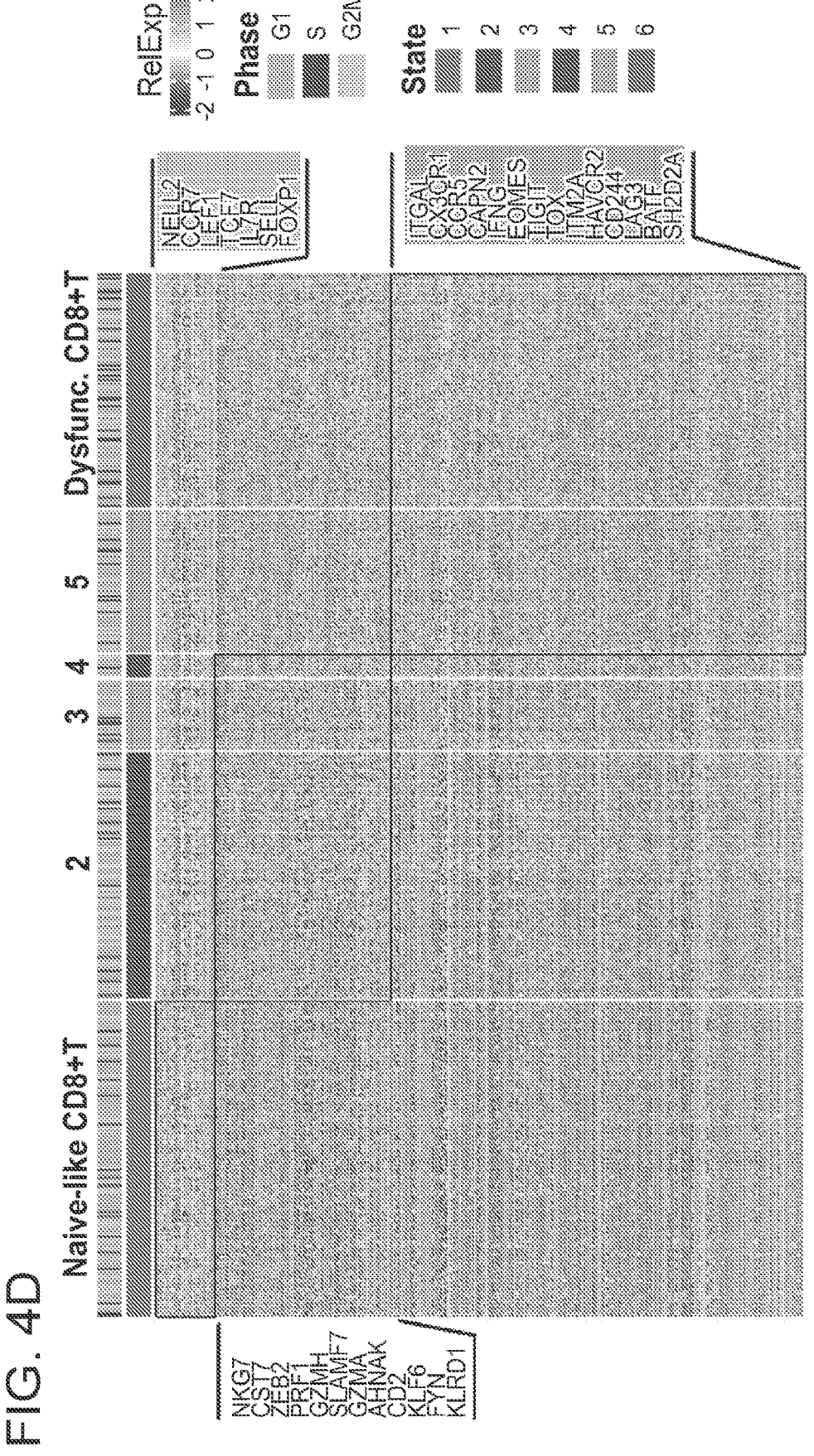
Figure 4F:
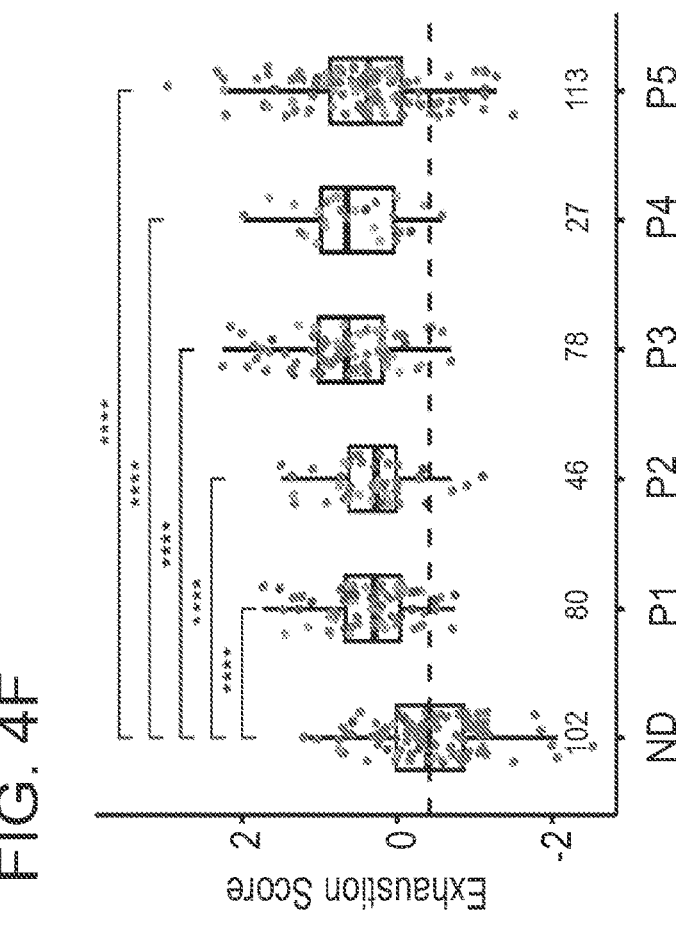
Figure 4E:
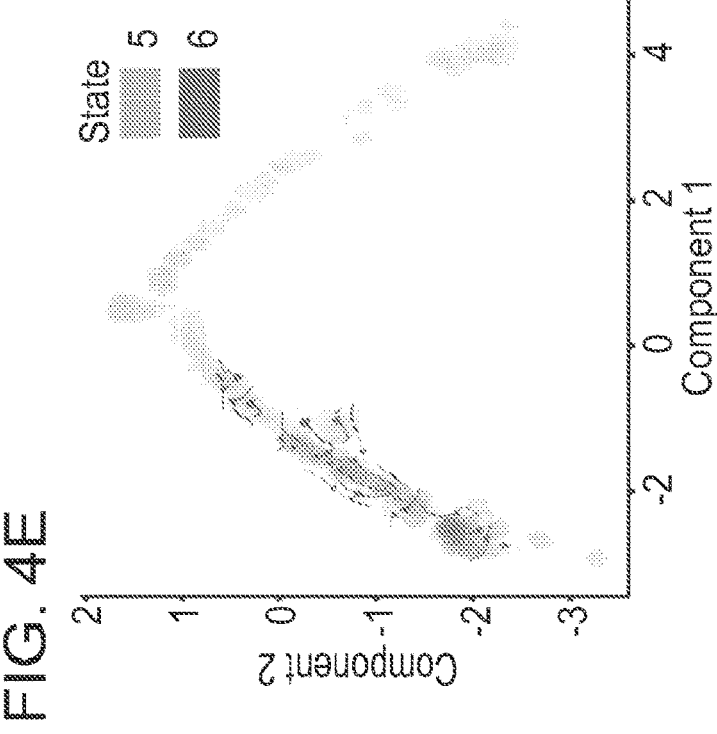

Immune Evasion Due to Galectin-9—HAVCR2 Interactions in the Leukemia Microenvironment The analyses so far suggest that the two dominant stem-like populations in ETP T-ALL can be targeted successfully by Notch and PI3K inhibition (FIG. 16A-FIG. 16E). However, the endpoint population that does not belong to any of the two root states (FIG. 2C) may escape Notch/PI3K inhibition. This population is more mature and harbors active transcriptional regulons driving immune modulation (FIG. 2D and FIG. 2E), indicating an unexpected interaction of leukemic cells with the immune microenvironment. Interestingly, this population carries prominent interferon signatures suggesting a particular role for T-cells (Marrack et al., 1999 J Exp Med, 189(3):521-530). It was assessed whether ETP T-ALL was associated with an altered T-cell function in the immune microenvironment. Interestingly, the T-cell receptor (TCR) repertoire of endogenous T cells in the leukemic patients was skewed toward oligoclonal TCR usage when comparing to normal donor T-cells (FIG. 4A). It was hypothesized that oligoclonal TCR usage reflects the presence of an expanded population of dysfunctional CD8$^+$ T-cells, as has been demonstrated in the microenvironment of several other malignancies (Tirosh et al., 2016 Science, 352(6282):189-196); Miller et al., 2019 Nat Immunol, 20(3):326-336). To determine CD8$^+$ T-cell differentiation states, an unsupervised pseudotime analysis was performed using monocle2 (Trapnell et al., 2014 Nat Biotechnol, 32(4):381-386) and identified six T-cell states that developed along a common trajectory (FIG. 4B). State 1 consisted mostly of CD8$^+$ T-cells from normal donors that expressed markers characteristic of naïve CD8$^+$ T-cells (CCR7, IL7R, NELL2, SELL, TCF7) (FIG. 4C-FIG. 4D). T-cells demonstrated gradually increased expression of activation markers from state2 through state4. In contrast, states5 and 6 contained mostly patient CD8$^+$ T-cells that exhibited increased expression of markers of T-cell exhaustion (PDCD1, TIGIT, LAG3, HAVCR2, CD244) when comparing state5 and state6, suggesting that these cells might be undergoing worsening dysfunction (FIG. 4D). Indeed, RNA velocity analyses confirmed the differentiation directionality from state5 toward the more dysfunctional state6 (FIG. 4E). To determine the extent of exhaustion, T-cell exhaustion scores were analyzed in all single CD8$^+$ T-cells (Tirosh et al., 2016 Science, 352(6282):189-196). High exhaustion scores were predominantly found in cells that showed oligoclonal TCR usage from ETP-ALL patients, whereas CD8$^+$ T-cells with high exhaustion scores were much less prevalent in normal donors (FIG. 4F).

Figure 5A:
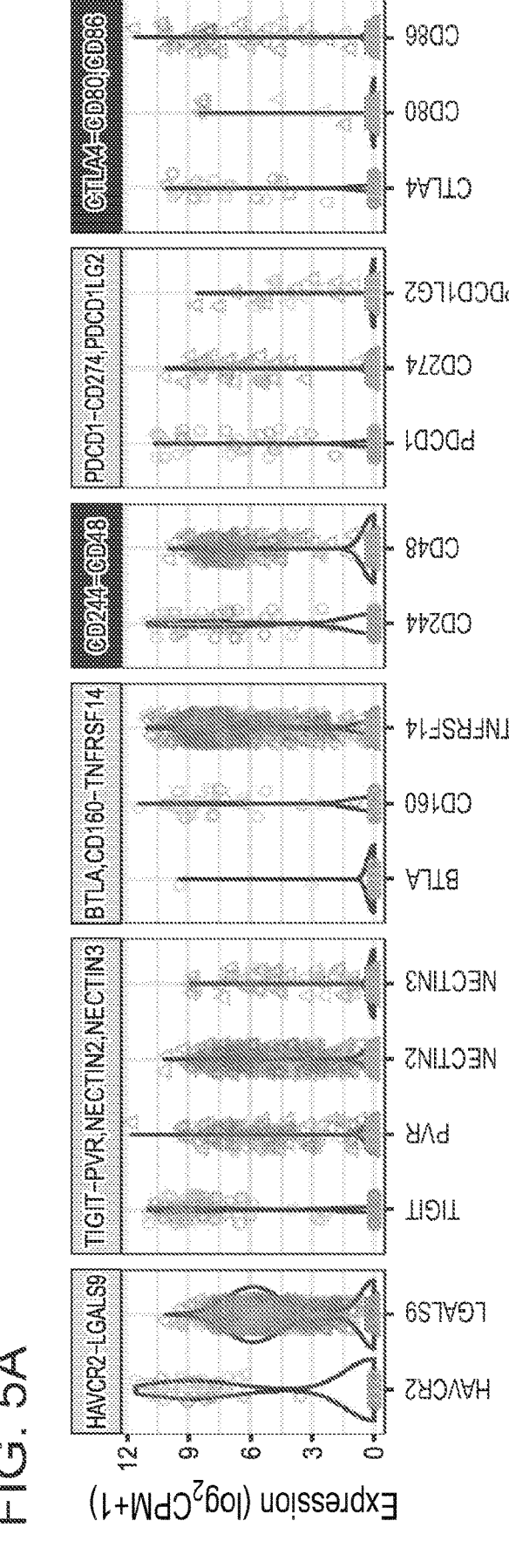
Figure 17A:
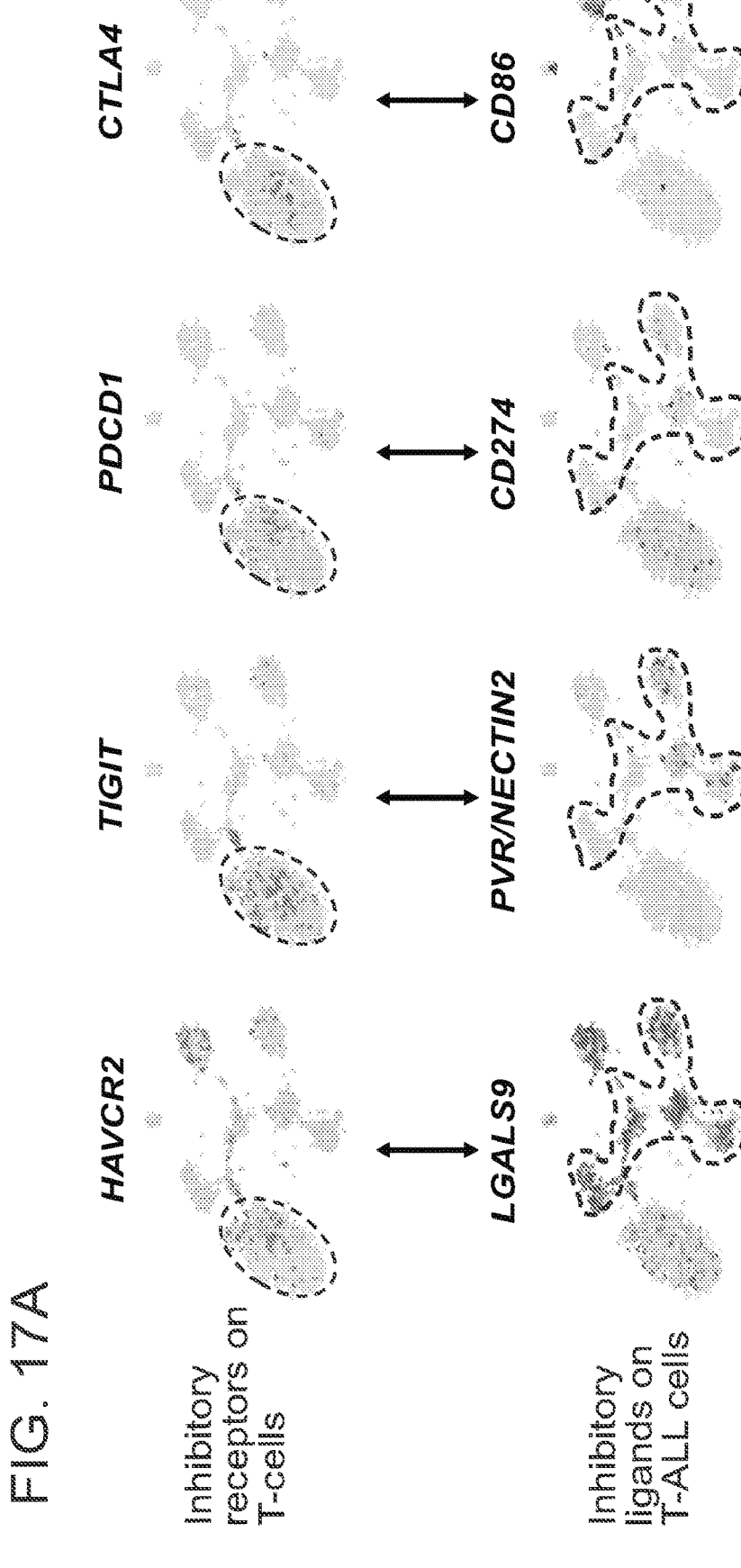
Figure 17B:
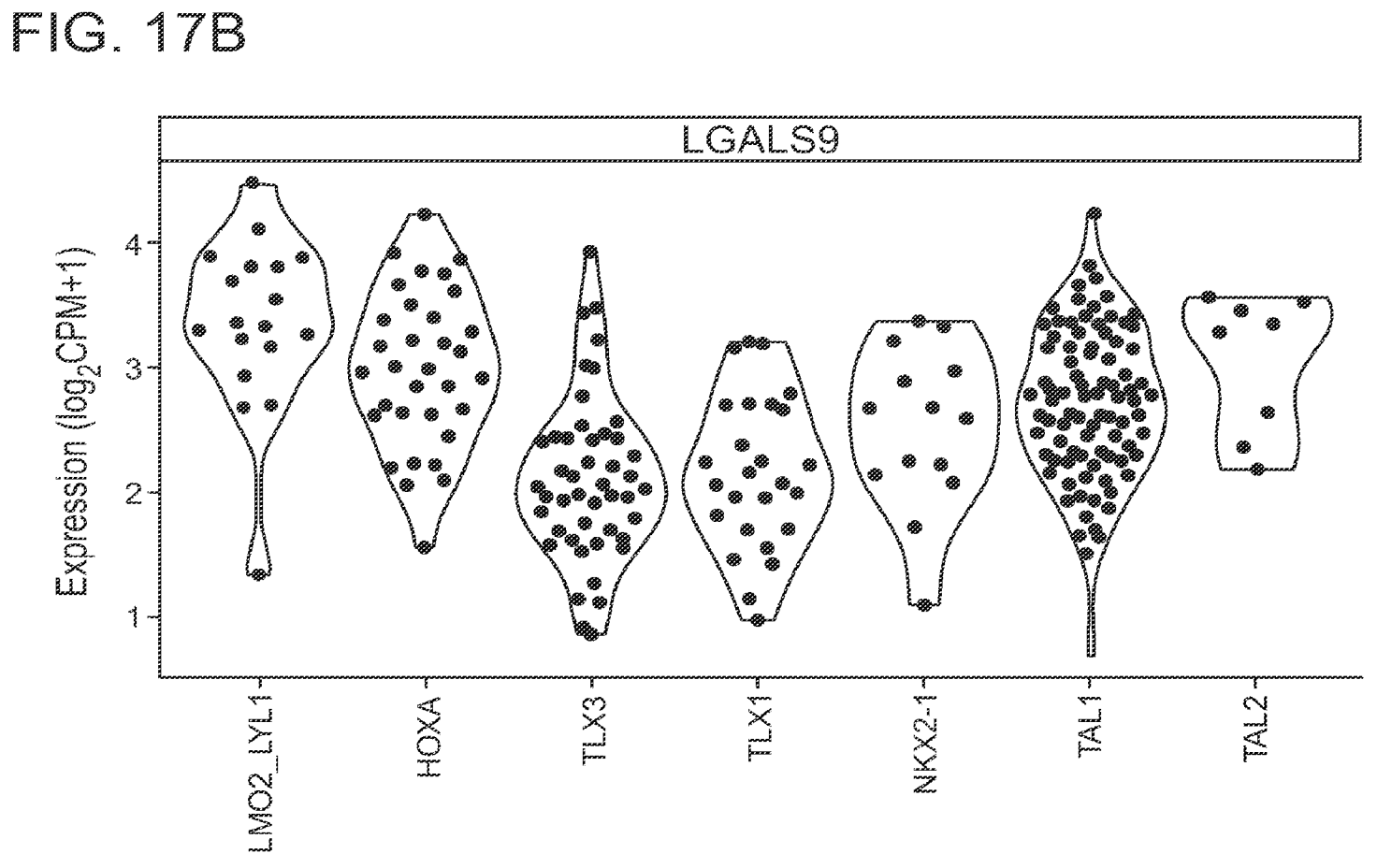
Figure 18A:
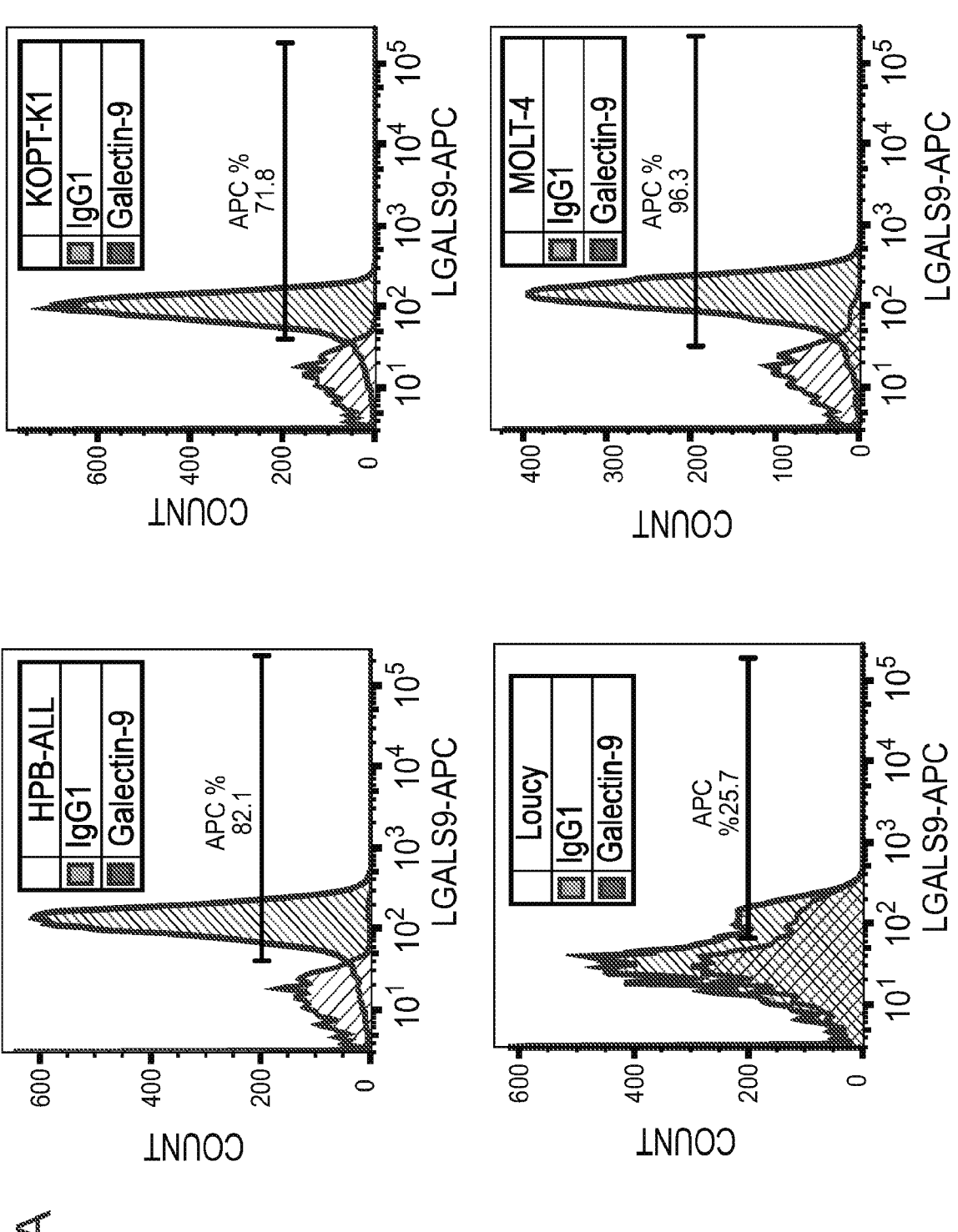
FIG. 18A-18C is a series of plots showing LGALS9 protein expression in T-ALL leukemia cell lines determined by flow cytometry. Intracellular LGALS9 fluorescence (dark gray) compared to mouse IgG1, κ (light gray) shown as histogram.
Figures 18B, 18C:
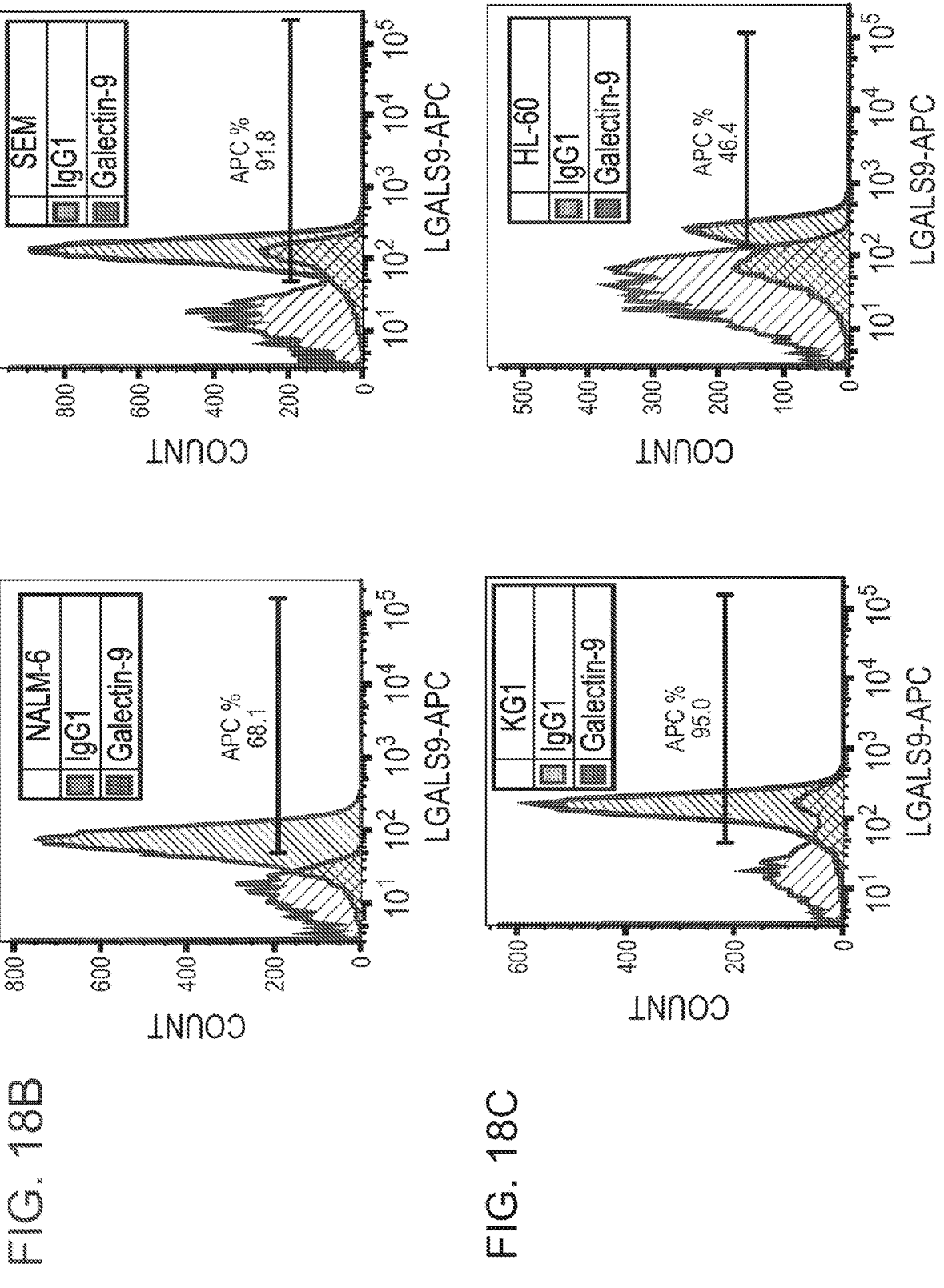

Maintenance of T-cell dysfunction requires signals that are generated by binding of ligands to inhibitory receptors on activated T-cells (Wherry et al., 2015 Nat Rev Immunol, 15(8):486-499). Previous studies in mice have described distinct categories of dysfunctional T-cells with differing susceptibilities to checkpoint inhibition, highlighting the need to identify specific ligand-receptor pairs across dysfunctional categories when considering therapeutic intervention (Miller et al., 2019 Nat Immunol, 20(3):326-336). In order to determine which ligands and receptors are potentially relevant to T-cell dysfunction in ETP-ALL, their expression levels were determined and computed interaction scores between inhibitory receptors on exhausted CD8$^+$ T-cells and their respective ligands in leukemia cells (FIG. 5A-FIG. 5B) (Kumar et al., 2018 Cell Rep, 25(6):1458-1468 e1454). The strongest interaction score was found for HAVCR2 (TIM-3) and its ligand LGALS9 (Galectin-9), with LGALS9 being universally expressed in all leukemic cells (FIG. 5B and FIG. 17A). Analysis of T-ALLs from the TARGET study confirmed high expression of LGALS9 in the LMO2/LYL1 category, which contains most of the ETP cases, and also in more mature types of T-ALL (FIG. 17B). Immunohistochemical (IHC) staining of bone marrow biopsies of ETP-ALL patients confirmed expression of LGALS9 on leukemic blasts and HAVCR2 on interspersed mononuclear cells (FIG. 5C, representative example). In contrast to recent reports in AML, where LGALS9 has been shown to be co-expressed with its receptor HAVCR2 creating an autocrine loop (Kikushige et al., 2015 Cell Stem Cell, 17(3):341-352), HAVCR2 and LGALS9 were not co-expressed on ETP-ALL blasts (FIG. 17A). IHC staining on a larger panel of ETP and T-ALL patients confirmed LGALS9 expression in almost all cases, although sometimes confined to a subset of cells. This might still suffice to blunt T-cell responses, as LGALS9 can be secreted and function in a paracrine manner (Zhu et al., 2005 Nat Immunol, 6(12):1245-1252; Yoshida et al., 2010 J Biol Chem, 285(47):36969-36976) (Table 4).

TABLE 4

IHC staining results for LGALS9 in ETP and T-ALL patients

| Case # | LGALS9 stain |
|---|---|
| ETP-ALL-1 | Positive |
| ETP-ALL-2 | Positive in minor subset |
| ETP-ALL-3 | Weakly positive in minor subset |
| ETP-ALL-4 | Positive in subset |
| ETP-ALL-5 | Weakly positive in subset |
| ETP-ALL-6 | Positive in subset |
| ETP-ALL-7 | Positive in subset |
| ETP-ALL-8 | Positive in subset |
| T-ALL-1 | Negative |
| T-ALL-2 | Weakly positive in subset |
| T-ALL-3 | Crush artifact, difficult to interpret |
| T-ALL-4 | Weakly positive |
| T-ALL-5 | Positive in subset |
| T-ALL-6 | Strongly positive |
| T-ALL-7 | Positive in subset |

Figure 19:
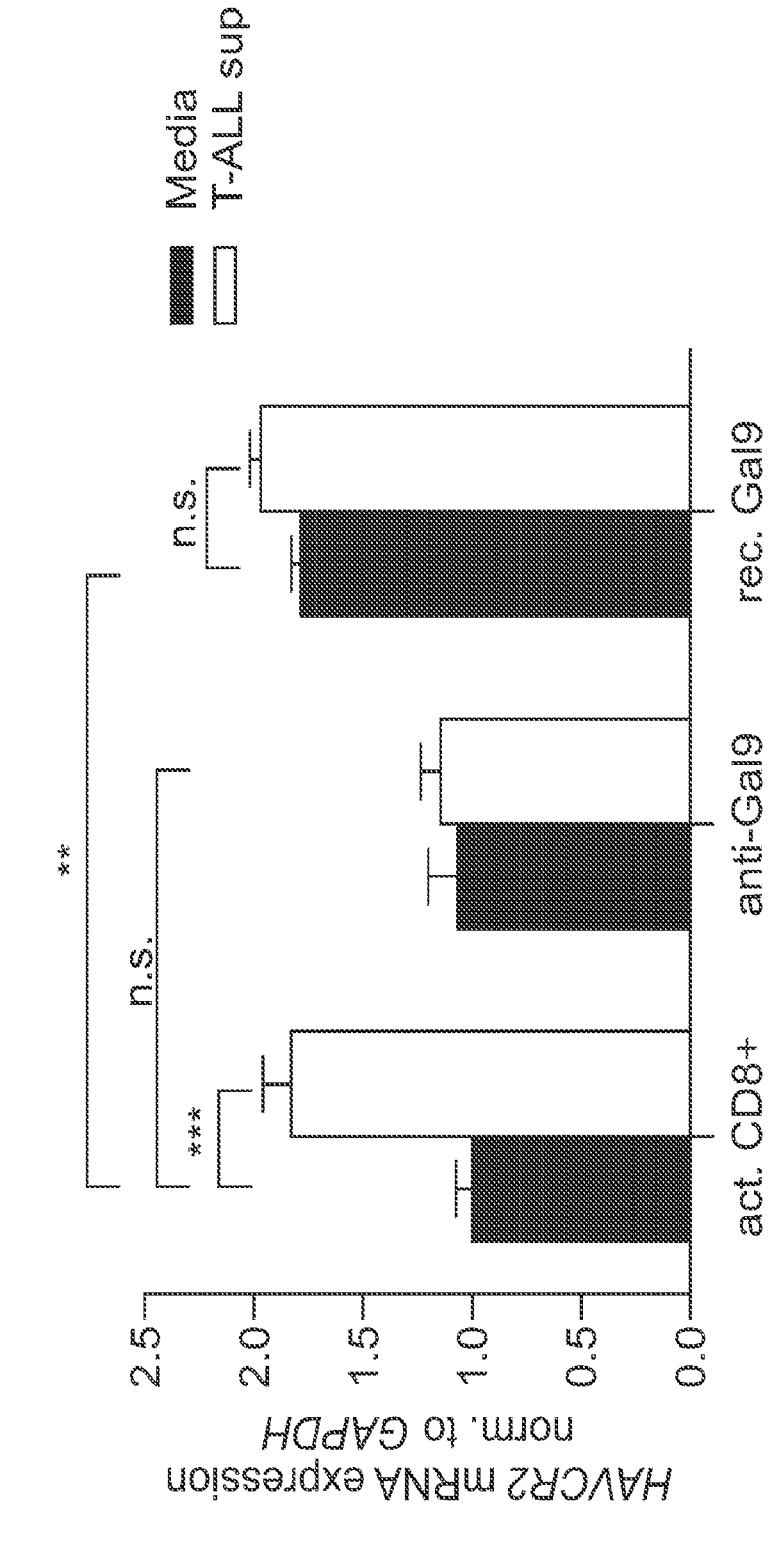
FIG. 19 is a bar graph showing the blockade of LGALS9 with neutralizing antibody inhibits HAVCR2 expression. HAVCR2 mRNA expression in activated CD8+ T-cells cultured with T-ALL supernatant (from DND-41 cells; orange) or control media (blue), in the presence/absence of anti-human Galectin-9 (10 μg/mL) or recombinant Galectin-9 (2.5 μg/mL). n.s. P>0.05, P≤0.01 and *P≤0.001, based on 3 technical replicates, using two-sided t-test.

To test whether T-ALL cells can cause T-cell dysfunction, it was first confirmed LGALS9 protein expression in T-ALL cell lines by flow cytometry (FIG. 5D, FIG. 18A-FIG. 18C). Activated polyclonal CD8$^+$ T-cells were cultured from normal donors with and without T-ALL supernatant (containing LGALS9) for three days. CD8$^+$ T-cells exposed to T-ALL supernatant showed down-regulation of GZMB (granzyme B), a main CD8$^+$ T-cell effector molecule, and up-regulation of the exhaustion markers HAVCR2 and TIGIT (FIG. 5E), effects that were abrogated by a neutralizing anti-LGALS9 antibody (FIG. 19). Moreover, upregulation of exhaustion markers was also observed when recombinant soluble LGALS9 was added to the culture (FIG. 19).

Figure 20A:
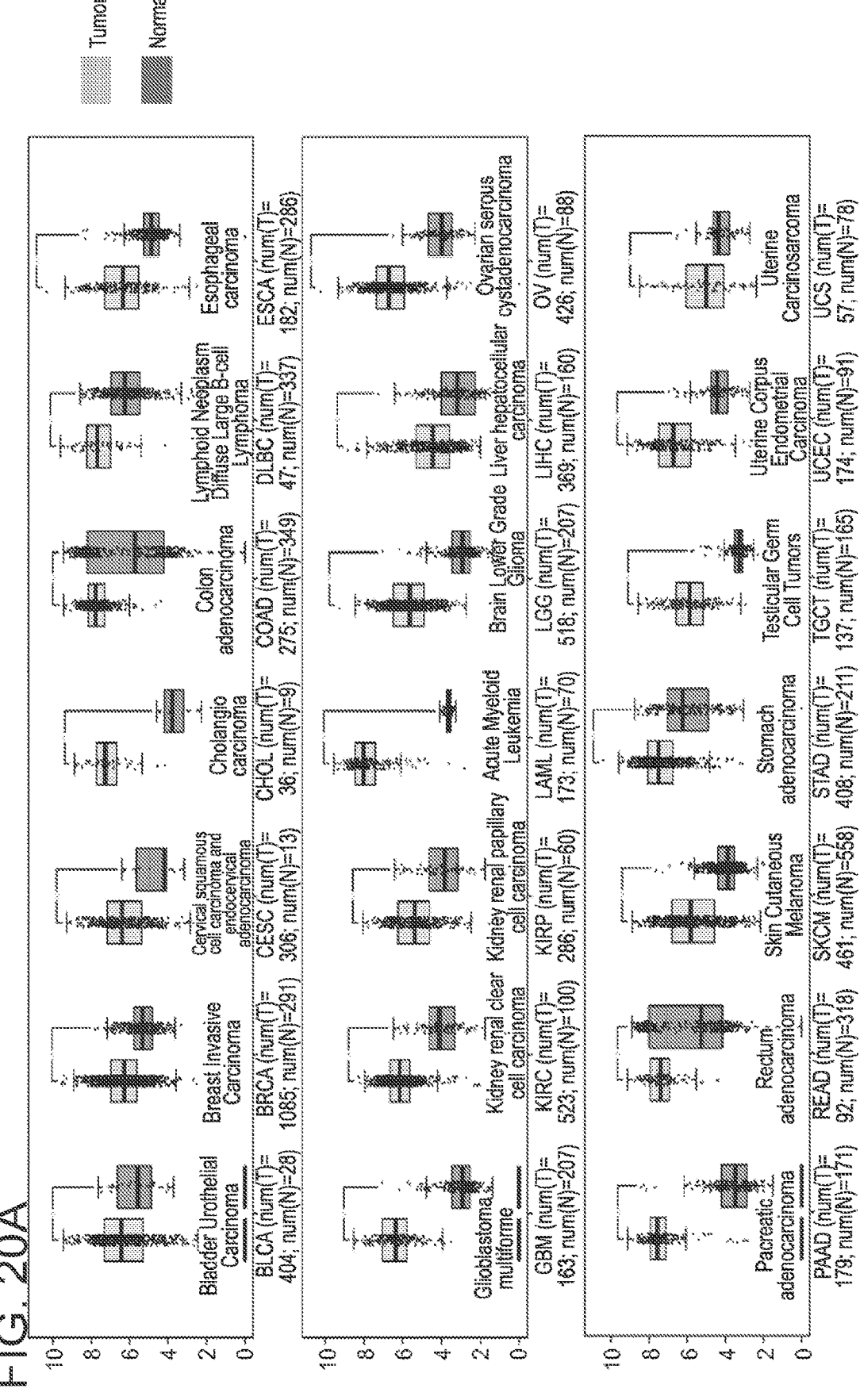
FIG. 20A-20B is a series of box and whisker plots and a line graph showing expression of LGALS9 in TCGA dataset.
Figure 20B:
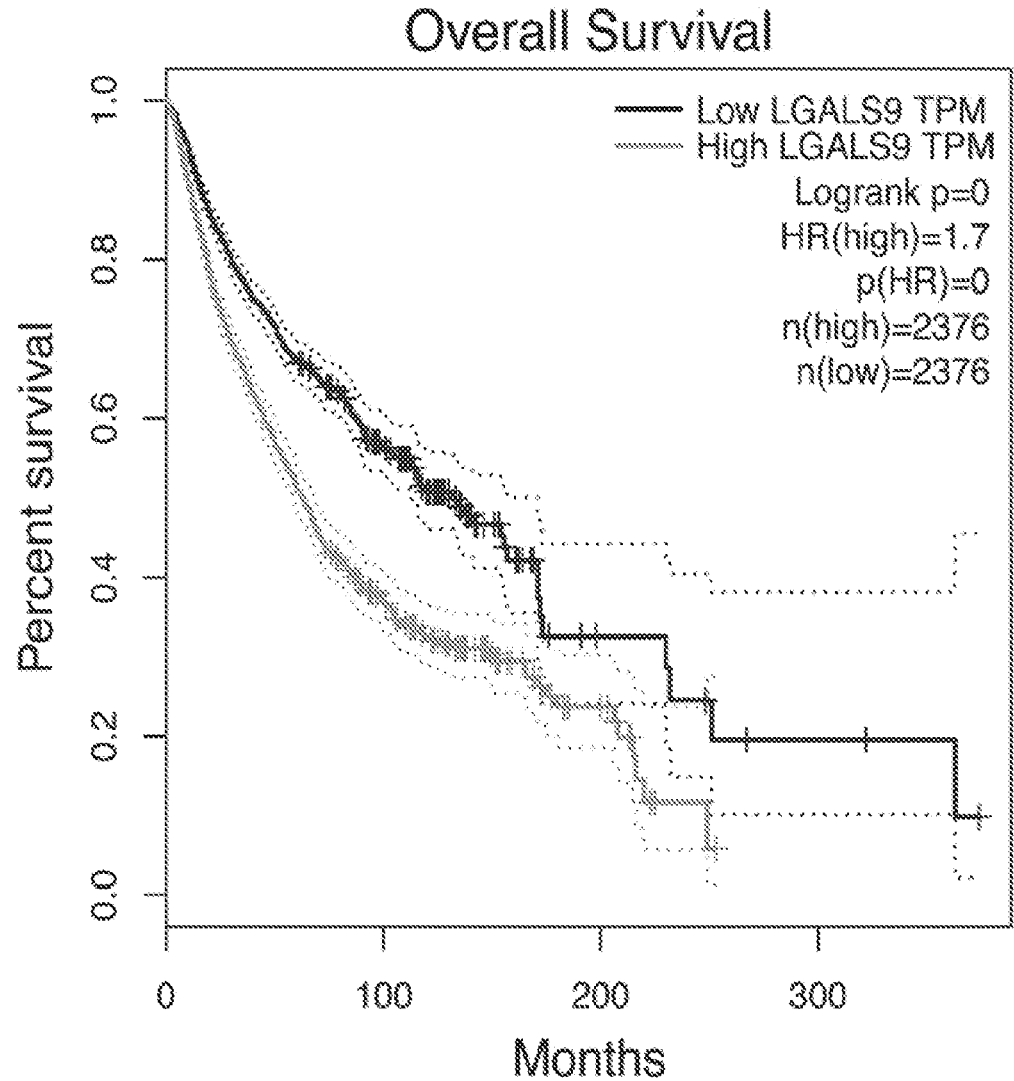
Figure 21:
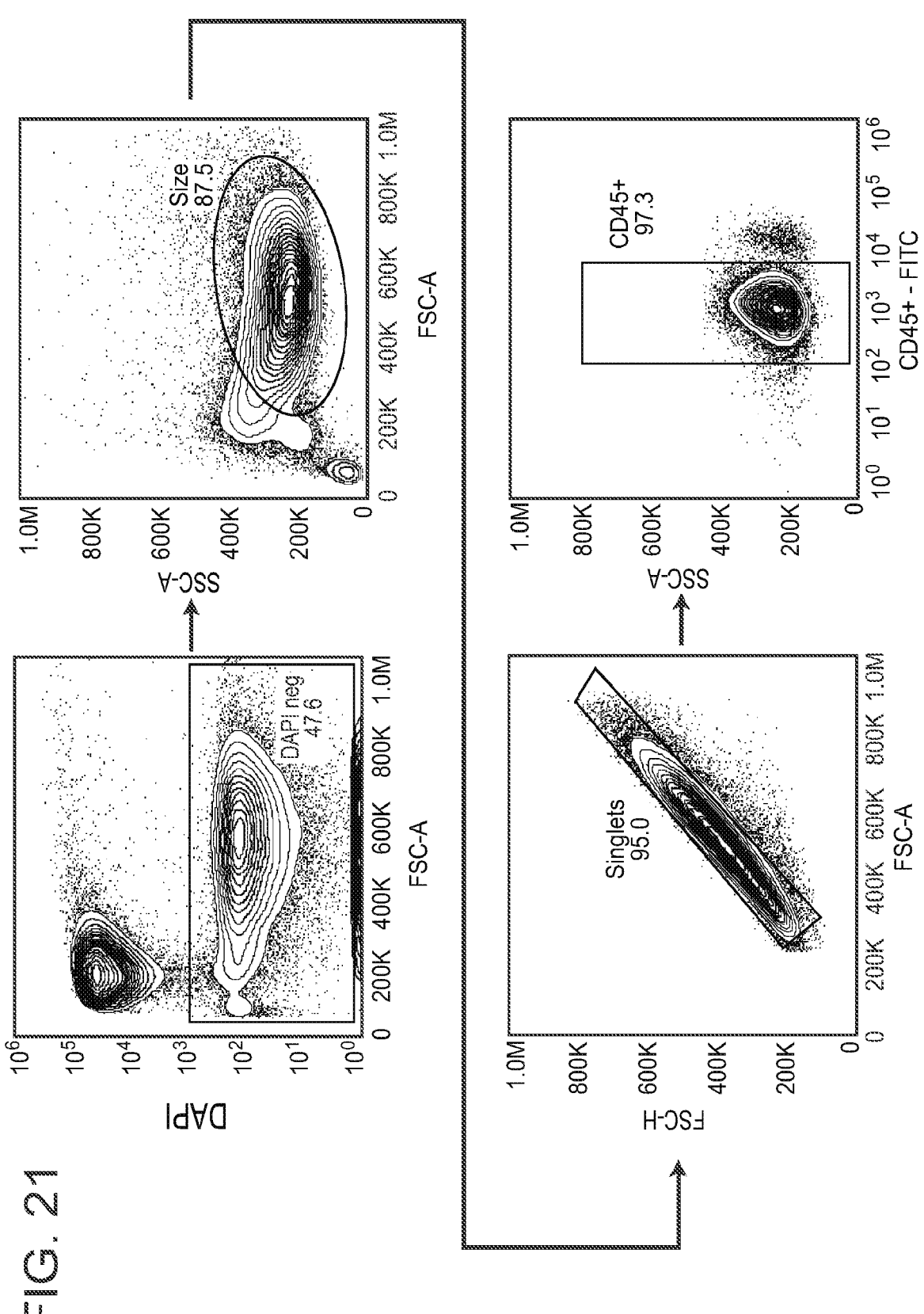
FIG. 21 is series of plots showing flow cytometry gating strategy of ETP T-ALL leukemic blasts. T-ALL samples were stained with anti-CD45 FITC and DAPI. CD45low expressing, DAPI negative single cells were sorted.
Figure 22:
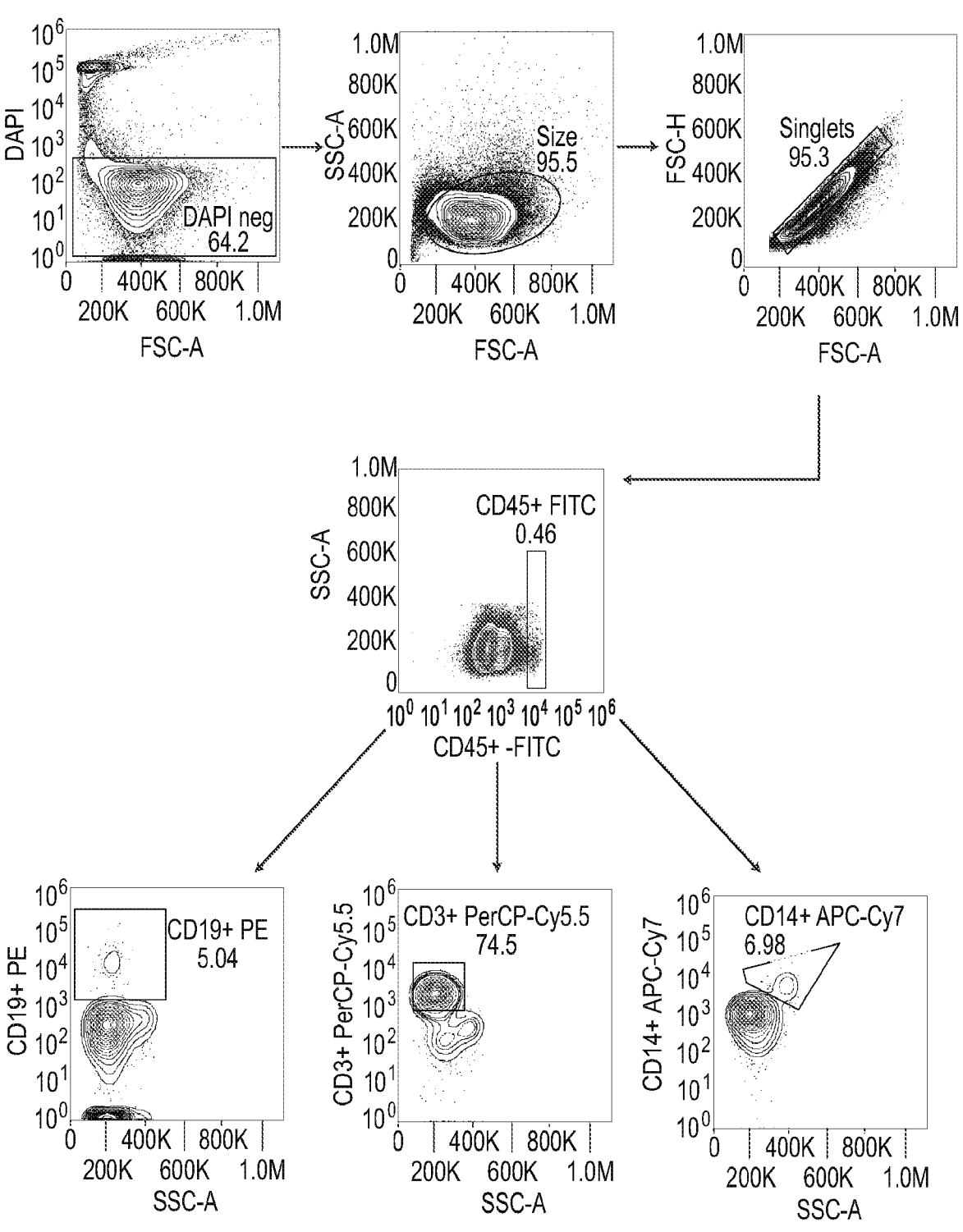
FIG. 22 is a series of plots showing flow cytometry gating strategy of normal immune cells. PBMCs were stained with DAPI, anti-CD45 FITC, anti-CD3 PerCP-Cy5.5, anti-CD19 PE, anti-CD14 APC-Cy7. CD45high CD3+ DAPI negative (T-cells), CD45high, CD19+, DAPI negative (B-cells), CD45high, CD14+, DAPI negative (monocytes) single cells were sorted.
Figure 23:
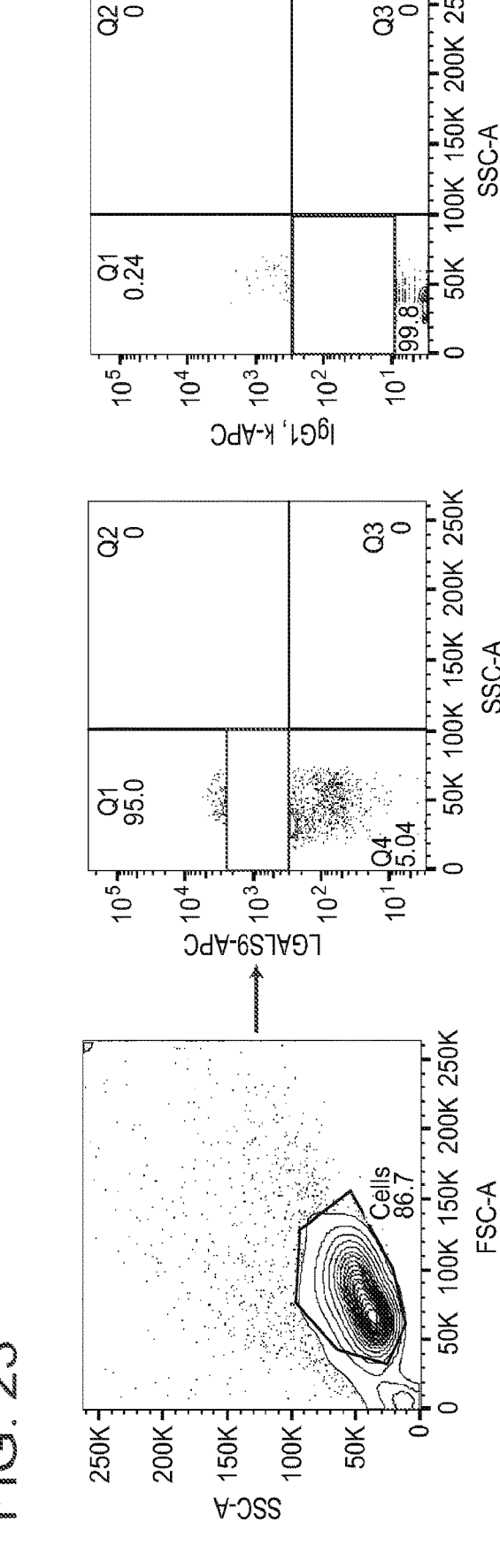
FIG. 23 is a series of plots showing flow cytometry gating strategy for flow staining of LGALS9. Cells were stained with anti-LGALS9 APC and data analyzed by gating on live cells based on FSC/SSC.

Finally, LGALS9 expression was examined across all cancers profiled in TCGA. LGALS9 expression is higher in the majority of cancers compared to matched normal tissue (FIG. 20A-FIG. 20B). Remarkably, high expression of LGALS9 is associated with inferior disease outcome (Tang et al., 2017 Nucleic Acids Res, 45(W1):W98-W102) (FIG. 20B).

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of decreasing T cell exhaustion in a subject having early T-cell precursor acute lymphoblastic leukemia (ETP T-ALL), the method comprising:
  identifying a subject having ETP T-ALL, and
  administering to the subject an effective amount of a neutralizing anti-Galectin-9 monoclonal antibody or a Galectin-9 binding antibody fragment thereof,
  thereby decreasing T cell exhaustion,
  wherein the anti-Galectin-9 antibody comprises Galectin-9 monoclonal antibody 9M1-3, D9R4A, or OT1D12.

2. The method of claim 1, wherein T cell effector function is increased.

3. The method of claim 1, further comprising obtaining a test sample from the subject; and identifying malignant early T-cell precursor acute lymphoblastic leukemic cells in the test sample.

4. The method of claim 3, wherein the test sample is obtained from a tumor tissue, a tumor microenvironment, a plasma sample, or a blood sample.

5. The method of claim 1, wherein the subject has relapsed or wherein the ETP T-ALL is refractory to treatment.

6. The method of claim 1, further comprising administering to the subject a chemotherapeutic agent, radiation therapy, cryotherapy, hormone therapy, or immunotherapy.

7. The method of claim 6, wherein the chemotherapeutic agent comprises thalidomide, lenalidomide, ixazomib, bortezomib, carfilzomib, melphalan, vincristine, cyclophosphamide, doxorubicin, liposomal doxorubicin, rituximab, etoposide or bendamustine.

8. The method of claim 6, wherein the chemotherapeutic agent is administered with a steroid.

9. The method of claim 8, wherein the steroid comprises prednisone or dexamethasone.

10. The method of claim 1, further comprising administering to the subject a combination chemotherapy agent.

11. The method of claim 10, wherein the combination chemotherapy agent comprises hyper-CVAD, hyper-CVAD+nelarabine or augmented Berlin-Frankfurt-Münster (aBFM) regimen.

12. The method of claim 1, further comprising administering an γ-secretase inhibitor selected from the group consisting of-BMS-906024, LY411,575, MK-0752, GSI MRK-003, GSI RO4929097, GSI PF-03084014, and BMS-708163.

13. The method of claim 1, further comprising administering a phosphoinositide 3-kinase (PI3-K) inhibitor selected from the group consisting of BAY80-6946/Copanlisib, Duvelisib/IPI-145, and δ/γ CAL-101/idelalisib.

14. The method of claim 1, wherein the subject is a human.

15. The method of claim 1, wherein the anti-Galectin-9 monoclonal antibody or Galectin-9 binding antibody fragment thereof is partially humanized, fully humanized, or chimeric.

* * * * *

SEQUENCE LISTING

<160> NUMBER OF SEQ ID NOS: 14

<210> SEQ ID NO 1
<211> LENGTH: 343
<212> TYPE: PRT
<213> ORGANISM: Homo sapiens

<400> SEQUENCE: 1

```
Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
                20                  25                  30

Val Asn Gly Thr Val Leu Ser Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
                100                 105                 110

Met Val Asn Gly Ile Leu Phe Val Gln Tyr Phe His Arg Val Pro Phe
                115                 120                 125

His Arg Val Asp Thr Ile Ser Val Asn Gly Ser Val Gln Leu Ser Tyr
    130                 135                 140

Ile Ser Phe Gln Asn Pro Arg Thr Val Pro Val Gln Pro Ala Phe Ser
145                 150                 155                 160

Thr Val Pro Phe Ser Gln Pro Val Cys Phe Pro Pro Arg Pro Arg Gly
                165                 170                 175

Arg Arg Gln Lys Thr Gln Thr Val Ile His Thr Val Gln Ser Ala Pro
                180                 185                 190

Gly Gln Met Phe Ser Thr Pro Ala Ile Pro Pro Met Met Tyr Pro His
                195                 200                 205

Pro Ala Tyr Pro Met Pro Phe Ile Thr Thr Ile Leu Gly Gly Leu Tyr
    210                 215                 220

Pro Ser Lys Ser Ile Leu Leu Ser Gly Thr Val Leu Pro Ser Ala Gln
225                 230                 235                 240

Arg Phe His Ile Asn Leu Cys Ser Gly Asn His Ile Ala Phe His Leu
                245                 250                 255

Asn Pro Arg Phe Asp Glu Asn Ala Val Val Arg Asn Thr Gln Ile Asp
                260                 265                 270

Asn Ser Trp Gly Ser Glu Glu Arg Ser Leu Pro Arg Lys Met Pro Phe
                275                 280                 285

Val Arg Gly Gln Ser Phe Ser Val Trp Ile Leu Cys Glu Ala His Cys
    290                 295                 300

Leu Lys Val Ala Val Asp Gly Gln His Leu Phe Glu Tyr Tyr His Arg
305                 310                 315                 320

Leu Arg Asn Leu Pro Thr Ile Asn Arg Leu Glu Val Gly Gly Asp Ile
                325                 330                 335

Gln Leu Thr His Val Gln Thr
                340
```

<210> SEQ ID NO 2
<211> LENGTH: 1696

-continued

```
<212> TYPE: DNA
<213> ORGANISM: Homo sapiens

<400> SEQUENCE: 2
ttctatttct ttgttaagtc gttccctcta caaaggactt cctagtgggt gtgaaaggca      60
gcggtggcca cagaggcggc ggagagatgg ccttcagcgg ttcccaggct ccctacctga     120
gtccagctgt cccctttct gggactattc aaggaggtct ccaggacgga cttcagatca      180
ctgtcaatgg gaccgttctc agctccagtg gaaccaggtt tgctgtgaac tttcagactg     240
gcttcagtgg aaatgacatt gccttccact caaccctcg gtttgaagat ggagggtacg      300
tggtgtgcaa cacgaggcag aacggaagct gggggcccga ggagaggaag acacacatgc     360
ctttccagaa ggggatgccc tttgacctct gcttcctggt gcagagctca gatttcaagg     420
tgatggtgaa cggggatcctc ttcgtgcagt acttccaccg cgtgcccttc caccgtgtgg    480
acaccatctc cgtcaatggc tctgtgcagc tgtcctacat cagcttccag aaccccgca     540 cagtccctgt tcagcctgcc ttctccacgg tgccgttctc ccagcctgtc tgtttcccac    600
ccaggcccag ggggcgcaga caaaaaaccc agacagtcat ccacacagtg cagagcgccc    660
ctggacagat gttctctact cccgccatcc cacctatgat gtaccccac cccgcctatc     720 cgatgccttt catcaccacc attctgggag ggctgtaccc atccaagtcc atcctcctgt    780
caggcactgt cctgcccagt gctcagaggt tccacatcaa cctgtgctct gggaaccaca    840
tcgccttcca cctgaacccc cgtttttgatg agaatgctgt ggtccgcaac acccagatcg    900
acaactcctg ggggtctgag gagcgaagtc tgccccgaaa aatgcccttc gtccgtggcc    960
agagcttctc agtgtggatc ttgtgtgaag ctcactgcct caaggtggcc gtggatggtc   1020
agcacctgtt tgaatactac catcgcctga ggaacctgcc caccatcaac agactggaag   1080
tggggggcga catccagctg acccatgtgc agacataggc ggcttcctgg ccctgggggcc   1140 gggggctggg gtgtggggca gtctgggtcc tctcatcatc cccacttccc aggcccagcc   1200
tttccaaccc tgcctgggat ctgggcttta atgcagaggc catgtccttg tctggtcctg   1260
cttctggcta cagccaccct ggaacggaga aggcagctga cggggattgc cttcctcagc   1320
cgcagcagca cctggggctc cagctgctgg aatcctacca tcccaggagg caggcacagc   1380
cagggagagg ggaggagtgg gcagtgaaga tgaagcccca tgctcagtcc cctcccatcc   1440
cccacgcagc tccaccccag tcccaagcca ccagctgtct gctcctggtg ggaggtggcc   1500
tcctcagccc ctcctctctg acctttaacc tcactctcac cttgcaccgt gcaccaaccc   1560
ttcacccctc ctggaaagca ggcctgatgg cttcccactg gcctccacca cctgaccaga   1620
gtgttctctt cagaggactg gctcctttcc cagtgtcctt aaaataaaga aatgaaaatg   1680
cttgttggca cattca                                                   1696

<210> SEQ ID NO 3
<211> LENGTH: 23
<212> TYPE: DNA
<213> ORGANISM: Artificial Sequence
<220> FEATURE:
<223> OTHER INFORMATION: Chemically Synthesized Primer

<400> SEQUENCE: 3
ctgctgctac tacttacaag gtc                                              23

<210> SEQ ID NO 4
<211> LENGTH: 20
<212> TYPE: DNA
```

-continued

```
<213> ORGANISM: Artificial Sequence
<220> FEATURE:
<223> OTHER INFORMATION: Chemically Sythesized Primer

<400> SEQUENCE: 4
gcagggcaga taggcattct                                              20

<210> SEQ ID NO 5
<211> LENGTH: 23
<212> TYPE: DNA
<213> ORGANISM: Artificial Sequence
<220> FEATURE:
<223> OTHER INFORMATION: Chemically Synthesized Primer

<400> SEQUENCE: 5
ggaatgatga caggcacaat aga                                          23

<210> SEQ ID NO 6
<211> LENGTH: 22
<212> TYPE: DNA
<213> ORGANISM: Artificial Sequence
<220> FEATURE:
<223> OTHER INFORMATION: Chemically Synthesized Primer

<400> SEQUENCE: 6
ccatcagggt aggtgtgata ga                                           22

<210> SEQ ID NO 7
<211> LENGTH: 21
<212> TYPE: DNA
<213> ORGANISM: Artificial Sequence
<220> FEATURE:
<223> OTHER INFORMATION: Chemically Synthesized Primer

<400> SEQUENCE: 7
taccattgag ttgtgcgtgg g                                            21

<210> SEQ ID NO 8
<211> LENGTH: 23
<212> TYPE: DNA
<213> ORGANISM: Artificial Sequence
<220> FEATURE:
<223> OTHER INFORMATION: Chemically Synthesized Primer

<400> SEQUENCE: 8
gccattgttt cgtccatagg aga                                          23

<210> SEQ ID NO 9
<211> LENGTH: 21
<212> TYPE: DNA
<213> ORGANISM: Artificial Sequence
<220> FEATURE:
<223> OTHER INFORMATION: Chemically Synthesized Primer

<400> SEQUENCE: 9
aactcctgtc ttgcattgca c                                            21

<210> SEQ ID NO 10
<211> LENGTH: 21
<212> TYPE: DNA
<213> ORGANISM: Artificial Sequence
<220> FEATURE:
<223> OTHER INFORMATION: Chemically Synthesized Primer

<400> SEQUENCE: 10
gctccagttg tagctgtgtt t                                            21
```

-continued

```
<210> SEQ ID NO 11
<211> LENGTH: 22
<212> TYPE: DNA
<213> ORGANISM: Artificial Sequence
<220> FEATURE:
<223> OTHER INFORMATION: Chemically Synthesized Primer

<400> SEQUENCE: 11
gtagcggata atggaactct tt                                          22

<210> SEQ ID NO 12
<211> LENGTH: 22
<212> TYPE: DNA
<213> ORGANISM: Artificial Sequence
<220> FEATURE:
<223> OTHER INFORMATION: Chemically Synthesized Primer

<400> SEQUENCE: 12
tttcgaagtc atctcgtttc tt                                          22

<210> SEQ ID NO 13
<211> LENGTH: 20
<212> TYPE: DNA
<213> ORGANISM: Artificial Sequence
<220> FEATURE:
<223> OTHER INFORMATION: Chemically Synthesized Primer

<400> SEQUENCE: 13
aatcccatca ccatcttcca                                             20

<210> SEQ ID NO 14
<211> LENGTH: 21
<212> TYPE: DNA
<213> ORGANISM: Artificial Sequence
<220> FEATURE:
<223> OTHER INFORMATION: Chemically Synthesized Primer

<400> SEQUENCE: 14
tgggactcca cgacgtactc a                                           21
```